US012729407B2

(12) United States Patent
Smet et al.

(10) Patent No.: US 12,729,407 B2
(45) Date of Patent: Sep. 8, 2026

(54) MUCINS AND ISOFORMS THEREOF IN DISEASES CHARACTERIZED BY BARRIER DYSFUNCTION

(71) Applicant: Universiteit Antwerpen, Antwerp (BE)

(72) Inventors: Annemieke Smet, Sint-Niklaas (BE); Benedicte De Winter, 's-Gravenwezel (BE); Tom Breugelmans, Turnhout (BE)

(73) Assignee: Universiteit Antwerpen, Antwerp (BE)

( * ) Notice: Subject to any disclaimer, the term of this patent is extended or adjusted under 35 U.S.C. 154(b) by 833 days.

(21) Appl. No.: 18/009,204

(22) PCT Filed: Jun. 30, 2021

(86) PCT No.: PCT/EP2021/068083

§ 371 (c)(1),
(2) Date: Dec. 8, 2022

(87) PCT Pub. No.: WO2022/003061

PCT Pub. Date: Jan. 6, 2022

(65) Prior Publication Data

US 2023/0340623 A1 Oct. 26, 2023

(30) Foreign Application Priority Data

Jun. 30, 2020 (WO) ................. PCT/EP2020/068340
Jan. 18, 2021 (EP) .................................... 21152072
Feb. 18, 2021 (EP) .................................... 21157750

(51) Int. Cl.
*C12Q 1/70* (2006.01)

(52) U.S. Cl.
CPC ......... *C12Q 1/70* (2013.01); *C12Q 2600/158* (2013.01); *C12Q 2600/16* (2013.01)

(58) Field of Classification Search
None
See application file for complete search history.

(56) References Cited

FOREIGN PATENT DOCUMENTS

WO 2016149368 A1 9/2016

OTHER PUBLICATIONS

Lu et al. (Journal of Medical Virology, 2021, p. 582-584).*
Moorsel et al. (Frontiers in Medicine, May 16, 2020, p. 1-8).*
Ko et al. (International Journal of Antimicrobial Agents Mar. 2020, p. 1-3).*
International Search Report and Written Opinion mailed Dec. 10, 2021 in reference to co-pending European Application PCT/EP2021/068083 filed Jun. 30, 2021.
Breugelmans, et al., "In-Depth Study of Transmembrane Mucins in Association with Intestinal Barrier Dysfunction During the Course of T Cell Transfer and DSS-Induced Colitis", Journal of Crohn's and Colitis, pp. 974-994, 2020.
Corman, et al., "Detection of 2019 novel coronavirus (2019-nCoV) by real-time RT-PCR", Research, pp. 1-8, 2020.
D'Alessandro, et al., "Serum KL-16 concentrations as a novel biomarker of severe COVID-19", Journal of Medical Virology, vol. 92, pp. 2216-2220.
Guan, et al., "Strategies for the prevention and management of coronavirus disease 2019", European Respiratory Journal, pp. 1-10, 2019.
Gupta, et al., "Analysis of Intestinal Permeability in Mice", Bio-protocol, vol. 4, Issue 22, pp. 1-4, Nov. 20, 2014.
Heylen, et al., "Colonoscopy and μPET/CT are Valid Techniques to Monitor Inflammation in the Adoptive Transfer Colitis Model in Mice", Inflamm Bowel Dis, vol. 19, No. 5, pp. 966-976, Apr. 5, 2013.
Hoffman, et al., "SARS-CoV-2 Cell Entry Depends on ACE2 and TMPRSS2 and Is Blocked by a Clinically Proven Protease Inhibitor", CellPress, vol. 181, pp. 271-280, 2020.
Huang, et al., "Clinical features of patients infected with 2019 novel coronavirus in Wuhan, China", Articles, vol. 395, pp. 497-506, Feb. 15, 2020.
Linden, et al., "Mucins in the mucosal barrier to infection", Nature Publishing Group, vol. 1, No. 3, pp. 183-197, May 2008.
Moehle, et al., "Aberrant intestinal expression and allelic variants of mucin genes associated with inflammatory bowel disease", Journal Mol. Medicine, vol. 84, pp. 1055-1066, 2006.
Moreels, et al., "Concurrent infection with Schistosoma mansoni attenuates inflammation induced changes in colonic morphology, cytokine levels, and smooth muscle contractility of trinitrobenzene sulphonic acid induced colitis in ats", Inflammatory Bowel Disease, vol. 53, pp. 99-107, 2004.
Obermair, et al., "Expression of Muc1 Splice Variants in Benign and Malignant Ovarian Tumours", Int. Journal of Cancer, vol. 100, pp. 166-171, 2002.
Sheng, et al., "MUC1 and MUC13 differentially regulate epithelial inflammation in response to inflammatory and Infectious stimuli", Nature Publishing Group Articles, vol. 6, No. 3, pp. 557-568, May 2013.
Sheng, et al., "The MUC13 cell-surface mucin protects against intestinal inflammation by inhibiting epithelial cell apoptosis", Intestinal Inflammation, vol. 60, pp. 1661-1670, 2011.
Vancamelbeke, et al., "Genetic and Transcriptomic Basis of Intestinal Epithelial Barrier Dysfunction in Inflammatory Bowel Disease", Inflamm. Bowel Dis., vol. 23, No. 10, pp. 1718-1729, Oct. 2017.

(Continued)

*Primary Examiner* — Agnieszka Boesen
(74) *Attorney, Agent, or Firm* — FRESH IP PLC; Michael H. Anderson

(57) ABSTRACT

Mucins and isoforms thereof are provided herein for use in the diagnosis, monitoring, prevention, and/or treatment of a disease characterized by barrier dysfunction, such as, but not limited to a gastrointestinal disorder (e.g. Inflammatory Bowel Disease (IBD), Irritable Bowel Syndrome (IBS), cancer, gastro-intestinal infections, obesitas, non-alcoholic fatty liver disease (NAFLD)), neurodegenerative disorders, respiratory infections, and more in particular coronaviral infections. In a specific embodiment, said mucins and/or isoforms thereof are selected from the list comprising: MUC16, MUC21, MUC20, MUC2, MUC4, MUC5AC, MUC5B, MUC13, and MUC1, and isoforms thereof.

19 Claims, 58 Drawing Sheets

Specification includes a Sequence Listing.

(56) References Cited

OTHER PUBLICATIONS

Wallace, et al., "Exacerbation of Experimental Colitis by Nonsteroidal Anti-Inflammatory Drugs is not Related to Elevated Leukotriene B4 Synthesis", Gastroenterology, vol. 102, pp. 18-27, 1992.
Lu, et al., "Elevated MUC1 and MUC5AC mucin protein levels in airway mucus of critical ill COVID-19 patients", Journal of Medical Virology, vol. 93, pp. 582-584, 2021.
Zaretsky, et al., "MUCI gene overexpressed in breast cancer: structure and transcriptional activity of MUCI promoter and role of estrogen receptor alpha (ERα) in regulation of the MUCI gene expression", Molecular Cancer, vol. 5, No. 57, pp. 1-14, 2006.
Zrihan-Licht, et al., "Characterization and molecular cloning of a novel MUCI protein, devoid of tandem repeats, expressed in human breast cancer tissue", Priority Paper, European Journal Biochem., vol. 224, pp. 787-795, 1994.
Wei, et al., "Elevations of serum cancer biomarkers correlate with severity of COVID-19", Journal of Medical Virology, vol. 92, pp. 2036-2041, 2020.
Bose, et al., "Mucin signature as a potential tool to predict susceptibility to COVID-19", Physiological Reports, vol. 9, No. 1, pp. 1-10, Dec. 29, 2020.
D'Alessandro, et al., "Serial KL-6 measurements in COVID-19 patients", Internal and Emergency Medicine, Springer Milan, Milan, vol. 16, No. 6, Jan. 16, 2021, pp. 1541-1545, XP037534829.

* cited by examiner

Fig. 2 - Continued
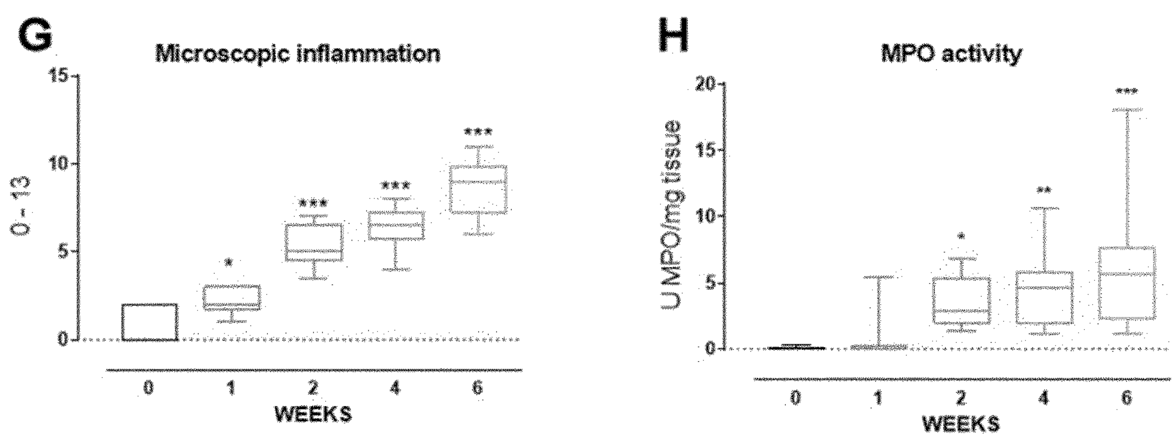

Fig. 3 - Continued
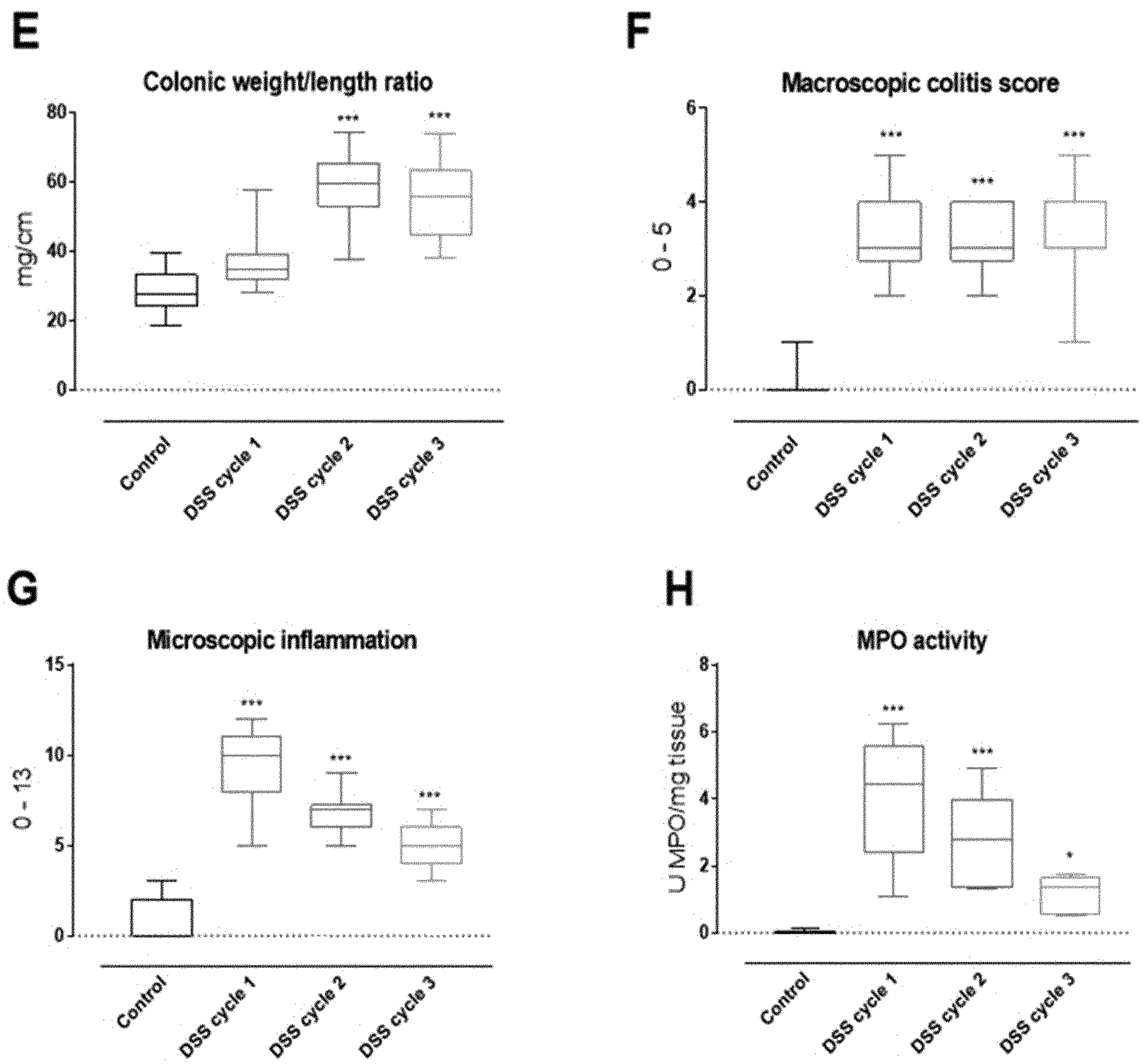

Fig. 4 - Continued
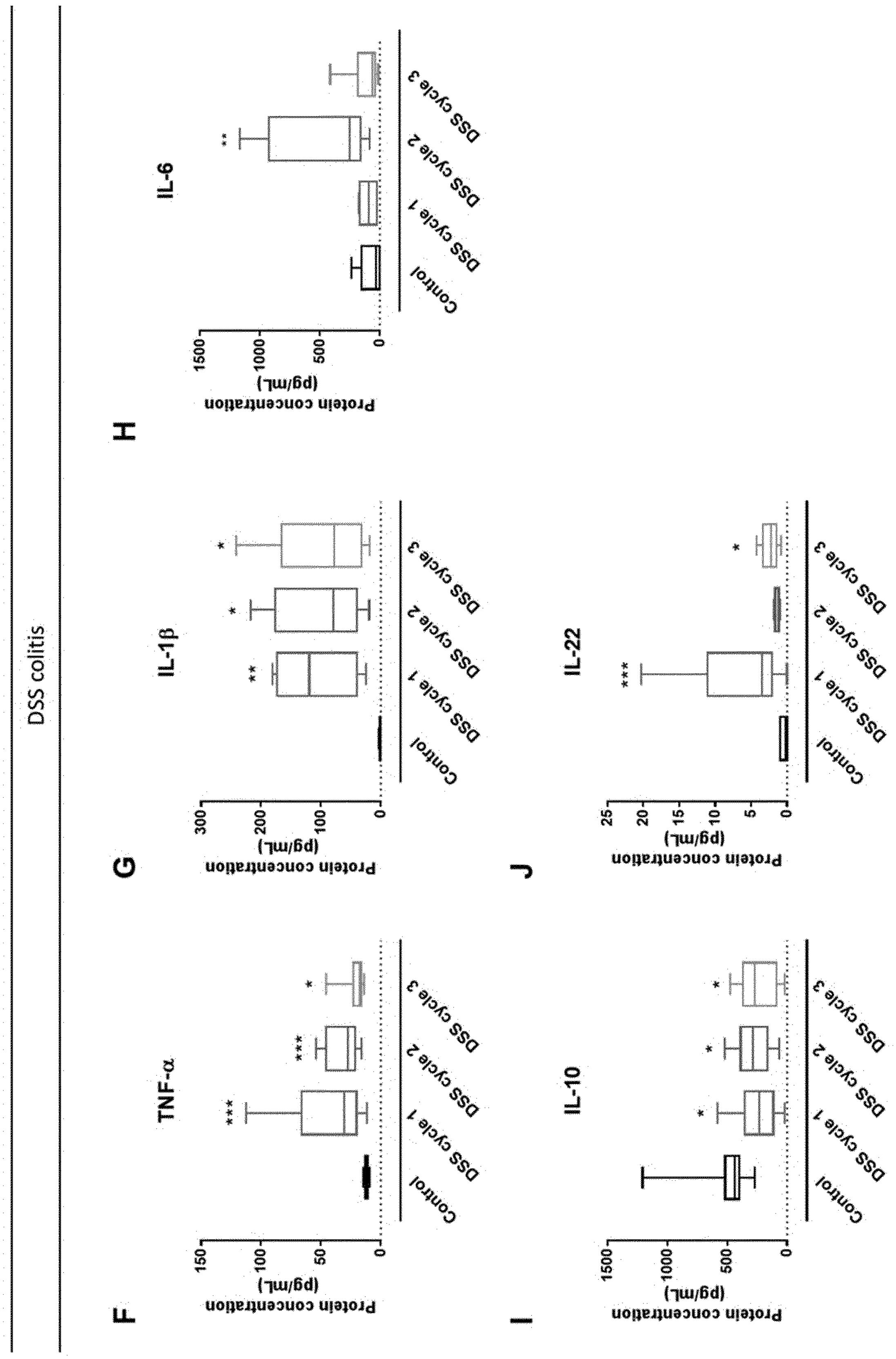

Fig. 8 - Continued
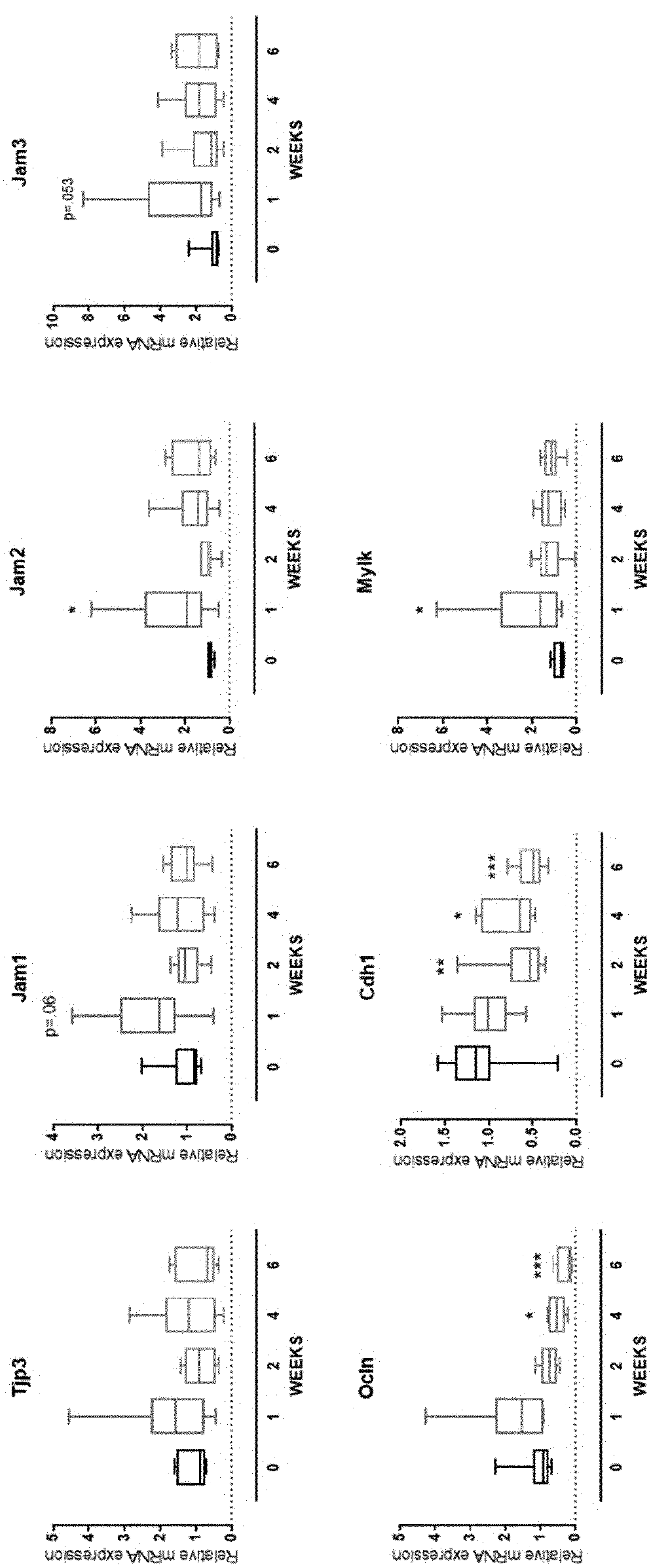

Fig. 9 - Continued
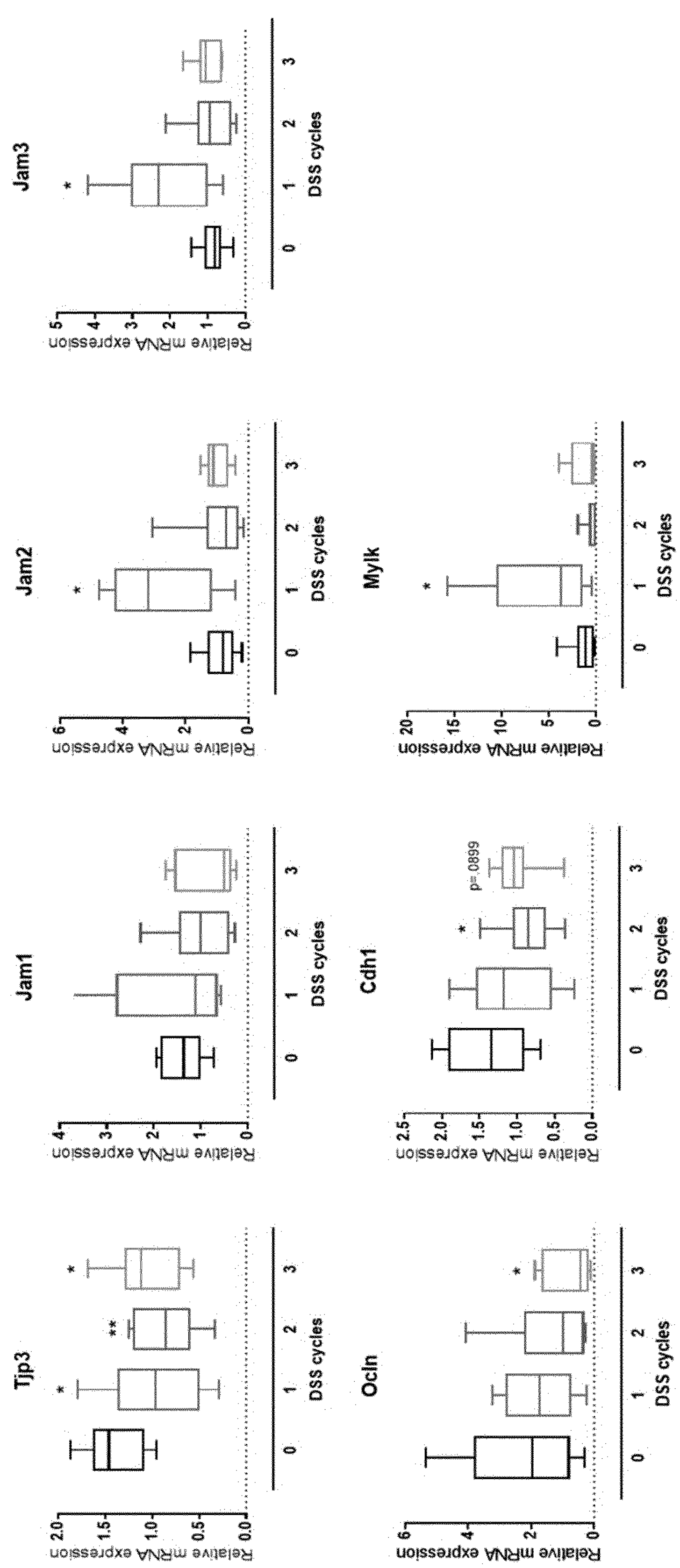

T cell transfer

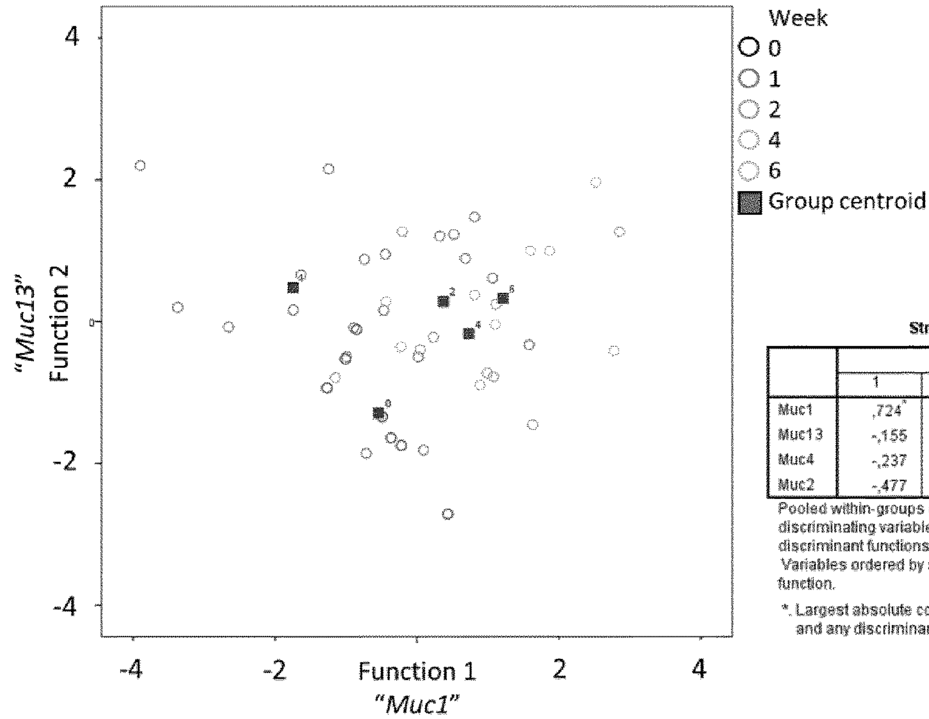

Structure Matrix

| | Function | | | |
|---|---|---|---|---|
| | 1 | 2 | 3 | 4 |
| Muc1 | ,724* | ,516 | ,389 | -,242 |
| Muc13 | -,155 | ,724* | ,040 | ,671 |
| Muc4 | -,237 | -,407 | ,829* | ,301 |
| Muc2 | -,477 | ,405 | ,614* | -,481 |

Pooled within-groups correlations between discriminating variables and standardized canonical discriminant functions
Variables ordered by absolute size of correlation within function.

*. Largest absolute correlation between each variable and any discriminant function

B

DSS-colitis

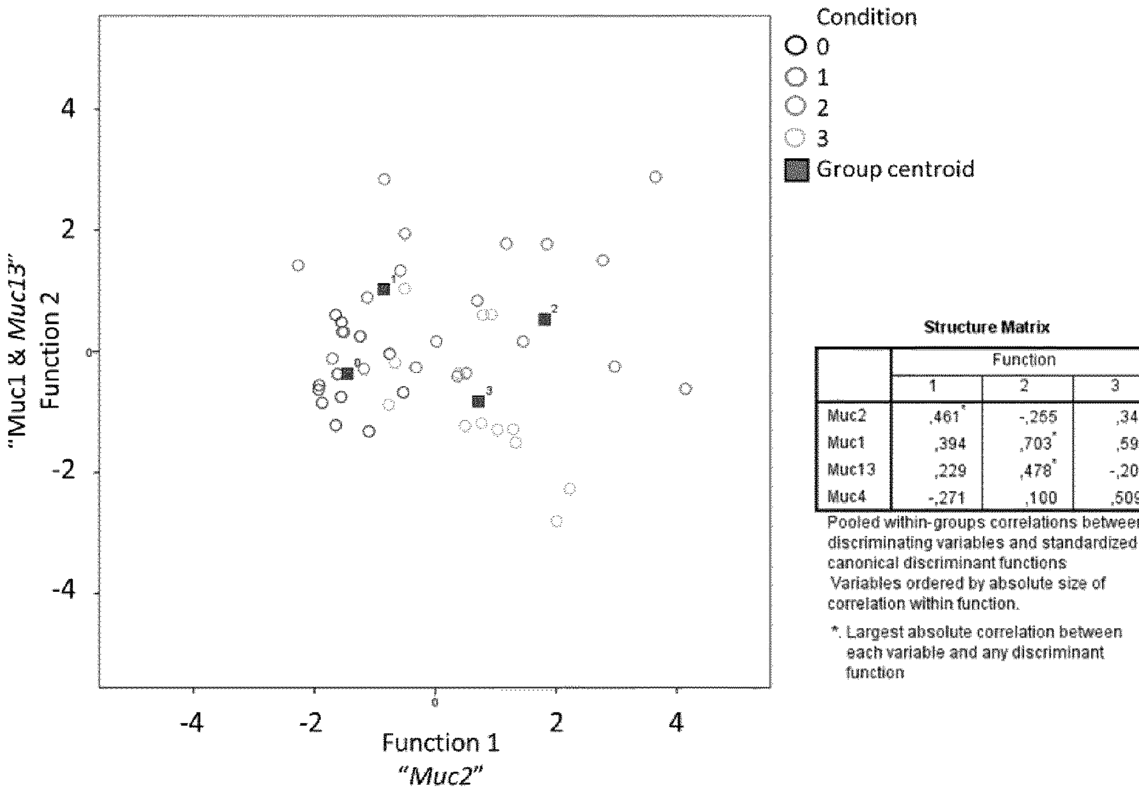

Structure Matrix

| | Function | | |
|---|---|---|---|
| | 1 | 2 | 3 |
| Muc2 | ,461* | -,255 | ,349 |
| Muc1 | ,394 | ,703* | ,591 |
| Muc13 | ,229 | ,478* | -,202 |
| Muc4 | -,271 | ,100 | ,509* |

Pooled within-groups correlations between discriminating variables and standardized canonical discriminant functions
Variables ordered by absolute size of correlation within function.

*. Largest absolute correlation between each variable and any discriminant function Fig. 12 - Continued
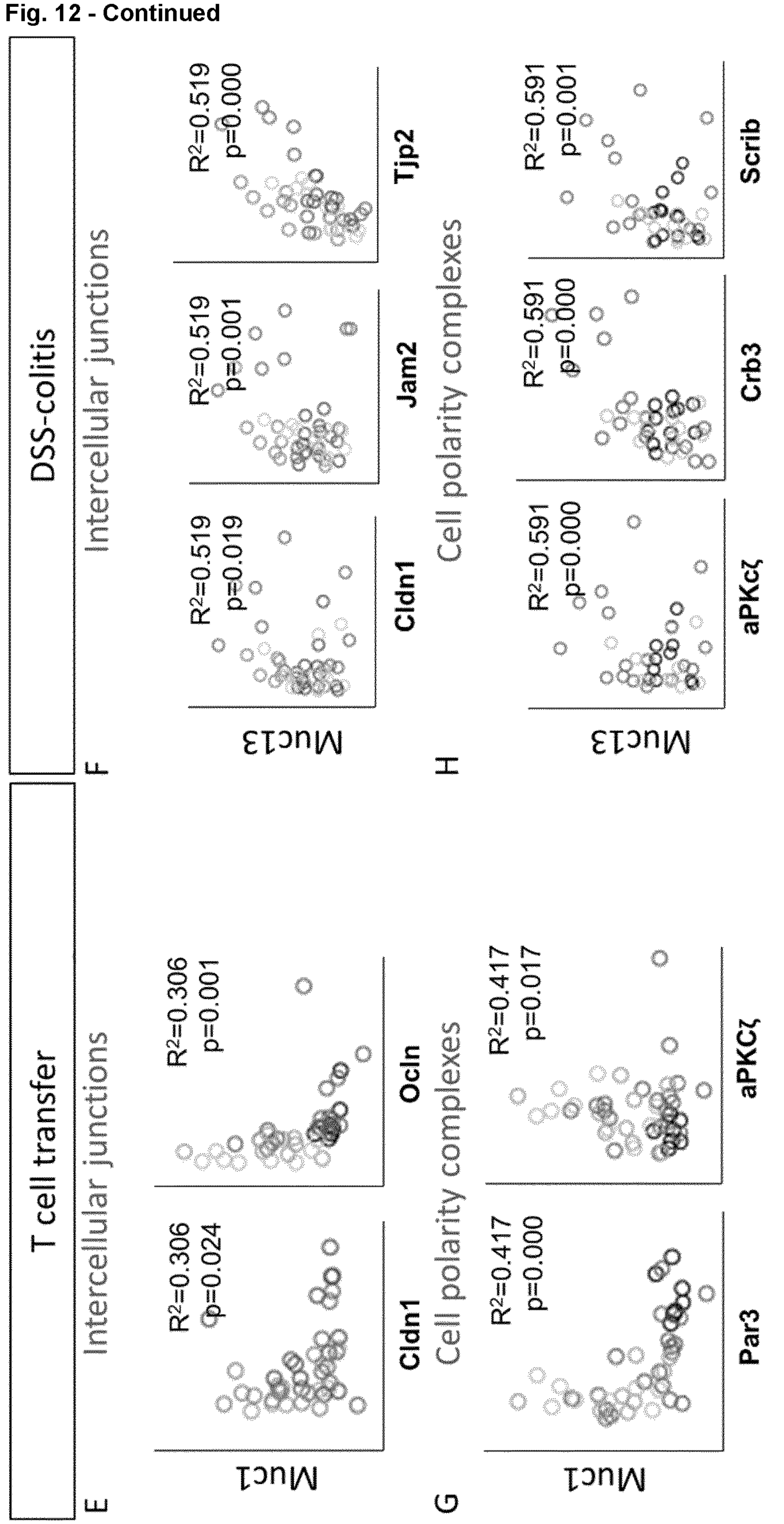

Fig. 21 - Continued
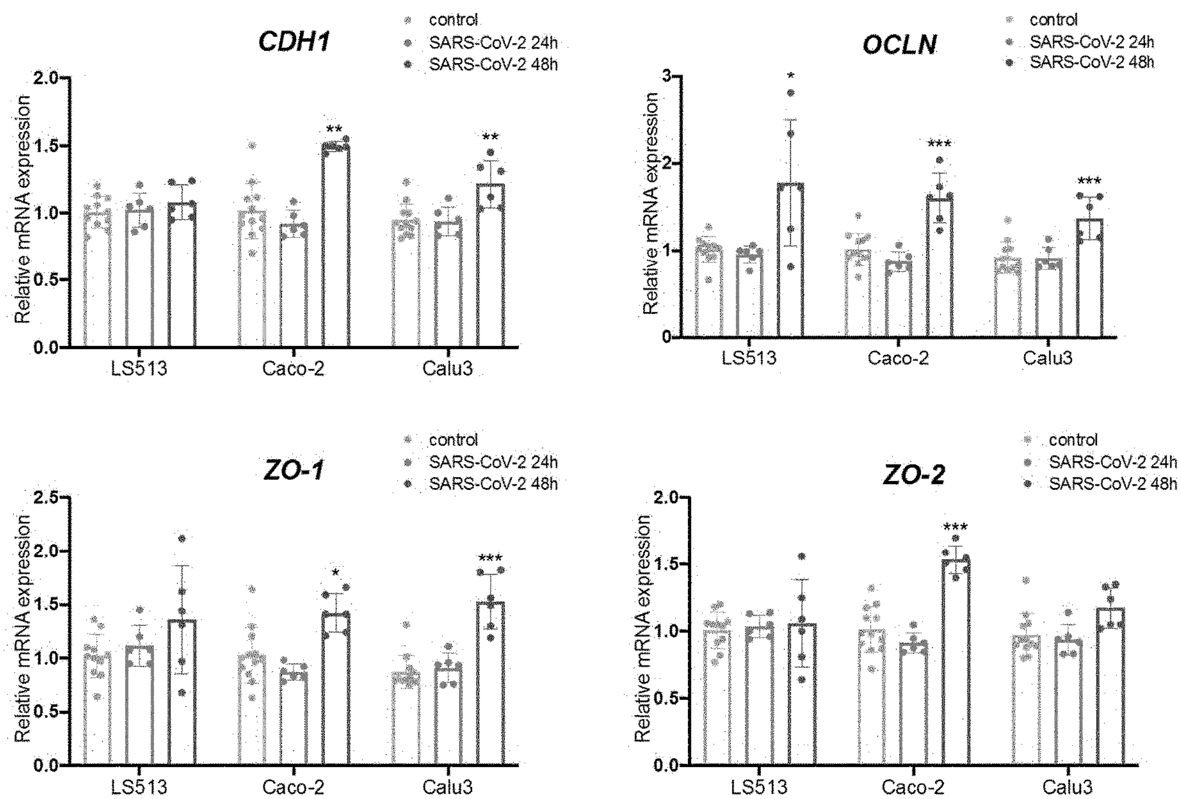

Fig. 23 - Continued
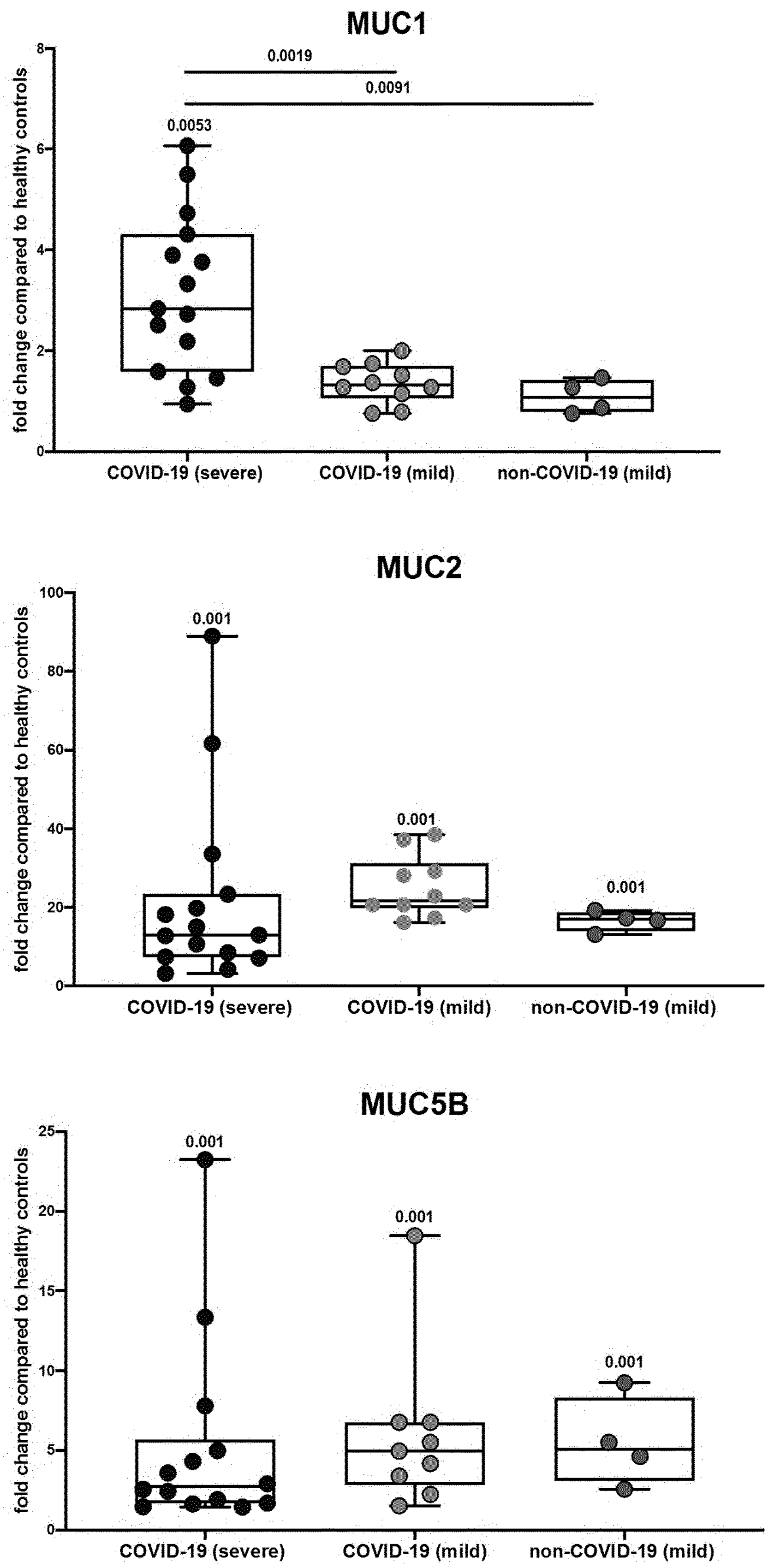

Fig.23 - Continued
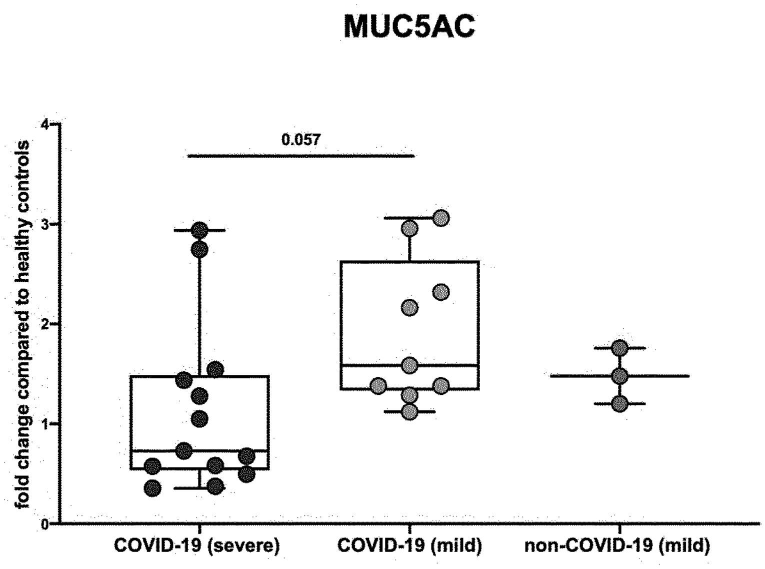
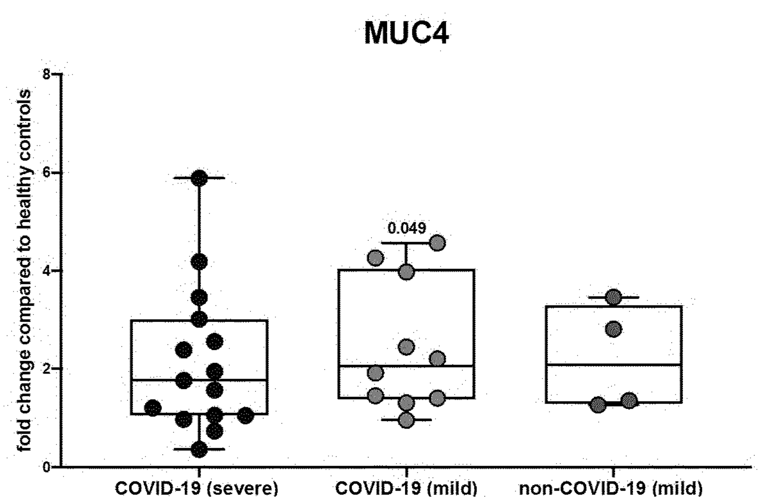

Fig. 24A

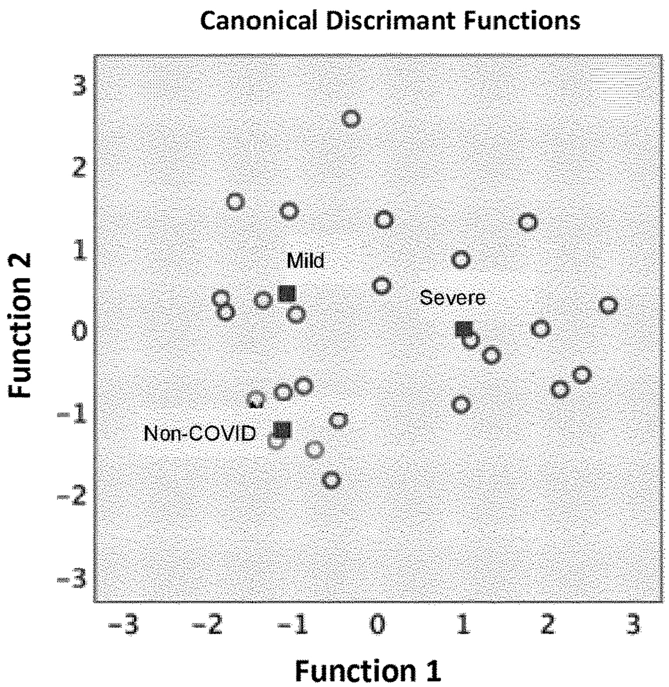

Structure Matrix

| | FUNCTION | |
|---|---|---|
| | 1 | 2 |
| MUC1 | .775* | .068 |
| MUC5AC | -.503* | .392 |
| MUC5B | .131* | -.076 |
| MUC21 | -.060 | .670* |
| MUC13 | -.187 | .669* |
| MUC2 | .027 | .253* |

Pooled within-groups correlations between discriminating variables and standardized canonical discriminant functions
Variables ordered by absolute size of correlation within function.

*. Largest absolute correlation between each variable and any discriminant function

Fig. 24B

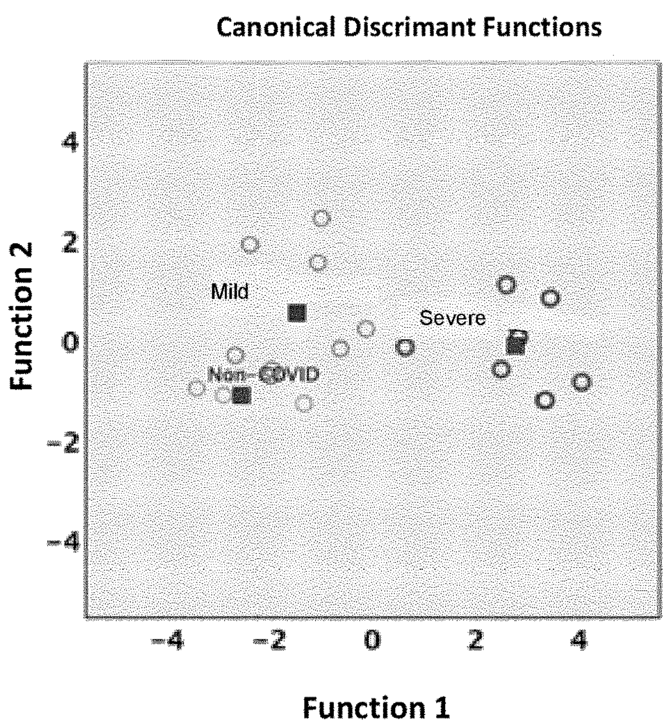

Structure Matrix

| | FUNCTION | |
|---|---|---|
| | 1 | 2 |
| MUC1 | .446* | -.230 |
| MUC16 | -.378* | .016 |
| MUC21 | .052 | .627* |
| MUC13 | -.034 | .626* |
| MUC5AC | -.144 | .352* |
| MUC5B | -.061 | .347* |
| MUC2 | .104 | .123* |

Pooled within-groups correlations between discriminating variables and standardized canonical discriminant functions
Variables ordered by absolute size of correlation within function.

*. Largest absolute correlation between each variable and any discriminant function Fig. 25 - Continued
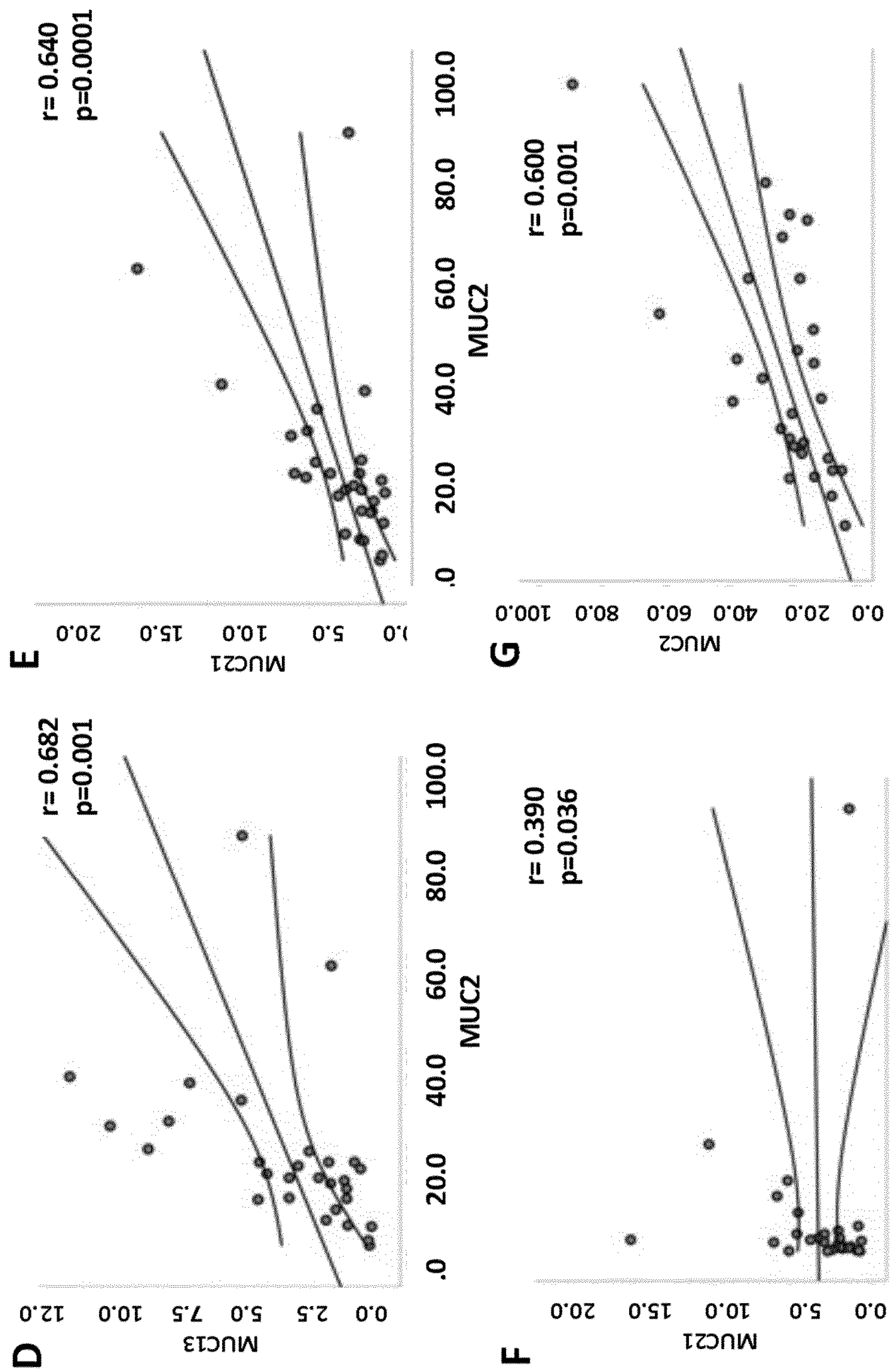

Fig. 27
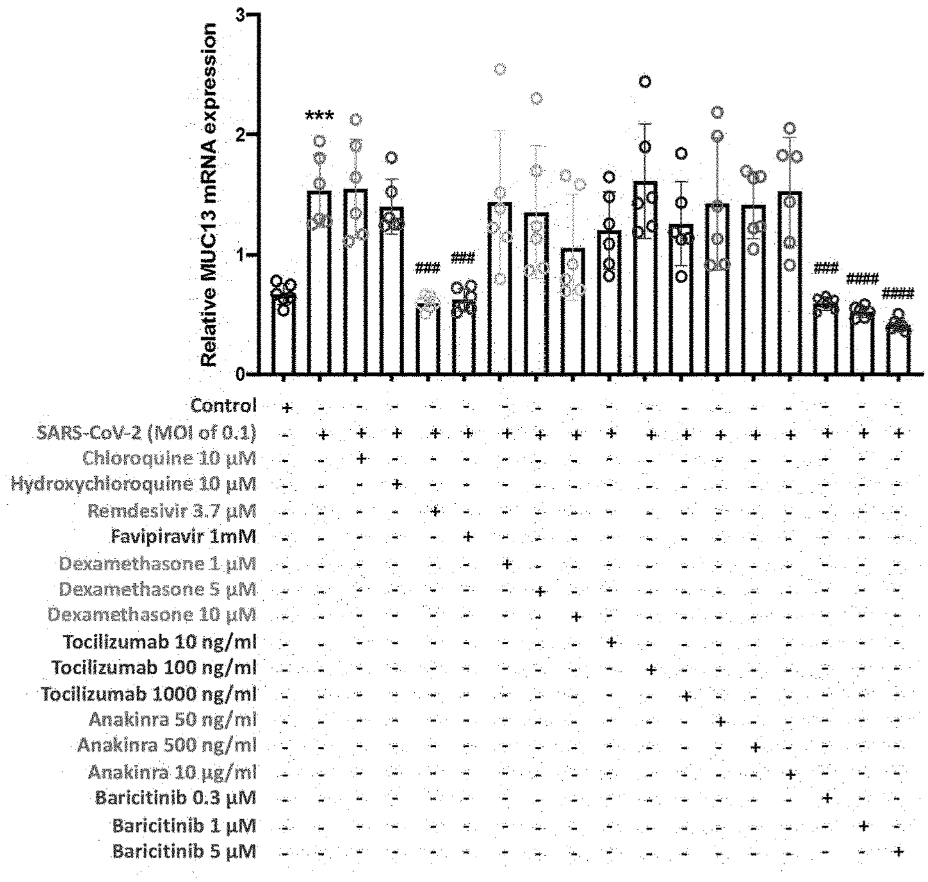
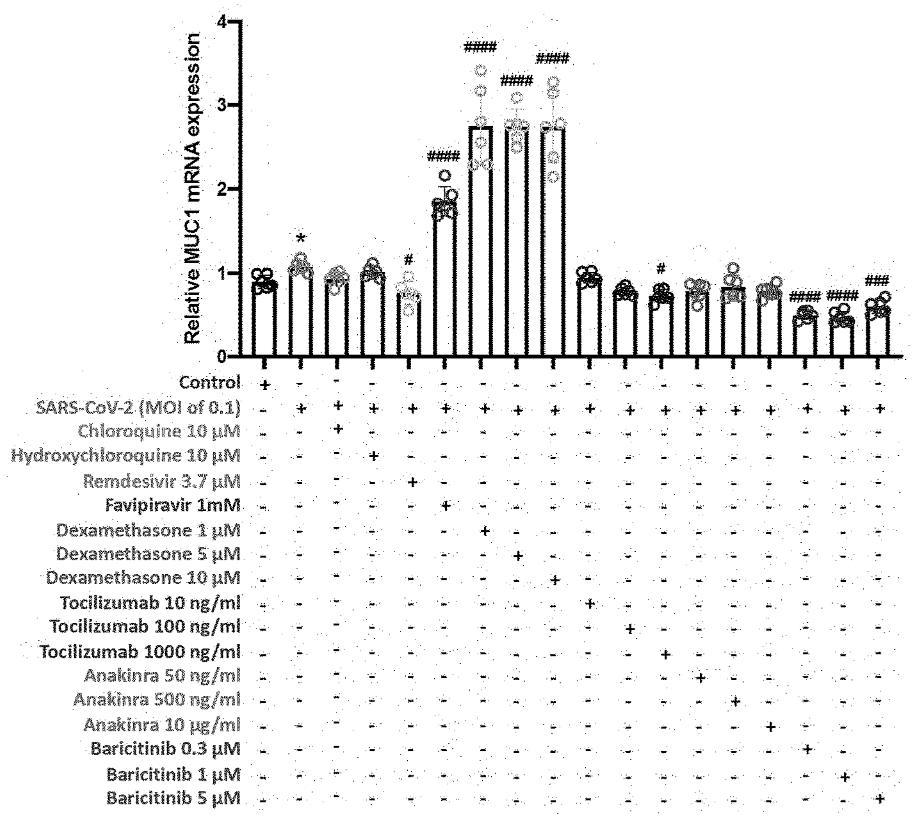

Fig. 27 - Continued
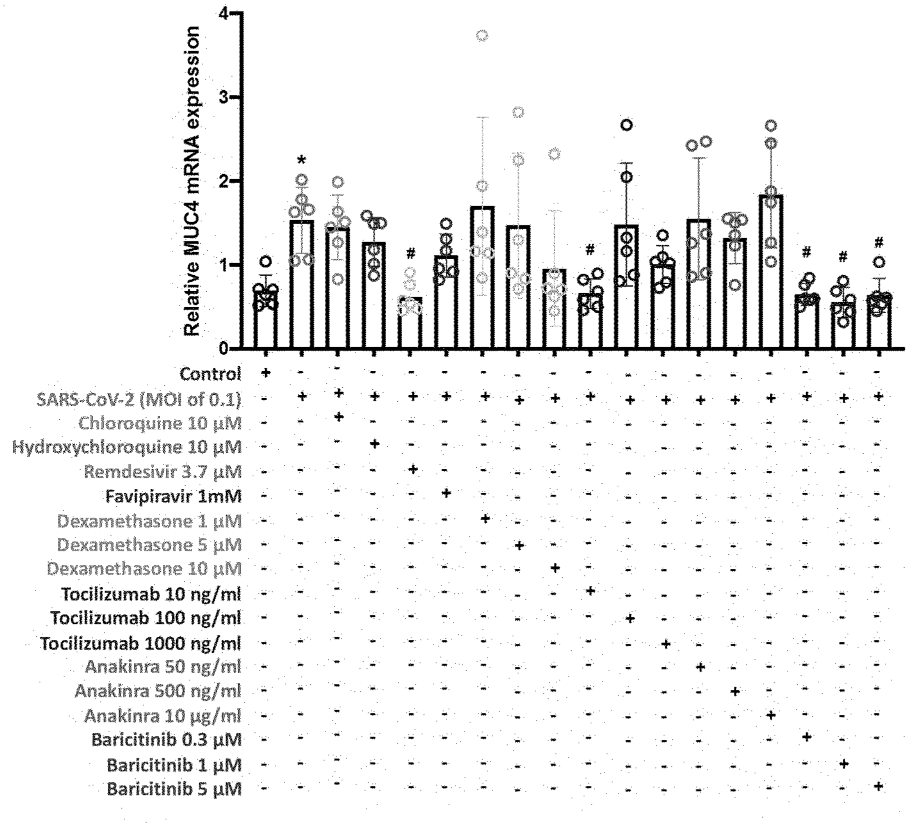
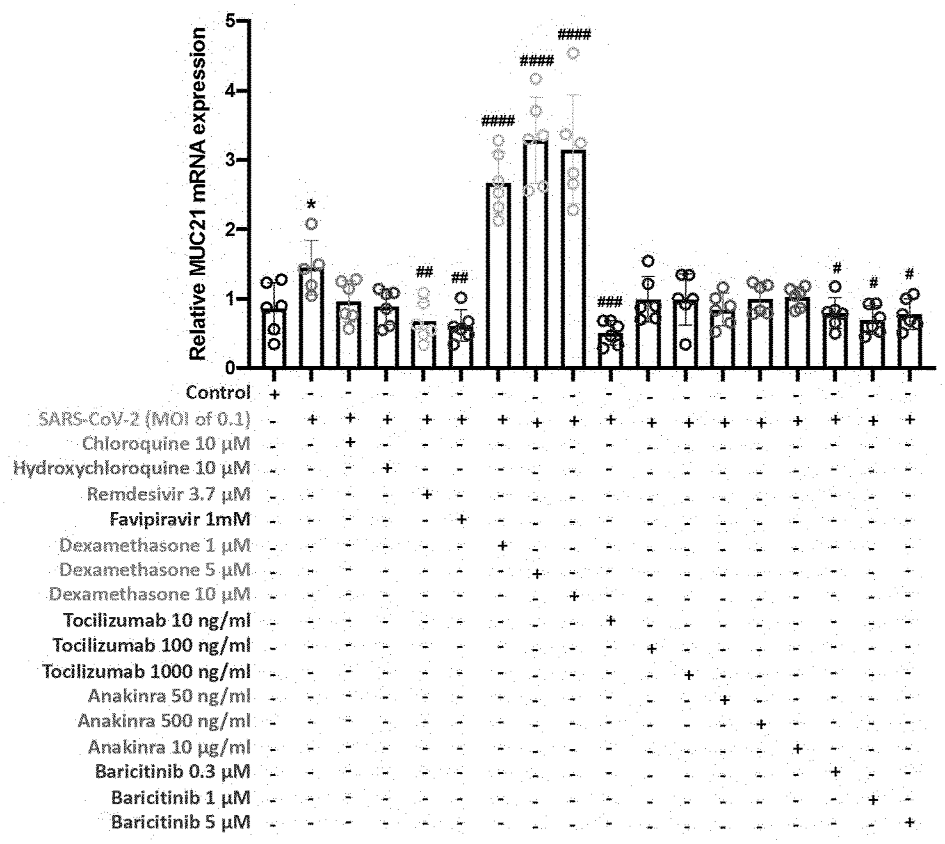

Fig. 27 - Continued
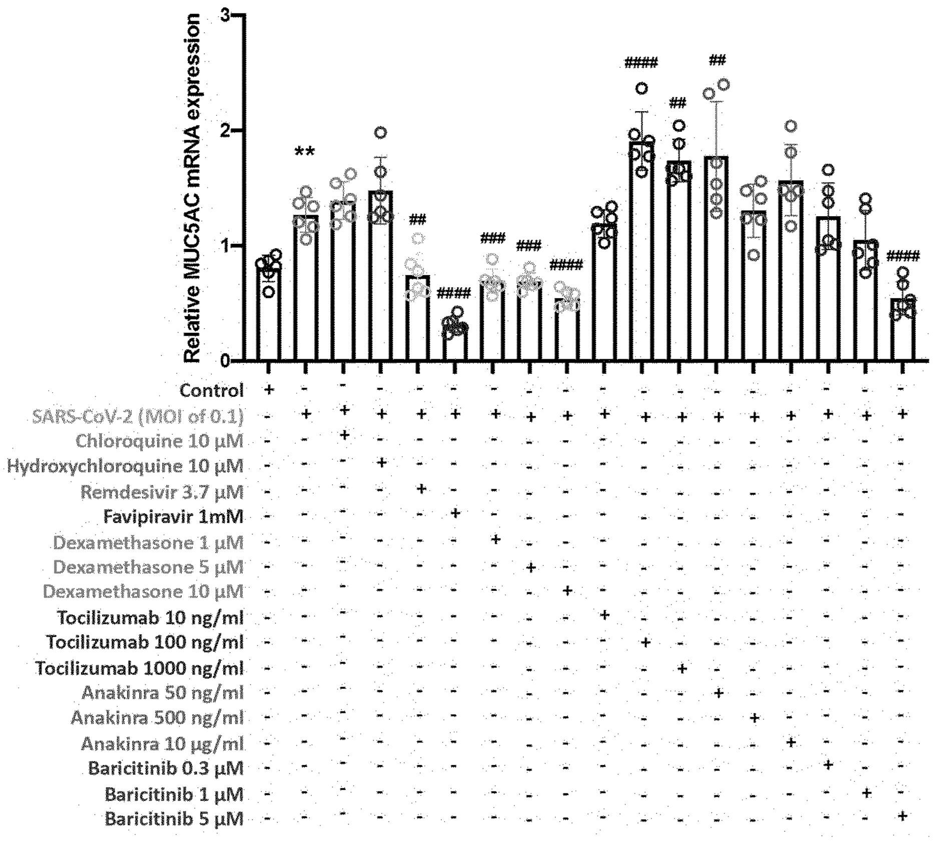
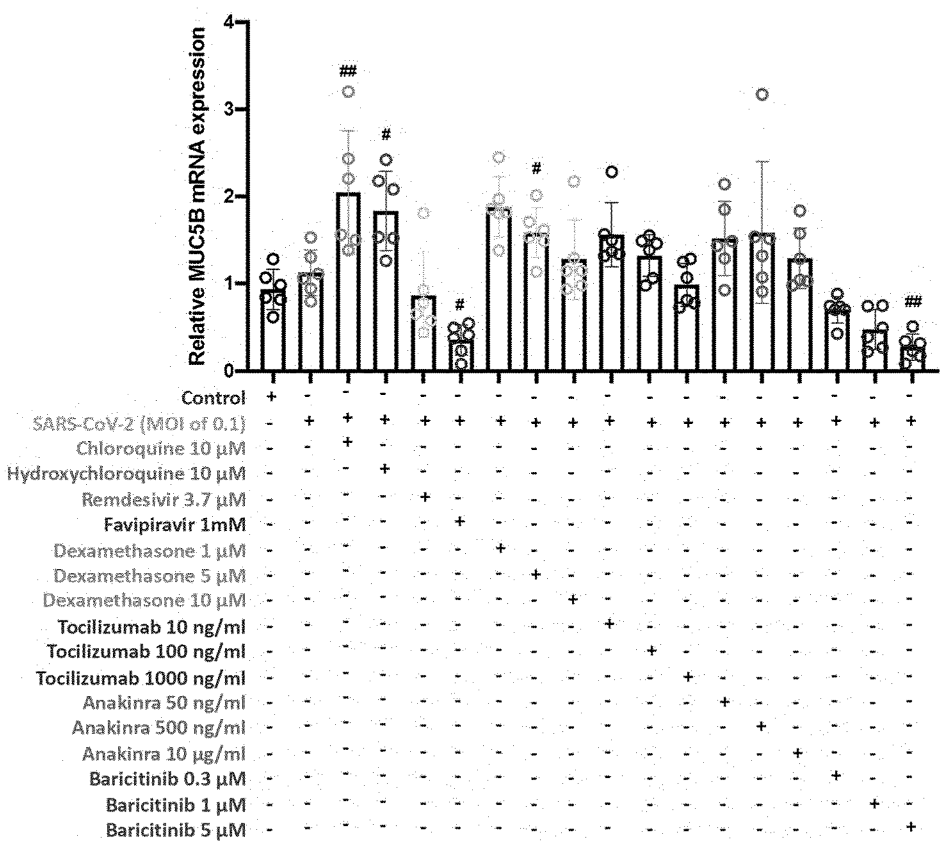

*MUC2*

Fig. 32 - Continued
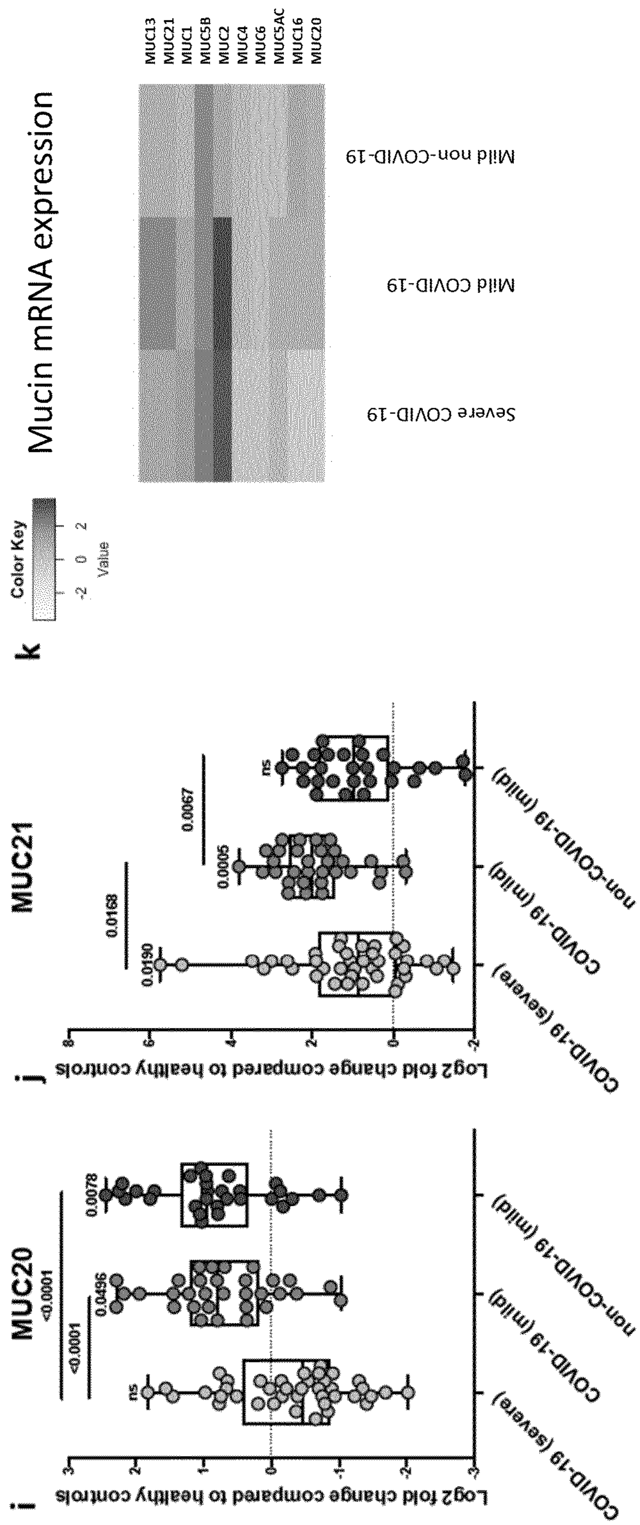

| | 1 | 2 |
|---|---|---|
| MUC16 | .384* | .350 |
| MUC1 | -.278* | -.019 |
| MUC5B | -.046* | .000 |
| MUC2 | -.566 | .656* |
| MUC13 | -.091 | .579* |
| MUC21 | -.049 | .496* |
| MUC20 | .432 | .438* |
| MUC5AC | -.017 | .209* |
| MUC6 | .041 | .127* |

Fig. 34
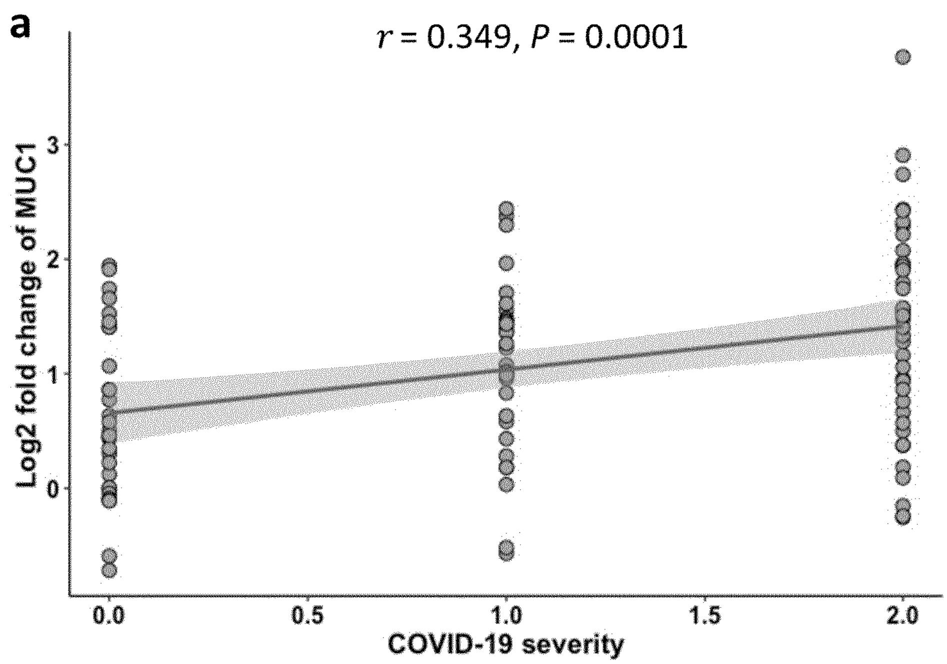
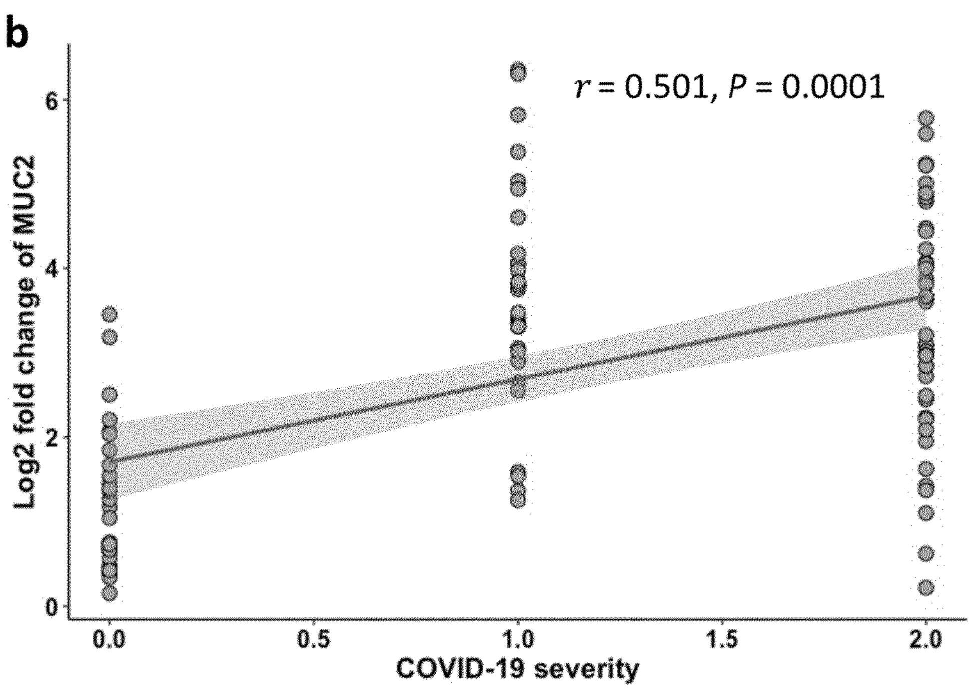

Fig. 34 - Continued
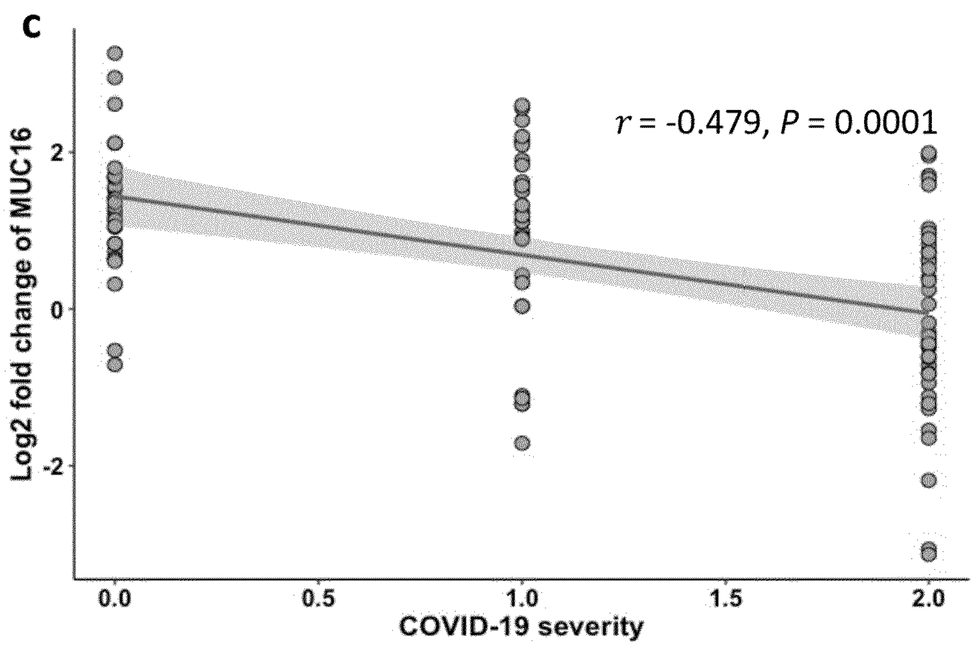
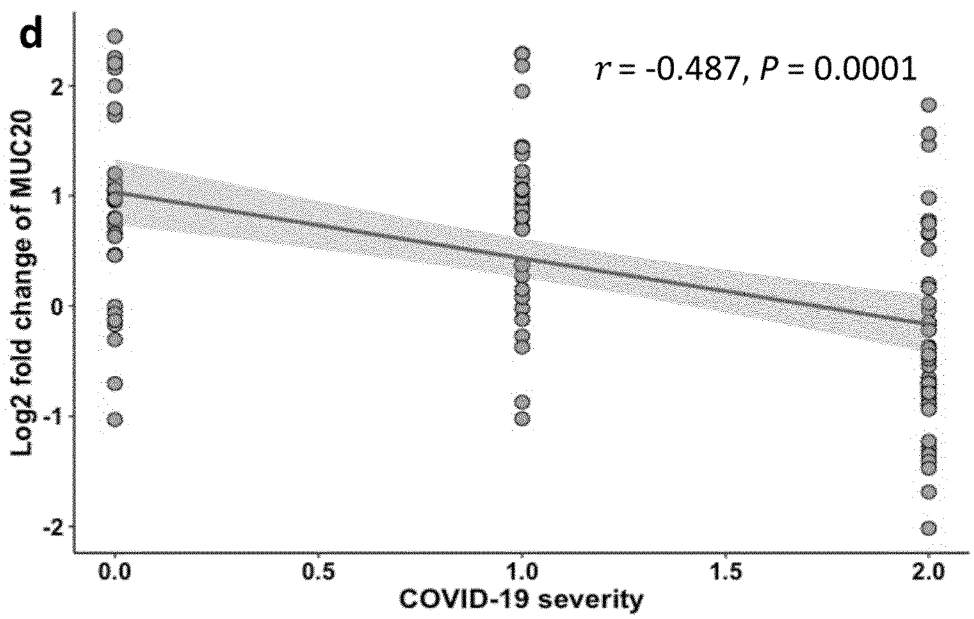

Fig. 34 – Continued
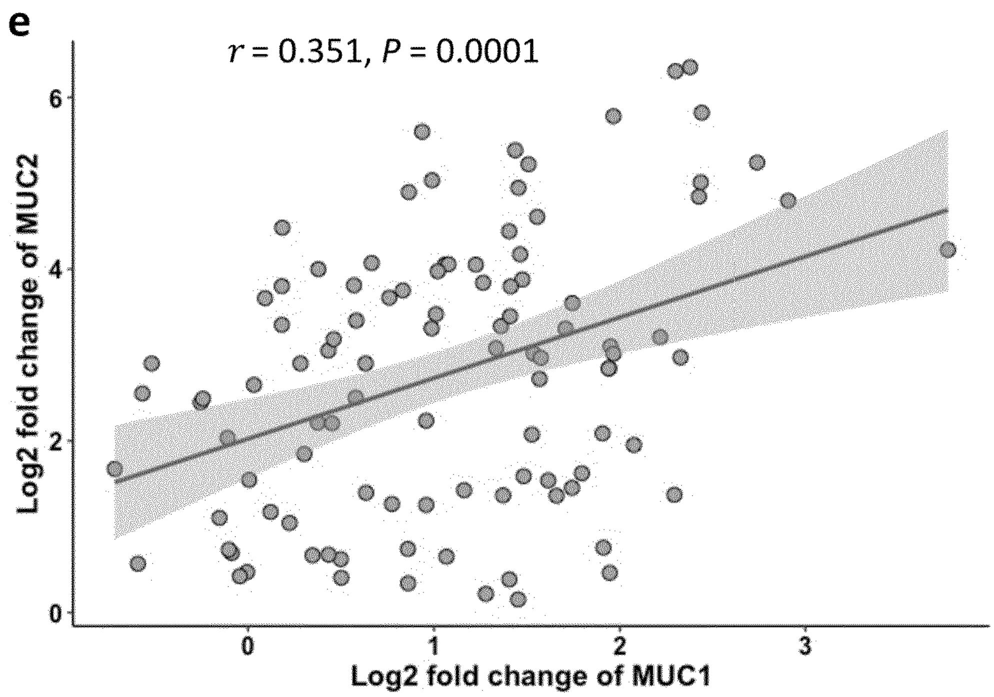
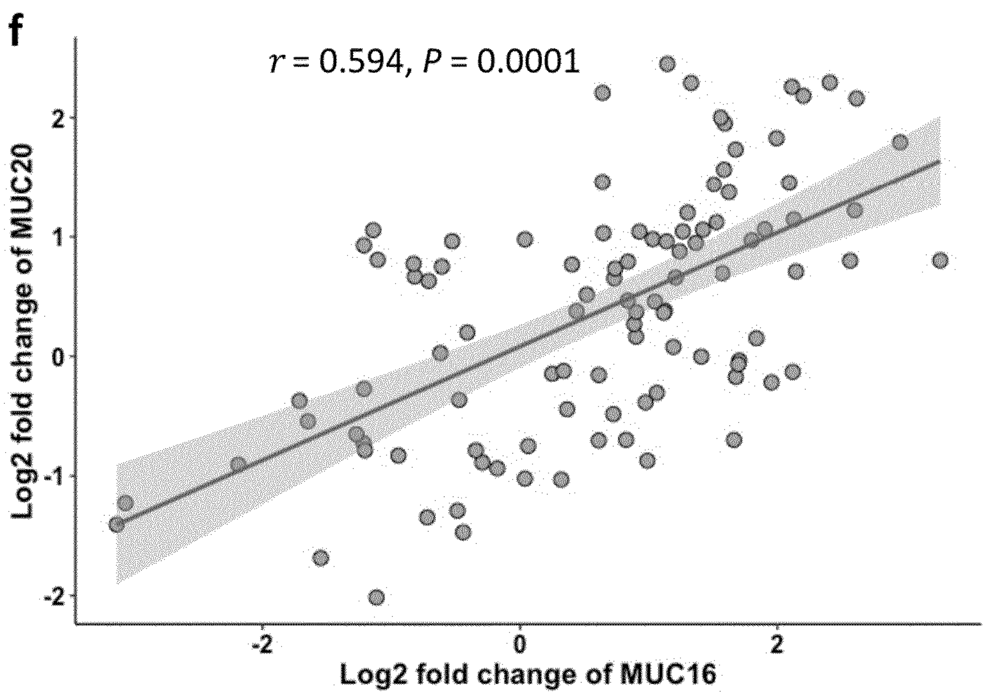

Fig. 34 - Continued
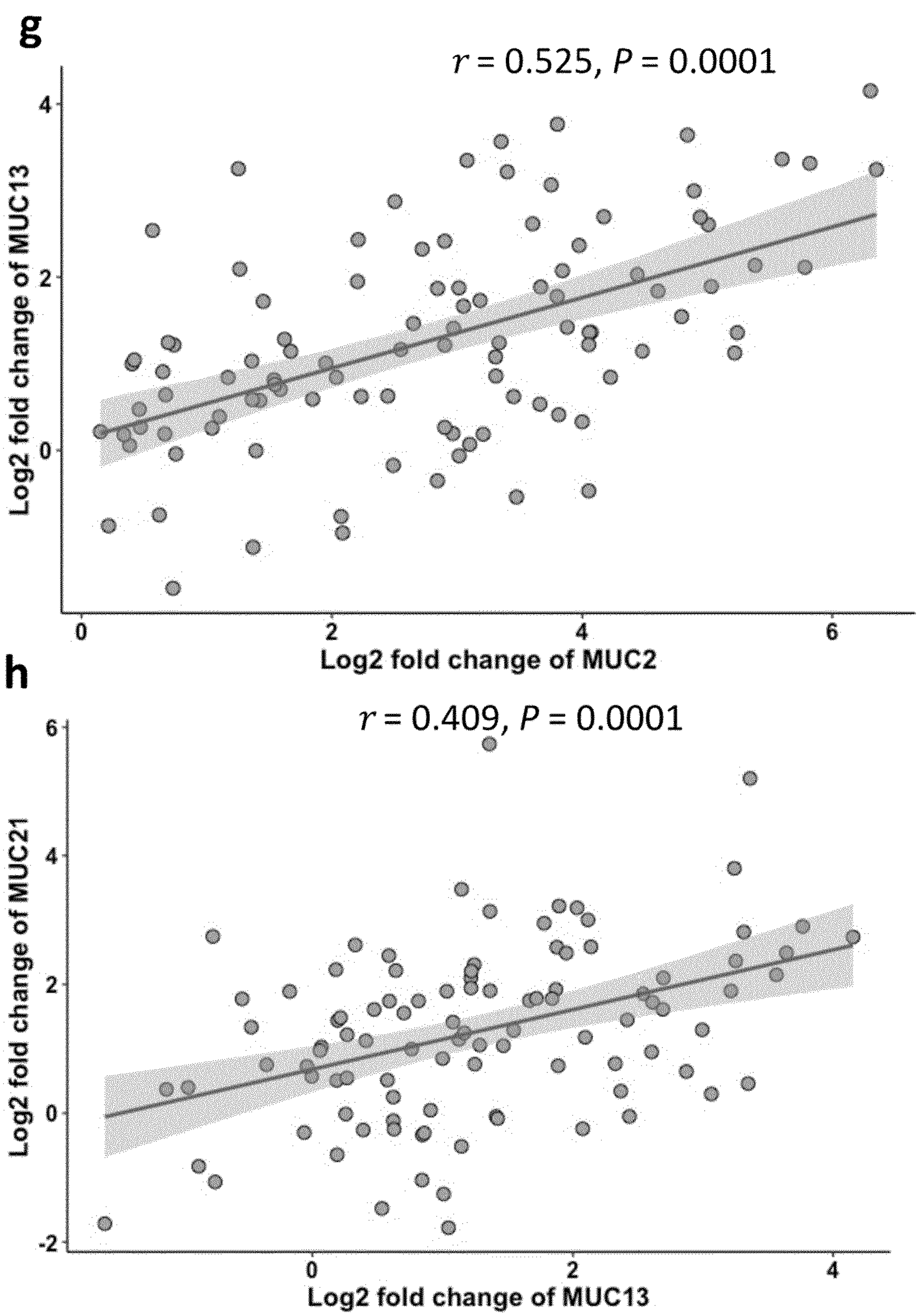

Fig. 35 - Continued
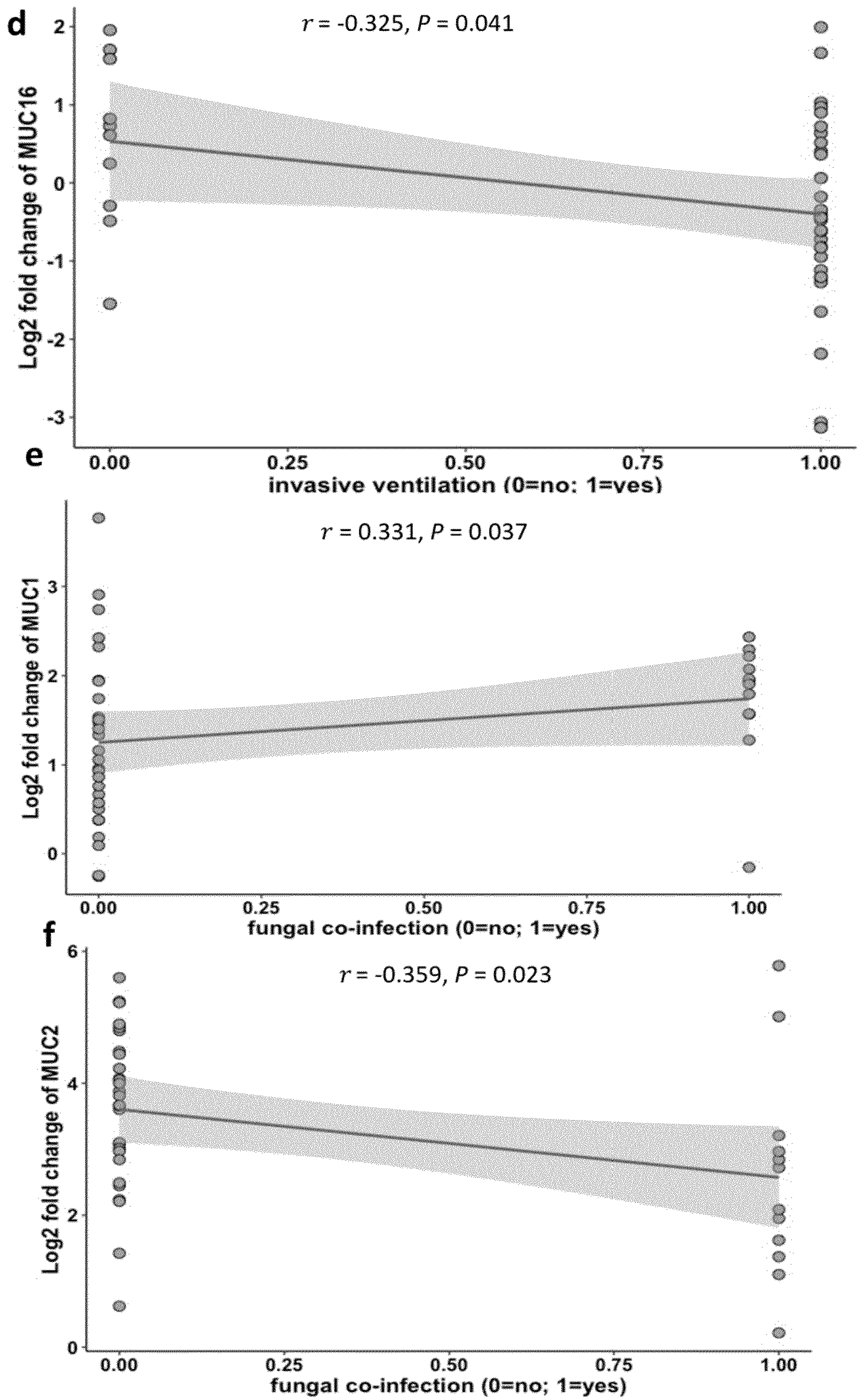

Fig. 35 - Continued
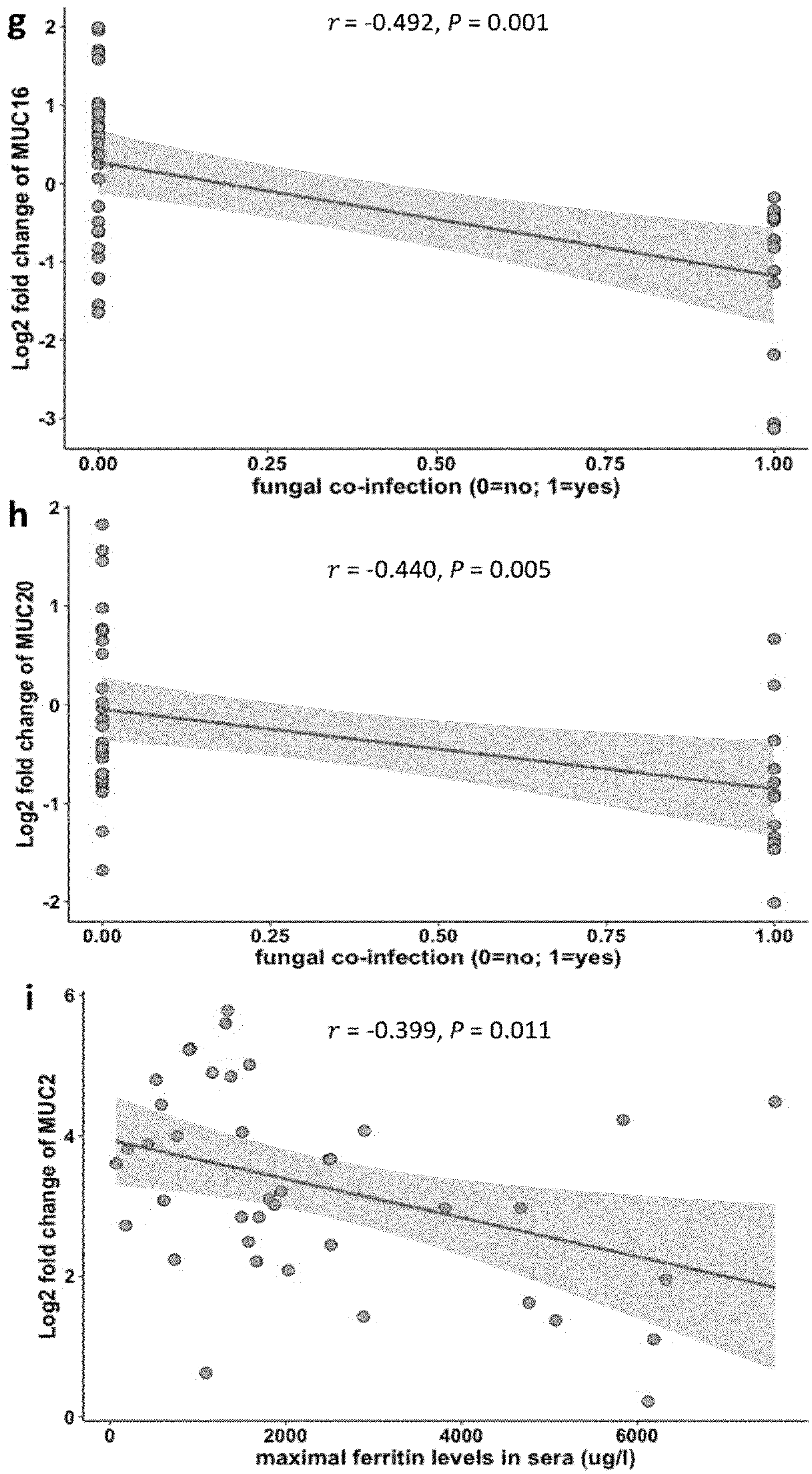

Fig. 35 – Continued
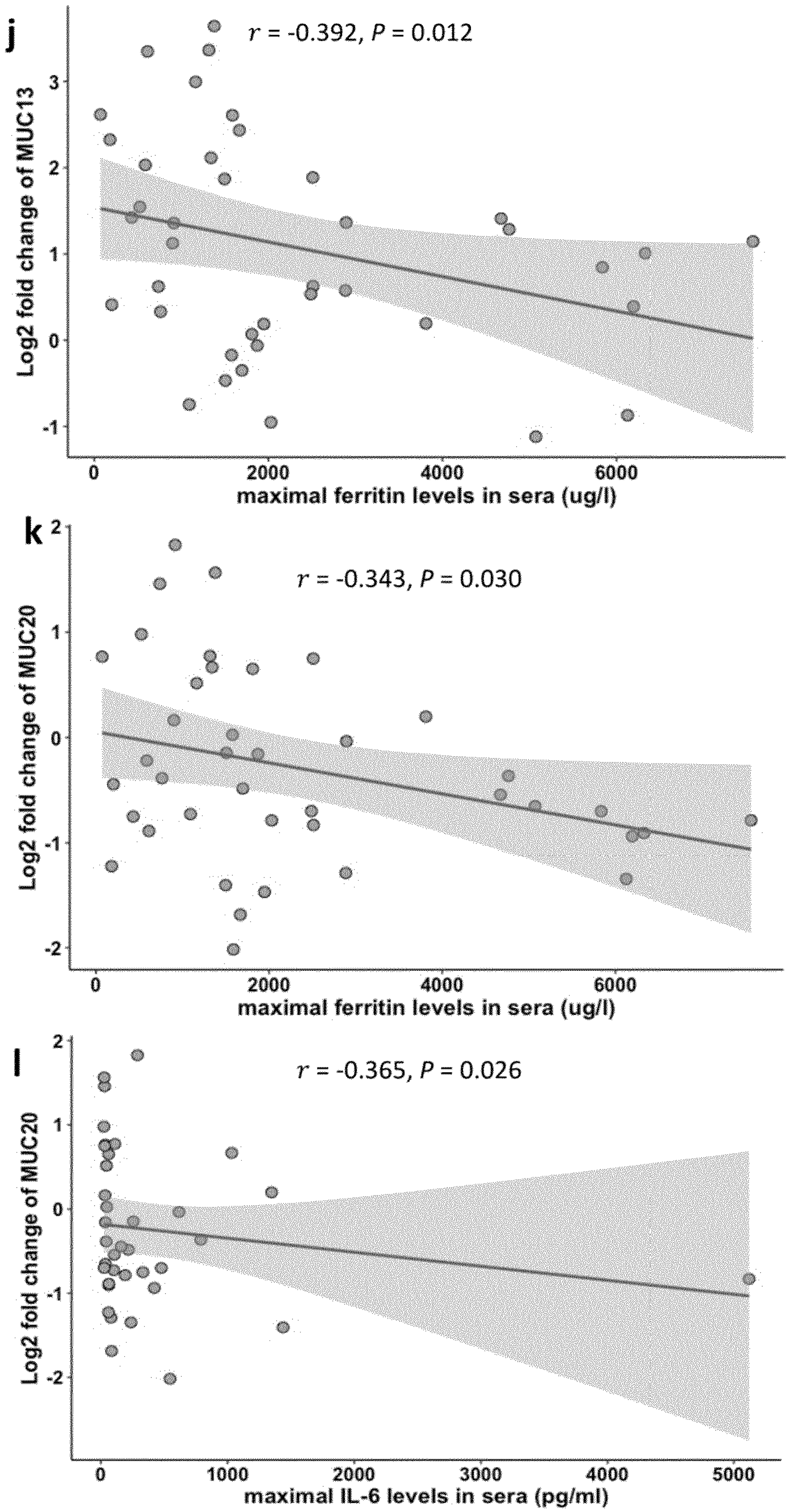

Fig. 35 – Continued
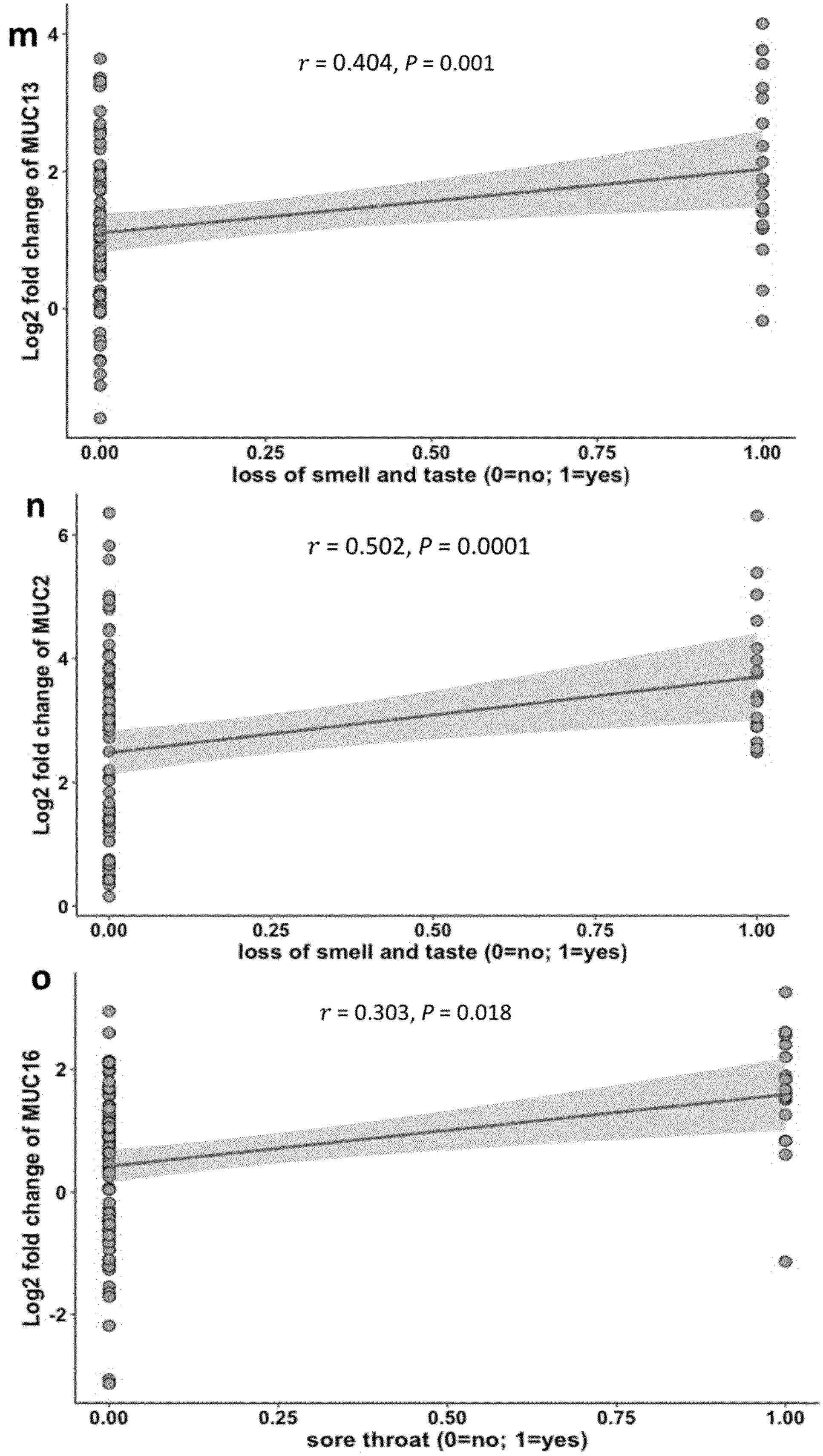

Fig. 35 – Continued
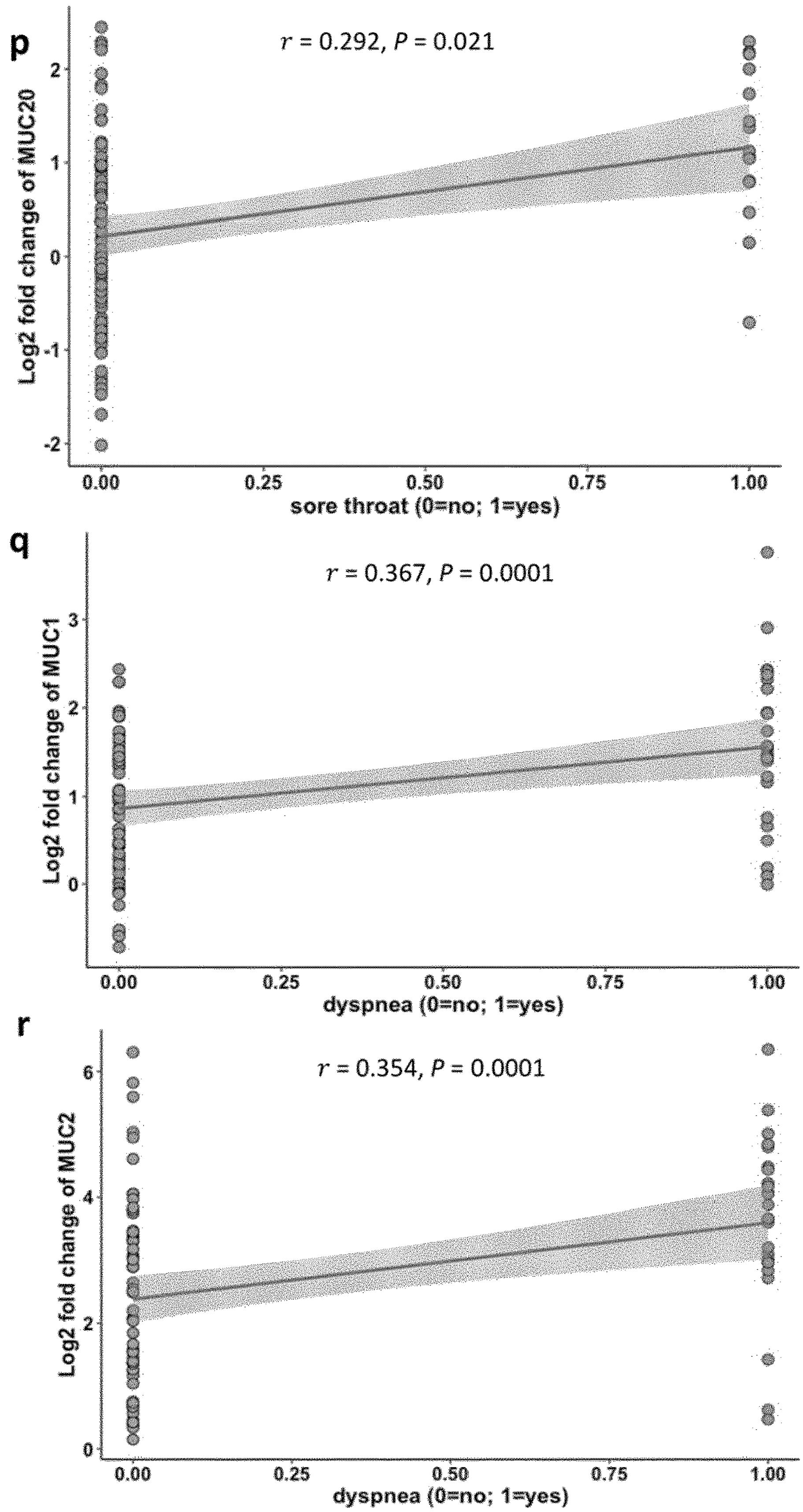

Fig. 37 – Continued
C
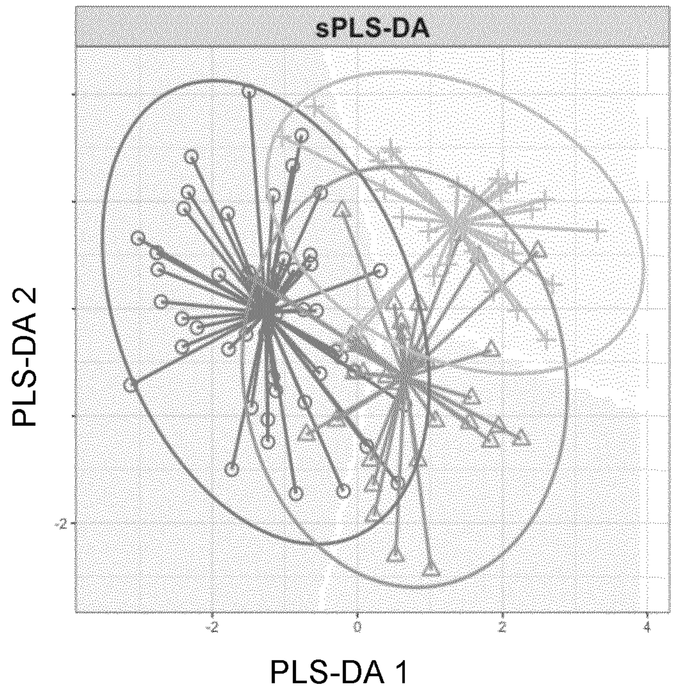
D
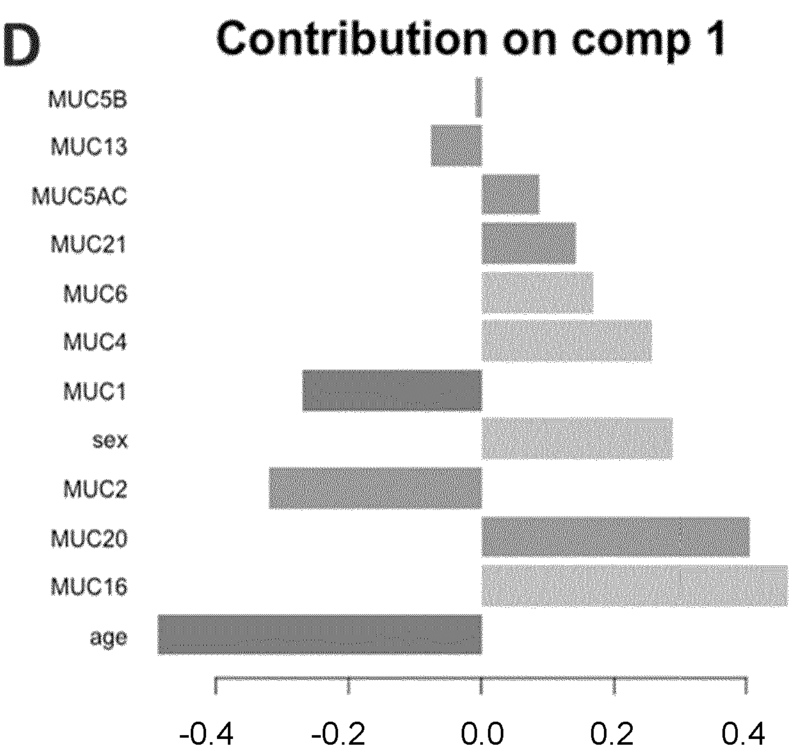

Fig. 37 – Continued
E
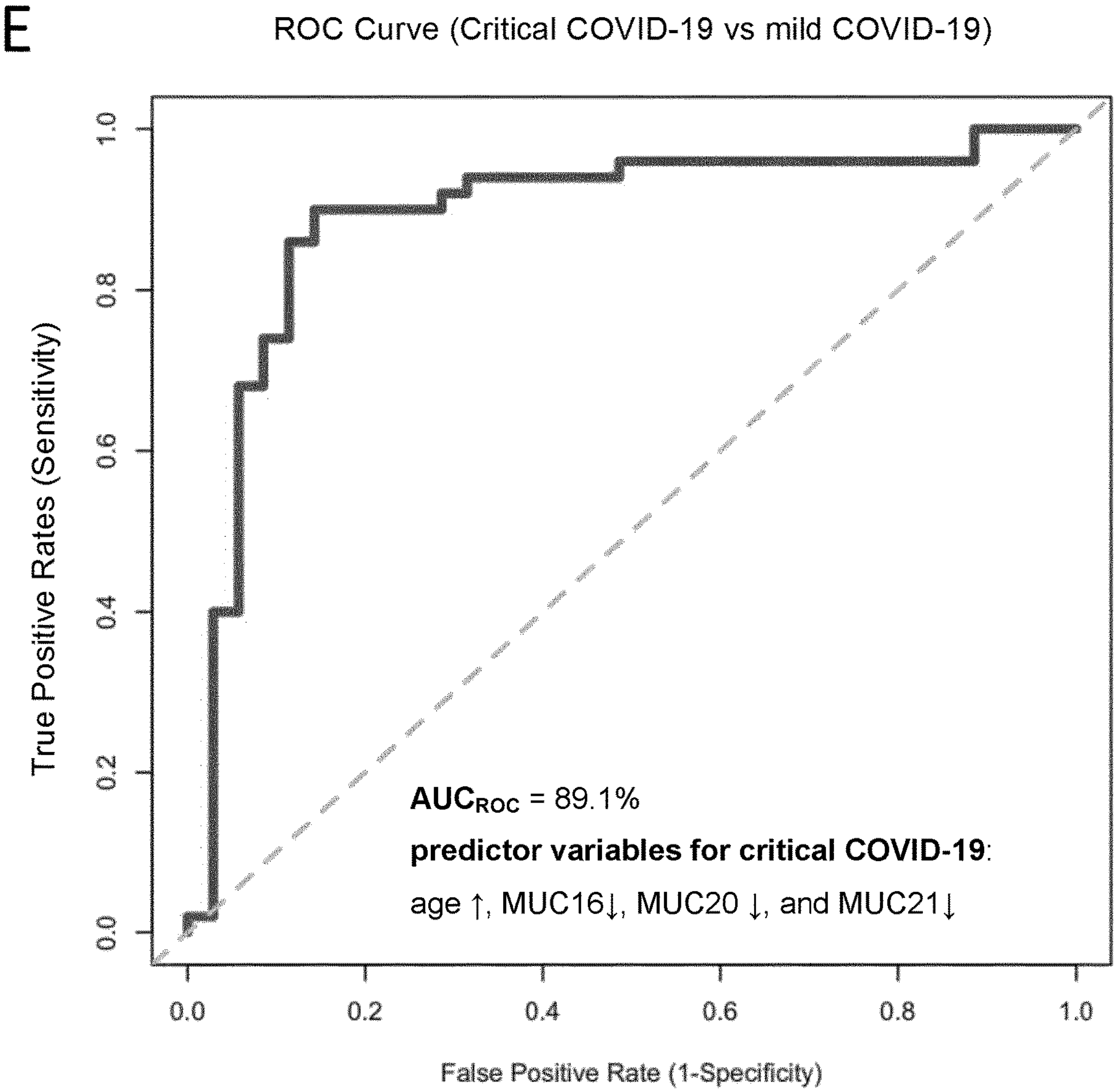

Fig. 37 – Continued
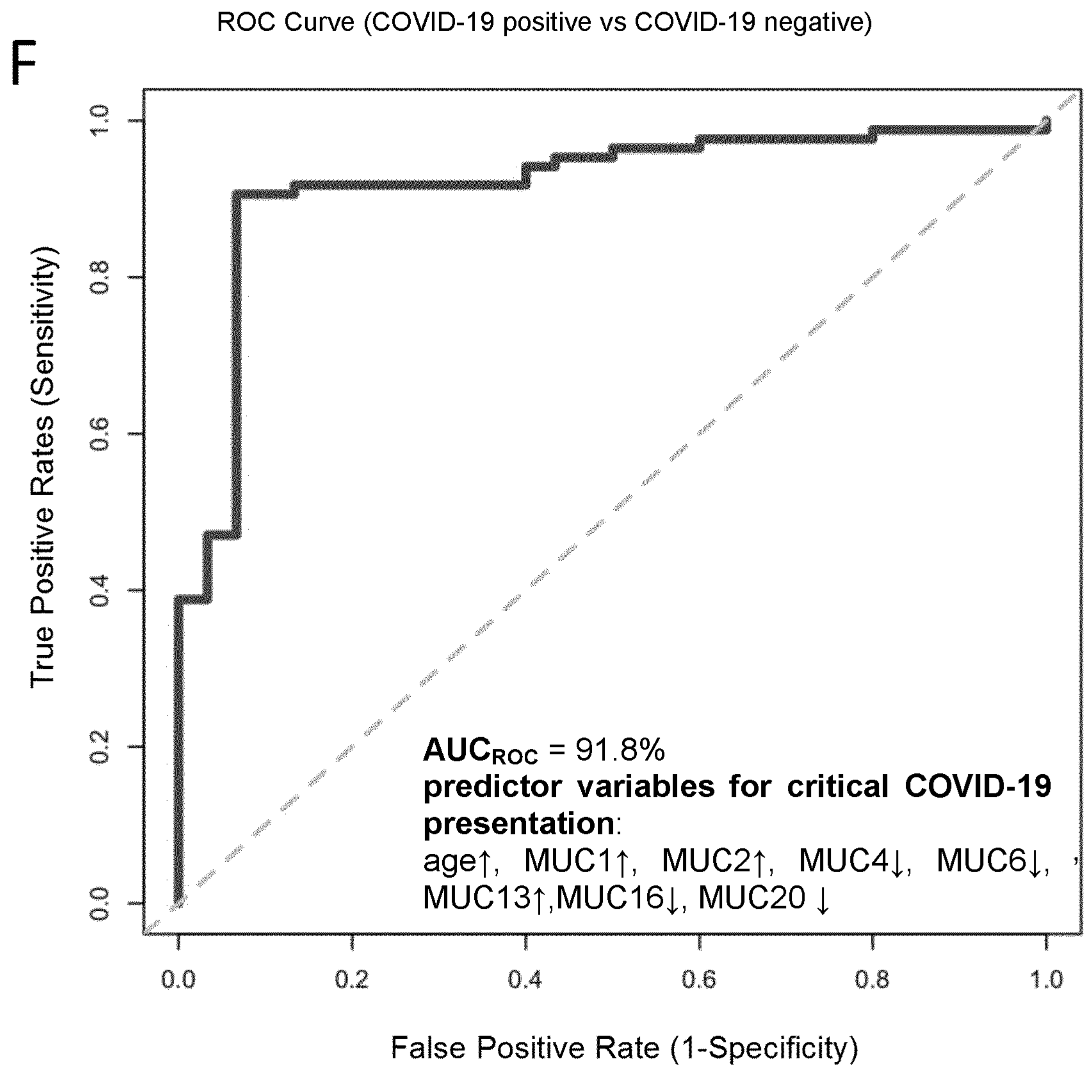

SEQUENCE LISTING

```
<160> NUMBER OF SEQ ID NOS: 78

<210> SEQ ID NO 1
<211> LENGTH: 21
<212> TYPE: DNA
<213> ORGANISM: Artificial Sequence
<220> FEATURE:
<223> OTHER INFORMATION: Cdh1 FW primer

<400> SEQUENCE: 1

cagttccgag gtctacacct t                                                21


<210> SEQ ID NO 2
<211> LENGTH: 22
<212> TYPE: DNA
<213> ORGANISM: Artificial Sequence
<220> FEATURE:
<223> OTHER INFORMATION: Cdh1 REV primer

<400> SEQUENCE: 2

tgaatcggga gtcttccgaa aa                                               22


<210> SEQ ID NO 3
<211> LENGTH: 21
<212> TYPE: DNA
<213> ORGANISM: Artificial Sequence
<220> FEATURE:
<223> OTHER INFORMATION: Cldn1 FW primer

<400> SEQUENCE: 3

tgccccagtg gaagatttac t                                                21


<210> SEQ ID NO 4
<211> LENGTH: 20
<212> TYPE: DNA
<213> ORGANISM: Artificial Sequence
<220> FEATURE:
<223> OTHER INFORMATION: Cldn1 REV primer

<400> SEQUENCE: 4

ctttgcgaaa cgcaggacat                                                  20


<210> SEQ ID NO 5
<211> LENGTH: 21
<212> TYPE: DNA
<213> ORGANISM: Artificial Sequence
```

-continued

<220> FEATURE:
<223> OTHER INFORMATION: Cldn2 FW primer

<400> SEQUENCE: 5
caactggtgg gctacatcct a 21

<210> SEQ ID NO 6
<211> LENGTH: 19
<212> TYPE: DNA
<213> ORGANISM: Artificial Sequence
<220> FEATURE:
<223> OTHER INFORMATION: Cldn2 REV primer

<400> SEQUENCE: 6
cccttggaaa agccaaccc 19

<210> SEQ ID NO 7
<211> LENGTH: 21
<212> TYPE: DNA
<213> ORGANISM: Artificial Sequence
<220> FEATURE:
<223> OTHER INFORMATION: Cldn3 FW primer

<400> SEQUENCE: 7
accaactgcg tacaagacga g 21

<210> SEQ ID NO 8
<211> LENGTH: 20
<212> TYPE: DNA
<213> ORGANISM: Artificial Sequence
<220> FEATURE:
<223> OTHER INFORMATION: Cldn3 REV primer

<400> SEQUENCE: 8
cgggcaccaa cgggttatag 20

<210> SEQ ID NO 9
<211> LENGTH: 19
<212> TYPE: DNA
<213> ORGANISM: Artificial Sequence
<220> FEATURE:
<223> OTHER INFORMATION: Cldn5 FW primer

<400> SEQUENCE: 9
gcaaggtgta tgaatctgt 19

<210> SEQ ID NO 10
<211> LENGTH: 22
<212> TYPE: DNA
<213> ORGANISM: Artificial Sequence
<220> FEATURE:
<223> OTHER INFORMATION: Cldn5 REV primer

<400> SEQUENCE: 10
gtcaaggtaa caaagagtgc ca 22

<210> SEQ ID NO 11
<211> LENGTH: 19
<212> TYPE: DNA
<213> ORGANISM: Artificial Sequence
<220> FEATURE:
<223> OTHER INFORMATION: Cldn7 FW primer

<400> SEQUENCE: 11
ggcctgatag cgagcactg 19

<210> SEQ ID NO 12
<211> LENGTH: 21
<212> TYPE: DNA
<213> ORGANISM: Artificial Sequence
<220> FEATURE:
<223> OTHER INFORMATION: Cldn7 REV primer

<400> SEQUENCE: 12
tggcgacaaa catggctaag a 21

<210> SEQ ID NO 13
<211> LENGTH: 21
<212> TYPE: DNA
<213> ORGANISM: Artificial Sequence
<220> FEATURE:
<223> OTHER INFORMATION: Cldn15 FW primer

<400> SEQUENCE: 13
attgcaggga ccctccacat a 21

<210> SEQ ID NO 14
<211> LENGTH: 21
<212> TYPE: DNA
<213> ORGANISM: Artificial Sequence
<220> FEATURE:
<223> OTHER INFORMATION: Cldn15 REV primer

<400> SEQUENCE: 14
gcccagttca tacttggttc c 21

<210> SEQ ID NO 15
<211> LENGTH: 21
<212> TYPE: DNA
<213> ORGANISM: Artificial Sequence
<220> FEATURE:
<223> OTHER INFORMATION: Crb3 FW primer

<400> SEQUENCE: 15
caccggaccc tttcacaaat a 21

<210> SEQ ID NO 16
<211> LENGTH: 21
<212> TYPE: DNA
<213> ORGANISM: Artificial Sequence
<220> FEATURE:
<223> OTHER INFORMATION: Crb3 REV primer

<400> SEQUENCE: 16
cccactgcta taaggaggac t 21

<210> SEQ ID NO 17
<211> LENGTH: 21
<212> TYPE: DNA
<213> ORGANISM: Artificial Sequence
<220> FEATURE:
<223> OTHER INFORMATION: Dlg1 FW primer

<400> SEQUENCE: 17
agtgacgaag tcggagtgat t 21

<210> SEQ ID NO 18
<211> LENGTH: 22
<212> TYPE: DNA
<213> ORGANISM: Artificial Sequence
<220> FEATURE:
<223> OTHER INFORMATION: Dlg1 REV primer

<400> SEQUENCE: 18
gtcagggatc tcccctttat ct 22

<210> SEQ ID NO 19
<211> LENGTH: 23
<212> TYPE: DNA
<213> ORGANISM: Artificial Sequence
<220> FEATURE:
<223> OTHER INFORMATION: Jam1 FW primer

<400> SEQUENCE: 19
tctcttcacg tctatgatcc tgg 23

<210> SEQ ID NO 20
<211> LENGTH: 21
<212> TYPE: DNA
<213> ORGANISM: Artificial Sequence
<220> FEATURE:
<223> OTHER INFORMATION: Jam1 REV primer

<400> SEQUENCE: 20
tttgatggac tcgttctggg g 21

<210> SEQ ID NO 21
<211> LENGTH: 22
<212> TYPE: DNA
<213> ORGANISM: Artificial Sequence
<220> FEATURE:
<223> OTHER INFORMATION: Jam2 FW primer

<400> SEQUENCE: 21
gtgcccactt ctgttatgac tg 22

<210> SEQ ID NO 22
<211> LENGTH: 21
<212> TYPE: DNA
<213> ORGANISM: Artificial Sequence
<220> FEATURE:
<223> OTHER INFORMATION: Jam2 REV primer

<400> SEQUENCE: 22
ttccctagca aacttgtgcc a 21

<210> SEQ ID NO 23
<211> LENGTH: 19
<212> TYPE: DNA
<213> ORGANISM: Artificial Sequence
<220> FEATURE:
<223> OTHER INFORMATION: Jam3 FW primer

<400> SEQUENCE: 23
ctgcgacttc gactgtacg 19

<210> SEQ ID NO 24
<211> LENGTH: 22
<212> TYPE: DNA
<213> ORGANISM: Artificial Sequence
<220> FEATURE:
<223> OTHER INFORMATION: Jam3 REV primer

<400> SEQUENCE: 24
ttcggttgct ggatttgaga tt 22

<210> SEQ ID NO 25

<211> LENGTH: 19
<212> TYPE: DNA
<213> ORGANISM: Artificial Sequence
<220> FEATURE:
<223> OTHER INFORMATION: Llgl1 FW primer

<400> SEQUENCE: 25
gcttccccaa tcagcccag 19

<210> SEQ ID NO 26
<211> LENGTH: 21
<212> TYPE: DNA
<213> ORGANISM: Artificial Sequence
<220> FEATURE:
<223> OTHER INFORMATION: Llgl1 REV primer

<400> SEQUENCE: 26
gcgcagccat tatgatggat g 21

<210> SEQ ID NO 27
<211> LENGTH: 24
<212> TYPE: DNA
<213> ORGANISM: Artificial Sequence
<220> FEATURE:
<223> OTHER INFORMATION: Muc1 FW primer

<400> SEQUENCE: 27
ggttgctttg gctatcgtct attt 24

<210> SEQ ID NO 28
<211> LENGTH: 21
<212> TYPE: DNA
<213> ORGANISM: Artificial Sequence
<220> FEATURE:
<223> OTHER INFORMATION: Muc1 REV primer

<400> SEQUENCE: 28
aaagatgtcc agctgcccat a 21

<210> SEQ ID NO 29
<211> LENGTH: 20
<212> TYPE: DNA
<213> ORGANISM: Artificial Sequence
<220> FEATURE:
<223> OTHER INFORMATION: Muc2 FW primer

<400> SEQUENCE: 29
atgcccacct cctcaaagac 20

<210> SEQ ID NO 30
<211> LENGTH: 23
<212> TYPE: DNA
<213> ORGANISM: Artificial Sequence
<220> FEATURE:
<223> OTHER INFORMATION: Muc2 REV primer

<400> SEQUENCE: 30
gtagtttccg ttggaacagt gaa 23

<210> SEQ ID NO 31
<211> LENGTH: 22
<212> TYPE: DNA
<213> ORGANISM: Artificial Sequence
<220> FEATURE:
<223> OTHER INFORMATION: Muc4 FW primer

<400> SEQUENCE: 31

-continued

```
acaggtgtaa ctagaagcct cg                                            22


<210> SEQ ID NO 32
<211> LENGTH: 21
<212> TYPE: DNA
<213> ORGANISM: Artificial Sequence
<220> FEATURE:
<223> OTHER INFORMATION: Muc4 REV primer

<400> SEQUENCE: 32

caggggtgct atgcactact g                                             21


<210> SEQ ID NO 33
<211> LENGTH: 21
<212> TYPE: DNA
<213> ORGANISM: Artificial Sequence
<220> FEATURE:
<223> OTHER INFORMATION: Muc13 FW primer

<400> SEQUENCE: 33

gccagtcctc ccaccacggt a                                             21


<210> SEQ ID NO 34
<211> LENGTH: 21
<212> TYPE: DNA
<213> ORGANISM: Artificial Sequence
<220> FEATURE:
<223> OTHER INFORMATION: Muc13 REV primer

<400> SEQUENCE: 34

ctgggacctg tgcttccacc g                                             21


<210> SEQ ID NO 35
<211> LENGTH: 21
<212> TYPE: DNA
<213> ORGANISM: Artificial Sequence
<220> FEATURE:
<223> OTHER INFORMATION: Mylk FW primer

<400> SEQUENCE: 35

tgggggacgt gaaactgttt g                                             21


<210> SEQ ID NO 36
<211> LENGTH: 19
<212> TYPE: DNA
<213> ORGANISM: Artificial Sequence
<220> FEATURE:
<223> OTHER INFORMATION: Mylk REV primer

<400> SEQUENCE: 36

ggggcagaat gaaagctgg                                                19


<210> SEQ ID NO 37
<211> LENGTH: 22
<212> TYPE: DNA
<213> ORGANISM: Artificial Sequence
<220> FEATURE:
<223> OTHER INFORMATION: Ocln FW primer

<400> SEQUENCE: 37

ggcggatata cagacccaag ag                                            22


<210> SEQ ID NO 38
<211> LENGTH: 24
<212> TYPE: DNA
```

<213> ORGANISM: Artificial Sequence
<220> FEATURE:
<223> OTHER INFORMATION: Ocln REV primer

<400> SEQUENCE: 38
gataatcatg aaccccagga caat 24

<210> SEQ ID NO 39
<211> LENGTH: 20
<212> TYPE: DNA
<213> ORGANISM: Artificial Sequence
<220> FEATURE:
<223> OTHER INFORMATION: Pals1 FW primer

<400> SEQUENCE: 39
tttgggcacc agaatgatgc 20

<210> SEQ ID NO 40
<211> LENGTH: 23
<212> TYPE: DNA
<213> ORGANISM: Artificial Sequence
<220> FEATURE:
<223> OTHER INFORMATION: Pals1 REV primer

<400> SEQUENCE: 40
aacaattcct tcttccgtgt caa 23

<210> SEQ ID NO 41
<211> LENGTH: 21
<212> TYPE: DNA
<213> ORGANISM: Artificial Sequence
<220> FEATURE:
<223> OTHER INFORMATION: Par3 FW primer

<400> SEQUENCE: 41
ggagatggcc gcatgaaagt t 21

<210> SEQ ID NO 42
<211> LENGTH: 21
<212> TYPE: DNA
<213> ORGANISM: Artificial Sequence
<220> FEATURE:
<223> OTHER INFORMATION: Par3 REV primer

<400> SEQUENCE: 42
ctccaagcga tgcacctgta t 21

<210> SEQ ID NO 43
<211> LENGTH: 20
<212> TYPE: DNA
<213> ORGANISM: Artificial Sequence
<220> FEATURE:
<223> OTHER INFORMATION: Par6 FW primer

<400> SEQUENCE: 43
tcagaaacgg gcagaaggtg 20

<210> SEQ ID NO 44
<211> LENGTH: 20
<212> TYPE: DNA
<213> ORGANISM: Artificial Sequence
<220> FEATURE:
<223> OTHER INFORMATION: Par6 REV primer

<400> SEQUENCE: 44
ccaggcggga gatgaagata 20

<210> SEQ ID NO 45
<211> LENGTH: 21
<212> TYPE: DNA
<213> ORGANISM: Artificial Sequence
<220> FEATURE:
<223> OTHER INFORMATION: Patj FW primer

<400> SEQUENCE: 45
ttcgatgggc accactatat c 21

<210> SEQ ID NO 46
<211> LENGTH: 21
<212> TYPE: DNA
<213> ORGANISM: Artificial Sequence
<220> FEATURE:
<223> OTHER INFORMATION: Patj REV primer

<400> SEQUENCE: 46
ggtgggggca cttctttaag g 21

<210> SEQ ID NO 47
<211> LENGTH: 21
<212> TYPE: DNA
<213> ORGANISM: Artificial Sequence
<220> FEATURE:
<223> OTHER INFORMATION: aPkc-lambda FW primer

<400> SEQUENCE: 47
cactttgagc cttccatctc c 21

<210> SEQ ID NO 48
<211> LENGTH: 19
<212> TYPE: DNA
<213> ORGANISM: Artificial Sequence
<220> FEATURE:
<223> OTHER INFORMATION: aPkc-lambda REV primer

<400> SEQUENCE: 48
gtgaccagct tgtggcact 19

<210> SEQ ID NO 49
<211> LENGTH: 21
<212> TYPE: DNA
<213> ORGANISM: Artificial Sequence
<220> FEATURE:
<223> OTHER INFORMATION: aPkc-zeta FW primer

<400> SEQUENCE: 49
gcgtggatgc catgacaaca t 21

<210> SEQ ID NO 50
<211> LENGTH: 21
<212> TYPE: DNA
<213> ORGANISM: Artificial Sequence
<220> FEATURE:
<223> OTHER INFORMATION: aPkc-zeta REV primer

<400> SEQUENCE: 50
ggctcttggg aaggcatgac a 21

<210> SEQ ID NO 51
<211> LENGTH: 21
<212> TYPE: DNA
<213> ORGANISM: Artificial Sequence
<220> FEATURE:

-continued

<223> OTHER INFORMATION: Rpl4 FW primer

<400> SEQUENCE: 51
ccgtcccctc atatcggtgt a 21

<210> SEQ ID NO 52
<211> LENGTH: 23
<212> TYPE: DNA
<213> ORGANISM: Artificial Sequence
<220> FEATURE:
<223> OTHER INFORMATION: Rpl4 REV primer

<400> SEQUENCE: 52
gcatagggct gtctgttgtt ttt 23

<210> SEQ ID NO 53
<211> LENGTH: 20
<212> TYPE: DNA
<213> ORGANISM: Artificial Sequence
<220> FEATURE:
<223> OTHER INFORMATION: Scrib FW primer

<400> SEQUENCE: 53
cctgggcatc agtatcgcag 20

<210> SEQ ID NO 54
<211> LENGTH: 20
<212> TYPE: DNA
<213> ORGANISM: Artificial Sequence
<220> FEATURE:
<223> OTHER INFORMATION: Scrib REV primer

<400> SEQUENCE: 54
gccctcgtca tctcctttgt 20

<210> SEQ ID NO 55
<211> LENGTH: 21
<212> TYPE: DNA
<213> ORGANISM: Artificial Sequence
<220> FEATURE:
<223> OTHER INFORMATION: Tjp1 FW primer

<400> SEQUENCE: 55
gagcgggcta ccttactgaa c 21

<210> SEQ ID NO 56
<211> LENGTH: 23
<212> TYPE: DNA
<213> ORGANISM: Artificial Sequence
<220> FEATURE:
<223> OTHER INFORMATION: Tjp1 REV primer

<400> SEQUENCE: 56
gtcatctctt tccgaggcat tag 23

<210> SEQ ID NO 57
<211> LENGTH: 20
<212> TYPE: DNA
<213> ORGANISM: Artificial Sequence
<220> FEATURE:
<223> OTHER INFORMATION: Tjp2 FW primer

<400> SEQUENCE: 57
atgggagcag tacaccgtga 20

<210> SEQ ID NO 58
<211> LENGTH: 22
<212> TYPE: DNA
<213> ORGANISM: Artificial Sequence
<220> FEATURE:
<223> OTHER INFORMATION: Tjp2 REV primer

<400> SEQUENCE: 58
tgaccaccct gtcattttct tg 22

<210> SEQ ID NO 59
<211> LENGTH: 21
<212> TYPE: DNA
<213> ORGANISM: Artificial Sequence
<220> FEATURE:
<223> OTHER INFORMATION: Tjp3 FW primer

<400> SEQUENCE: 59
ctgtggagaa cgtcacatct g 21

<210> SEQ ID NO 60
<211> LENGTH: 20
<212> TYPE: DNA
<213> ORGANISM: Artificial Sequence
<220> FEATURE:
<223> OTHER INFORMATION: Tjp3 REV primer

<400> SEQUENCE: 60
cggggacgct tcactgtaac 20

<210> SEQ ID NO 61
<211> LENGTH: 73
<212> TYPE: DNA
<213> ORGANISM: Artificial Sequence
<220> FEATURE:
<223> OTHER INFORMATION: dt_BC1001_PB
<220> FEATURE:
<221> NAME/KEY: unsure
<222> LOCATION: (73)..(73)
<223> OTHER INFORMATION: /note="v is A or C or G" /note="n is any nucleotide"
<220> FEATURE:
<221> NAME/KEY: misc_feature
<222> LOCATION: (73)..(73)
<223> OTHER INFORMATION: n is a, c, g, or t

<400> SEQUENCE: 61
aagcagtggt atcaacgcag agtaccacat atcagagtgc gttttttttt tttttttttt 60
tttttttttt tvn 73

<210> SEQ ID NO 62
<211> LENGTH: 73
<212> TYPE: DNA
<213> ORGANISM: Artificial Sequence
<220> FEATURE:
<223> OTHER INFORMATION: dt_BC1002_PB
<220> FEATURE:
<221> NAME/KEY: unsure
<222> LOCATION: (73)..(73)
<223> OTHER INFORMATION: /note="v is A or C or G" /note="n is any nucleotide"
<220> FEATURE:
<221> NAME/KEY: misc_feature
<222> LOCATION: (73)..(73)
<223> OTHER INFORMATION: n is a, c, g, or t

<400> SEQUENCE: 62
aagcagtggt atcaacgcag agtacacaca cagactgtga gttttttttt tttttttttt 60

-continued tttttttttt tvn 73

<210> SEQ ID NO 63
<211> LENGTH: 73
<212> TYPE: DNA
<213> ORGANISM: Artificial Sequence
<220> FEATURE:
<223> OTHER INFORMATION: dt_BC1003_PB
<220> FEATURE:
<221> NAME/KEY: unsure
<222> LOCATION: (73)..(73)
<223> OTHER INFORMATION: /note="v is A or C or G" /note="n is any nucleotide"
<220> FEATURE:
<221> NAME/KEY: misc_feature
<222> LOCATION: (73)..(73)
<223> OTHER INFORMATION: n is a, c, g, or t

<400> SEQUENCE: 63
aagcagtggt atcaacgcag agtacacaca tctcgtgaga gttttttttt tttttttttt 60
tttttttttt tvn 73

<210> SEQ ID NO 64
<211> LENGTH: 73
<212> TYPE: DNA
<213> ORGANISM: Artificial Sequence
<220> FEATURE:
<223> OTHER INFORMATION: dt_BC1004_PB
<220> FEATURE:
<221> NAME/KEY: unsure
<222> LOCATION: (73)..(73)
<223> OTHER INFORMATION: /note="v is A or C or G" /note="n is any nucleotide"
<220> FEATURE:
<221> NAME/KEY: misc_feature
<222> LOCATION: (73)..(73)
<223> OTHER INFORMATION: n is a, c, g, or t

<400> SEQUENCE: 64
aagcagtggt atcaacgcag agtaccacgc acacacgcgc gttttttttt tttttttttt 60
tttttttttt tvn 73

<210> SEQ ID NO 65
<211> LENGTH: 73
<212> TYPE: DNA
<213> ORGANISM: Artificial Sequence
<220> FEATURE:
<223> OTHER INFORMATION: dt_BC1005_PB
<220> FEATURE:
<221> NAME/KEY: unsure
<222> LOCATION: (73)..(73)
<223> OTHER INFORMATION: /note="v is A or C or G" /note="n is any nucleotide"
<220> FEATURE:
<221> NAME/KEY: misc_feature
<222> LOCATION: (73)..(73)
<223> OTHER INFORMATION: n is a, c, g, or t

<400> SEQUENCE: 65
aagcagtggt atcaacgcag agtaccactc gactctcgcg tttttttttt tttttttttt 60
tttttttttt tvn 73

<210> SEQ ID NO 66
<211> LENGTH: 73
<212> TYPE: DNA
<213> ORGANISM: Artificial Sequence
<220> FEATURE:
<223> OTHER INFORMATION: dt_BC1006_PB
<220> FEATURE:

<221> NAME/KEY: unsure
<222> LOCATION: (73)..(73)
<223> OTHER INFORMATION: /note="v is A or C or G" /note="n is any nucleotide"
<220> FEATURE:
<221> NAME/KEY: misc_feature
<222> LOCATION: (73)..(73)
<223> OTHER INFORMATION: n is a, c, g, or t

<400> SEQUENCE: 66
aagcagtggt atcaacgcag agtaccatat atatcagctg tttttttttt tttttttttt 60
tttttttttt tvn 73

<210> SEQ ID NO 67
<211> LENGTH: 73
<212> TYPE: DNA
<213> ORGANISM: Artificial Sequence
<220> FEATURE:
<223> OTHER INFORMATION: dT_BC1001_PB
<220> FEATURE:
<221> NAME/KEY: unsure
<222> LOCATION: (73)..(73)
<223> OTHER INFORMATION: /note="n is any nucleotide" /note="v is A or C or G"
<220> FEATURE:
<221> NAME/KEY: misc_feature
<222> LOCATION: (73)..(73)
<223> OTHER INFORMATION: n is a, c, g, or t

<400> SEQUENCE: 67
aagcagtggt atcaacgcag agtaccacat atcagagtgc gttttttttt tttttttttt 60
tttttttttt tvn 73

<210> SEQ ID NO 68
<211> LENGTH: 73
<212> TYPE: DNA
<213> ORGANISM: Artificial Sequence
<220> FEATURE:
<223> OTHER INFORMATION: dT_BC1002_PB
<220> FEATURE:
<221> NAME/KEY: unsure
<222> LOCATION: (73)..(73)
<223> OTHER INFORMATION: /note="n is any nucleotide" /note="v is A or C or G"
<220> FEATURE:
<221> NAME/KEY: misc_feature
<222> LOCATION: (73)..(73)
<223> OTHER INFORMATION: n is a, c, g, or t

<400> SEQUENCE: 68
aagcagtggt atcaacgcag agtacacaca cagactgtga gttttttttt tttttttttt 60
tttttttttt tvn 73

<210> SEQ ID NO 69
<211> LENGTH: 73
<212> TYPE: DNA
<213> ORGANISM: Artificial Sequence
<220> FEATURE:
<223> OTHER INFORMATION: dt_BC1003_PB
<220> FEATURE:
<221> NAME/KEY: unsure
<222> LOCATION: (73)..(73)
<223> OTHER INFORMATION: /note="n is any nucleotide" /note="v is A or C or G"
<220> FEATURE:
<221> NAME/KEY: misc_feature
<222> LOCATION: (73)..(73)
<223> OTHER INFORMATION: n is a, c, g, or t

<400> SEQUENCE: 69
aagcagtggt atcaacgcag agtacacaca tctcgtgaga gttttttttt tttttttttt 60
tttttttttt tvn 73

<210> SEQ ID NO 70
<211> LENGTH: 73
<212> TYPE: DNA
<213> ORGANISM: Artificial Sequence
<220> FEATURE:
<223> OTHER INFORMATION: dT-BC1004_PB
<220> FEATURE:
<221> NAME/KEY: unsure
<222> LOCATION: (73)..(73)
<223> OTHER INFORMATION: /note="n is any nucleotide" /note="v is A or C or G"
<220> FEATURE:
<221> NAME/KEY: misc_feature
<222> LOCATION: (73)..(73)
<223> OTHER INFORMATION: n is a, c, g, or t

<400> SEQUENCE: 70
aagcagtggt atcaacgcag agtaccacgc acacacgcgc gttttttttt tttttttttt 60
tttttttttt tvn 73

<210> SEQ ID NO 71
<211> LENGTH: 73
<212> TYPE: DNA
<213> ORGANISM: Artificial Sequence
<220> FEATURE:
<223> OTHER INFORMATION: dT_BC1005_PB
<220> FEATURE:
<221> NAME/KEY: unsure
<222> LOCATION: (73)..(73)
<223> OTHER INFORMATION: /note="n is any nucleotide" /note="v is A or G or C"
<220> FEATURE:
<221> NAME/KEY: misc_feature
<222> LOCATION: (73)..(73)
<223> OTHER INFORMATION: n is a, c, g, or t

<400> SEQUENCE: 71
aagcagtggt atcaacgcag agtaccactc gactctcgcg tttttttttt tttttttttt 60
tttttttttt tvn 73

<210> SEQ ID NO 72
<211> LENGTH: 73
<212> TYPE: DNA
<213> ORGANISM: Artificial Sequence
<220> FEATURE:
<223> OTHER INFORMATION: dT_BC1006_PB
<220> FEATURE:
<221> NAME/KEY: unsure
<222> LOCATION: (73)..(73)
<223> OTHER INFORMATION: /note="n is any nucleotide" /note="v is A or G or C"
<220> FEATURE:
<221> NAME/KEY: misc_feature
<222> LOCATION: (73)..(73)
<223> OTHER INFORMATION: n is a, c, g, or t

<400> SEQUENCE: 72
aagcagtggt atcaacgcag agtaccatat atatcagctg tttttttttt tttttttttt 60
tttttttttt tvn 73

<210> SEQ ID NO 73
<211> LENGTH: 74
<212> TYPE: DNA
<213> ORGANISM: Artificial Sequence

```
<220> FEATURE:
<223> OTHER INFORMATION: dT_BC1007_PB
<220> FEATURE:
<221> NAME/KEY: unsure
<222> LOCATION: (74)..(74)
<223> OTHER INFORMATION: /note="n is any nucleotide" /note="v is A or G
      or C"
<220> FEATURE:
<221> NAME/KEY: misc_feature
<222> LOCATION: (74)..(74)
<223> OTHER INFORMATION: n is a, c, g, or t

<400> SEQUENCE: 73

aagcagtggt atcaacgcag agtactctgt atctctatgt gttttttttt tttttttttt     60

tttttttttt ttvn                                                       74


<210> SEQ ID NO 74
<211> LENGTH: 74
<212> TYPE: DNA
<213> ORGANISM: Artificial Sequence
<220> FEATURE:
<223> OTHER INFORMATION: dT_BC1008_PB
<220> FEATURE:
<221> NAME/KEY: unsure
<222> LOCATION: (74)..(74)
<223> OTHER INFORMATION: /note="n is any nucleotide" /note="v is A or C
      or G"
<220> FEATURE:
<221> NAME/KEY: misc_feature
<222> LOCATION: (74)..(74)
<223> OTHER INFORMATION: n is a, c, g, or t

<400> SEQUENCE: 74

aagcagtggt atcaacgcag agtacacagt cgagcgctgc gttttttttt tttttttttt     60

tttttttttt ttvn                                                       74


<210> SEQ ID NO 75
<211> LENGTH: 74
<212> TYPE: DNA
<213> ORGANISM: Artificial Sequence
<220> FEATURE:
<223> OTHER INFORMATION: dT_BC1009_PB
<220> FEATURE:
<221> NAME/KEY: unsure
<222> LOCATION: (74)..(74)
<223> OTHER INFORMATION: /note="n is any nucleotide" /note="v is A or C
      or G"
<220> FEATURE:
<221> NAME/KEY: unsure
<222> LOCATION: (74)..(74)
<223> OTHER INFORMATION: /note="n is any nucleotide" /note="v is A or C
      or G"
<220> FEATURE:
<221> NAME/KEY: misc_feature
<222> LOCATION: (74)..(74)
<223> OTHER INFORMATION: n is a, c, g, or t

<400> SEQUENCE: 75

aagcagtggt atcaacgcag agtacacaca cgcgagacag attttttttt tttttttttt     60

tttttttttt ttvn                                                       74


<210> SEQ ID NO 76
<211> LENGTH: 74
<212> TYPE: DNA
<213> ORGANISM: Artificial Sequence
<220> FEATURE:
<223> OTHER INFORMATION: dT_BC1010_PB
<220> FEATURE:
<221> NAME/KEY: unsure
<222> LOCATION: (74)..(74)
```

-continued

```
<223> OTHER INFORMATION: /note="n is any nucleotide" /note="v is A or G
      or C"
<220> FEATURE:
<221> NAME/KEY: misc_feature
<222> LOCATION: (74)..(74)
<223> OTHER INFORMATION: n is a, c, g, or t

<400> SEQUENCE: 76

aagcagtggt atcaacgcag agtacacgcg ctatctcaga gttttttttt ttttttttt     60

ttttttttt ttvn                                                       74


<210> SEQ ID NO 77
<211> LENGTH: 73
<212> TYPE: DNA
<213> ORGANISM: Artificial Sequence
<220> FEATURE:
<223> OTHER INFORMATION: dT_BC1011_PB
<220> FEATURE:
<221> NAME/KEY: unsure
<222> LOCATION: (73)..(73)
<223> OTHER INFORMATION: /note="n is any nucleotide" /note="v is A or G
      or C"
<220> FEATURE:
<221> NAME/KEY: misc_feature
<222> LOCATION: (73)..(73)
<223> OTHER INFORMATION: n is a, c, g, or t

<400> SEQUENCE: 77

aagcagtggt atcaacgcag agtacctata cgtatatcta ttttttttt ttttttttt      60

ttttttttt tvn                                                        73


<210> SEQ ID NO 78
<211> LENGTH: 73
<212> TYPE: DNA
<213> ORGANISM: Artificial Sequence
<220> FEATURE:
<223> OTHER INFORMATION: dT_BC1012_PB
<220> FEATURE:
<221> NAME/KEY: unsure
<222> LOCATION: (73)..(73)
<223> OTHER INFORMATION: /note="n is any nucleotide" /note="v is A or G
      or C"
<220> FEATURE:
<221> NAME/KEY: misc_feature
<222> LOCATION: (73)..(73)
<223> OTHER INFORMATION: n is a, c, g, or t

<400> SEQUENCE: 78

aagcagtggt atcaacgcag agtacacact agatcgcgtg ttttttttt ttttttttt      60

ttttttttt tvn                                                        73
```

MUCINS AND ISOFORMS THEREOF IN DISEASES CHARACTERIZED BY BARRIER DYSFUNCTION

CROSS-REFERENCES TO RELATED APPLICATIONS

This application is a national-stage application under 35 U.S.C. § 371 of International Application No. PCT/EP2021/068083, filed Jun. 30, 2021, which claims benefit of priority to International Application No. PCT/EP2020/068340, filed Jun. 30, 2020, to European Patent Application No. 21152072.1, filed Jan. 18, 2021, and to European Patent Application No. 21157750.7, filed Feb. 18, 2021.

SEQUENCE LISTING

A computer-readable form (CRF) sequence listing having file name SubstituteSequenceListingANW0022PA.txt (19,781 bytes), created Jul. 7, 2023, is incorporated herein by reference. The nucleic acid sequences and amino acid sequences listed in the accompanying sequence listing are shown using standard abbreviations as defined in 37 C.F.R. § 1.822.

FIELD OF THE INVENTION

The present invention relates to the field of mucins and mRNA isoforms thereof, more in particular for use in the diagnosis, monitoring, prevention and/or treatment of a disease characterized by barrier dysfunction, such as but not limited to a gastrointestinal disorder (e.g. Inflammatory Bowel Disease (IBD), Irritable Bowel Syndrome (IBS), cancer, gastrointestinal infections, obesitas, non-alcoholic fatty liver disease (NAFLD)), neurodegenerative disorders, respiratory infections, . . . more in particular coronaviral infections. In a specific embodiment, said mucins and/or mRNA isoforms thereof are selected from the list comprising: MUC13, MUC16, MUC21, MUC20, MUC2, MUC4, MUC5AC, MUC5B and MUC1 and mRNA isoforms thereof.

BACKGROUND TO THE INVENTION

All epithelial tissues in the human body are covered by a mucus layer consisting of secreted and membrane-bound mucins that are a family of large molecular weight glycoproteins. Besides providing a protective function to the underlying epithelium by the formation of a physical barrier, transmembrane mucins also participate in the intracellular signal transduction. Mucins contain multiple exonic regions that encode for various functional domains. More specifically, they possess a large extracellular domain (ECD) consisting of variable number of tandem repeat (VNTR) regions rich in proline, threonine and serine (i.e. PTS domains) and heavily glycosylated. In addition, transmembrane mucins also contain extracellular epidermal growth factor (EGF)-like domains, a transmembrane region (TMD) and a shorter cytoplasmic tail (CT) that contains multiple phosphorylation sites. Binding of the ECD to the TMD is mediated by a sea urchin sperm protein, enterokinase and agrin (SEA) domain that is present in all transmembrane mucins except for MUC4. This SEA domain is autoproteolytically cleaved in the endoplasmic reticulum resulting in the noncovalent binding of the α-chain (ECD) and β-chain (TMD and CT).

Aberrant expression of transmembrane mucins has been observed during chronic inflammation and cancer. Of particular interest are MUC1 and MUC13. These transmembrane mucins are upregulated in the inflamed colonic mucosa from patients with inflammatory bowel disease (IBD) and in the tumor tissue of patients with gastric and colorectal cancer. Furthermore, emerging evidence suggests that their aberrant expression upon inflammation is associated with loss of mucosal epithelial barrier integrity.

Due to their polymorphic nature, the presence of genetic differences (i.e. single nucleotide polymorphisms (SNPs)) in mucin genes can result in different mRNA isoforms or splice variants due to alternative splicing. While most mRNA isoforms encode similar biological functions, others have the potential to alter the protein function resulting in progression toward disease. Although still poorly understood, differential expression of mucin mRNA isoforms could be involved in the pathophysiology of inflammatory diseases and cancer involving loss of barrier integrity.

SUMMARY OF THE INVENTION

In a first aspect, the present invention provides a mucin or mucin mRNA isoform thereof for use in the diagnosis, monitoring, prevention and/or treatment of a disease characterized by barrier dysfunction, in particular a coronaviral infection or coronaviral infectious disease, wherein the mucin or mRNA isoform thereof is selected from the list comprising: MUC16, MUC21, MUC2, MUC4, MUC5AC, MUC5B, MUC13, MUC20, MUC1, MUC16 mRNA isoforms, MUC21 mRNA isoforms, MUC2 mRNA isoforms, MUC4 mRNA isoforms, MUC5AC mRNA isoforms, MUC5B mRNA isoforms, MUC13 mRNA isoforms, MUC20 mRNA isoforms, or MUC1 mRNA isoforms.

In another particular embodiment, the present invention provides one or more mucin for use in the diagnosis, monitoring, prevention and/or treatment of a disease characterized by barrier dysfunction, in particular a coronaviral infection or coronaviral infectious disease, wherein the mucin is selected from the list comprising: MUC1, MUC2, MUC3A, MUC4, MUC5AC, MUC5B, MUC6, MUC7, MUC8, MUC12, MUC13, MUC15, MUC16, MUC17, MUC19, MUC20, MUC21, MUC22.

Particularly interesting mucins for use in the diagnosis or determination of a coronaviral infection or coronaviral infectious disease may be selected from the list comprising: MUC1, MUC2, MUC4, MUC6, MUC13, MUC16 and MUC20.

Particularly interesting mucins for use in the prognosis of severity of a coronaviral infection or coronaviral infectious disease may be selected from the list comprising: MUC1, MUC2, MUC5AC, MUC5B, MUC13, MUC16, MUC20 and MUC21.

In another particular embodiment, the present invention provides one or more mucin mRNA isoform for use in the diagnosis, monitoring, prevention and/or treatment of a disease characterized by barrier dysfunction, in particular a coronaviral infection or coronaviral infectious disease, wherein the mucin mRNA isoform is selected from the list comprising: MUC1 mRNA isoforms, MUC2 mRNA isoforms, MUC3A mRNA isoforms, MUC4 mRNA isoforms, MUC5AC mRNA isoforms, MUC5B mRNA isoforms, MUC6 mRNA isoforms, MUC7 mRNA isoforms, MUC8 mRNA isoforms, MUC12 mRNA isoforms, MUC13 mRNA isoforms, MUC15 mRNA isoforms, MUC16 mRNA isoforms, MUC17 mRNA isoforms, MUC19 mRNA isoforms, MUC20 mRNA isoforms, MUC21 mRNA isoforms, MUC22 mRNA isoforms.

In a particular embodiment, the present invention provides an in vitro method for diagnosing and/or determining the severity of a coronaviral infection or coronaviral infectious disease and/or associated co-infections, said method comprising:

a) providing a biological sample from a subject suspected of having a coronaviral infection or coronaviral infectious disease and/or associated co-infections, and b) determining the presence and/or quantity of one or more mucins selected from the list comprising: MUC16, MUC21, MUC2, MUC4, MUC5AC, MUC5B, MUC13, MUC20, optionally in combination with MUC1;

wherein the presence and/or quantity of the one or more mucins is indicative for the presence and/or severity of a coronaviral infection or coronaviral infectious disease.

In another particular embodiment, the present invention provides an in vitro method for diagnosing and/or determining the severity of a coronaviral infection or coronaviral infectious disease and/or associated co-infections, said method comprising:

a) providing a biological sample from a subject suspected of having a coronaviral infection or coronaviral infectious disease and/or associated co-infections, and b) determining the presence and/or quantity of one or more mucins selected from the list comprising: MUC16, MUC21, MUC2, MUC4, MUC5AC, MUC5B, MUC6, MUC13, MUC20, optionally in combination with MUC1;

wherein the presence and/or quantity of the one or more mucins is indicative for the presence and/or severity of a coronaviral infection or coronaviral infectious disease.

In a specific embodiment, said method comprises determining the presence and/or quantity of MUC13 and MUC21; and wherein high levels of MUC13 and MUC21 are indicative of a coronaviral infection or coronaviral infectious disease.

In a specific embodiment, said method comprises determining the presence and/or quantity of MUC1, MUC2, MUC16 and/or MUC20; and wherein high levels of MUC1, high levels of MUC2, high levels of MUC20 and/or low levels of MUC16 are indicative of a coronaviral infection or coronaviral infectious disease.

In a specific embodiment, said method comprises determining the presence and/or quantity of MUC1, MUC2, MUC16 and/or MUC20; and wherein high levels of MUC1, high levels of MUC2, low levels of MUC20 and/or low levels of MUC16 are indicative of a coronaviral infection or coronaviral infectious disease.

In another particular embodiment, said method comprises determining the presence and/or quantity of MUC1, MUC2, MUC4, MUC6, MUC13, MUC16 and MUC20; and wherein high levels of MUC1, high levels of MUC2, low levels of MUC4, low levels of MUC6, high levels of MUC13, low levels of MUC16 and/or low levels of MUC20 are indicative of a coronaviral infection or coronaviral infectious disease.

In another particular embodiment, said method comprises determining the presence and/or quantity of MUC2, MUC13, MUC20 and/or MUC21; and wherein high levels of MUC2, high levels of MUC13, high levels of MUC20 and/or high levels of MUC21 are indicative of a mild coronaviral infection or coronaviral infectious disease.

In yet a further embodiment, said method comprises determining the presence and/or quantity of MUC2, MUC5AC, MUC5B, MUC13, MUC16, MUC20 and MUC21; and wherein high levels of MUC2, high levels of MUC5AC, high levels of MUC5B, high levels of MUC13, high levels of MUC16, high levels of MUC20 and/or high levels of MUC21 are indicative of a mild coronaviral infection or coronaviral infectious disease.

In another specific embodiment, said method comprises determining the presence and/or quantity of MUC1, MUC5B and/or MUC16; and high levels of MUC1, high levels of MUC5B and/or low levels of MUC16 are indicative of a more severe coronaviral infection or coronaviral infectious disease.

In a further embodiment, said method further comprises determining the presence and/or quantity of MUC2, MUC13, MUC20 and/or MUC21; and wherein high levels of MUC2, MUC13, MUC20 and/or MUC21 are indicative of a mild coronaviral infection or coronaviral infectious disease.

In a further embodiment, said method comprises determining the presence and/or quantity of MUC1, MUC16, MUC20 and MUC21; and wherein high levels of MUC1, low levels of MUC16, low levels of MUC20 and/or low levels of MUC21 are indicative of a more severe coronaviral infection or coronaviral infectious disease.

In another particular embodiment, the present invention provides an in vitro method for diagnosing and/or determining the severity of a coronaviral infection or coronaviral infectious disease and/or associated co-infections, said method comprising:

a) providing a biological sample from a subject suspected of having a coronaviral infection or coronaviral infectious disease and/or associated co-infections, and b) determining the presence and/or quantity of one or more mucin isoforms; selected from the group comprising MUC16 mRNA isoforms, MUC21 mRNA isoforms, MUC2 mRNA isoforms, MUC4 mRNA isoforms, MUC5AC mRNA isoforms, MUC5B mRNA isoforms, MUC13 mRNA isoforms, MUC20 mRNA isoforms or MUC1 mRNA isoforms;

wherein the presence and/or quantity of the one or more mucin mRNA isoforms is indicative for the presence and/or severity of a coronaviral infection or coronaviral infectious disease.

In a particular embodiment, the method of the present invention may further comprise determining the presence and/or quantity of one or more mucin isoforms; selected from the group comprising MUC3A mRNA isoforms, MUC6 mRNA isoforms, MUC7 mRNA isoforms, MUC8 mRNA isoforms, MUC12 mRNA isoforms, MUC15 mRNA isoforms, MUC17 mRNA isoforms, MUC19 mRNA isoforms and MUC22 mRNA isoforms.

In a specific embodiment, said one or more mucin mRNA isoforms are selected from the group comprising MUC1 mRNA isoforms, MUC13 mRNA isoforms, MUC16 mRNA isoforms, or MUC21 mRNA isoforms.

In yet a further embodiment at least 2, preferably at least 3 mucin mRNA isoforms are determined and/or quantified.

In a further embodiment, of the present invention, the presence and/or quantity of MUC1 mRNA isoforms, MUC13 mRNA isoforms, MUC16 mRNA isoforms and MUC21 mRNA isoforms are determined and wherein the presence and/or quantity of said mucin mRNA isoforms is indicative for the presence and/or severity of a coronaviral infection or coronaviral infectious disease.

In yet a further embodiment of the present invention, the presence and/or quantity of MUC13 mRNA isoforms and/or MUC21 mRNA isoforms is determined and wherein the presence and/or quantity of MUC13 mRNA isoforms and/or MUC21 mRNA isoforms is indicative for the diagnosis of a coronaviral infection or coronaviral infectious disease.

In another embodiment of the present invention, said method comprises determining the presence and/or quantity of MUC1 mRNA isoforms, MUC2 mRNA isoforms, MUC16 mRNA isoforms and/or MUC20 mRNA isoforms; and wherein high levels of MUC1 mRNA isoforms, high levels of MUC2 mRNA isoforms, high levels of MUC20 mRNA isoforms and/or low levels of MUC16 mRNA isoforms is indicative of a coronaviral infection or coronaviral infectious disease.

In another embodiment of the present invention, the presence and/or quantity of MUC1 mRNA isoforms, MUC5B mRNA isoforms and/or MUC16 mRNA isoforms is determined and wherein high levels of MUC1 mRNA isoforms, high levels of MUC5B mRNA isoforms and/or low levels of MUC16 mRNA isoforms is indicative of a more severe coronaviral infection or coronaviral infectious disease.

In a further embodiment, said method further comprises determining the presence and/or quantity of MUC2 mRNA isoforms, MUC13 mRNA isoforms, MUC20 mRNA isoforms and/or MUC21 mRNA isoforms; and wherein high levels of MUC2 mRNA isoforms, MUC13 mRNA isoforms, MUC20 mRNA isoforms and/or MUC21 mRNA isoforms are indicative of a mild coronaviral infection or coronaviral infectious disease.

The present invention further provides one or more mucin mRNA isoforms for use in the diagnosis and/or monitoring of a coronaviral infection or coronaviral infectious disease, wherein the one or more mucin mRNA isoforms are selected from the list comprising: MUC1 mRNA isoforms, MUC2 mRNA isoforms, MUC4 mRNA isoforms, MUC5AC mRNA isoforms, MUC5B mRNA isoforms, MUC13 isoforms, MUC16 mRNA isoforms, MUC20 mRNA isoforms, and MUC 21 mRNA isoforms.

In a specific embodiment, the method of the present invention provides the determination of the presence and/or quantity of MUC1 mRNA isoforms, MUC2 mRNA isoforms, MUC3A mRNA isoforms, MUC4 mRNA isoforms, MUC5AC mRNA isoforms, MUC5B mRNA isoforms, MUC6 mRNA isoforms, MUC7 mRNA isoforms, MUC8 mRNA isoforms, MUC12 mRNA isoforms, MUC13 mRNA isoforms, MUC15 mRNA isoforms, MUC16 mRNA isoforms, MUC17 mRNA isoforms, MUC19 mRNA isoforms, MUC20 mRNA isoforms, MUC21 mRNA isoforms and/or MUC22 mRNA isoforms in a mucus sample and wherein the presence and/or quantity of one or more of said mRNA isoforms is indicative of the presence and/or severity of a coronaviral infection or coronaviral infectious disease.

In a specific embodiment, the method of the present invention provides the determination of MUC1 mRNA isoforms, MUC3A mRNA isoforms, MUC4 mRNA isoforms, MUC5B mRNA isoforms, MUC7 mRNA isoforms, MUC12 mRNA isoforms, MUC13 mRNA isoforms, MUC15 mRNA isoforms, MUC16 mRNA isoforms, MUC17 mRNA isoforms, MUC19 mRNA isoforms, and/or MUC20 mRNA isoforms is determined in a blood sample and wherein the presence and/or quantity of one or more of said mRNA isoforms is indicative of the presence and/or severity of a coronaviral infection or coronaviral infectious disease.

In a specific embodiment, the method of the present invention provides the determination of MUC1 mRNA isoforms, MUC12 mRNA isoforms, MUC13 mRNA isoforms, MUC16 mRNA isoforms, MUC19 mRNA isoforms, and/or MUC20 mRNA isoforms is determined in a blood sample and wherein the presence and/or quantity of one or more of said mRNA isoforms is indicative of the presence and/or severity of a coronaviral infection or coronaviral infectious disease.

In a particular embodiment, said mucin mRNA isoform is a transmembrane mucin.

In a specific embodiment, the one or more mucin mRNA isoforms for use in the present invention are selected from the list comprising: MUC1 mRNA isoforms, MUC13 isoforms, MUC16 mRNA isoforms, or MUC21 mRNA isoforms; optionally in combination with one or more of MUC2 mRNA isoforms, MUC4 mRNA isoforms, MUC20 mRNA isoforms, MUC5AC mRNA isoforms or MUC5B mRNA isoforms.

The present invention also provides a combination of MUC1 mRNA isoforms, MUC13 mRNA isoforms, MUC16 mRNA isoforms and MUC21 mRNA isoforms for use in the diagnosis and/or monitoring of a coronaviral infection or coronaviral infectious disease.

The present invention also provides a combination of MUC1 mRNA isoforms, MUC2 mRNA isoforms, MUC13 mRNA isoforms, MUC16 mRNA isoforms and/or MUC20 mRNA isoforms for use in the diagnosis and/or monitoring of a coronaviral infection or coronaviral infectious disease.

The present invention also provides a combination of one or more mRNA isoforms selected from the list comprising: MUC3A mRNA isoforms, MUC4 mRNA isoforms, MUC6 mRNA isoforms, MUC7 mRNA isoforms, MUC8 mRNA isoforms, MUC12 mRNA isoforms, MUC15 mRNA isoforms, MUC17 mRNA isoforms, MUC19 mRNA isoforms and MUC22 mRNA isoforms.

Furthermore, the present invention provides a MUC1 mRNA isoform and MUC16 mRNA isoform for use in determining the severity of a coronaviral infection or coronaviral infectious disease.

The present invention also provides a combination of MUC13 mRNA isoforms and MUC21 mRNA isoforms for use in the diagnosis of a coronaviral infection or coronaviral disease.

In another embodiment, the coronaviral infection or coronaviral disease is a SARS-CoV-2 infection or SARS-CoV-2 associated disease.

The invention also provides a diagnostic kit for performing the in vitro method according to the present invention, said kit comprising agents for detecting the presence of one or more mucins and/or mucin mRNA isoforms as defined herein.

In another particular embodiment, the present invention provides a mucin mRNA isoform as defined herein, for use as a biomarker for diagnosis and disease surveillance or monitoring.

In another particular embodiment, the present invention provides a mucin mRNA isoform as defined herein, for use as a new therapeutic target. In particular, said mucin mRNA isoform may be specifically targeted by monoclonal antibodies, small molecules or antisense technology.

In a specific embodiment of the present invention, said disease characterized by barrier dysfunction is a gastrointestinal disorder such as selected from the list comprising: Inflammatory Bowel Disease (IBD), Irritable Bowel Syndrome (IBS), cancer, gastro-intestinal infections, obesitas, non-alcoholic fatty liver disease (NAFLD); a neurodegenerative disorder; or a respiratory infection.

In another particular embodiment of the present invention, said cancer may be selected from the list comprising: esophageal cancer, gastric cancer, colorectal cancer, pancreas cancer, liver cancer, kidney cancer, lung cancer, ovarian cancer, colon cancer and prostate cancer.

In a further embodiment of the present invention, said gastro-intestinal infection may be selected from the list comprising: *Helicobacter* infection, *Campylobacter* infection, *Clostridioides difficile* infection and *Salmonella* infection.

In yet a further embodiment of the present invention, said neurodegenerative disorder may be selected from the list comprising: Parkinson's disease, Alzheimer's disease, Multiple Sclerosis (MS) and Autism.

In another embodiment of the present invention, said Inflammatory Bowel Disease may be selected from the list comprising: Crohn's disease and ulcerative colitis.

In yet a further embodiment, said respiratory infection may be selected from the list comprising: respiratory syncytial viral infections, influenza viral infections, rhinoviral infections, metapneumoviral infections, *Pseudomonas aeruginosa* viral infections and coronaviral infections. Said coronaviral infection for example being a SARS-CoV-2 infection.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

FIG. 11. Discriminant analysis with mRNA expression values of Muc1, Muc2, Muc4 and Muc13 as predictors. Discriminant analysis for the T cell transfer and DSS models to predict healthy controls and colitis groups (week 0, 1, 2, 4, 6; DSS cycle 1, DSS cycle 2, DSS cycle 3). The main predictor variables for each function are stated in the structure matrix. (A) For the T cell transfer model, the different experimental groups were mainly discriminated by Muc1 (function 1) and Muc13 (function 2). Individual mice were correctly annotated to their respective groups in 57.8% of the cases. (B) For the DSS-colitis model, the different experimental groups were primary discriminated by Muc2 (function 1) followed by Muc1 and Muc13 (function 2). Individual mice were correctly annotated to their respective groups in 69.6% of the cases.

The gray mRNA transcripts highlight transcripts that are found in only one condition (i.e. inflamed or non-inflamed). On the right panel, the isoform identity number can be found of which the details are shown in table 5 (n=3 paired samples).

Figure 16:
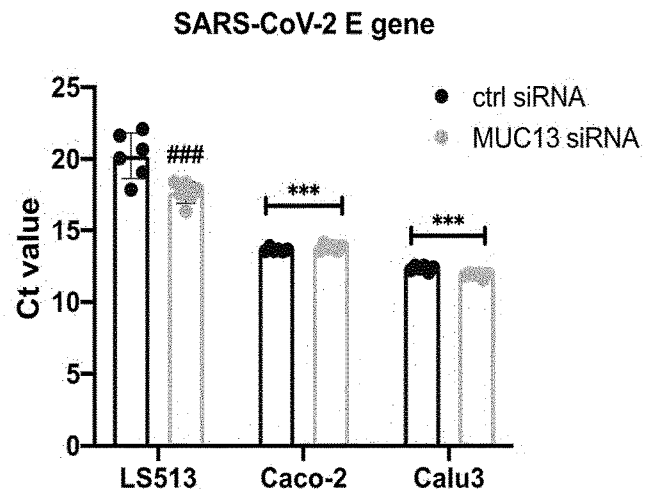

FIG. 16: RT-qPCR results to detect the SARS-CoV-2 E in the supernatants of ctrl and MUC13 siRNA transfected intestinal (LS513 and Caco2) and pulmonary (Calu3) epithelial cells infected with SARS-CoV-2 at 0.1 MOI for 48 h. Cycle threshold values are shown. Significant differences between ctrl and MUC13 siRNA transfected cells within a cell line are indicated by ###p<0.001 and between different transfected cell lines are indicated by *** p<0.001. (One-Way ANOVA, Tukey's post-hoc multiple comparison test, N=6). Error bars indicate SEM.

Figure 17:
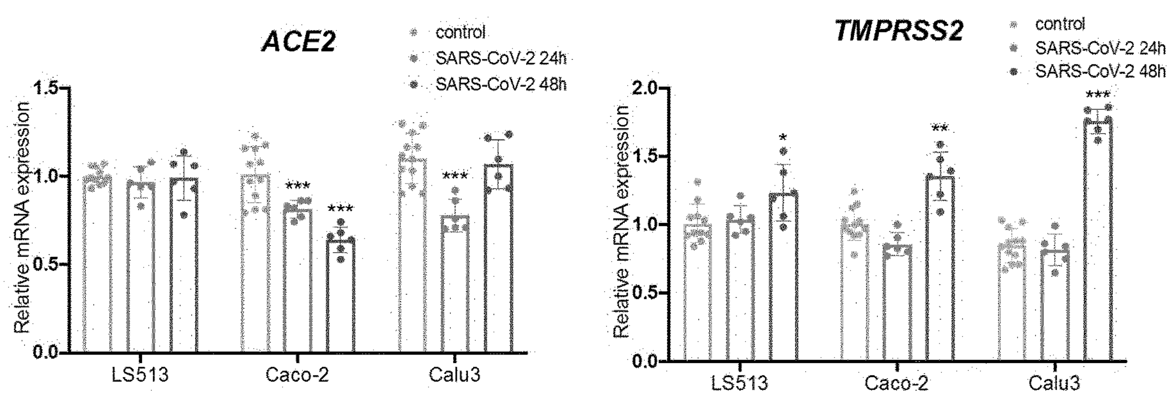

FIG. 17: Relative mRNA expression of ACE2 and TMPRSS2 in intestinal (LS513 and Caco2) and pulmonary (Calu3) epithelial cells infected with SARS-CoV-2 at 0.1 MOI for 24 h and 48 h. Cells treated with the growth medium of the virus were included as controls. Significant differences between SARS-CoV-2-infected and uninfected cells are indicated by *p<0.05; p<0.01; *p<0.001 (One-Way ANOVA, Tukey's post-hoc multiple comparison test, N=6). Error bars indicate SEM.

Figure 18:
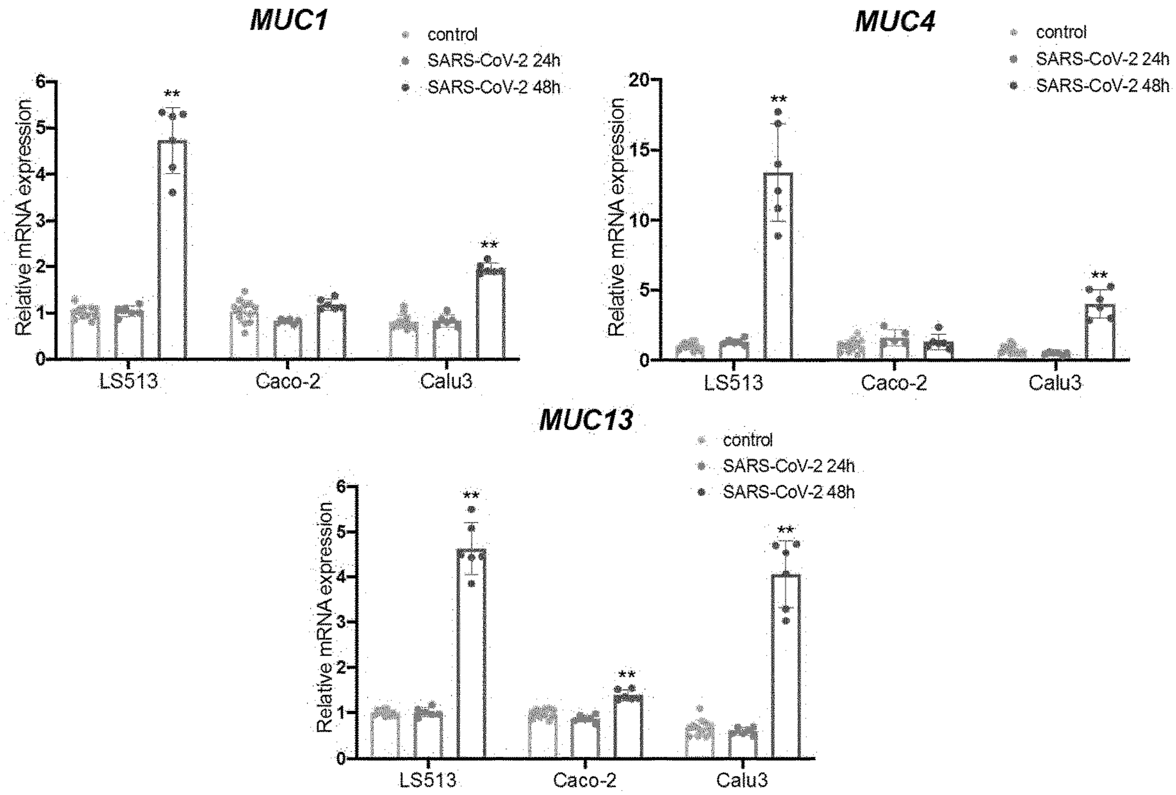

FIG. 18: Relative mRNA expression of the transmembrane mucins (MUC1, MUC4 and MUC13) in intestinal (LS513 and Caco2) and pulmonary (Calu3) epithelial cells infected with SARS-CoV-2 at 0.1 MOI for 24 h and 48 h. Cells treated with the growth medium of the virus were included as controls. Significant differences between SARS-CoV-2-infected and uninfected cells are indicated by *p<0.05; p<0.01; *p<0.001 (One-Way ANOVA, Tukey's post-hoc multiple comparison test, N=6). Error bars indicate SEM.

Figure 19:
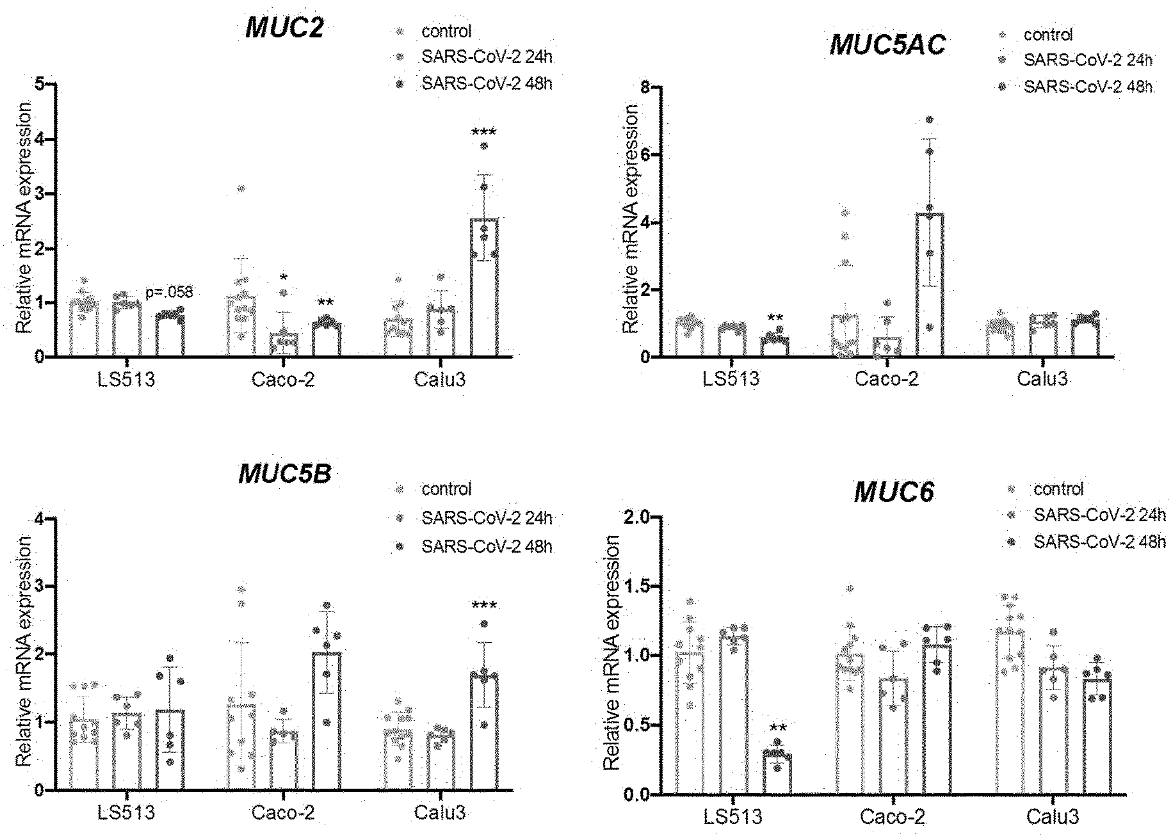

FIG. 19: Relative mRNA expression of the secreted mucins (MUC2, MUC5AC, MUC5B and MUC6) in intestinal (LS513 and Caco2) and pulmonary (Calu3) epithelial cells infected with SARS-CoV-2 at 0.1 MOI for 24 h and 48 h. Cells treated with the growth medium of the virus were included as controls. Significant differences between SARS-CoV-2-infected and uninfected cells are indicated by *p<0.05; p<0.01; *p<0.001 (One-Way ANOVA, Tukey's post-hoc multiple comparison test, N=6). Error bars indicate SEM.

Figure 20:
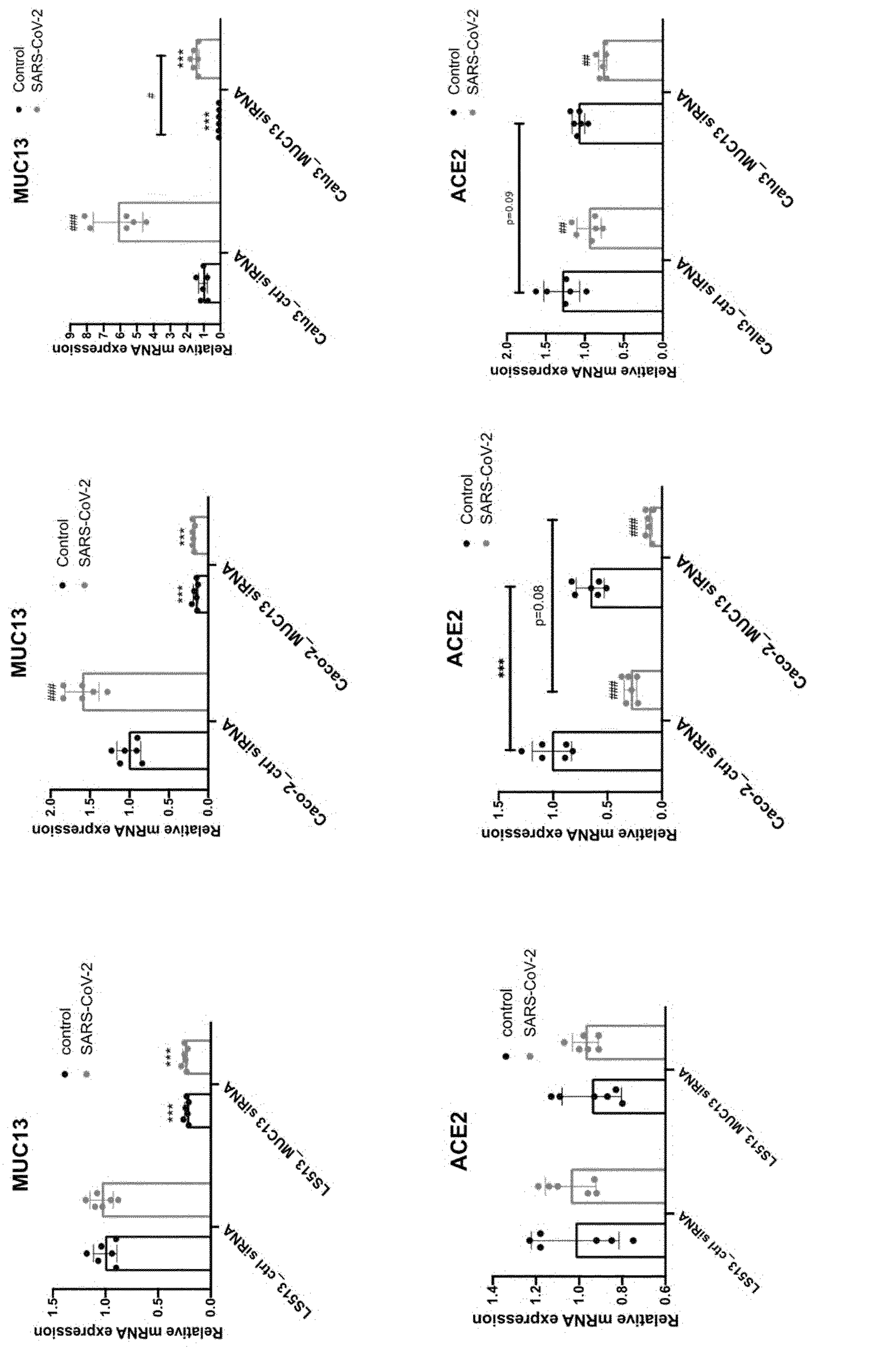

FIG. 20: Relative mRNA expression of MUC13 and ACE2 in ctrl siRNA and MUC13 siRNA transfected intestinal (LS513 and Caco-2) and pulmonary (Calu3) epithelial cells infected with SARS-CoV-2 at 0.1 MOI for 48 h. Transfected cells treated with the growth medium of the virus were included as controls. Significant differences between SARS-CoV-2-infected and uninfected transfected cells are indicated by #p<0.05; ##p<0.01; ###p<0.001. Significant differences between ctrl siRNA and MUC13 siRNA transfected cells infected or uninfected with SARS-CoV-2 are indicated by ***p<0.001. One-Way ANOVA, Tukey's post-hoc multiple comparison test, N=6. Error bars indicate SEM.

Figure 21:
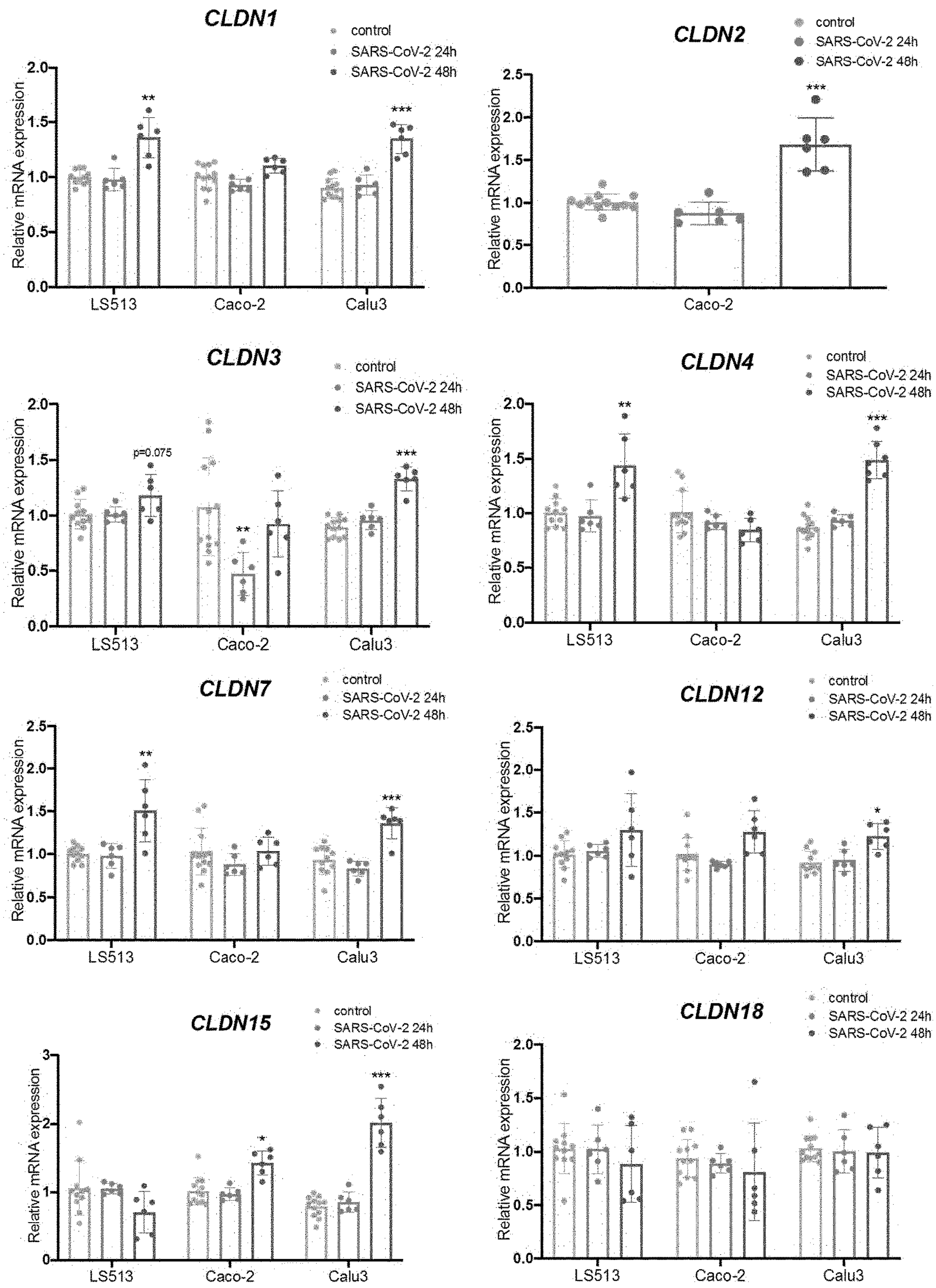

FIG. 21: Relative mRNA expression of junctional proteins (CLDN1, CLDN2, CLDN3, CLDN4, CLDN7, CLDN12, CLDN15, CLDN18, OCLN, ZO-1 and ZO-2 and CHD1 (E-cadherin)) in intestinal (LS513 and Caco2) and pulmonary (Calu3) epithelial cells infected with SARS-CoV-2 at 0.1 MOI for 24 h and 48 h. Cells treated with the growth medium of the virus were included as controls. Significant differences between SARS-CoV-2-infected and uninfected cells are indicated by *p<0.05; p<0.01; *p<0.001 (One-Way ANOVA, Tukey's post-hoc multiple comparison test, N=6). Error bars indicate SEM.

Figure 22A:
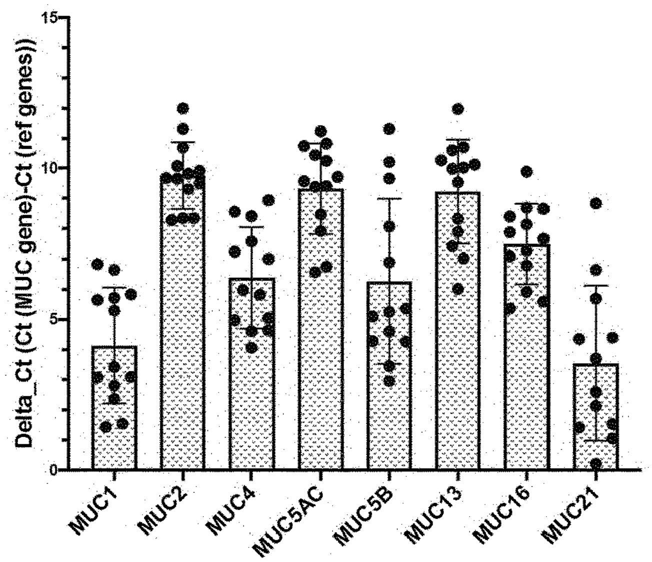
Figure 22B:
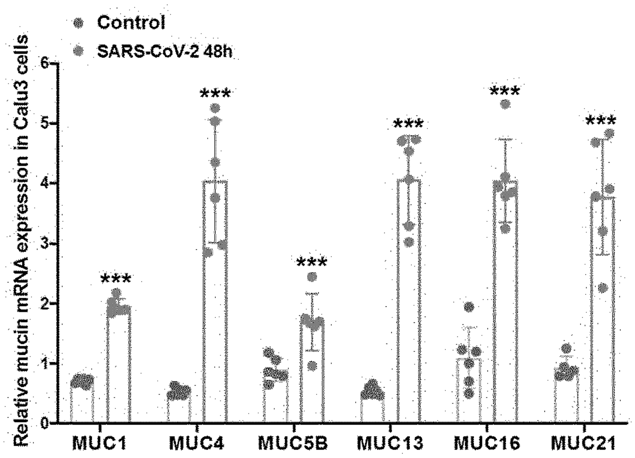

FIG. 22: A, Box plots of mucin mRNA expression (expressed as delta_Ct values) in mucus (endotracheal tubes) from mechanically ventilated ICU COVID-19 patients (N=10). The lower the delta_Ct value, the higher the mucin expression levels. Particularly MUC2, MUC4, MU5B, MUC5AC, MUC13, MUC16, MUC21 and MUC1 could be detected in mucus secretions from COVID-19 patients. B, Relative mRNA expression of MUC1, MUC4, MUC5B, MUC13, MUC16 and MUC21 in Calu3 cells infected with SARS-CoV-2 at 0.1 MOI for 48 h. C, Relative mRNA expression of ACE2 and the junctional proteins: claudin-1 (CLDN1), CLDN4, zonula occludens 1 (ZO-1) and E-cadherin (CDH1) in ctrl siRNA and MUC13 siRNA transfected Calu3 cells infected with SARS-CoV-2 at 0.1 MOI for 48 h. Significant differences between SARS-CoV-2-infected and uninfected (transfected) cells are indicated by p<0.01; *p<0.001 and between ctrl siRNA and MUC13 siRNA transfected cells infected or uninfected with SARS-CoV-2 are indicated by #p<0.05; ##p<0.01. (ANOVA, N=6). Error bars indicate SEM.

Figure 23:
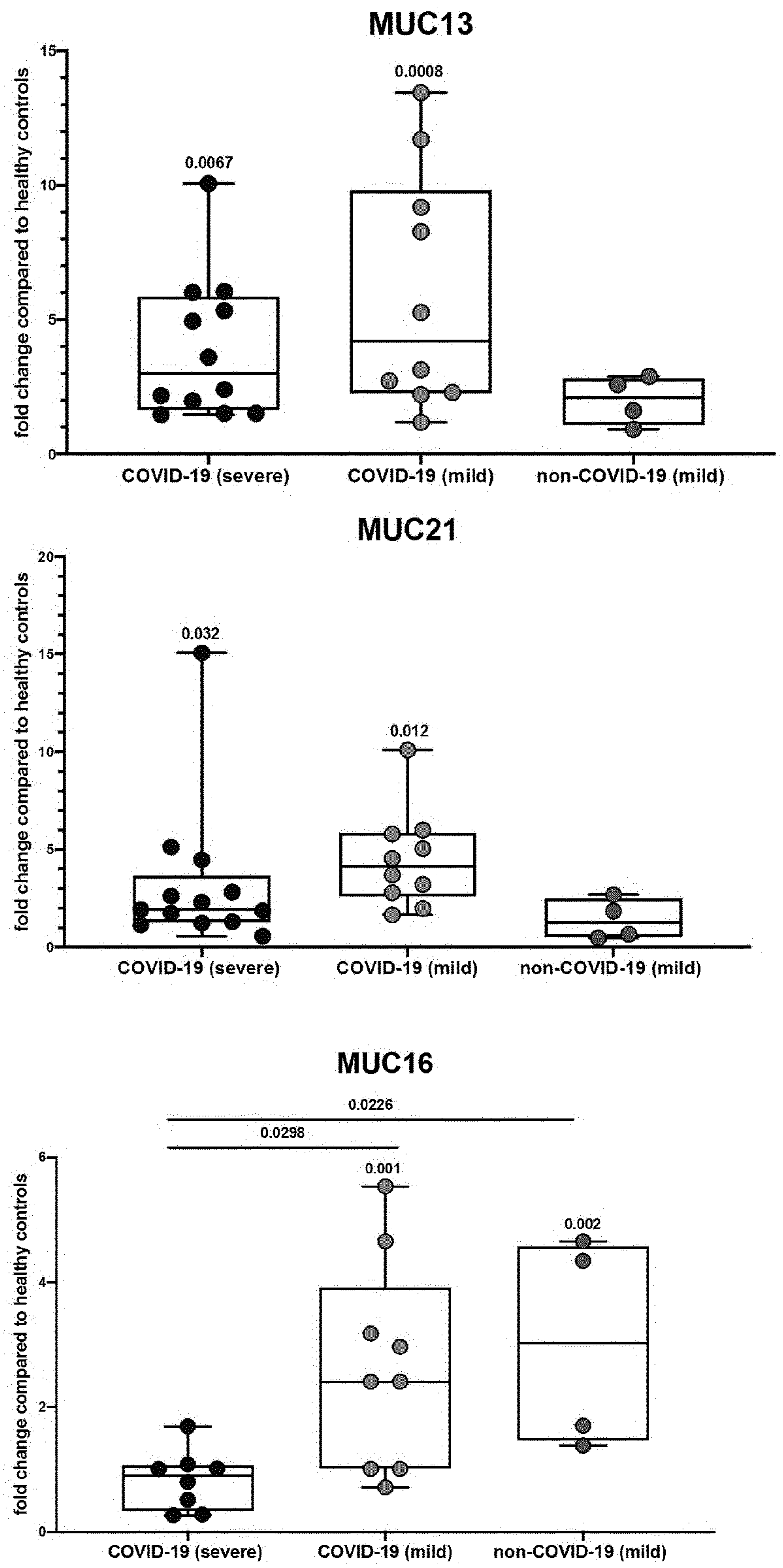

FIG. 23: Fold change mRNA expression levels of the mucins MUC13, MUC2, MUC4, MUC5AC, MUC5B, MUC1, MUC16 and MUC21 in blood from severely ill COVID-19 patients (N=15, blue bullets), ambulatory COVID-19 (N=10, orange bullets) and non-COVID-19 (N=4, green bullets) patients compared to healthy controls (N=4). Significant differences between severely ill COVID-19 patients, ambulatory COVID-19 or non-COVID-19 patients and healthy controls as well as among the different patients groups (i.e. COVID-19 (severe), COVID-19 (mild) and non-COVID-19 (mild)) are indicated by p-value (One-Way ANOVA, Tukey's post-hoc multiple comparison test). Error bars indicate SEM.

FIG. 24: A, Discriminant analysis with mRNA expression values of MUC1, MUC2, MUC5AC, MUC5B, MUC13 and MUC21 as predictors for COVID-19 positivity and severity. The main predictor variables for each function (MUC1=function 1; MUC13 and MUC21=function 2) are stated in the structure matrix. Individual patients were correctly annotated to their respective groups (i.e. mild non-COVID-19, mild COVID-19 and severe COVID-19) in 84% of the cases. B, Discriminant analysis with mRNA expression values of MUC1, MUC2, MUC5AC, MUC5B, MUC13, MUC16 and MUC21 as predictors for COVID-19 diagnosis and severity. The main predictor variables for each function (MUC1 and MUC16=function 1; MUC13 and MUC21=function 2) are stated in the structure matrix. Individual patients were correctly annotated to their respective groups (i.e. mild non-COVID-19, mild COVID-19 and severe COVID-19) in 94.4% of the cases.

Figure 25:
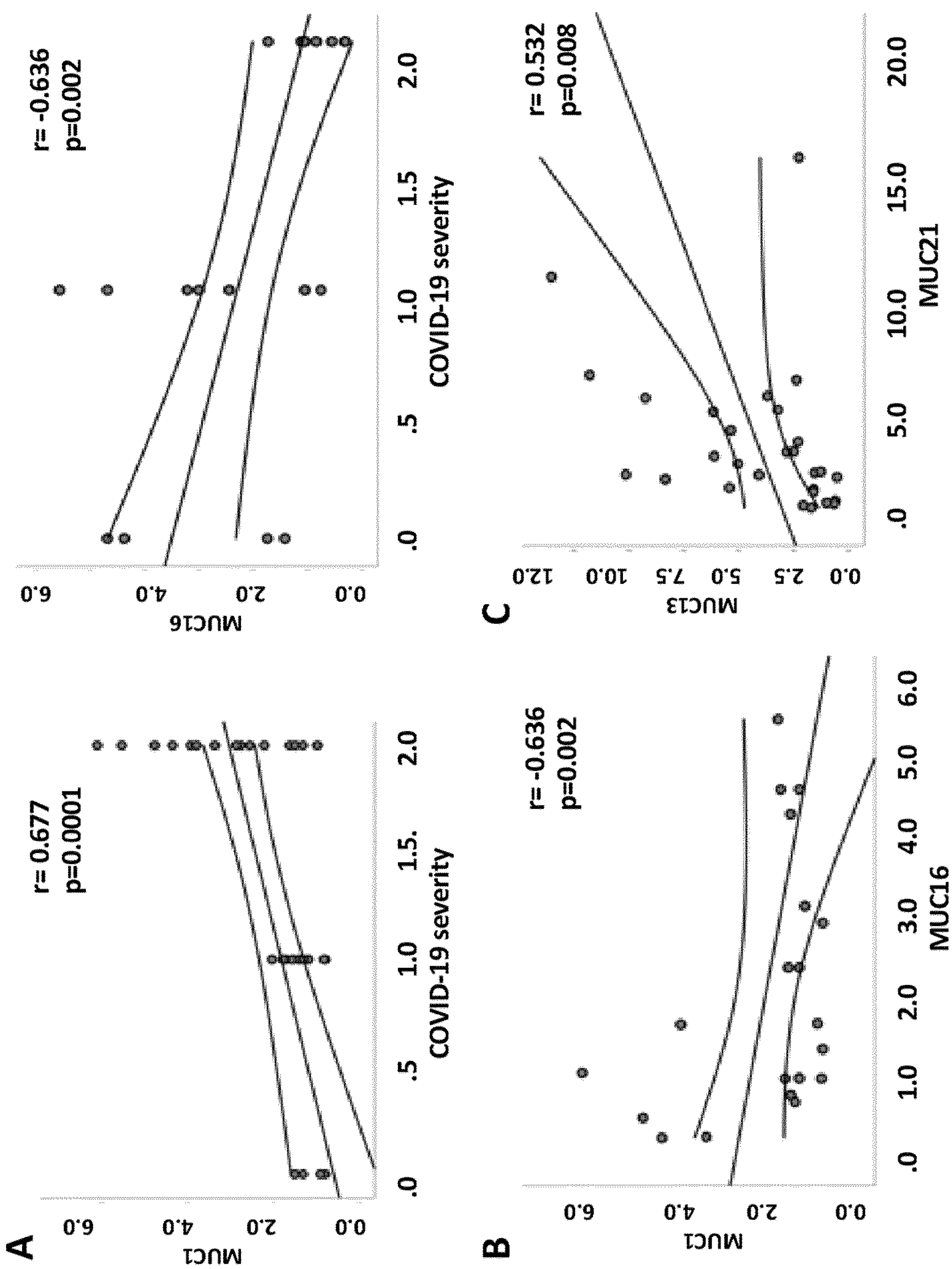

FIG. 25: Scatter plots of the correlation data on mucin expression among the different patient groups (severe COVID-19, mild COVID-19, mild non-COVID-19). A, correlation of MUC1 and MUC16 mRNA expression levels with COVID-19 severity. B, Correlation between MUC1 and MUC16 mRNA expression. C, Correlation between MUC13 and MUC21 mRNA expression. D, Correlation between MUC13 and MUC2 mRNA expression. E, Correlation between MUC21 and MUC2 mRNA expression. F, Correlation between MUC21 and MUC5B mRNA expression. G, Correlation between MUC2 and MUC4 mRNA expression. Results from Spearman correlation tests are displayed as well as a linear regression line with 95% confidence interval.

Figure 26:
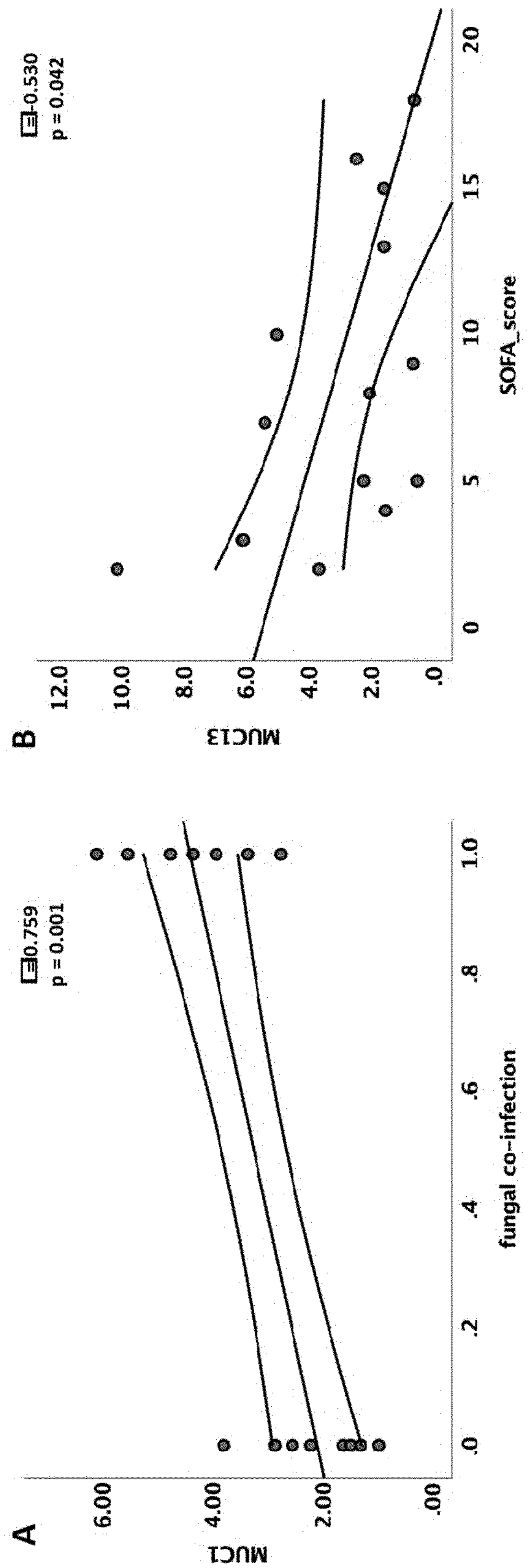

FIG. 26: Scatter plots of correlation data between mucin expression and clinical patient data. A, Correlation between MUC1 expression levels and fungal co-infection. B, Correlation of MUC13 expression levels with the SOFA score. Results from Spearman correlation tests are displayed as well as a linear regression line with 95% confidence interval.

FIG. 27: Relative mRNA expression of MUC1, MUC4, MUC5B, MUC13, MUC16 and MUC21 in Calu3 cells infected with SARS-CoV-2 at 0.1 MOI for 2 h and thereafter treated with a COVID-19 drug at different concentrations for 48 h. These include: Remdesivir (antiviral; 3.7 μM); favipiravir (antiviral; 1 mM), (Hydroxy)chloroquine (10 μM); Dexamethasone (corticosteroid able to reduce mucin expression; 1-5-10 μM); Tocilizumab (anti-IL6; 10-100-1000 ng/ml); Anakinra (anti-IL1; 50-500 ng/ml, 10 μg/ml); and Baricitinib (JAK1/2 inhibitor; 0.3-1-5 μM). Significant differences between SARS-CoV-2-infected and uninfected cells are indicated by *$p<0.05$; $p<0.01$; *$p<0.001$. Significant differences between treated and untreated cells upon SARS-CoV-2 infection are indicated by #$p<0.05$; ##$p<0.01$; ###$p<0.001$. (One-Way ANOVA, Tukey's post-hoc multiple comparison test, N=6). Error bars indicate SEM.

Figure 28:
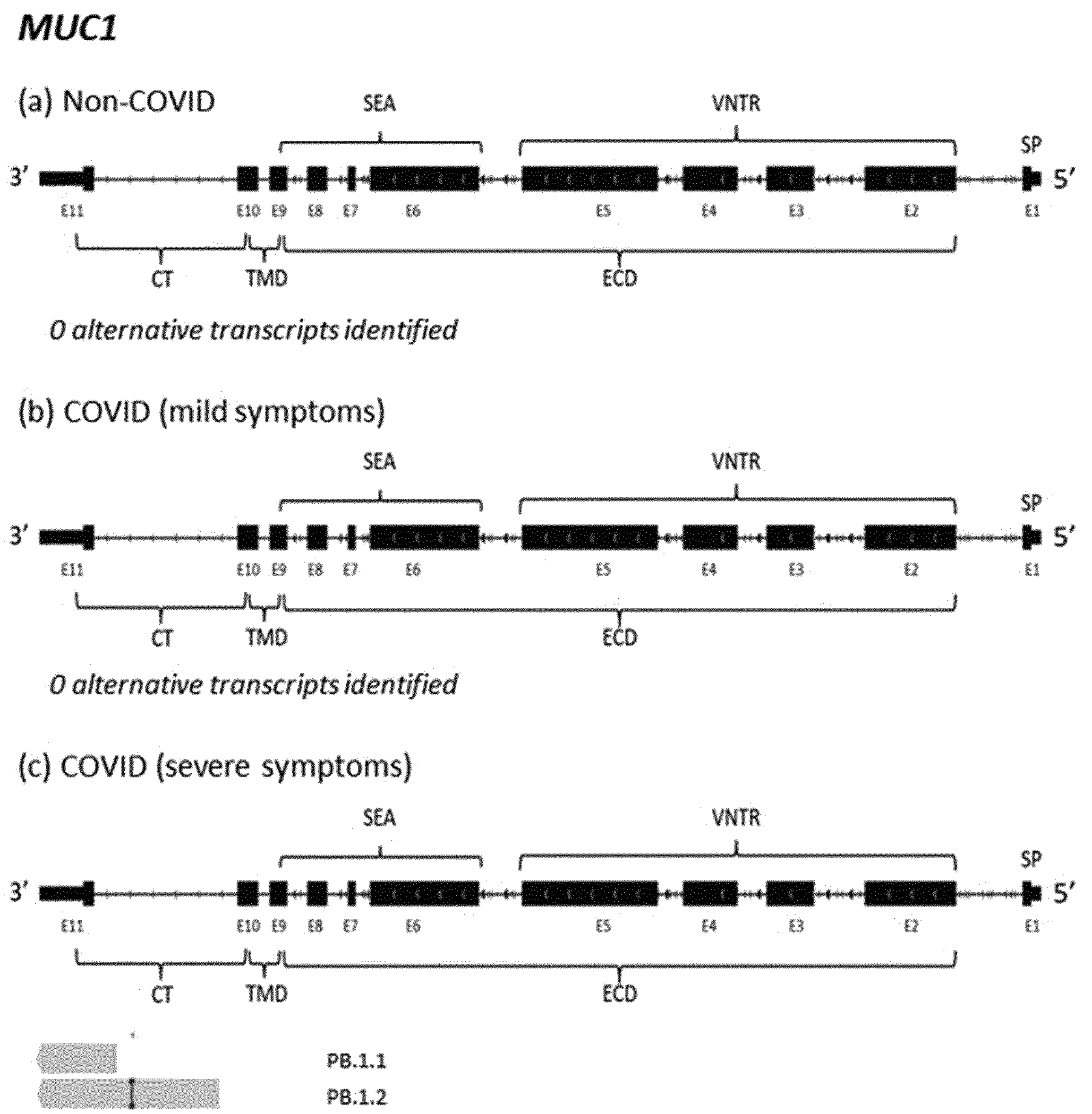

FIG. 28. Alternative mRNA transcripts of MUC1 in the blood of (a) non-COVID19 and COVID19 patients with (b) mild and (c) severe symptoms. The gene structure highlighted in blue illustrates the overall exonic structure of MUC1 with the corresponding exon numbers and coding domains (CT=cytoplasmic tail; TMD=transmembrane domain; ECD=extracellular domain; EGF=epidermal growth factor; SEA=sea urchin sperm protein, enterokinase and agrin; VNTR=variable number tandem repeat; SP=signal peptide). The gray mRNA transcripts highlight the alternative mRNA isoforms that are found in the blood of a particular condition (i.e. non-COVID19 (n=2) or COVID19 with mild (n=5) or severe (n=5) symptoms). On the right panel, the isoform identity number can be found of which the details are shown in table 11.

Figure 29:
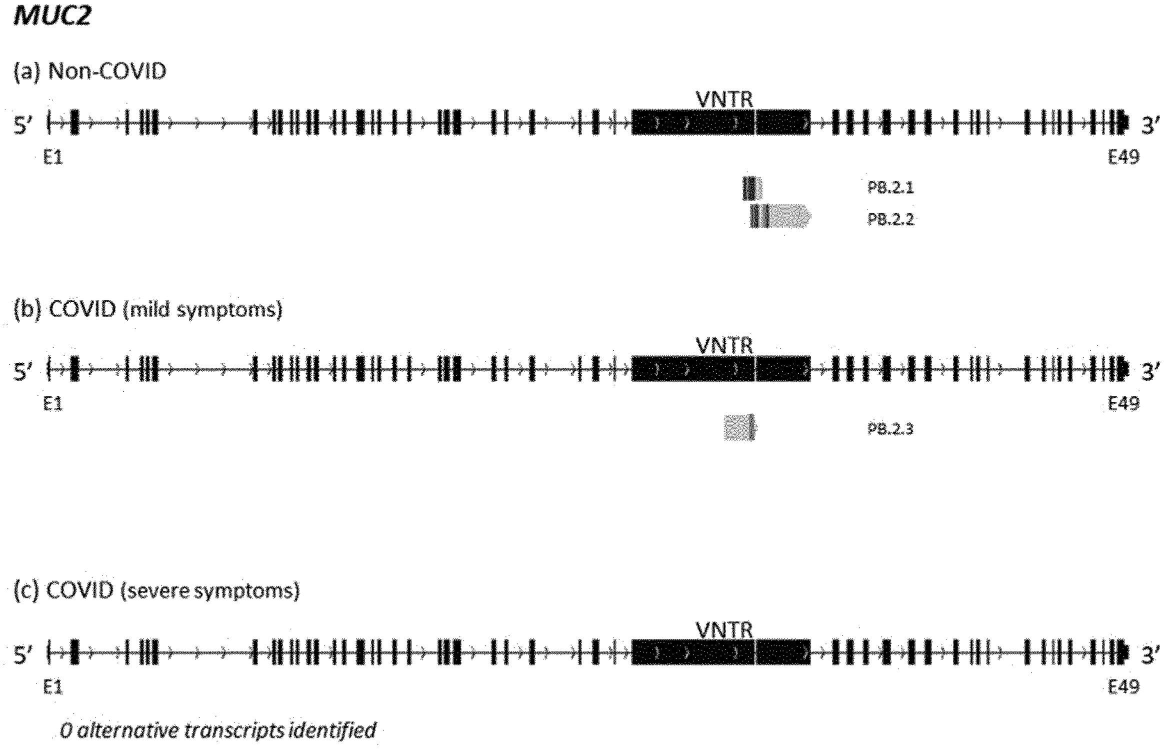

FIG. 29. Alternative mRNA transcripts of MUC2 in the blood of (a) non-COVID19 and COVID19 patients with (b) mild and (c) severe symptoms. The gene structure highlighted in blue illustrates the overall exonic structure of MUC2 with the corresponding exon numbers and coding domains (VNTR=variable number tandem repeat). The gray mRNA transcripts highlight the alternative mRNA isoforms that are found in the blood of a particular condition (i.e. non-COVID19 (n=2) or COVID19 with mild (n=5) or severe (n=5) symptoms). On the right panel, the isoform identity number can be found of which the details are shown in table 11.

Figure 30:
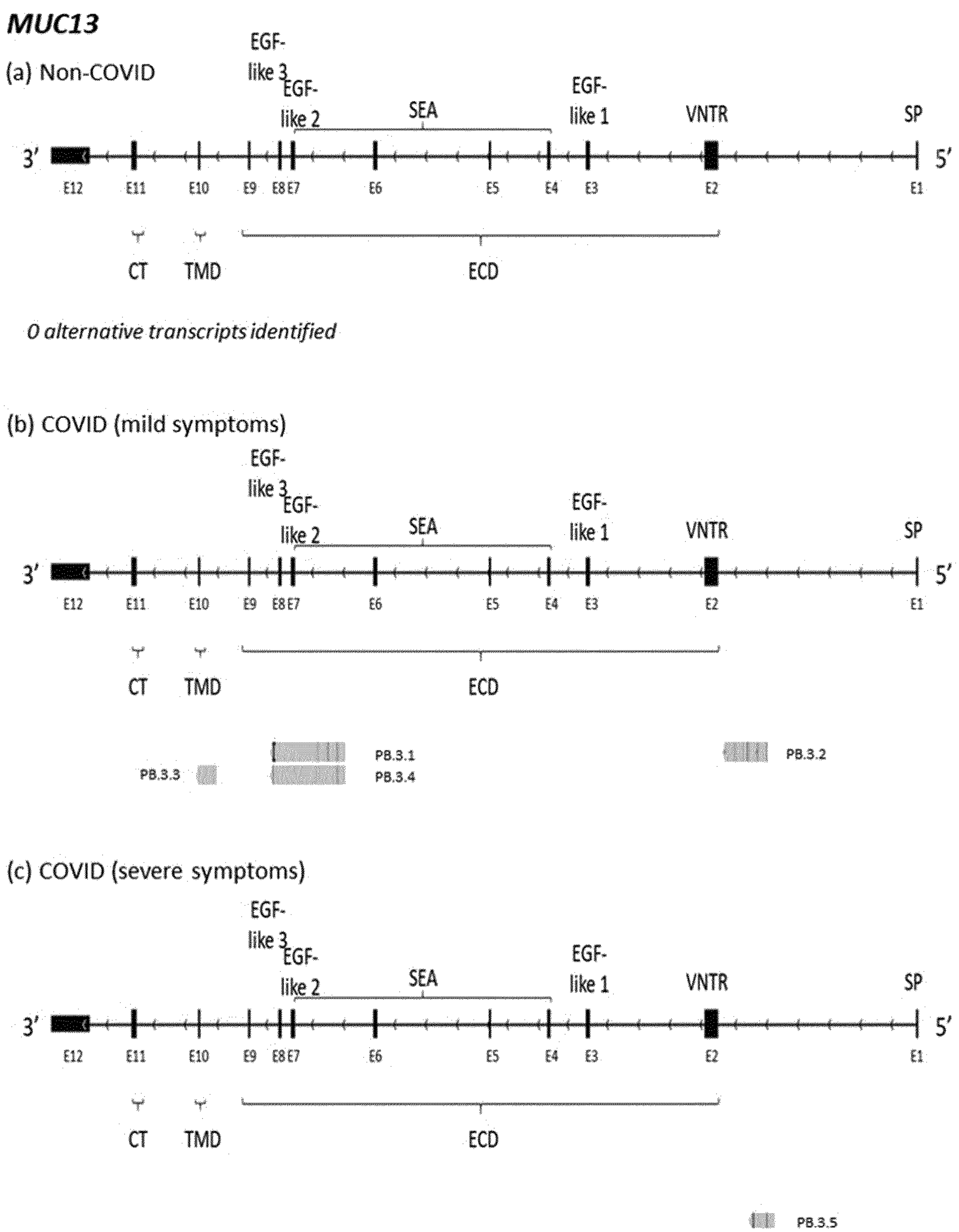

FIG. 30. Alternative mRNA transcripts of MUC13 in the blood of (a) non-COVID19 and COVID19 patients with (b) mild and (c) severe symptoms. The gene structure highlighted in blue illustrates the overall exonic structure of MUC13 with the corresponding exon numbers and coding domains (VNTR=variable number tandem repeat). The gray mRNA transcripts highlight the alternative mRNA isoforms that are found in the blood of a particular condition (i.e. non-COVID19 (n=2) or COVID19 with mild (n=5) or severe (n=5) symptoms). The isoform identity number can be found next to the mRNA isoform of which the details are shown in table 11.

Figure 31:
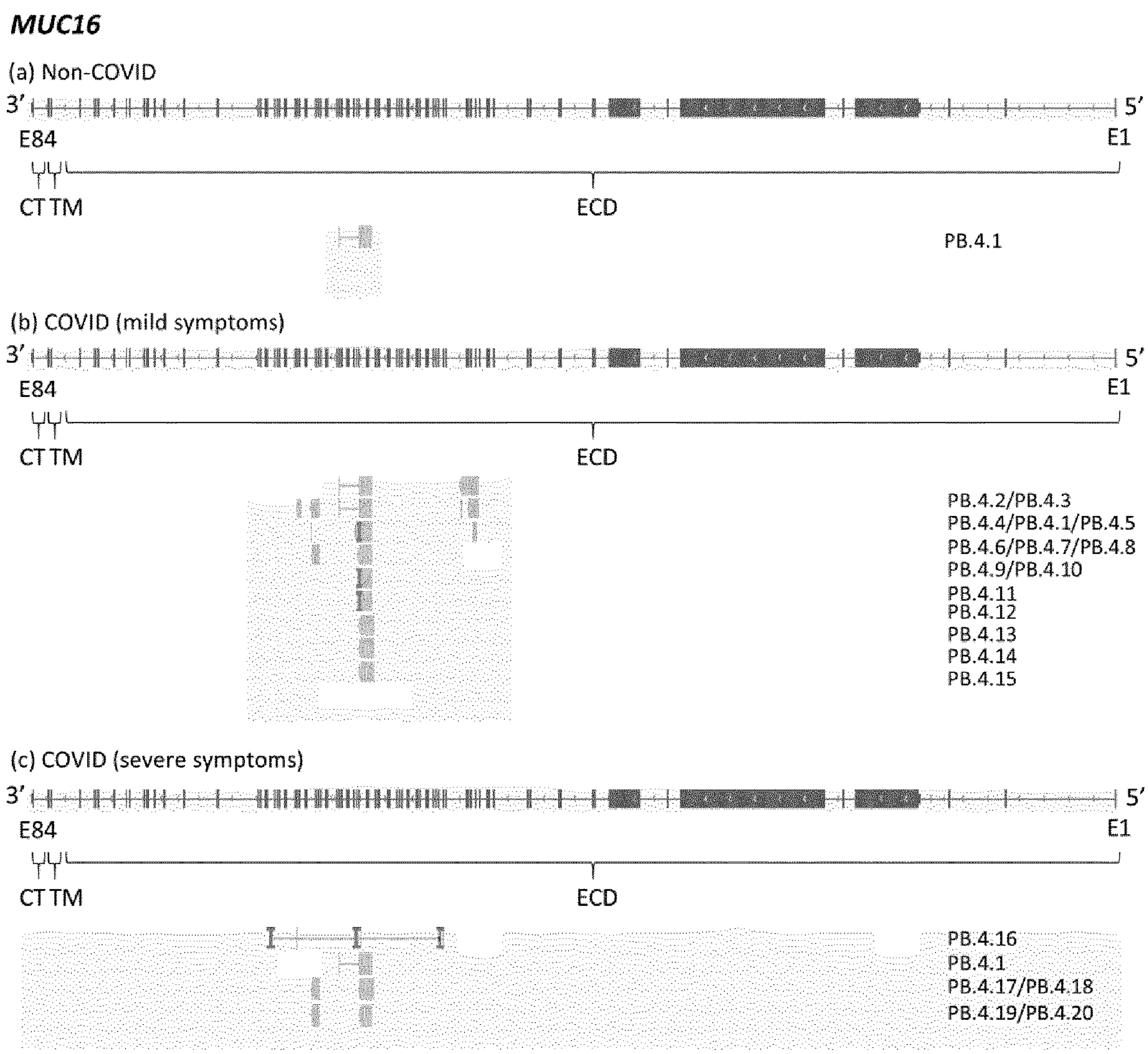

FIG. 31. Alternative mRNA transcripts of MUC16 in the blood of (a) non-COVID19 and COVID19 patients with (b) mild and (c) severe symptoms. The gene structure highlighted in blue illustrates the overall exonic structure of MUC16 with the corresponding exon numbers and coding domains (VNTR=variable number tandem repeat). The gray mRNA transcripts highlight the alternative mRNA isoforms that are found in the blood of a particular condition (i.e. non-COVID (n=2) or COVID with mild (n=5) or severe (n=5) symptoms). The isoform identity number can be found next to the mRNA isoform of which the details are shown in table 11.

Figure 32:
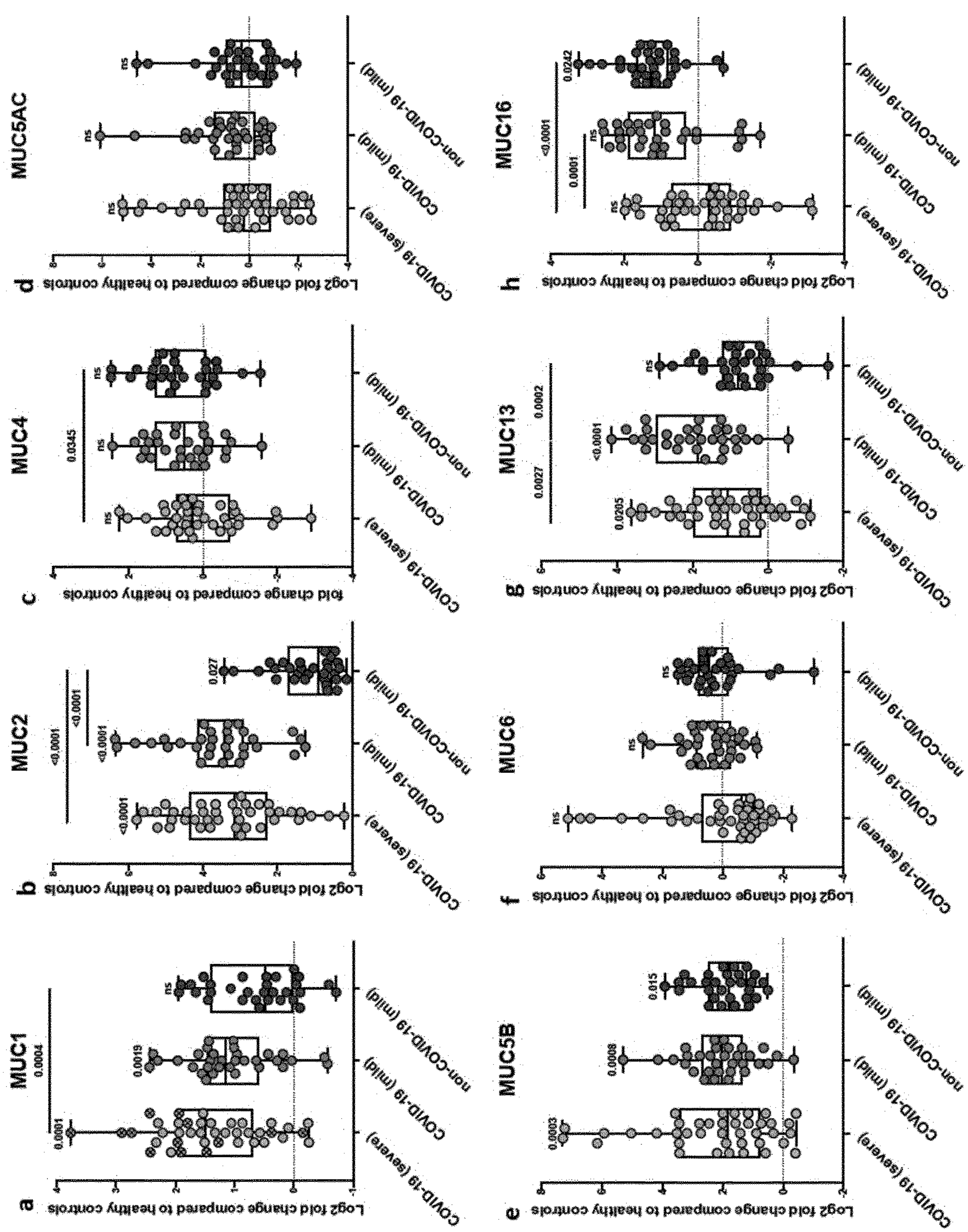

FIG. 32. Mucin mRNA expression in the blood of patients with severe COVID-19 (n=40), mild COVID-19 (n=32) and mild non-COVID-19 (n=30). a, Log 2 fold change of MUC1 relative to healthy controls. b, Log 2 fold change of MUC2 relative to healthy controls. c, Log 2 fold change of MUC4 relative to healthy controls. d, Log 2 fold change of MUC5AC relative to healthy controls. e, Log 2 fold change of MUC5B relative to healthy controls. f, Log 2 fold change of MUC6 relative to healthy controls. g, Log 2 fold change of MUC13 relative to healthy controls. h, Log 2 fold change of MUC16 relative to healthy controls. i, Log 2 fold change of MUC20 relative to healthy controls. j, Log 2 fold change of MUC21 relative to healthy controls. k, Heatmap of the fold change mucin expression data in the different patient cohorts. Box plots denote median and $25^{th}$ to $75^{th}$ percentiles (boxes) and $10^{th}$ to $90^{th}$ percentiles (whiskers). Each filled circle represents a patient and a blue filled circle with a cross, as shown for MUC1, denoted deceased patients in the severe COVID-19 group. Significant differences between severely ill COVID-19 patients, ambulatory COVID-19 or non-COVID-19 patients and healthy controls as well as among the different patient groups (i.e. severe COVID-19, mild COVID-19 and mild non-COVID-19) are indicated by a p-value (One-Way ANOVA, Tukey's post-hoc multiple comparison test). ns=not significant. Error bars indicate SEM.

Figure 33:
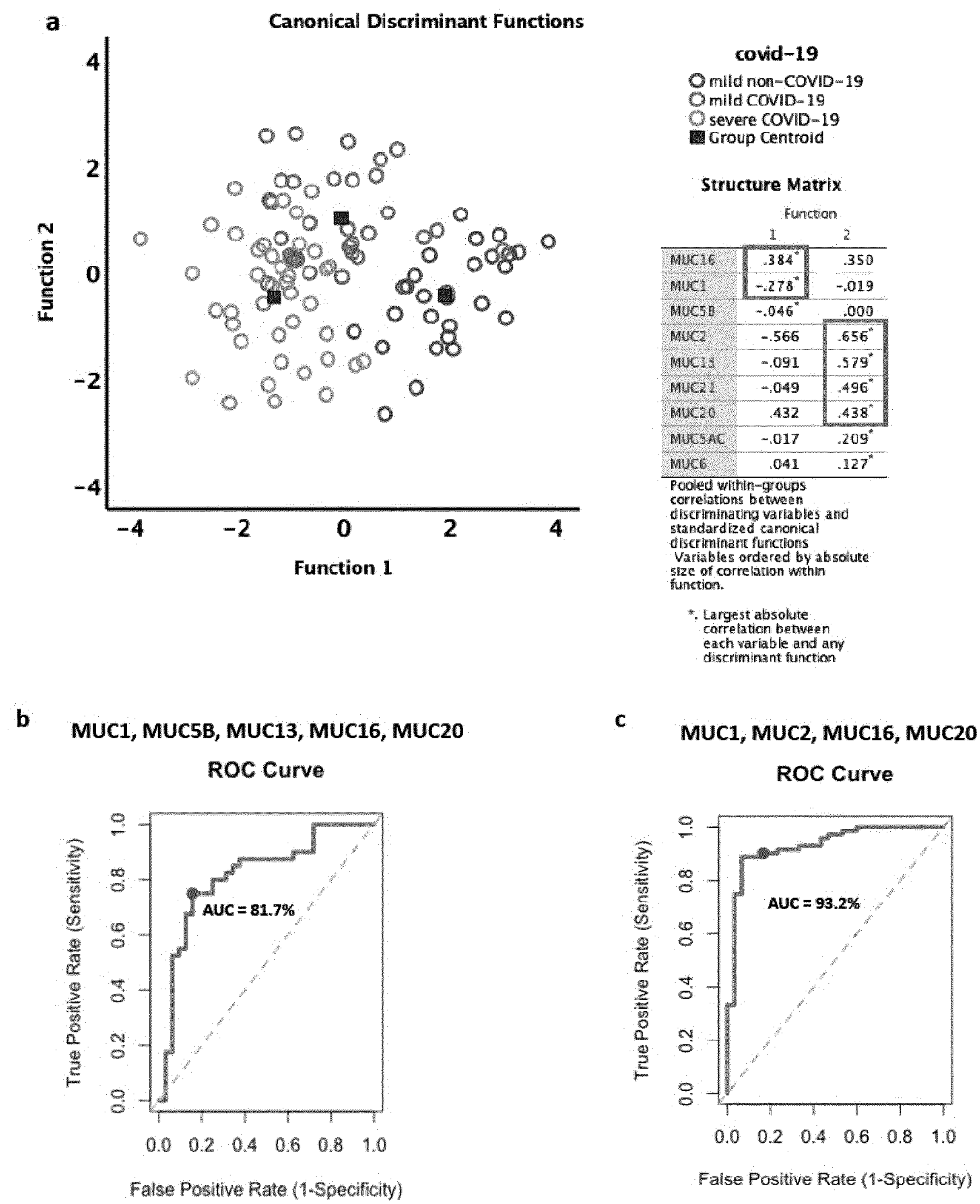

FIG. 33. Mucin mRNA expression as predictive variable for COVID-19 severity and presentation. a, Discriminant analysis with mRNA expression values of MUC1 and MUC16 as major predictors for severe COVID-19 and MUC2, MUC13, MUC20 and MUC21 mRNA expression as major predictors for mild COVID-19. The main predictor variables for each function (MUC1 and MUC16=function 1; MUC2, MUC13, MUC20 and MUC21=function 2) are stated in the structure matrix. Individual patients were correctly annotated to their respective groups (i.e. mild non-COVID-19, mild COVID-19 and severe COVID-19) in 82.8% of the cases. b, ROC curve and area under the curve (AUC) for the prediction model of COVID-19 severity obtained by the LASSO logistic regression. Included predictors were: mRNA expression of MUC1, MUC5B, MUC13, MUC16 and MUC20, with an AUC of 81.7% (95% Cl: 70.9%-91.2%), a sensitivity of 75.0% (95% Cl: 60.0%-86.5%) and a specificity of 84.4% (95% Cl: 68.7%-94.0%). c, ROC curve and area under the curve (AUC) for the prediction model of COVID-19 presentation obtained by the LASSO logistic regression. Included predictors were: mRNA expression of MUC1, MUC2, MUC16 and MUC20, with an AUC of 93.2% (95% Cl: 87.3%-97.8%), a sensitivity of 88.9% (95% Cl: 80.0%-94.7%) and a specificity of 83.3% (95% Cl: 79.7%-98.9%).

FIG. 34. Scatter plots of the correlation data showing the relationship between mucin expression and disease severity (severe COVID-19, mild COVID-19, mild non-COVID-19). a-i, Correlation between MUC1 mRNA expression and COVID-19 severity (0=mild non-COVID-19, 1=mild COVID-19, 2=severe COVID-19) (a), MUC2 mRNA expression and COVID-19 severity (0=mild non-COVID-19, 1=mild COVID-19, 2=severe COVID-19) (b), MUC16 mRNA expression and COVID-19 severity (0=mild non- COVID-19, 1=mild COVID-19, 2=severe COVID-19) (c), MUC20 mRNA expression and COVID-19 severity (0=mild non-COVID-19, 1=mild COVID-19, 2=severe COVID-19) (d), MUC1 and MUC2 mRNA expression (e), MUC16 and MUC20 mRNA expression (f), MUC2 and MUC13 mRNA expression (g), MUC13 and MUC21 mRNA expression (h). Results from Spearman correlation tests are displayed as well as a linear regression line with 95% confidence interval.

Figure 35:
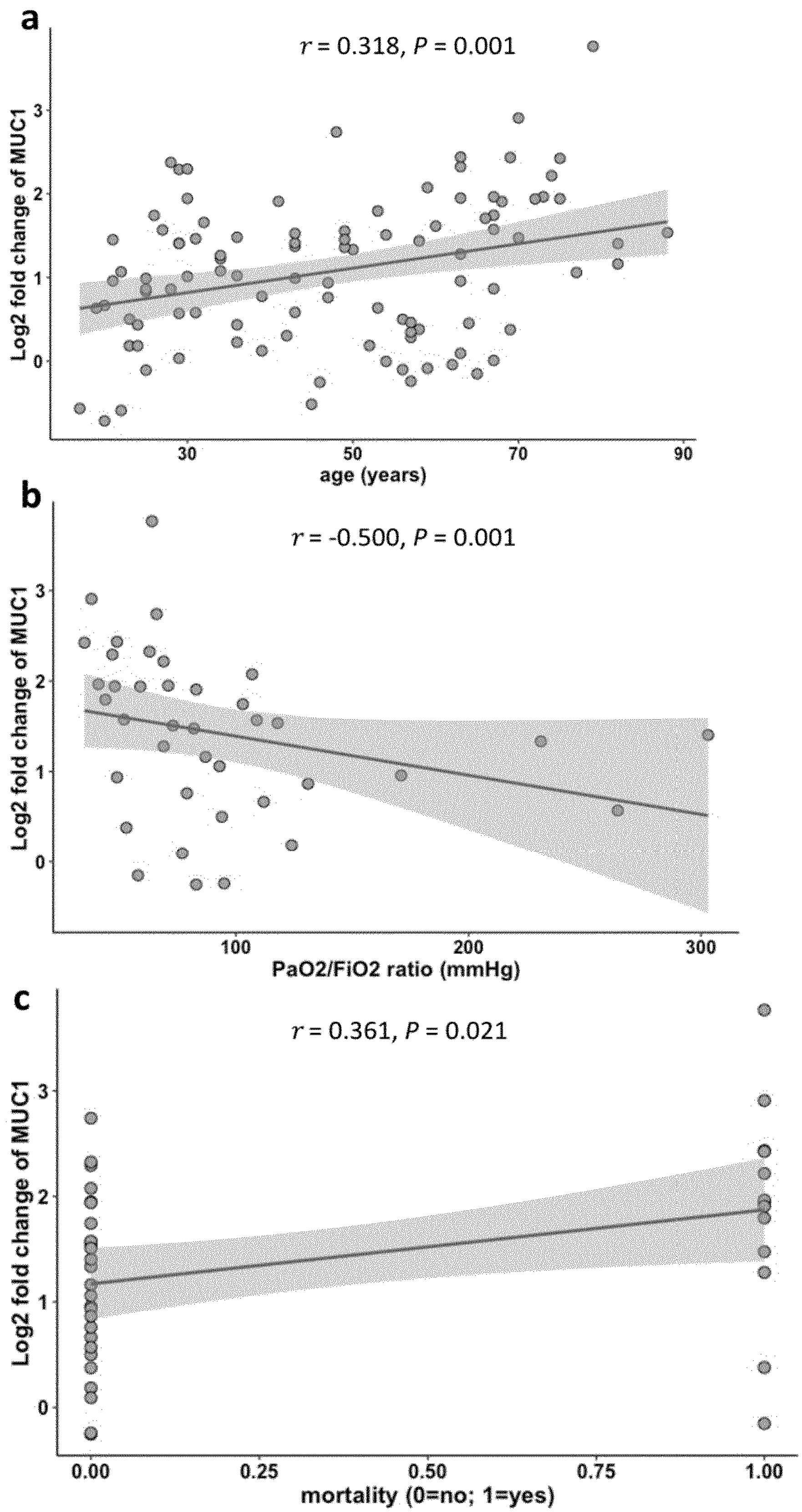

FIG. 35. Scatter plots of correlation data showing the relationship between mucin expression and clinical data of severe COVID-19 patients and between mucin expression and the symptoms among the different patient groups (severe COVID-19, mild COVID-19, mild non-COVID-19). a-n, Correlations between MUC1 mRNA expression and age (a), MUC1 mRNA expression and the lowest $P_aO_2/F_iO_2$ ratio (b), MUC1 mRNA expression and mortality (c), MUC16 mRNA expression and necessity for invasive ventilation (d), MUC1 mRNA expression and occurrence of fungal co-infection (e), MUC2 mRNA expression and fungal co-infection (f), MUC16 mRNA expression and fungal co-infection (g), MUC20 mRNA expression and fungal co-infection (h), MUC2 mRNA expression and maximum ferritin levels in the serum (i), MUC13 mRNA expression and maximum ferritin levels in the serum (j), MUC20 mRNA expression and maximum ferritin levels in the serum (k), MUC20 mRNA expression and maximum IL-6 levels in the serum (1), MUC13 mRNA expression and loss of smell and taste (m), MUC2 mRNA expression and loss of smell and taste (n), MUC16 mRNA expression and sore throat (o), MUC20 mRNA expression and sore throat (p), MUC1 mRNA expression and dyspnea (q) and MUC2 mRNA expression and dyspnea (r). Results from Spearman correlation tests are displayed as well as a linear regression line with 95% confidence interval.

Figure 36:
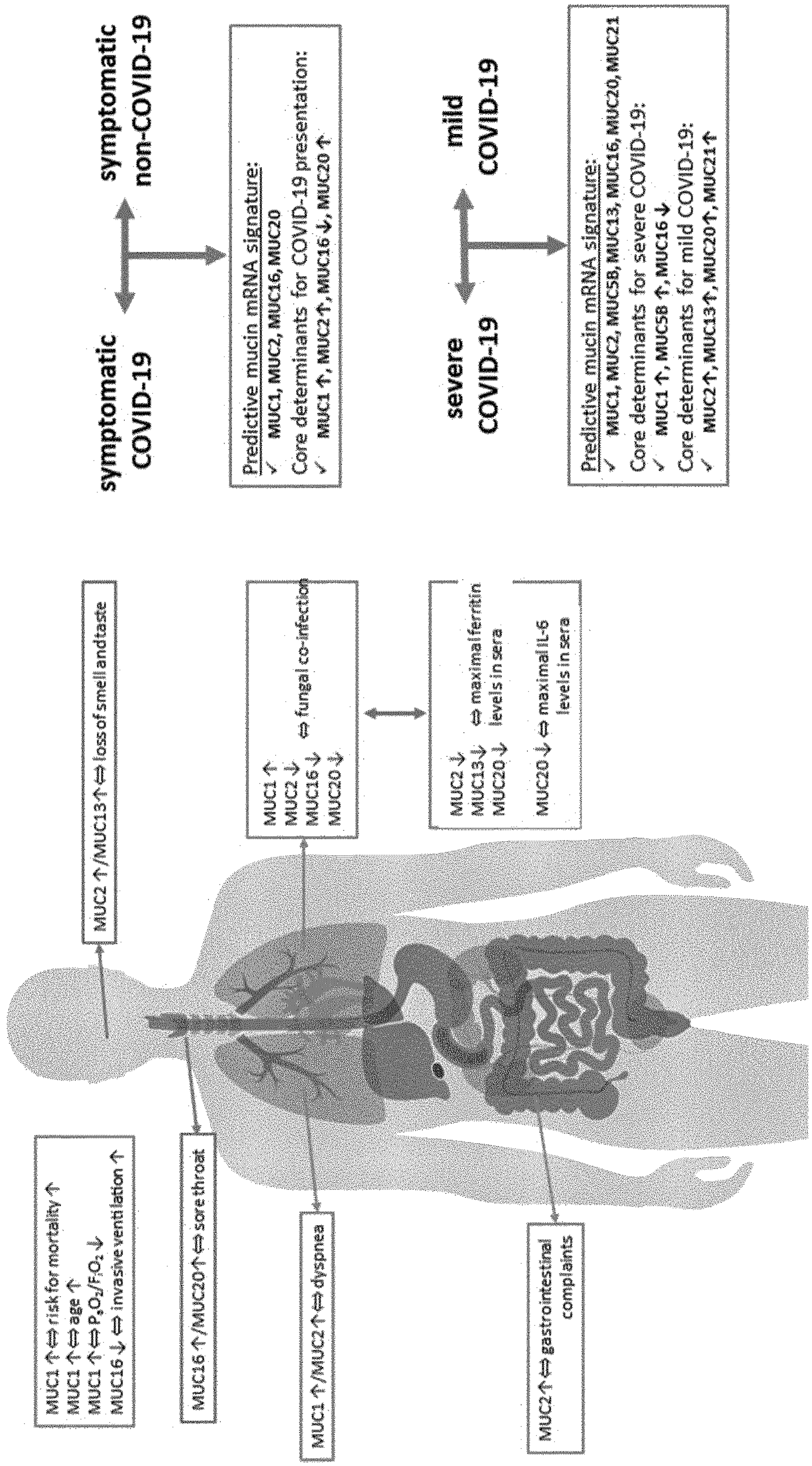

FIG. 36. A dynamic peripheral blood mucin mRNA signature predictive for COVID-19 presentation and prognosis. Symptomatic COVID-19 patients are segregated from symptomatic non-COVID-19 patients based on the expression of MUC1, MUC2, MUC16 and MUC20 whereas mild and severe COVID-19 patients are discriminated based on expression of MUC1, MUC2, MUC5B, MUC13, MUC16 and MUC20. Differences in the transcriptional landscape of mucins in severe cases compared to mild cases identify links with COVID-19 clinical outcome parameters.

Figure 37:
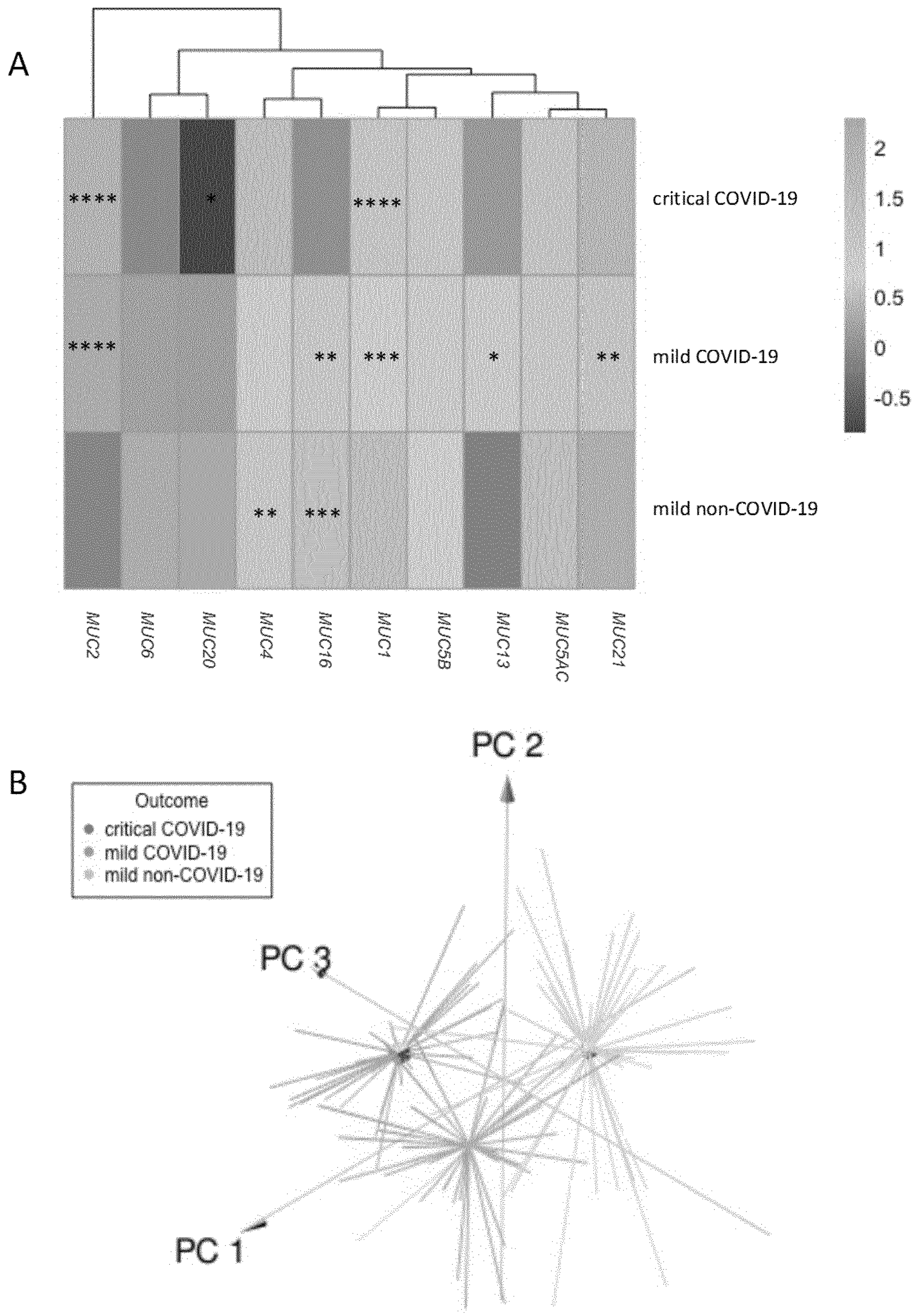

FIG. 37. Peripheral mucin mRNA expression levels as predictive variables for COVID-19 severity and presentation. (A) Heatmap of the log 2 fold change mucin expression data in the different patient cohorts. Significant differences between critically ill COVID-19 patients, mild COVID-19 or non-COVID-19 patients and healthy controls (heatmap) are indicated by * (p<0.05),  (p<0-01), * (p<0-001), **** (p<0-0001). (B) 3D PCA plot based on mucin expression values, age and sex from critically ill COVID-19 patients (n=50), mild COVID-19 patients (n=35) and mild non-COVID-19 patients (n=30). PC1 explains 28-7% the variation, while PC2 explains 17-8% of the variation. (C) sPLD-DA plot based on mucin mRNA expression values, age and sex as major predictors for critical COVID-19, mild COVID-19 and mild non-COVID-19. (D) Contribution plot indicating the main predictor variables contributing to component 1 of the sPLS-DA plot that discriminate between critical COVID-19 (i.e. age and MUC1), mild COVID-19 (i.e. MUC2, MUC5AC, MUC5B, MUC13, MUC20 and MUC21) and mild non-COVID-19 (i.e. MUC4, MUC6, MUC16 and age) patients. (E) ROC curve and area under the curve (AUC) for the prediction model of COVID-19 severity (i.e. critical COVID-19 (n=50) or mild COVID-19 (n=35)) obtained by LASSO logistic regression. Included predictors were: age and mRNA expression of MUC16, MUC20 and MUC21, with an AUC of 89-1% (95% Cl: 80-4%-96-1%), a sensitivity of 90-0% (95% Cl: 79-3%-96-2%) and a specificity of 85-7% (95% Cl: 71-2%-94-6%). (F) ROC curve and area under the curve (AUC) for the prediction model of COVID-19 presentation (COVID-19 positive (n=85) or COVID-19 negative (n=30)) obtained by the LASSO logistic regression. Included predictors were: age and mRNA expression of MUC1, MUC2, MUC4, MUC6, MUC13, MUC16 and MUC20, with an AUC of 91-8% (95% Cl: 85-2%-97-1%), a sensitivity of 90.6% (95% Cl: 83-0%-95-5%) and a specificity of 93-3% (95% Cl: 79-7%-98-9%).

DETAILED DESCRIPTION OF THE INVENTION

As already detailed herein above, in a first aspect, the present invention provides a mucin or mucin mRNA isoform for use in the diagnosis, monitoring, prevention and/or treatment of a disease characterized by barrier dysfunction, wherein the mucin or mucin mRNA isoform is selected from the list comprising: MUC1, MUC13, MUC1 isoforms and MUC13 isoforms; or alternatively from the list comprising MUC16, MUC21, MUC2, MUC4, MUC5AC, MUC5B, MUC6, MUC13, MUC1, MUC20; MUC16 mRNA isoforms, MUC21 mRNA isoforms, MUC2 mRNA isoforms, MUC4 mRNA isoforms, MUC5AC mRNA isoforms, MUC5B mRNA isoforms, MUC6 mRNA isoforms, MUC13 mRNA isoforms, MUC20 mRNA isoforms, or MUC1 mRNA isoforms.

In the context of the present invention, several correlations between mucins and mRNA isoforms thereof on the one hand, and coronaviral related aspects on the other hand have been identified.

In particular MUC1, MUC2, MUC16 and MUC20 (as well as mRNA isoforms thereof) are discriminators between symptomatic COVID-19 and symptomatic non-COVID-19 patients. In particular, said combination is highly suitable in the diagnosis of COVID-19 patients. More in particular, upregulation or high expression of MUC1, MUC2, and/or MUC20 (and mRNA isoforms thereof); either or not in combination with downregulation or low expression of MUC16 (and mRNA isoforms thereof) is indicative of a coronaviral infection or infectious disease.

Moreover, the combination of MUC1, MUC2, MUC4, MUC6, MUC13, MUC16 and MUC20 (as well as mRNA isoforms thereof) were also found to be discriminators between symptomatic COVID-19 and symptomatic non-COVID-19 patients. In particular, said combination is highly suitable in the diagnosis of COVID-19 patients. More in particular, upregulation or high expression of MUC1, MUC2 and/or MUC13 (and mRNA isoforms thereof); either or not in combination with downregulation or low expression of MUC4, MUC6, MUC16 and MUC20 (and mRNA isoforms thereof) is indicative of a coronaviral infection or infectious disease.

In addition MUC1, MUC2, MUC5B, MUC13, MUC16, MUC20 and MUC21 (or mRNA isoforms thereof) are discriminators between severe and mild COVID-19 disease, with MUC1 or MUC1 mRNA isoform and MUC5B or MUC5B mRNA isoform upregulation/high expression and MUC16 or MUC16 mRNA isoform downregulation/low expression being the core determinants for severe COVID- 19; high expression of MUC2, MUC13, MUC20 and/or MUC21 (or mRNA isoforms thereof) being the core determinants for mild COVID-19.

Also the combination of MUC1, MUC2, MUC5AC, MUC5B, MUC13, MUC16, MUC20 and/or MUC21 (or mRNA isoforms thereof) are discriminators between severe and mild COVID-19 disease, with MUC1 (or MUC1 mRNA isoform) upregulation/high expression and MUC16 (or MUC16 mRNA isoform), MUC20 (or MUC20 mRNA isoform) and/or MUC21 (or MUC21 mRNA isoform) downregulation/low expression being the core determinants for severe or critical COVID-19; while high expression of MUC2, MUC5AC, MUC5B, MUC13, MUC16, MUC20 and/or MUC21 (or mRNA isoforms thereof) being the core determinants for mild COVID-19.

Additional correlations were found with COVID-19 related symptoms, in particular:

MUC16 and/or MUC20 (or mRNA isoforms thereof) upregulation/high expression are associated with sore throat symptoms MUC2 and/or MUC13 (or mRNA isoforms thereof) upregulation/high expression are associated with loss of smell and taste MUC2 (or mRNA isoforms thereof) upregulation/high expression is associated with gastrointestinal complaints MUC1 and/or MUC2 (or mRNA isoforms thereof) upregulation/high expression are associated with dyspnea The risk to and/or development of co-infections were associated with MUC1 (or mRNA isoforms thereof) upregulation/high expression and MUC2, MUC16 and/or MUC20 downregulation/low expression. MUC1 upregulation/high levels were further associated with a higher risk of mortality The above defined correlations are further illustrated in FIG. 36.

In a particular embodiment, the present invention provides a mucin or mucin mRNA isoform for use in the diagnosis, monitoring, prevention and/or treatment of coronaviral infection or coronaviral infectious disease, wherein the mucin or mucin mRNA isoform is selected from the list comprising: MUC16, MUC21, MUC2, MUC4, MUC5AC, MUC5B, MUC13, MUC1, MUC20; MUC16 mRNA isoforms, MUC 21 mRNA isoforms, MUC2 mRNA isoforms, MUC4 mRNA isoforms, MUC5AC mRNA isoforms, MUC5B mRNA isoforms, MUC13 mRNA isoforms, MUC20 mRNA isoforms, or MUC1 mRNA isoforms.

In another particular embodiment, the present invention provides a mucin or mucin mRNA isoform for use in the diagnosis, monitoring, prevention and/or treatment of coronaviral infection or coronaviral infectious disease, wherein the mucin or mucin mRNA isoform is selected from the list comprising: MUC1, MUC2, MUC3A, MUC4, MUC5AC, MUC5B, MUC6, MUC7, MUC8, MUC12, MUC13, MUC15, MUC16, MUC17, MUC19, MUC20, MUC21, MUC22, MUC1 mRNA isoforms, MUC2 mRNA isoforms, MUC3A mRNA isoforms, MUC4 mRNA isoforms, MUC5AC mRNA isoforms, MUC5B mRNA isoforms, MUC6 mRNA isoforms, MUC7 mRNA isoforms, MUC8 mRNA isoforms, MUC12 mRNA isoforms, MUC13 mRNA isoforms, MUC15 mRNA isoforms, MUC16 mRNA isoforms, MUC17 mRNA isoforms, MUC19 mRNA isoforms, MUC20 mRNA isoforms, MUC21 mRNA isoforms, MUC22 mRNA isoforms.

Mature mucins are composed of 2 distinct regions: the amino- and carboxy-terminal regions which are lightly glycosylated but rich in cysteines which participate in establishing disulfide linkages within and among mucin monomers; and a large central region formed of multiple tandem repeats of 10 to 80 residue sequences which are rich in serine and threonine. This area becomes saturated with hundreds of O-linked oligosaccharides.

In the context of the present invention, the term “mucin isoform” or alternatively termed “mucin mRNA isoform” is meant to be a member of a set of similar mRNA molecules or encoded proteins thereof, which originate from a single mucin gene and that are the result of genetic differences. These isoforms may be formed from alternative splicing, variable promoter usage, or other post-transcriptional modifications of the gene. Through RNA splicing mechanisms, mRNA has the ability to select different protein-coding segments (exons) of a gene, or even different parts of exons from RNA to form different mRNA sequences, i.e. isoforms. Each unique sequence produces a specific form of a protein. The presence of genetic differences in mucin genes can result in different mRNA isoforms (i.e. splice variants via alternative splicing) produced from the same mucin gene locus. While most isoforms encode similar biological functions, others have the potential to alter the protein function resulting in progression toward disease. Accordingly, the present invention is specifically directed to the identification and/or use of such mucin isoforms in various disorders. The present invention in particular provides mucin isoforms as defined herein below in the examples part, specifically those referred to in tables 5, 6, 11, S2 and S3; as well as FIGS. 14, 15, 28, 29, 30 and 31. It further provides uses of such mucin isoforms as detailed in the present application.

The term “isoform” according to the present invention encompasses transcript variants (which are mRNA molecules) as well as the corresponding polypeptide variants (which are polypeptides) of a gene. Such transcription variants result, for example, from alternative splicing or from a shifted transcription initiation. Based on the different transcript variants, different polypeptides are generated. It is possible that different transcript variants have different translation initiation sites. A person skilled in the art will appreciate that the amount of an isoform can be measured by adequate techniques for the quantification of mRNA as far as the isoform relates to a transcript variant which is an mRNA. Examples of such techniques are polymerase chain reaction-based methods, in situ hybridization-based methods, microarray-based techniques and whole transcriptome long-read sequencing. Further, a person skilled in the art will appreciate that the amount of an isoform can be measured by adequate techniques for the quantification of polypeptides as far as the isoform relates to a polypeptide. Examples of such techniques for the quantification of polypeptides are ELISA (Enzyme-linked Immunosorbent Assay)-based, gel-based, blot-based, mass spectrometry-based, and flow cytometry-based methods.

In a particular embodiment, said mucin isoform is a transmembrane mucin, which is a type of integral membrane protein that spans the entirety of the cell membrane. These mucins form a gateway to permit/prevent the transport of specific substances across the membrane.

In a particular embodiment, the present invention provides an in vitro method for diagnosing and/or determining the severity of a coronaviral infection or coronaviral infectious disease and/or associated co-infections, said method comprising:

a) providing a biological sample from a subject suspected of having a coronaviral infection or coronaviral infectious disease and/or associated co-infections, and b) determining the presence and/or quantity of one or more mucins selected from the list comprising: MUC16, MUC21, MUC2, MUC4, MUC5AC, MUC5B, MUC6, MUC13 or MUC20, optionally in combination with MUC1;

wherein the presence and/or quantity of the one or more mucins is indicative for the presence and/or severity of a coronaviral infection or coronaviral infectious disease.

In the context of the present invention, the term 'biological sample' or 'sample' is meant to be sample obtained from a subject, such as for example a blood sample, a serum sample, a nasal swab sample, a nasopharyngeal wash/aspirate sample, a nasal wash/aspirate sample, a saliva sample, a sputum sample, a mucus sample or a tissue sample.

In the context of the present invention, the phrase 'determining the presence and/or quantity of mucins', is meant to be a step in the method in which the expression level of mucins is determined, in order to detect the presence and/or amount of expression of such mucins. This can be determined on the level of protein or mRNA expression levels, by means of suitable techniques including but not limited to: western blotting, ELISA assays, RT-PCR methods, mass spectrometry, . . . .

In yet a further embodiment the presence and/or quantity of at least 2, preferably at least 3 mucins are determined and/or quantified. Accordingly, the present invention provides different combinations of mucins such as but not limited to MUC1 and MUC2, MUC1 and MUC4, MUC1 and MUC5AC, MUC1 and MUC5B, MUC1 and MUC13, MUC1 and MUC16, MUC1 and MUC21, MUC2 and MUC4, MUC2 and MUC5AC, MUC2 and MUC5B, MUC2 and MUC13, MUC2 and MUC16, MUC2 and MUC21, MUC4 and MUC5AC, MUC4 and MUC5B, MUC4 and MUC13, MUC4 and MUC16, MUC4 and MUC21, MUC5AC and MUC5B, MUC5AC and MUC13, MUC5AC and MUC16, MUC5AC and MUC21, MUC5B and MUC13, MUC5B and MUC16, MUC5B and MUC21, MUC13 and MUC16, MUC13 and MUC21, MUC16 and MUC21, MUC1 and MUC20, MUC2 and MUC20, MUC4 and MUC20, MUC5A and MUC20, MUC5B and MUC20, MUC16 and MUC20, MUC21 and MUC20, either or not further in combination with one or more other mucins selected from the list comprising MUC1, MUC2, MUC4, MUC5AC, MUC5B, MUC13, MUC16, MUC20 or MUC21.

In a specific embodiment, said method comprises determining the presence and/or quantity of MUC13 and MUC21; and wherein high levels of MUC13 and MUC21 are indicative of a coronaviral infection or coronaviral infectious disease.

In another particular embodiment, said method comprises determining the presence and/or quantity of MUC1, MUC2, MUC16 and MUC20; and wherein high levels of MUC1, MUC2 and MUC20, in combination with low levels of MUC16 is indicative of a coronaviral infection or coronaviral infectious disease.

In another particular embodiment, said method comprises determining the presence and/or quantity of MUC1, MUC2, MUC4, MUC6, MUC13, MUC16 and MUC20; and wherein high levels of MUC1, high levels of MUC2, low levels of MUC4, low levels of MUC6, high levels of MUC13, low levels of MUC16 and/or low levels of MUC20 are indicative of a coronaviral infection or coronaviral infectious disease.

In yet a further embodiment, said method comprises determining the presence and/or quantity of MUC1, MUC5B and/or MUC16; and wherein high levels of MUC1 and MUC5B and low levels of MUC16 are indicative of a more severe coronaviral infection or coronaviral infectious disease. In yet a further embodiment, said method further comprises determining the presence and/or quantity of MUC2, MUC13, MUC20 and/or MUC21; and wherein high levels of MUC2, MUC13, MUC20 and/or MUC21 are indicative of a mild coronaviral infection or coronaviral infectious disease.

In a specific embodiment, said one or more mucin mRNA isoforms are selected from the group comprising MUC1 mRNA isoforms, MUC13 mRNA isoforms, MUC16 mRNA isoforms, or MUC21 mRNA isoforms.

In yet a further embodiment at least 2, preferably at least 3 mucin mRNA isoforms are determined and/or quantified. Accordingly, the present invention provides different combinations of mucin isoforms such as but not limited to MUC1 and MUC2 mRNA isoforms, MUC1 and MUC4 mRNA isoforms, MUC1 and MUC5AC mRNA isoforms, MUC1 and MUC5B mRNA isoforms, MUC1 and MUC13 mRNA isoforms, MUC1 and MUC16 mRNA isoforms, MUC1 and MUC21 mRNA isoforms, MUC2 and MUC5AC mRNA isoforms, MUC2 and MUC5B mRNA isoforms, MUC2 and MUC13 mRNA isoforms, MUC2 and MUC16 mRNA isoforms, MUC2 and MUC21 mRNA isoforms, MUC4 and MUC5AC mRNA isoforms, MUC4 and MUC5B mRNA isoforms, MUC4 and MUC13 mRNA isoforms, MUC4 and MUC16 mRNA isoforms, MUC4 and MUC21 mRNA isoforms, MUC5AC and MUC5B mRNA isoforms, MUC5AC and MUC13 mRNA isoforms, MUC5AC and MUC16 mRNA isoforms, MUC5AC and MUC21 mRNA isoforms, MUC5B and MUC13 mRNA isoforms, MUC5B and MUC16 mRNA isoforms, MUC5B and MUC21 mRNA isoforms, MUC13 and MUC16 mRNA isoforms, MUC13 and MUC21 mRNA isoforms, MUC16 and MUC21 mRNA isoforms, MUC1 mRNA isoforms and MUC20 mRNA isoforms, MUC2 mRNA isoforms and MUC20 mRNA isoforms, MUC4 mRNA isoforms and MUC20 mRNA isoforms, MUC5A mRNA isoforms and MUC20 mRNA isoforms, MUC5B mRNA isoforms and MUC20 mRNA isoforms, MUC16 mRNA isoforms and MUC20 mRNA isoforms, MUC21 mRNA isoforms and MUC20 mRNA isoforms, either or not further in combination with one or more other mRNA isoforms selected from the list comprising MUC1 mRNA isoforms, MUC2 mRNA isoforms, MUC4 mRNA isoforms, MUC5AC mRNA isoforms, MUC5B mRNA isoforms, MUC13 mRNA isoforms, MUC16 mRNA isoforms, MUC20 mRNA isoforms or MUC21 mRNA isoforms.

In a further embodiment, of the present invention, the presence and/or quantity of MUC1 mRNA isoforms, MUC13 mRNA isoforms, MUC16 mRNA isoforms and MUC21 mRNA isoforms are determined and wherein the presence and/or quantity of said mucin mRNA isoforms is indicative for the presence and/or severity of a coronaviral infection or coronaviral infectious disease.

In yet a further embodiment of the present invention, the presence and/or quantity of MUC13 mRNA isoforms and/or MUC21 mRNA isoforms is determined and wherein the presence and/or quantity of MUC13 mRNA isoforms and/or MUC21 mRNA isoforms is indicative for the diagnosis of a coronaviral infection or coronaviral infectious disease.

In a further embodiment, said method comprises determining the presence and/or quantity of MUC1 mRNA isoforms, MUC2 mRNA isoforms, MUC16 mRNA isoforms and/or MUC20 mRNA isoforms; and wherein high levels of MUC1 mRNA isoforms, high levels of MUC2 mRNA isoforms, high levels of MUC20 mRNA isoforms, and/or low levels of MUC16 mRNA isoforms is indicative of a coronaviral infection or coronaviral infectious disease.

In a further embodiment, said method comprises determining the presence and/or quantity of MUC2 mRNA isoforms, MUC13 mRNA isoforms, MUC20 mRNA isoforms and/or MUC21 mRNA isoforms; and wherein high levels of MUC2 mRNA isoforms, high levels of MUC13 mRNA isoforms, high levels of MUC20 mRNA isoforms, and/or high levels of MUC21 mRNA isoforms is indicative of a mild coronaviral infection or coronaviral infectious disease.

In a further embodiment, said method comprises determining the presence and/or quantity of MUC2, MUC5AC, MUC5B, MUC13, MUC16, MUC20 and MUC21; and wherein high levels of MUC2, high levels of MUC5AC, high levels of MUC5B, high levels of MUC13, high levels of MUC16, high levels of MUC20 and/or high levels of MUC21 are indicative of a mild coronaviral infection or coronaviral infectious disease.

In a further embodiment, said method comprises determining the presence and/or quantity of MUC1, MUC16, MUC20 and MUC21; and wherein high levels of MUC1, low levels of MUC16, low levels of MUC20 and/or low levels of MUC21 are indicative of a more severe coronaviral infection or coronaviral infectious disease.

The present invention further provides one or more mucin mRNA isoforms for use in the diagnosis and/or monitoring of a coronaviral infection or coronaviral infectious disease, wherein the one or more mucin mRNA isoforms are selected from the list comprising: MUC1 mRNA isoforms, MUC2 mRNA isoforms, MUC4 mRNA isoforms, MUC5AC mRNA isoforms, MUC5B mRNA isoforms, MUC13 isoforms, MUC16 mRNA isoforms, MUC20 mRNA isoforms, MUC21 mRNA isoforms.

In a particular embodiment, the method of the present invention may further comprise determining the presence and/or quantity of one or more mucin isoforms; selected from the group comprising MUC3A mRNA isoforms, MUC6 mRNA isoforms, MUC7 mRNA isoforms, MUC8 mRNA isoforms, MUC12 mRNA isoforms, MUC15 mRNA isoforms, MUC17 mRNA isoforms, MUC19 mRNA isoforms and MUC22 mRNA isoforms.

In another embodiment of the present invention, the presence and/or quantity of MUC1 mRNA isoforms, MUC5B mRNA isoforms, and/or MUC16 mRNA isoforms is determined and wherein high levels of MUC1 mRNA isoforms, high levels of MUC5B mRNA isoforms and/or low levels of MUC16 mRNA isoforms is indicative for a more severe coronaviral infection or coronaviral infectious disease.

In a specific embodiment, the present invention provides the determination of the presence and/or quantity of MUC1 mRNA isoforms, MUC2 mRNA isoforms, MUC3A mRNA isoforms, MUC4 mRNA isoforms, MUC5AC mRNA isoforms, MUC5B mRNA isoforms, MUC6 mRNA isoforms, MUC7 mRNA isoforms, MUC8 mRNA isoforms, MUC12 mRNA isoforms, MUC13 mRNA isoforms, MUC16 mRNA isoforms, MUC16 mRNA isoforms, MUC17 mRNA isoforms, MUC19 mRNA isoforms, MUC20 mRNA isoforms, MUC21 mRNA isoforms and/or MUC22 mRNA isoforms is determined in a mucus sample and the presence and/or quantity of one or more of said mRNA isoforms is indicative of the presence and/or severity of a coronaviral infection or coronaviral infectious disease.

In yet a further specific embodiment, the present invention provides the determination of the presence and/or quantity of MUC1 mRNA isoforms, MUC3A mRNA isoforms, MUC4 mRNA isoforms, MUC5B mRNA isoforms, MUC7 mRNA isoforms, MUC12 mRNA isoforms, MUC13 mRNA isoforms, MUC15 mRNA isoforms, MUC16 mRNA isoforms, MUC17 mRNA isoforms, MUC19 mRNA isoforms, and/or MUC20 mRNA isoforms is determined in a blood sample and the presence and/or quantity of one or more of said mRNA isoforms is indicative of the presence and/or severity of a coronaviral infection or coronaviral infectious disease.

In a particular embodiment, said mucin mRNA isoform is a transmembrane mucin.

In a specific embodiment, the one or more mucin mRNA isoforms for use in the present invention are selected from the list comprising: MUC1 mRNA isoforms, MUC13 isoforms, MUC16 mRNA isoforms, or MUC21 mRNA isoforms.

The present invention also provides a combination of MUC1 mRNA isoforms, MUC13 mRNA isoforms, MUC16 mRNA isoforms and MUC21 mRNA isoforms for use in the diagnosis and/or monitoring of a coronaviral infection or coronaviral infectious disease.

The present invention also provides a combination of MUC1 mRNA isoforms, MUC2 mRNA isoforms, MUC13 mRNA isoforms, MUC16 mRNA isoforms and MUC20 mRNA isoforms for use in the diagnosis and/or monitoring of a coronaviral infection or coronaviral infectious disease.

Furthermore, the present invention provides a MUC1 mRNA isoform and/or MUC16 mRNA isoform for use in determining the severity of a coronaviral infection or coronaviral infectious disease.

The present invention also provides a combination of MUC13 mRNA isoforms and MUC21 mRNA isoforms for use in the diagnosis of a coronaviral infection or coronaviral disease.

In another embodiment, the coronaviral infection or coronaviral disease is a SARS-CoV-2 infection or SARS-CoV-2 associated disease.

The invention also provides a diagnostic kit for performing the in vitro method according to present invention, said kit comprising agents for detecting the presence of one or more mucin mRNA isoforms selected from the list comprising MUC1 mRNA isoforms, MUC2 mRNA isoforms, MUC4 mRNA isoforms, MUC5AC mRNA isoforms, MUC5B mRNA isoforms, MUC13 isoforms, MUC16 mRNA isoforms, MUC21 mRNA isoforms.

Particularly interesting mucin mRNA isoforms are those listed below. Accordingly, the present invention also provides the use of one or more of the following mRNA isoforms in the diagnosis or determination of a disorder characterized by barrier dysfunction, in particular a coronaviral infection or coronaviral infectious disease:

- MUC1 variant ENST00000338684.9; in particular for determining the severity of the disorder, i.e. it is associated with mild coronaviral infections
- MUC1 variants ENST00000485118.5 and ENST00000462215.5; in particular for determining the severity of the disorder, i.e. they are associated with severe/critical coronaviral infections
- MUC1 variants ENST00000614519.4; in particular for diagnosing coronaviral infections, i.e. it is associated with mild and severe coronaviral infections but not with controls
- MUC1 variant ENST00000438413.5; in particular for diagnosing past infections, i.e. it is associated with post-coronaviral infections MUC1 variant NST00000462317.5; in particular for diagnosing coronaviral infections, i.e. it is not associated with coronaviral infections, but with non-COVID-19 controls only MUC 1 variants ENST00000337604.6, ENST00000368390.7, ENST00000368392.7, ENST00000467134.5, ENST00000468978.2, ENST00000620103.4; in particular for diagnosing coronaviral infections, i.e. it is associated with coronaviral infections but not with controls MUC12 variant ENST00000473098.5; in particular for diagnosing coronaviral infections, i.e. it is not associated with mild and severe coronaviral infections nor with post-coronaviral infections; but only with controls MUC13 variants ENST00000616727.4 & ENST00000490147.1; in particular for determining the severity of the disorder, i.e. it is associated with mild coronaviral infections MUC16 variants ENST00000596768.5 & ENST00000599436.1; in particular for determining the severity of the disorder, i.e. it is associated with mild coronaviral infections MUC16 variant ENST00000397910.8; in particular for diagnosing coronaviral infections, i.e. it is associated with coronaviral infections but not with controls MUC19 variant ENST00000484665.2; in particular for diagnosing past infections, i.e. it is associated with post-coronaviral infections MUC19 variant ENST00000546043.2; in particular for determining the severity of the disorder, i.e. it is associated with severe/critical coronaviral infections MUC20 variant ENST00000445522.6; in particular for determining the severity of the disorder, i.e. it is associated with mild coronaviral infections The specific set of disorders focused on in this application, is that they are characterized by barrier dysfunction. The term barrier dysfunction is meant to be the partial or complete disruption of the natural function of an internal barrier of a subject. Such barriers may for example include the brain barriers, the gastrointestinal mucosal barrier, the respiratory mucosal barrier, the reproductive mucosal barrier and the urinary mucosal barrier.

The gastrointestinal mucosal barrier separates the luminal content from host tissues and plays a pivotal role in the communication between the microbial flora and the mucosal immune system. Emerging evidence suggests that loss of barrier integrity, also referred to 'leaky gut', is a significant contributor to the pathophysiology of gastrointestinal diseases, including IBD (Inflammatory Bowel Diseases).

The blood-brain barrier is a highly selective semipermeable border of endothelial cells that prevents solutes in the circulating blood from non-selectively crossing into the extracellular fluid of the central nervous system. The blood-brain barrier restricts the passage of pathogens, the diffusion of solutes in the blood and large or hydrophilic molecules into the cerebrospinal fluid, while allowing diffusion of hydrophobic molecules (e.g. $O_2$, $CO_2$, hormones . . . ) and small polar molecules. Accordingly, an improperly functioning blood-brain barrier can be linked to neurological disorders, in particular neurodegenerative disorders. Not only the blood-brain barrier may have a role in neurological disorders, also other brain barriers, such as the blood-cerebrospinal fluid barrier, may be linked to neurological disorders.

The respiratory mucosal barrier's main function is to form a physical barrier, between the environment and the inside of an organism. It is the first barrier against continuously inhaled substances such as pathogens and allergens. Increased mucus production is often associated with respiratory infections or respiratory diseases, such as for example COPD (Chronic Obstructive Pulmonary Disease). It was moreover found that severely ill COVID-19 patients (i.e. having a SARS-CoV-2 infection) requiring intensive care, may specifically develop mucus hyperproduction in the bronchioles and alveoli of the lungs, an observation which hampers ICU stay and recovery. Accordingly, the present invention may have a significant impact on the diagnosis, monitoring, prevention and/or treatment of respiratory infections, in particular coronaviral infections such as SARS-CoV-2 infections.

Therefore, in a specific embodiment of the present invention, said disease characterized by barrier dysfunction may be a gastrointestinal disorder; a neurodegenerative disorder; cancer, or a respiratory infection.

In a particular embodiment, said gastrointestinal disorder may be selected from the list comprising: Inflammatory Bowel Disease (IBD), Irritable Bowel Syndrome (IBS), cancer, gastro-intestinal infections, obesitas, non-alcoholic fatty liver disease (NAFLD). In another embodiment of the present invention, said Inflammatory Bowel Disease may be selected from the list comprising: Crohn's disease and ulcerative colitis.

In another particular embodiment of the present invention, said cancer may be selected from the list comprising: esophageal cancer, gastric cancer, colorectal cancer, pancreas cancer, liver cancer, kidney cancer, lung cancer, ovarian cancer, colon cancer and prostate cancer.

In a further embodiment of the present invention, said gastro-intestinal infection may be selected from the list comprising: *Helicobacter* infection, *Campylobacter* infection, *Clostridioides difficile* infection and *Salmonella* infection.

In yet a further embodiment of the present invention, said neurodegenerative disorder may be selected from the list comprising: Parkinson's Disease, Alzheimer's Disease, Multiple Sclerosis (MS) and Autism.

In yet a further embodiment, said respiratory infection may be selected from the list comprising: respiratory syncytial viral infections, influenza viral infections, rhinoviral infections, metapneumoviral infections, *Pseudomonas aeruginosa* viral infections and coronaviral infections. Said coronaviral infection for example being a SARS-CoV-2 infection.

As used herein, the terms "treatment", "treating", "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease or condition in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

A "therapeutically effective amount" of an agent described herein is an amount sufficient to provide a therapeutic benefit in the treatment of a condition or to delay or minimize one or more symptoms associated with the condition. A therapeutically effective amount of an agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

Prevention of a disease may involve complete protection from disease, for example as in the case of prevention of infection with a pathogen or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "diagnosing" as used herein means assessing whether a subject suffers from a disease as disclosed herein or not. As will be understood by those skilled in the art, such an assessment is usually not intended to be correct for all (i.e. 100%) of the subjects to be identified. The term, however, requires that a statistically significant portion of subjects can be identified. The term diagnosis also refers, in some embodiments, to screening. Screening for diseases, in some embodiments, can lead to earlier diagnosis in specific cases and diagnosing the correct disease subtype can lead to adequate treatment.

In another particular embodiment, the present invention provides a mucin isoform as defined herein, for use as a biomarker for diagnosis and disease surveillance or monitoring.

By monitoring the progression and change of MUC mRNA isoform status of the individual using the methods of the present invention, the clinician or practitioner is able to make informed decisions relating to the treatment approach adopted for any one individual. For example, in certain embodiments, it may be determined that patients having specific mucin isoforms may or may not react to a particular treatment. Thus, by monitoring the response of mucin isoform carriers to various treatment approaches using the methods of the present invention, it is also possible to tailor an approach which combines two or more treatments, each targeting different subsets of isoforms in the individual.

In another particular embodiment, the present invention provides a mucin isoform as defined herein, for use as a new therapeutic target. In particular, said mucin isoform may be specifically targeted by monoclonal antibodies, small molecules or antisense technology.

EXAMPLES

Example 1: In-Depth Study of Transmembrane Mucins in Association with Intestinal Barrier Dysfunction During the Course of T Cell Transfer and DSS-Induced Colitis

1. Background to the Invention

Inflammatory bowel diseases (IBD), including Crohn's disease (CD) and ulcerative colitis (UC), remain disease entities with a high morbidity burden and are characterized by perpetual chronic relapsing inflammation of the intestines. At this moment, there is no curative treatment for IBD, which is why patients require life-long medication and often need surgery. Treatment mainly focuses on immunosuppression and still a substantial number of patients fail to respond or obtain full remission.

Figure 1:
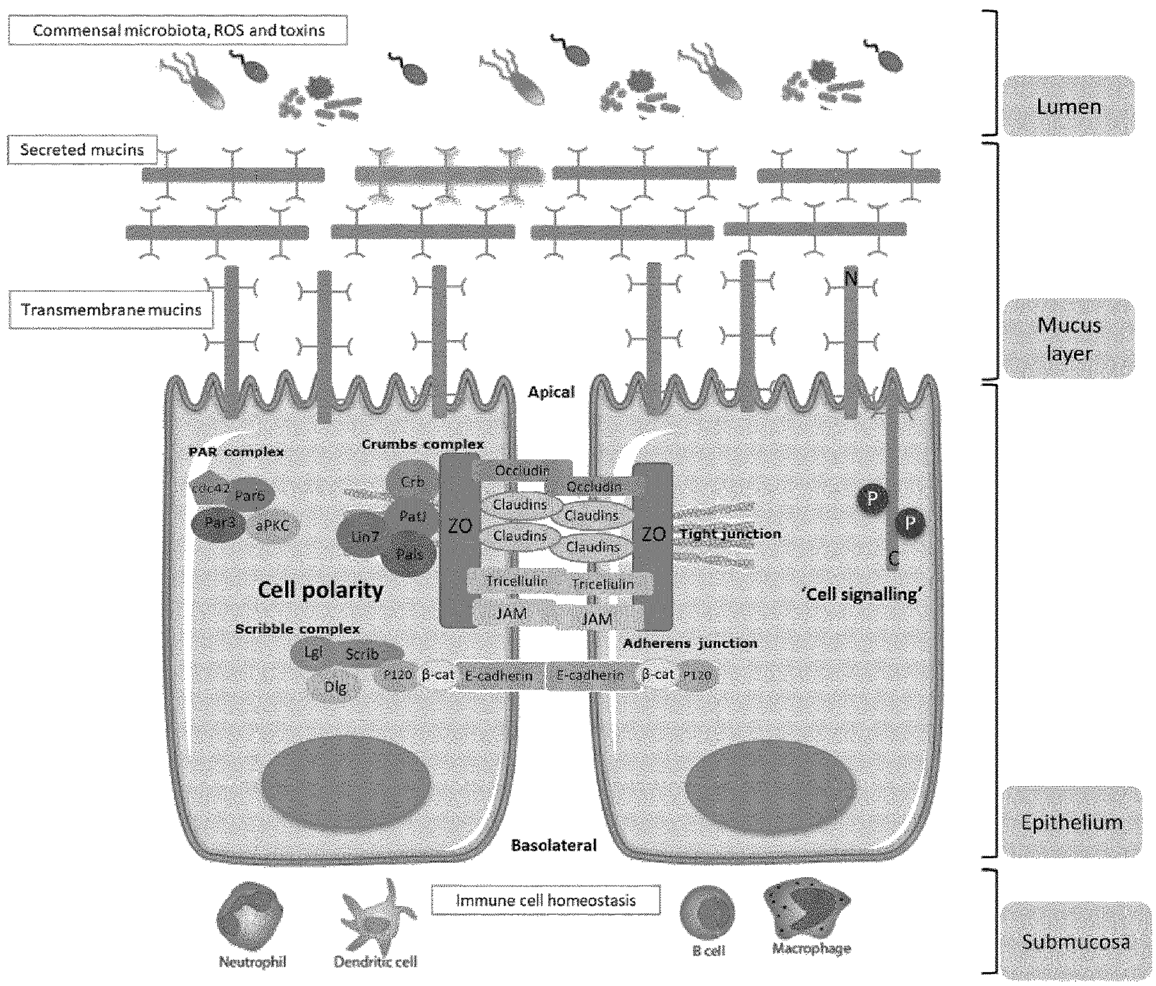
FIG. 1. Schematic representation of the intestinal mucosal barrier. The intestinal barrier comprises a thick layer of mucus, a single layer of epithelial cells and the inner lamina propria hosting innate and adaptive immune cells. Secreted and transmembrane mucins (MUCs) represent the major components of the mucus barrier. Besides having a protective function, transmembrane mucins also participate in intracellular signal transduction. The epithelium underneath plays an active role in innate immunity via secretion and expression of mucins and antimicrobial peptides as well as by hosting antigen presenting cells. Intestinal epithelial cells are tightly linked to each other by intercellular junctions: i.e. tight junctions (claudins (CLDNs), occludin (OCLN) and junctional adhesion molecules (JAMs)) and adherens junctions (E-cadherin and β-catenin). The PAR, Crumbs and Scribble polarity complexes regulate the polarized expression of membrane proteins in the epithelial cells.

The etiology and pathogenesis of IBD are believed to involve inappropriate immune responses to the complex microbial flora in the gut in genetically predisposed persons. The intestinal mucosal barrier separates the luminal content from host tissues and plays a pivotal role in the communication between the microbial flora and the mucosal immune system. Emerging evidence suggests that loss of barrier integrity, also referred to 'leaky gut', is a significant contributor to the pathophysiology of IBD. The intestinal mucosal barrier comprises a thick layer of mucus, a single layer of epithelial cells and the lamina propria hosting innate and adaptive immune cells. Integrity of this barrier is maintained in several ways as depicted in FIG. 1. Secreted (e.g. MUC2) and transmembrane (e.g. MUC1, MUC4, MUC13) mucins represent the major components of the mucus barrier and are characterized by domains rich in proline, threonine, and serine that are heavily glycosylated (i.e. PTS domains). In addition to having a protective function, transmembrane mucins possess extracellular EGF-like domains and intracellular phosphorylation sites which enable them to also participate in the intracellular signal transduction. In this way, they can modulate intestinal inflammation by affecting epithelial cell proliferation, survival, differentiation and cell-cell interactions.

The intestinal epithelium underneath plays an active role in innate immunity via the secretion and expression of mucins and antimicrobial peptides as well as by hosting antigen presenting cells. At this level, intense communication takes place between intestinal epithelial cells (IECs), immune cells, the microbiome and environmental antigens shaping immune responses towards tolerance or activation. IECs are mechanically tied to one another and are constantly renewed to maintain proper barrier function. This linkage is achieved by three types of intercellular junctions, listed from the apical to basal direction: tight junctions, adherens junctions and desmosomes. Whereas the adherens junctions and desmosomes are essential to maintain cell-cell adhesion by providing mechanical strength to the epithelium, tight junctions regulate paracellular permeability and seal the intestinal barrier. Tightjunctions mainly consist of claudins (CLDNs), occludin (OCLN) and junctional adhesion molecules (JAMs). Apart from linking neighbouring cells, they associate with peripheral intracellular membrane proteins, such as zonula occludens (ZO) proteins, which anchor them to the actin cytoskeleton. Furthermore, tight junctions are also involved in regulating cell polarity which is established by the mutual interaction of three evolutionary conserved complexes: defective partitioning (PAR; PAR3-PAR6-aPKC), Crumbs (CRB3-PALS1-PATJ) and Scribble (SCRIB DLG-LGL) complexes (FIG. 1). The Crumbs complex defines the apical membrane whereas the PAR and Scribble complexes are responsible for the establishment of the apical-lateral junctions between cells and the basolateral membrane, respectively. These polarity complexes are thus complementary and act together to initiate and maintain apical-basal polarity.

To date, the mechanisms underlying altered function of the intestinal mucosal barrier in IBD remain largely unexplored, particularly the role of mucins. Moehle et al., 2006 described a downregulation of MUC2 mRNA in the colon of CD patients and increased colonic mRNA levels of MUC13 in patients with UC. This latter finding was also confirmed by another study (Sheng et al., 2011), whereas Vancamelbeke and colleagues showed a stable upregulation of MUC1 and MUC4 mRNA in both the ileum and colon of IBD patients compared to controls (Vancamelbeke et al., 2017). Upon inflammation, MUC1 and MUC13 have been shown to possess divergent actions to modulate mucosal epithelial signalling, with MUC1 being anti-inflammatory and MUC13 pro-inflammatory (Linden et al., 2008; Sheng et al., 2012). Initially, elevated MUC13 during inflammation inhibits epithelial cell apoptosis, and impairment of its expression could lower the level of protection (Sheng et al., 2011). Similarly, MUC1 protects the gastrointestinal epithelial cells from infection-induced apoptosis and enhances the rate of wound healing after injury. It should also be noted that inappropriate overexpression of transmembrane mucins could affect barrier integrity by modulating apical-basal cell polarity and cell-cell interactions, resulting in tight junction dysfunction, and may thus be responsible for the progression from local inflammation to more severe diseases, including IBD.

Therefore, in order to enhance our understanding of the role of transmembrane mucins as novel players in intestinal mucosal barrier dysfunction in IBD, we conducted an in vivo study to characterize changes in barrier components affecting integrity during the course of colitis using two complementary mouse models.

2. Material and Methods

2.1. Animals

Eight- to nine-week-old female immunocompromised SCID (C.B-17/lcr-Prkdc$^{scid}$/lcrlcoCrl) and BALB/c mice (T cell transfer model) and 7- to 8-week-old male C57BL/6J mice (DSS model) were purchased from Charles River (France). All animals were housed in a conventional animal facility with ad libitum access to food and water and a light cycle of 12 hours. After arrival in the animal facility, mice were allowed to acclimatize for 7 days before the onset of the experiments.

2.2. Colitis Models and Experimental Design

Mouse models of colitis have been major tools in understanding the pathogenesis of IBD, yet each separate model has its limitations in that it not fully recapitulates the complexity of this human disease. Among these, the adoptive T cell transfer model has mainly been used to investigate the immunological mechanisms of intestinal inflammation mediated by T cells, and to a lesser extent to study barrier integrity. By contrast, the dextran sodium sulphate (DSS) model has been described as a useful model to examine the innate immune mechanisms involved in the development of intestinal inflammation and barrier dysfunction. More specifically, DSS is toxic to the colonic epithelium and oral administration of this chemical compound causes epithelial cell injury and innate immune responses which alter mucosal barrier integrity. As each colitis model provides valuable insights into a certain aspect of IBD, using multiple models with different initiation of pathology will thus yield a broader picture of the pathophysiology of these diseases, including barrier dysfunction.

T-cell transfer model: colitis was induced in SCID mice by the adoptive transfer of CD4$^+$ CD25$^-$ CD62L$^+$ T cells isolated from the spleens of BALB/c donor mice as described before (FIG. 2A). To monitor disease progression, animals were weighed every week and clinically scored based on the following clinical disease parameters: weight loss, piloerection, stool consistency and mobility. Each parameter was graded from 0 to 2 according to disease severity (0=absent, 1=moderate, 2=severe, for weight loss, 0=weight gain, 1=stable, 2=weight loss). The cumulative score hence ranged from 0 to 8. In addition, intestinal inflammation was also monitored in a continuous manner in individual mice by colonoscopy at fixed time points (weeks 0, 2, 4 and 6) using a flexible Olympus URF type P5 ureteroscope with an outer diameter of 3.0 mm (Olympus Europe GmbH). Briefly, mice were sedated with a mixture of ketamine (60 mg/kg, Ketalar, Pfizer) and xylazine (6.67 mg/kg, Rompun, Bayer) (intraperitoneally (i.p.)) and placed in prone position. The anal sphincter was lubricated with gel (RMS-endoscopy) to facilitate insertion of the endoscope. Subsequently, the scope was carefully inserted through the anus as far as possible into the colon of the sedated mouse. A score was given during the withdrawal of the scope for the following parameters: morphology of the vascular pattern, bowel wall translucency, fibrin attachment and presence of loose stools (each ranging from 0 to 3), with a cumulative minimum of 0 (no inflammation) and a maximum of 12 (severe inflammation).

DSS-induced colitis model: acute colitis was induced by administering 2% DSS (36-50 kDa) to autoclaved drinking water for 7 days ad libitum. This cycle was repeated two more times with intermediate recovery phases of normal drinking water for 7 days to induce more chronic forms of colitis. Control mice received only autoclaved drinking water (FIG. 3A). Water levels were checked every day and were refreshed every other day. Each day, an individual disease activity index (DAI) was calculated by analysing weight loss (0=<1%, 1=1-5%, 2=5-10%, 3=10-20%, 4=>20%), stool consistency (0=normal, 1=semi-solid, 2=loose stools, 4=diarrhea) and rectal bleeding (0=no bleeding, 2=blood visible, 4=gross bleeding) to obtain a cumulative score of these parameters ranging from 0 (healthy) to 12 (severe colitis).

At 1, 2, 4 and 6 weeks post-transfer and at the end of each DSS treatment (FIGS. 2A & 3A), 10-14 animals per group (control, T cell transfer and DSS) were sacrificed by exsanguination under anesthesia (90 mg/kg ketamine and 10 mg/kg xylazine; i.p.). The collected blood was centrifuged to obtain serum for further analysis. Subsequently, the colon was resected, feces were removed and the weight as well as the length of the colon were determined and expressed as the weight/length ratio (mg/cm). Macroscopic inflammation was then scored based on the following parameters: presence of ulcerations, hyperemia, bowel wall thickening and mucosal edema. For the T cell transfer model, each parameter was scored from 0 to 3 depending on the severity, leading to a maximum cumulative score of 12 as described by Heylen et al., 2013. For the DSS model, the macroscopic scoring system of Wallace et al., 1992. was used resulting in a score from 0 to 5. Thereafter, different samples from the colon (distal side) were taken and processed immediately or stored in RNA later, snapfrozen or embedded in paraffin or cryoprotectant until further analysis (see below).

2.3. Myeloperoxidase (MPO) Activity Assay

Myeloperoxidase (MPO) activity was measured in colonic tissue as a parameter for neutrophil infiltration (Heylen et al., 2013). Briefly, colonic samples were immersed in potassium phosphate (pH 6.0) containing 0.5% hexadecyltrimethylammonium bromide (0.02 mL/mg tissue). Thereafter, samples were homogenized, subjected to two freeze-thawing cycles and subsequently centrifuged at 15000 rpm for 15 min at 4° C. An aliquot (0.1 mL) of the supernatant was then added to 2.9 mL of o-dianisidine solution (i.e. 16.7 mg of o-dianosidine dihydrochloride in 1 mL of methyl alcohol, 98 mL of 50 mM potassium phosphate buffer at pH 6.0 and 1 mL of 0.005% $H_2O_2$ solution).

Immediately afterwards, the change in absorbance of the samples was read at 460 nm over 60 sec using a Spectronic Genesys 5 spectrophotometer (Milton Roy). One unit of MPO activity equals the amount of enzyme able to convert 1 mmol of $H_2O_2$ to $H_2O$ per min at 25° C.

2.4. RNA Extraction and RT-qPCR for Gene Expression

Total RNA from colonic tissue stored in RNA later, was extracted using the NucleoSpin® RNA plus kit (Macherey-Nagel) following the manufacturer's instructions. The concentration and quality of the RNA were evaluated using the NanoDrop® ND-1000 UV-Vis Spectrophotometer (Thermo Fisher Scientific). Subsequently, 1 μg RNA was converted to cDNA by reverse transcription using the SensiFast™ cDNA synthesis kit (Bioline). Relative gene expression was then determined by SYBR Green RT-qPCR using the GoTaq qPCR master mix (Promega) on a QuantStudio 3 Real-Time PCR instrument (Thermo Fisher Scientific). Primer sequences are shown in Supplementary Table 1.

Supplementary table S1: Primer sequences used in qPCR assays

| Gene name | Primer | SEQ ID No | Primer sequence (5'-3') |
|---|---|---|---|
| Cdh1 | FW | 1 | CAGTTCCGAGGTCTACACCTT |
| | REV | 2 | TGAATCGGGAGTCTTCCGAAAA |
| Cldn1 | FW | 3 | TGCCCCAGTGGAAGATTTACT |
| | REV | 4 | CTTTGCGAAACGCAGGACAT |
| Cldn2 | FW | 5 | CAACTGGTGGGCTACATCCTA |
| | REV | 6 | CCCTTGGAAAAGCCAACCC |
| Cldn3 | FW | 7 | ACCAACTGCGTACAAGACGAG |
| | REV | 8 | CGGGCACCAACGGGTTATAG |
| Cldn5 | FW | 9 | GCAAGGTGTATGAATCTGT |
| | REV | 10 | GTCAAGGTAACAAAGAGTGCCA |
| Cldn7 | FW | 11 | GGCCTGATAGCGAGCACTG |
| | REV | 12 | TGGCGACAAACATGGCTAAGA |
| Cldn15 | FW | 13 | ATTGCAGGGACCCTCCACATA |
| | REV | 14 | GCCCAGTTCATACTTGGTTCC |
| Crb3 | FW | 15 | CACCGGACCCTTTCACAAATA |
| | REV | 16 | CCCACTGCTATAAGGAGGACT |
| Dlg1 | FW | 17 | AGTGACGAAGTCGGAGTGATT |
| | REV | 18 | GTCAGGGATCTCCCCTTTATCT |
| Jam1 | FW | 19 | TCTCTTCACGTCTATGATCCTGG |
| | REV | 20 | TTTGATGGACTCGTTCTGGGG |
| Jam2 | FW | 21 | GTGCCCACTTCTGTTATGACTG |
| | REV | 22 | TTCCCTAGCAAACTTGTGCCA |
| Jam3 | FW | 23 | CTGCGACTTCGACTGTACG |
| | REV | 24 | TTCGGTTGCTGGATTTGAGATT |
| Ligl1 | FW | 25 | GCTTCCCCAATCAGCCCAG |
| | REV | 26 | GCGCAGCCATTATGATGGATG |
| Muc1 | FW | 27 | GGTTGCTTTGGCTATCGTCTATTT |
| | REV | 28 | AAAGATGTCCAGCTGCCCATA |
| Muc2 | FW | 29 | ATGCCCACCTCCTCAAAGAC |
| | REV | 30 | GTAGTTTCCGTTGGAACAGTGAA |
| Muc4 | FW | 31 | ACAGGTGTAACTAGAAGCCTCG |
| | REV | 32 | CAGGGGTGCTATGCACTACTG |
| Muc13 | FW | 33 | GCCAGTCCTCCCACCACGGTA |
| | REV | 34 | CTGGGACCTGTGCTTCCACCG |
| Mylk | FW | 35 | TGGGGGACGTGAAACTGTTTG |
| | REV | 36 | GGGGCAGAATGAAAGCTGG |
| Ocln | FW | 37 | GGCGGATATACAGACCCAAGAG |
| | REV | 38 | GATAATCATGAACCCCAGGACAAT |
| Pals1 | FW | 39 | TTTGGGCACCAGAATGATGC |
| | REV | 40 | AACAATTCCTTCTTCCGTGTCAA |
| Par3 | FW | 41 | GGAGATGGCCGCATGAAAGTT |
| | REV | 42 | CTCCAAGCGATGCACCTGTAT |
| Par6 | FW | 43 | TCAGAAACGGGCAGAAGGTG |
| | REV | 44 | CCAGGCGGGAGATGAAGATA |

-continued

Supplementary table S1: Primer sequences used in qPCR assays

| Gene name | Primer | SEQ ID No | Primer sequence (5'-3') |
|---|---|---|---|
| Patj | FW | 45 | TTCGATGGGCACCACTATATC |
| | REV | 46 | GGTGGGGGCACTTCTTTAAGG |
| aPkcλ | FW | 47 | CACTTTGAGCCTTCCATCTCC |
| | REV | 48 | GTGACCAGCTTGTGGCACT |
| aPkcζ | FW | 49 | GCGTGGATGCCATGACAACAT |
| | REV | 50 | GGCTCTTGGGAAGGCATGACA |
| Rpl4 | FW | 51 | CCGTCCCCTCATATCGGTGTA |
| | REV | 52 | GCATAGGGCTGTCTGTTGTTTTT |
| Scrib | FW | 53 | CCTGGGCATCAGTATCGCAG |
| | REV | 54 | GCCCTCGTCATCTCCTTTGT |
| Tjp1 | FW | 55 | GAGCGGGCTACCTTACTGAAC |
| | REV | 56 | GTCATCTCTTTCCGAGGCATTAG |
| Tjp2 | FW | 57 | ATGGGAGCAGTACACCGTGA |
| | REV | 58 | TGACCACCCTGTCATTTTCTTG |
| Tjp3 | FW | 59 | CTGTGGAGAACGTCACATCTG |
| | REV | 60 | CGGGGACGCTTCACTGTAAC |

All RT-qPCR reactions were performed in duplicate and involved an initial DNA polymerase activation step for 2 min at 95° C., followed by 40 cycles of denaturation at 95° C. for 15 sec and annealing/extension for 1 min at 60° C. Analysis and quality control were performed using qbase+ software (Biogazelle). Relative expression of the target genes was normalized to the expression of the housekeeping genes Actb and Rp/4.

2.5. Quantification of Intestinal Permeability

To assess in vivo intestinal permeability, the FITC-dextran intestinal permeability assay was performed as described by Gupta et al., 2014. In brief, mice were intragastrically inoculated 4 hours prior to euthanasia with FITC-dextran (44 mg/100 g body weight (T cell transfer), 60 mg/100 g body weight (DSS model), 4 kDa, Sigma). Upon euthanasia, blood was collected via cardiac puncture and transferred into SSTII Advance Blood Collection Tubes (BD Vacutainer). After centrifugation (10000 rpm, 5 min), serum was collected and equally diluted with PBS. Subsequently, aliquots of 100 μl were added in duplo to a 96-well microplate and the concentration of FITC was measured by spectrophotofluorometry (Fluoroskan Microplate Fluorometer, Thermo Fisher Scientific) at an excitation wavelength of 480 nm and an emission wavelength of 530 nm. The exact FITC-dextran concentration per well was calculated using a standard curve with serially diluted FITC-dextran solutions.

2.6. Cytokine Measurements

To determine colonic inflammatory mediators at protein level, two different approaches were applied. First, fresh colonic segments were rinsed with PBS, blotted dry and weighed. Subsequently, the samples were stored on ice until further processing in a Tris-EDTA buffer (i.e. PBS containing 10 mM Tris, 1 mM EDTA, 0.5% v/v Tween-20 and a protease-inhibitor cocktail (Sigma-Aldrich)) at a ratio of 100 mg tissue per ml buffer. Samples were then homogenized, centrifuged (11 000 rpm, 10 min, 4° C.) and the supernatants were stored at −80° C. until further analysis. Colonic cytokine levels were quantified using cytometric bead arrays (CBA) (BD Biosciences) for Tumour Necrosis Factor (TNF)-α, Interferon (IFN)-γ, Interleukin (IL)-1β and IL-6 according to the manufacturer's instructions. Fluorescence detection was performed on a BD Accuri C6 flow cytometer and the FCAP Array software was used for data analysis.

Second, snap frozen colonic tissues were homogenized using beads and total protein was extracted in ice cold NP-40 buffer (i.e. 20 mM Tris HCl (pH 8), 137 mM NaCl, 10% glycerol, 1% nonidet-40, 2 mM EDTA) supplemented with protease and phosphatase inhibitor cocktail tablets (Roche). After centrifugation (14.000 rpm, 10 min, 4° C.) to remove cell debris, the protein concentration was determined using the Pierce BCA protein assay kit (Thermo Fisher Scientific). Enzyme-Linked ImmunoSorbent Assay (ELISA) was then performed to quantify colonic cytokine expression at the protein level. To this end, the mouse uncoated ELISA kits (Invitrogen) were used according to the manufacturer's instructions to measure protein concentrations of IL-1β, TNF-α, IL-6, IL-10 and IL-22. A standard curve was created by performing 2-fold serial dilutions of the top standards included in the kits. For each sample, 100 μl of a 2.5 μg/ml protein solution was analysed by ELISA in duplicate.

2.7. Histopathology and Immunohistochemistry

In order to evaluate inflammation at the microscopic level, full thickness colonic segments were fixed for 24 h in 4% formaldehyde and subsequently embedded in paraffin. Cross sections (5 μm thick) were deparaffinized and rehydrated. Sections were then stained with Hematoxylin Gill III Prosan (Merck) and Eosin Yellow (VWR) according to the standardized protocols. Inflammation was scored based on the degree of inflammatory infiltrates (0-3), presence of goblet cells (0-1), crypt architecture (0-3), mucosal erosion and/or ulceration (0-2), presence of crypt abscesses (0-1) and the number of layers affected (0-3), resulting in a cumulative score ranging from 0 to 13 (Moreels et al., 2004). Periodic Acid-Schiff (PAS) staining was performed to detect mucin glycoproteins in paraffin-embedded colon sections. In brief, rehydrated 5 μm thick colon sections were placed in Schiff reagent for 15 min after an initial oxidation step in 0.5% periodic acid solution for 5 min. Then, colon sections were washed with tap water, counterstained with hematoxylin and analysed by light microscopy (Olympus BX43).

Several immunohistochemical mucin stainings were also applied on paraffin-embedded colonic tissue using the following primary antibodies: the polyclonal rabbit Muc1 (Abcam (ab15481), 1/1000), Muc2 (Novus Biologicals (NBP1-31231), 1/3000), Muc4 (Novus Biologicals (NBP1-52193SS), 1/3000) and the in-house Muc13 (1/2000) antibodies. Briefly, heat-induced antigen retrieval was performed in EDTA (pH 8) (MUC1 and MUC13) or citrate buffer (10 mM, pH 6) (MUC2 and MUC4). Subsequently, endogenous peroxidase activity was blocked by incubating the slides with 3% $H_2O_2$ in methanol (5 min). Primary antibody incubation was performed overnight at 4° C. Subsequently, the mucins were visualized by incubating the colon sections with a goat anti-rabbit biotinylated secondary antibody (EnVision detection system for MUC13) for 60 min at room temperature, followed by incubation with HRP-avidin complexes. Finally, visualization of the target antigen was performed by a short incubation with aminoethyl carbazole (AEC), after which the sections were counterstained with hematoxylin. Washing steps were performed using Tris-buffered saline containing 0.1% Triton X-100 (pH 7.6). The stainings were analysed by light microscopy (Olympus BX43).

To visualize tight junctions in the colon, fresh colonic tissue was transversally placed and immersed in Richard-Allan Scientific™ Neg-50™ Frozen Section Medium (Thermo Fisher Scientific) and snap frozen, after which 6 μm cryosections were mounted on SuperFrost slides (Thermo Fisher Scientific). After a short fixation period of 5 min in aceton, the sections were dried and rinsed with Tris-buffered saline supplemented with 1% albumin. The sections were then incubated overnight with the following primary antibodies: ZO-1 (Invitrogen (61-7300), 1/1000) and CLDN1 (abcam (ab15098), 1/2000).

The next day, secondary antibody incubation was performed for 60 min using a goat anti-rabbit Alexa Fluor 594 secondary antibody (Invitrogen, 1/800). After rinsing in distilled water, the colon sections were counterstained and protected against fading using Vectashield mounting medium containing DAPI (Vector Laboratories). Washing steps were performed using Tris-buffered saline supplemented with 0.1% Triton X-100. For visualization, a Nikon Eclipse Ti inverted fluorescence microscope equipped with a Nikon DS-Qi2 camera was used. All sections were blinded to obtain the representative images.

2.8. Statistics

Statistical analysis using the GraphPad Prism 8.00 software (licence DFG170003) was performed to determine significant differences between control and the different colitis groups within a certain model (T cell transfer or DSS). Data were analysed by the One-way Analysis of Variance (ANOVA) and non-parametric Kruskal-Wallis tests and are presented as means±standard error of mean (SEM) or boxplots (min to max), unless stated otherwise. Significance levels are indicated on the graphs by *p<0.05, <0.01, *p<0.001 and were corrected for multiple testing using the Tukey-Kramer's and Dunn's post-hoc multiple comparisons tests.

A discriminant function analysis was performed to determine whether colitis mice could be distinguished from control animals based on a set of predictor variables (i.e. the expression of cytokines, mucins or other barrier mediators). The results are depicted as scatter plots showing the two main discriminant functions (i.e. function 1 and function 2) with the according main predictor variables summarized in a table. Furthermore, a multiple linear regression analysis was carried out to investigate associations (1) between changes in barrier integrity and the expression of mucins, cytokines and barrier mediators; (2) between the expression of mucins, cytokines and barrier mediators. Scatter plots are shown distinguishing between different experimental groups with the corresponding p-value of the regression model. A p-value below 0.05 was considered statistically significant. These analyses were performed using IBM SPSS Statistics 24 software.

3. Results

Figure 2:
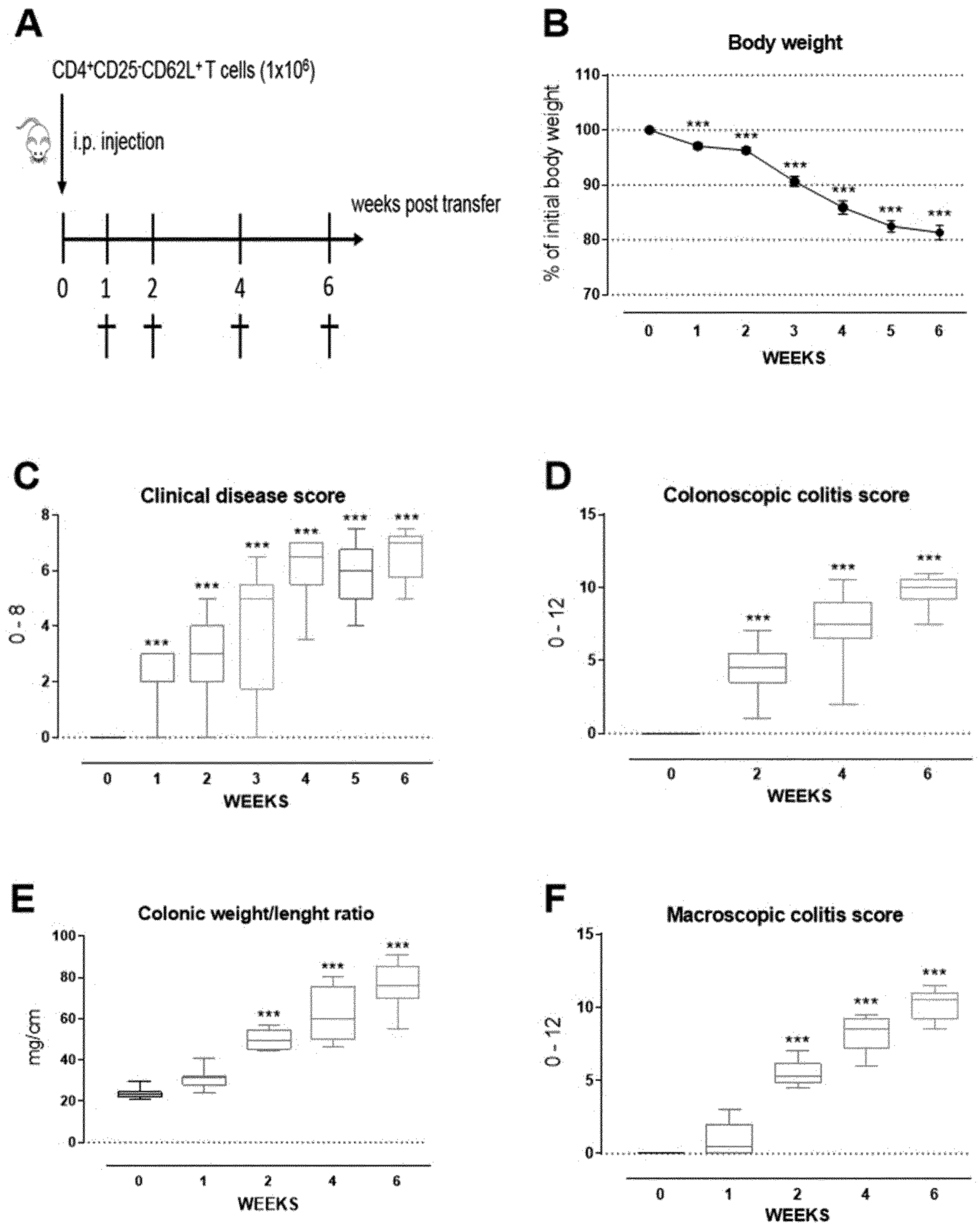
FIG. 2. Analysis of intestinal inflammation in the adoptive T cell transfer model. (A) Schematic overview and timeline of the adoptive T cell transfer model. (B) Relative changes in body weight after T cell transfer. (C) Weekly determination of the clinical disease score by the assessment of body weight loss, pilo-erection, mobility and stool consistency. (D) Colitis severity was scored every two weeks by endoscopy and was based on the morphology of the vascular pattern, bowel wall translucency, fibrin attachment and the presence of loose stools. (E) The colon weight/length ratio. (F) At sacrifice, the colon was longitudinally opened and visually inspected for the presence of ulcerations, hyperemia, bowel wall thickening and oedema. (G) H&E stained colon sections were evaluated blinded focusing on crypt destruction, epithelial erosion, goblet cell loss and immune cell infiltration. (H) Neutrophil infiltration in the colon was assessed by measuring MPO activity. Significant differences between control and colitis mice are indicated by $*p<0.05$, $<0.01$, $*p<0.001$ (One-Way ANOVA, Tukey's multiple comparison post-hoc test).

3.1. Macroscopic and Microscopic Observations of Colitis Evolution Over Time In the T cell transfer model, SCID mice started to develop clinical signs of colitis one week after the adoptive transfer of naïve T cells. Body weight was decreased at 1 week post-transfer compared to the initial body weight pre-transfer and this decrease gradually continued until week 6 (FIG. 2B). The clinical disease score increased over time starting from week 1 to week 4, while stagnating afterwards (FIG. 2C). A colonoscopy was performed every 2 weeks to monitor signs of colitis in the bowel wall, showing a time-dependent increase in inflammatory scores at weeks 2, 4 and 6 post-transfer compared to the control mice (FIG. 1D). After sacrifice, the mucosal damage in the colon was scored at both a macro- and microscopic level. Mice that were sacrificed at 2, 4- and 6-weeks post-transfer showed a gradual increase in macroscopic inflammation (FIG. 2F). This phenomenon was also seen for another macroscopic marker of colonic inflammation, the colonic weight/length ratio, which is a quantification of colonic edema (FIG. 2E). In contrast, the infiltration of neutrophils and lymphocytes became already visible on H&E-stained colonic segments of colitis mice at week 1 post-transfer (FIG. 2G). This mucosal and submucosal infiltration of immune cells gradually increased and was associated with a remarkable increase in colon thickness as disease progressed to weeks 2, 4 and 6 (FIG. 2G). Furthermore, MPO activity, which is caused by neutrophil infiltration in the mucosa, was increased starting from 2 weeks post-transfer, with a gradual increase overtime to weeks 4 and 6 (FIG. 2H).

Figure 3:
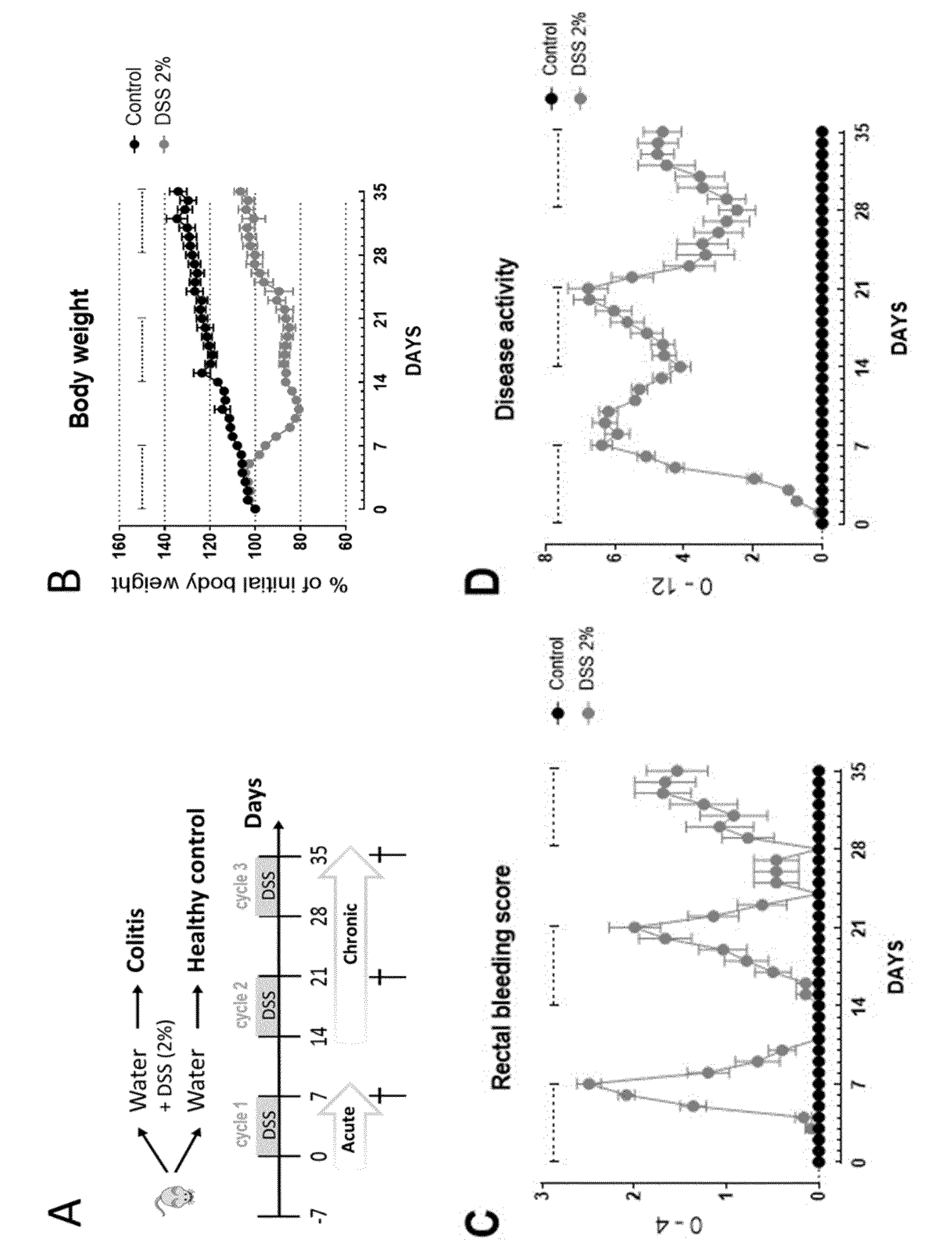
FIG. 3. Analysis of intestinal inflammation in the DSS-induced colitis model. (A) Schematic overview and timeline of the DSS-induced colitis model. (B) Body weight was daily assessed and shown as percentage of the initial body weight. (C) Daily determination of the disease activity index (DAI), which is the cumulative score of body weight loss, the extent of rectal bleeding and changes in stool consistency. The horizontal bars indicate periods of DSS administration. (D) Rectal bleeding score. (E) The colon weight/length ratio. (F) At sacrifice, the colon was longitudinally opened and inspected for the presence of ulcerations, hyperemia, bowel wall thickening and oedema. (G) Microscopic colonic inflammation score which was based on crypt loss, epithelial erosion, goblet cell loss, immune cell infiltration and colonic hyperplasia. (H) Colonic MPO activity to assess neutrophil infiltration in the colon. N=8-14 mice/group (control, DSS cycle 1, DSS cycle 2, DSS cycle 3). Significant differences between control and colitis mice are indicated by $*p<0.05$, $<0.01$, $*p<0.001$ (One-Way ANOVA, Tukey's multiple comparison post-hoc test).

In the DSS colitis model, mice treated with DSS started to lose weight after 5 days of DSS administration in the first cycle. The body weight further decreased when normal drinking water was reintroduced at day 8, with a maximal weight loss at day 11 of the experimental protocol (FIG. 3B). The colitis mice started to regain weight at the end of the second DSS cycle (day 21) until the initial body weight was reached at the end of the experiment. Healthy control mice gained weight over time (FIG. 3B). As a result of DSS administration, mice in each DSS group showed maximal changes in stool consistency and rectal bleeding after 7 days of DSS administration, which decreased and completely disappeared in the recovery phase (FIG. 3). The above-described parameters to assess clinical disease in this model (body weight, stool consistency and rectal bleeding) are combined in the DAI score, which is shown in FIG. 3D. Control mice did not show any signs of disease throughout the experiment, whereas administration of 2% DSS for 7 days stably induced a mild acute colitis after DSS cycle 1. The two subsequent DSS cycles, however, led to the development of a chronic colitis with an increased interindividual variability.

To assess the effect of DSS-induced colitis on macro- and microscopic inflammatory parameters of the colon, a group of mice was sacrificed after each cycle of DSS administration (DSS cycle 1, DSS cycle 2 and DSS cycle 3, respectively, FIG. 3A). The colonic weight/length ratio was increased in all three groups (cycles 1, 2 and 3) compared to the control group. The macroscopic inflammation score was increased in all DSS cycles (FIG. 3F) with hyperemia and ulcerations abundantly present after DSS cycle 1, whereas colon thickening appeared after DSS cycles 2 and 3. Microscopic inflammation was present in all DSS groups as scored on H&E-stained colon sections (FIG. 3G) and showed crypt loss, epithelial erosions and marked infiltration of neutrophils in the colon of acute DSS treated mice (data not shown). At the end of DSS cycles 2 and 3, the colon sections showed epithelial regeneration compared to the acute stage, yet with remarkable hyperplasia. Infiltration of neutrophils and lymphocytes in the submucosa and mucosa could also be observed (data not shown). In addition, some mice even showed massive focal ulcerations in the colon. At the molecular level, MPO activity was increased during DSS-induced colitis progression (FIG. 3H), which confirmed the infiltration of neutrophils into the colon due to DSS administration. Interestingly, mice treated with 3 DSS cycles showed a significant lower colonic MPO activity compared to mice treated only once.

3.2. Colonic Inflammatory Markers

Figure 4:
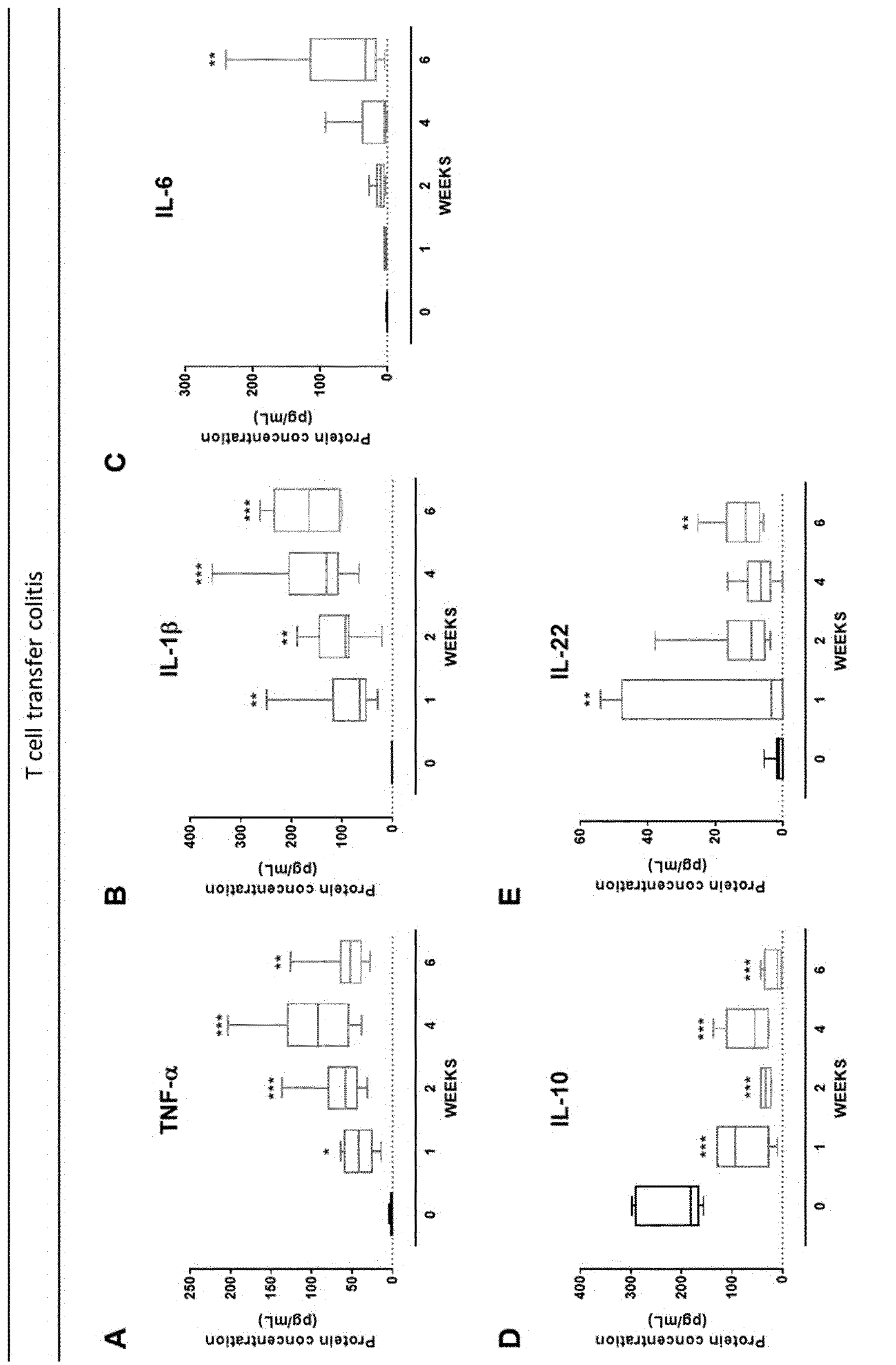
FIG. 4. Colonic cytokine expression in the T cell transfer and DSS-induced colitis models. Protein expression of pro- and anti-inflammatory cytokines in the colon of controls and T cell transfer- or DSS-induced colitis mice. Results are shown for TNF-α (A&F), IL-1β (B&G), IL-6 (C&H), IL-10 (D&I) and IL-22 (E&J). Significant differences between control and colitis mice are indicated by $*p<0.05$; $p<0.01$; $*p<0.001$ (N=5-10 mice/group (week 0 (control), 1, 2, 4 & 6) for the T cell transfer model; N=6-13 mice/group (control, DSS cycle 1, DSS cycle 2, DSS cycle 3) for the DSS model; One-Way ANOVA or Kruskal-Wallis, Tukey's and Dunn's multiple comparison post-hoc test).

In both colitis models, colonic protein levels of several inflammatory markers were quantified as shown in FIG. 4. At all timepoints post-transfer and after each cycle of DSS administration, expression of IL-1β and TNF-α was increased whereas IL-10 was reduced in expression (FIG. 4A-B, D, F-G, I). Interestingly, IL-22 protein levels were only increased at 1 and 6 weeks post-transfer and at the end of DSS cycles 1 and 3 (FIG. 4E, J). In contrast, expression of IL-6 was only increased in the more chronic phase of colitis, i.e. at week 6 post-transfer (FIG. 4C) and after the second cycle of DSS administration (FIG. 4H).

3.3. Mucosal Barrier Function During Colitis Progression

Figure 5:
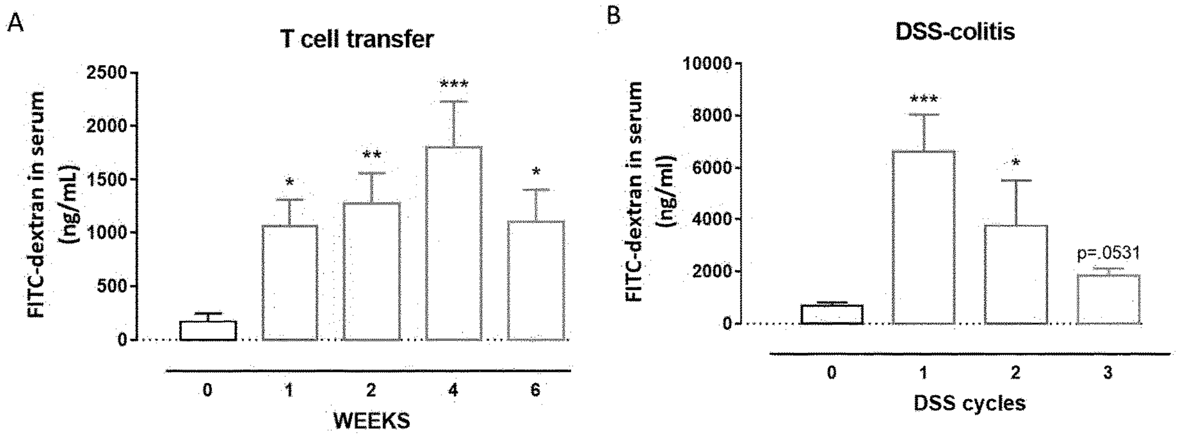
FIG. 5. Analysis of intestinal permeability in the T-cell transfer and DSS-induced colitis models. Relative gastrointestinal permeability of control mice compared to colitis animals: (A) T cell transfer model (N=7-10 mice/group (week 0 (control), 1, 2, 4 & 6)); (B) DSS model (N=8-13 mice/group (control, DSS cycle 1, DSS cycle 2, DSS cycle 3)). Significant differences between control and colitis mice are indicated by $*p<0.05$; $p<0.01$; $*p<0.001$ (Kruskal-Wallis test, Dunn's post-hoc multiple comparison test).

As loss of intestinal barrier integrity is recognized as a major hallmark of the IBD pathophysiology[18], changes in barrier permeability during colitis progression were investigated in both models. Results of the FITC-dextran intestinal permeability assays showed that integrity of the intestinal mucosal barrier was affected in both models (FIG. 5). More specifically, intestinal permeability progressively increased during colitis progression in the T cell transfer model levelling off at week 6, but remaining increased as compared to control mice (FIG. 5A). In the DSS model, intestinal permeability showed a strong increase after the first cycle of DSS administration, after which it declined in the chronic stages of colitis with only a significant increase left after the second DSS cycle but not after the third cycle (FIG. 5B).

To further substantiate intestinal mucosal barrier dysfunction upon colitis, the expression of several components that are the building stones of and regulate the mucosal barrier were measured.

Figure 6:
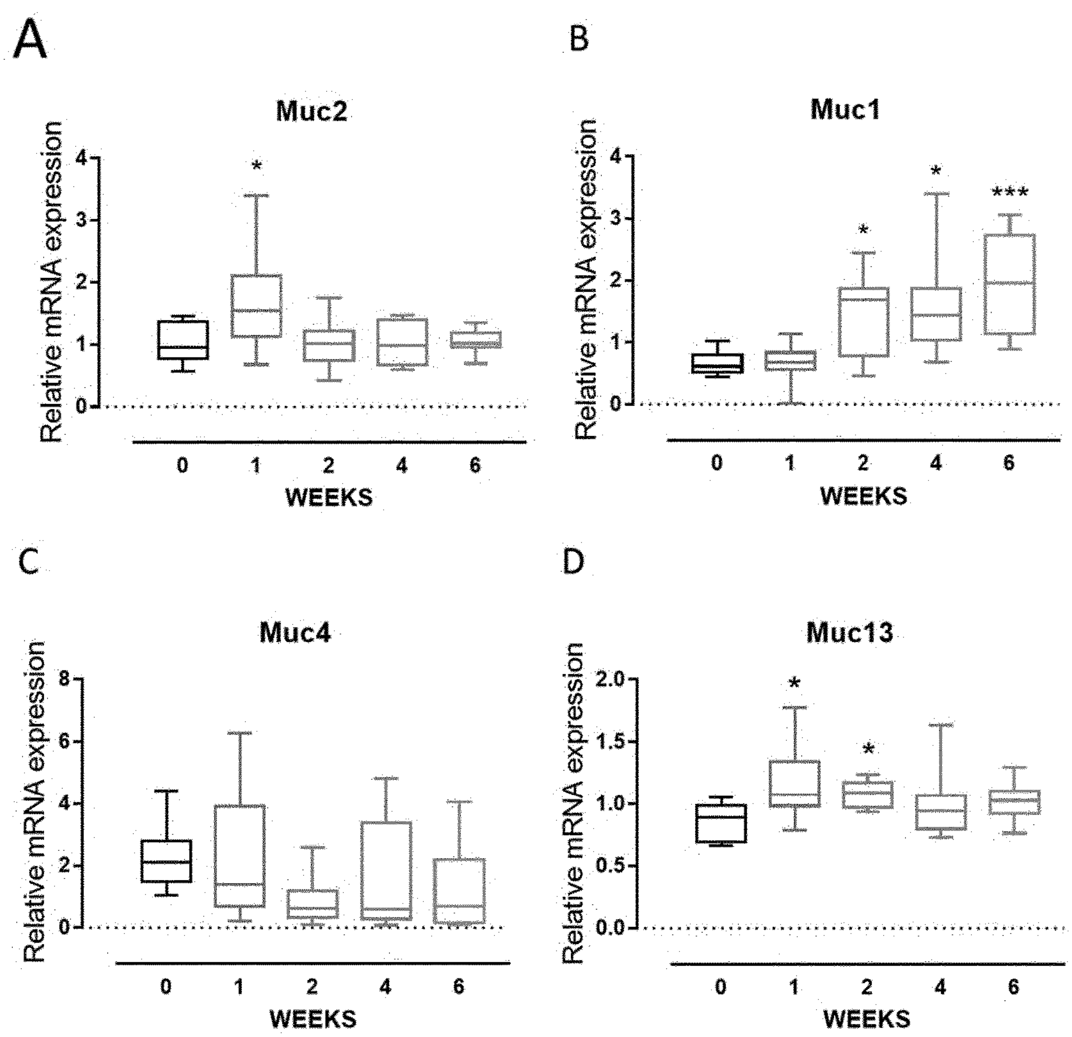
FIG. 6. Colonic mucin expression in the adoptive T cell transfer model. (A-D) mRNA expression of Muc1, Muc2, Muc4 and Muc13 (N=7-10 mice/group (week 0 (control), 1, 2, 4 & 6)) in the colon of controls and T cell transfer-induced colitis mice. Significant differences between control and colitis mice are indicated by $*p<0.05$; $p<0.01$; $*p<0.001$ (One-Way ANOVA, Tukey's post-hoc multiple comparison test).
Figure 7:
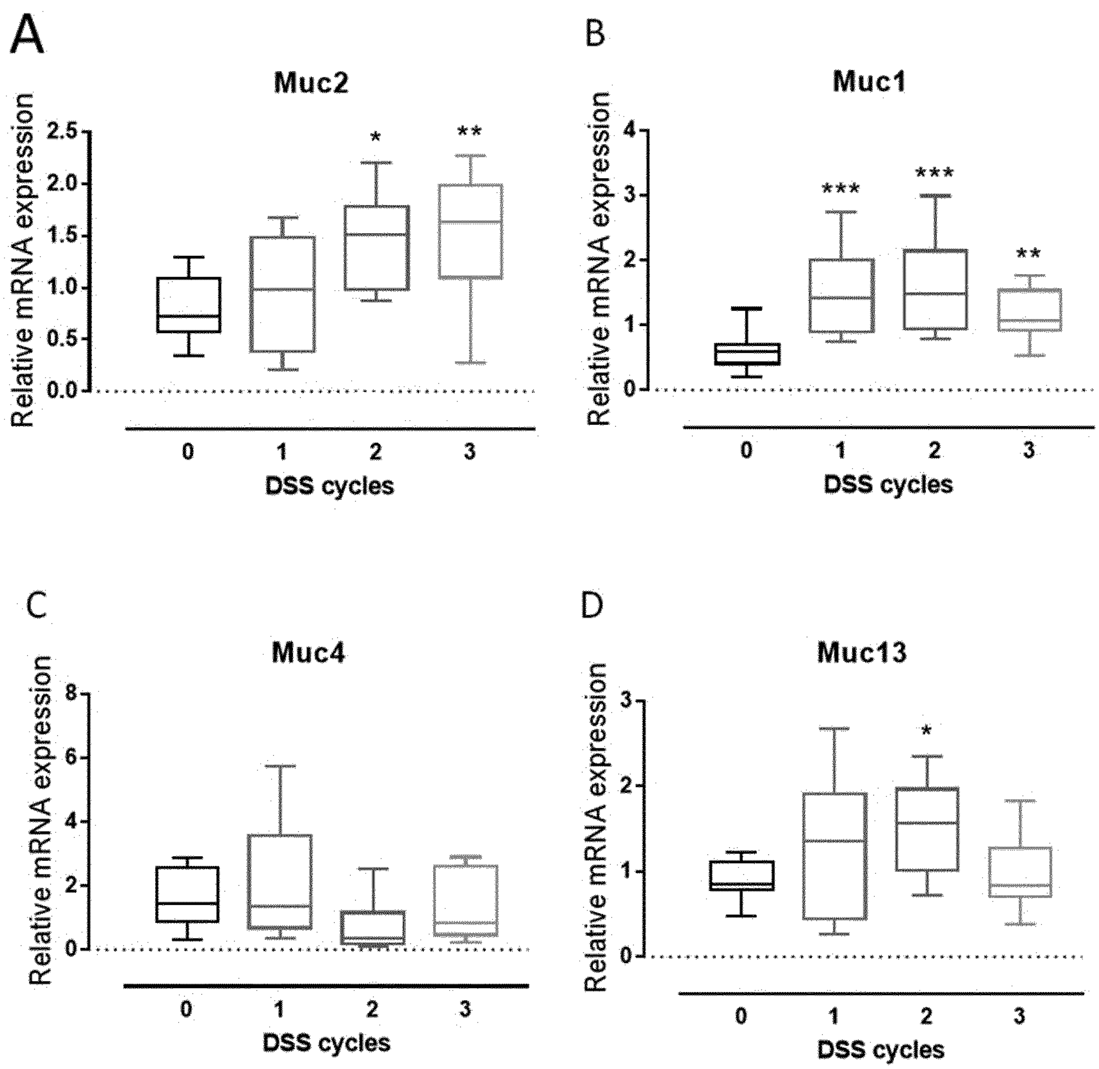
FIG. 7. Colonic mucin expression in the DSS-induced colitis model. (A-D) mRNA expression of Muc1, Muc2, Muc4 and Muc13 (N=10-13 mice/group (control, DSS cycle 1, DSS cycle 2, DSS cycle 3)) in the colon of controls and DSS-induced colitis mice. Significant differences between control and colitis mice are indicated by *$p<0.05$; $p<0.01$; *$p<0.001$ (One-Way ANOVA, Tukey's post-hoc multiple comparison test).

We first investigated mucin expression since mucins constitute the main part of the mucus layer and are the first barrier luminal pathogens and toxins encounter. Muc2 (i.e. the main secreted mucin of the large intestine) mRNA expression was increased after 1 week post-transfer (FIG. 6A) whereas it was upregulated during the chronic stages of DSS-induced colitis (FIG. 7A). mRNA expression of Muc1, a transmembrane mucin expressed only at low levels in the healthy intestines, was upregulated after 2, 4 and 6 weeks post-transfer (FIG. 6B) and after all cycles of DSS administration (FIG. 7B). The transmembrane Muc13 mucin, which is normally expressed in the healthy intestines, showed aberrant expression patterns at the RNA level in both models with an increased expression seen at 1 and 2 weeks after T cell transfer and DSS cycle 2 (FIGS. 6D & 7D). In contrast, mRNA expression of Muc4, another membrane-bound mucin, was not significantly altered during experimental colitis in either model (FIGS. 6C & 7C). The changes in mucin mRNA expression were verified at protein level by immunohistochemical stainings (data not shown). In the DSS model, we observed increased Muc2 staining intensity during colitis progression, whereas in the T cell transfer model, overall Muc2 staining intensities were not altered compared to control animals. In control animals, Muc1 was mainly observed on the apical side of epithelial cells lining the villi, whereas colitis induction was associated with increased Muc1 staining intensities in the cytoplasm and the crypts in both colitis models. Muc13 intensity was mainly increased after the first two cycles of DSS administration and from week 2 post-transfer in the T cell transfer model. Concerning its cellular localisation, Muc13 showed a strong apical staining intensity in intestinal epithelial cells, which became apparent in the cytoplasm during colitis. For Muc4, no clear changes were observed during colitis progression compared to control animals.

Figure 8:
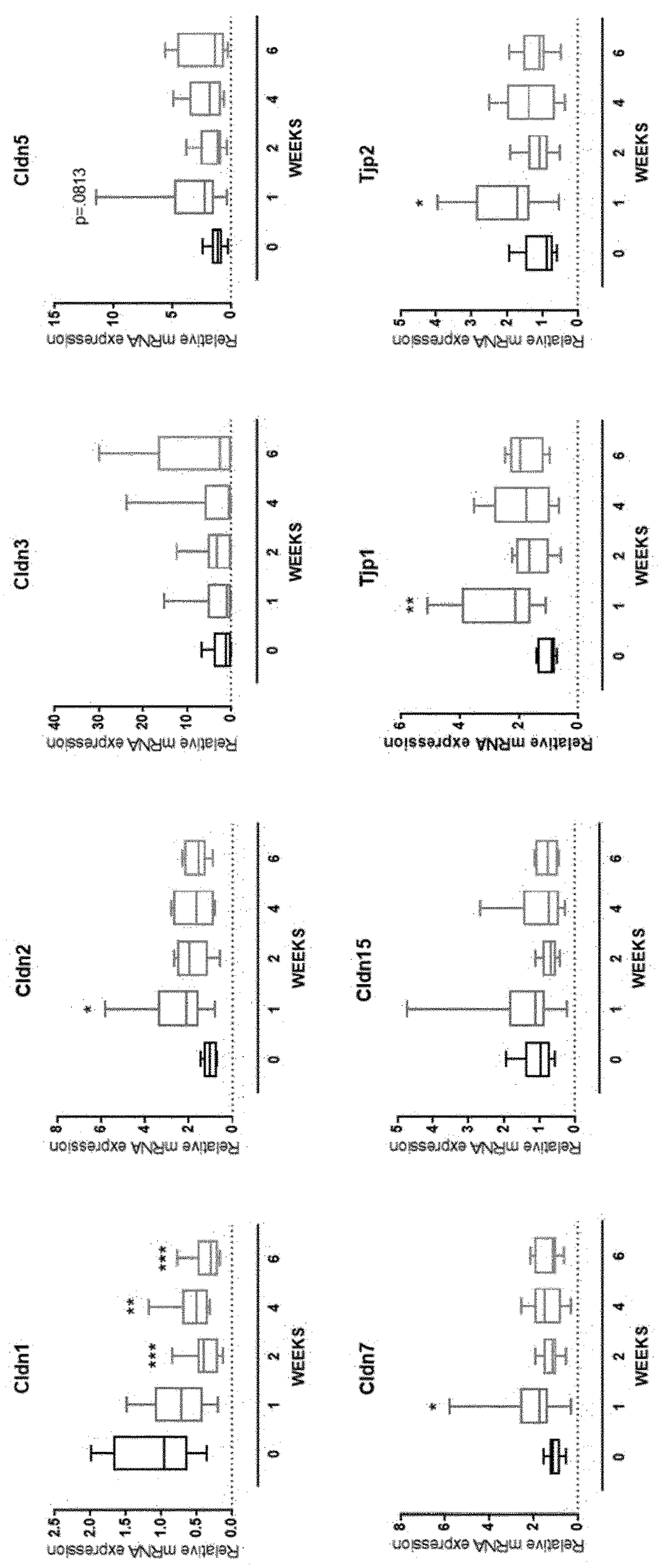
FIG. 8. Colonic intercellular junction expression in the adoptive T cell transfer model. mRNA expression of several Claudins (Cldn), Zonula-Occludens (Zo/Tjp), Junctional Adhesion Molecules (Jam), Occludin (Ocln), E-cadherin (Cdh1) and Myosin light chain kinase (My/k) in the colon of controls and T cell transfer-induced colitis mice. Significant differences between healthy control and colitis mice is indicated by *$p<0.05$; $p<0.01$; *$p<0.001$ (N=10-13 mice/group (week 0 (control), 1, 2, 4 & 6); One-Way ANOVA or Kruskal-Wallis, Tukey's and Dunn's multiple comparison post-hoc test).
Figure 9:
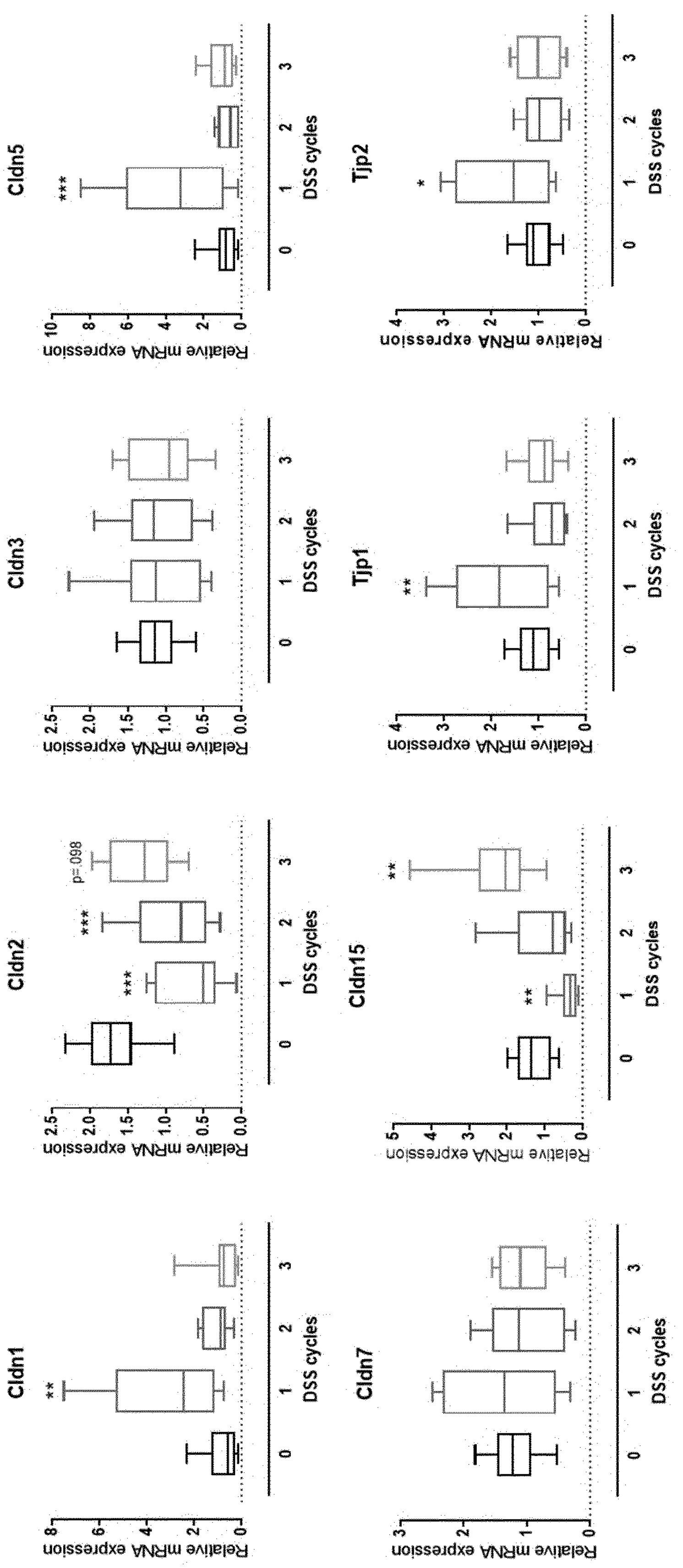
FIG. 9. Colonic intercellular junction expression in the DSS model. mRNA expression of several Claudins (C/dn), Zonula-Occludens (Zo/Tjp), Junctional Adhesion Molecules (Jam), Occludin (Ocln), E-cadherin (Cdh1) and Myosin light chain kinase (My/k) in the colon of controls and DSS-induced colitis mice. Significant differences between control and colitis mice are indicated by *$p<0.05$; $p<0.01$; *$p<0.001$ (N=10-13 mice/group (control, DSS cycle 1, DSS cycle 2, DSS cycle 3); One-Way ANOVA or Kruskal-Wallis, Tukey's and Dunn's multiple comparison post-hoc test).

Several interesting alterations were observed in both models as far as the expression patterns of junction constituents at RNA level were concerned (FIGS. 8 & 9). mRNA expression levels of Zol (Tjp1), Tjp2, Jam2, Jam3 and Myosin Light Chain Kinase (My/k) were significantly increased at week 1 post-transfer and after the first cycle of DSS administration (FIGS. 8 & 9). E-cadherin (Cdh1) and Ocln mRNA expression levels were significantly decreased during the more chronic stages of experimental colitis in both models (FIGS. 8 & 9). mRNA levels of Cldn1, a major regulator of paracellular permeability, were elevated after the first DSS cycle, whereas it decreased throughout colitis progression in the T cell transfer model (FIGS. 8 & 9). In contrast, Cldn2 mRNA expression was increased at 1 week post-transfer, yet its expression declined at the end of each DSS cycle (FIGS. 8 & 9). In addition, Cldn5 and Cldn7 showed a model-specific response. More specifically, expression of Cldn7 and Cldn5 mRNA was upregulated at the initial stage of colitis in the T cell transfer and the DSS model, respectively (FIGS. 8 & 9). Furthermore, Tjp3 mRNA expression was reduced throughout colitis progression in the DSS-induced colitis model only, whereas Cldn15 mRNA expression was significantly decreased during the acute phase of DSS-induced colitis and became significantly increased in the chronic phases (FIG. 9). Expression of Cldn3 and Jam1 was not altered throughout colitis progression in either model (FIGS. 8 & 9). Immunohistochemical stainings for ZO-1 and CLDN1 were also performed to analyse alterations in intercellular junctions at the protein level. These results showed that mainly CLDN1 showed an increased staining intensity during the course of colitis in both models highlighting dysfunction of this tight junction protein, whereas no clear alterations could visually be observed for ZO-1 (data not shown).

Figure 10:
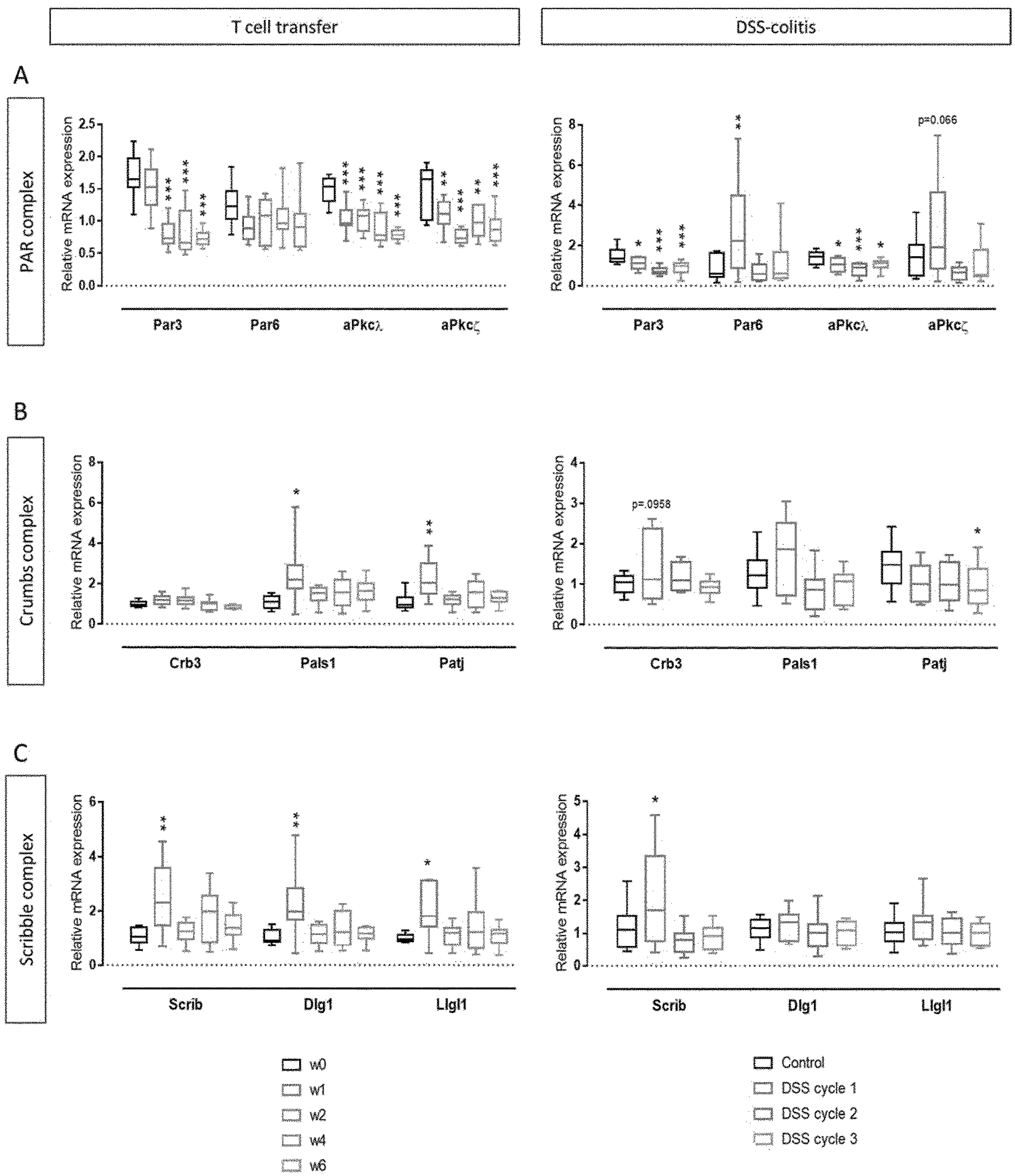
FIG. 10. Colonic expression of cell polarity proteins during the course of colitis. mRNA expression of (A) Par3, Par6, aPkcλ and aPkcç (PAR complex) (B) Crb3, Pals1 and Patj (Crumbs complex) and (C) Scrib, Dlg1 and Llgl1 (Scribble complex) in the T cell transfer (N=7-10 mice/group (week 0 (control), 1, 2, 4 & 6)) and DSS-induced colitis model (N=10-13 mice/group (control, DSS cycle 1, DSS cycle 2, DSS cycle 3)). Significant differences between control and colitis mice are indicated by *$p<0.05$; $p<0.01$; *$p<0.001$ (One-Way ANOVA, Tukeys post-hoc multiple comparison test).

In addition to appropriate expression of intercellular junctions, a well organised apical-to-basal cell polarity is indispensable for the formation of a functional and tight intestinal epithelial cell monolayer. Gene expression analysis showed that subunits of the different polarity complexes were affected in both our experimental colitis mouse models (FIG. 10). The expression of Par3 and aPkcλ, two major coordinators of tight junction localization, was downregulated at all DSS cycles and time points post-transfer (FIG. 10A). On the other hand, aPkcçmRNA expression was only decreased in the T cell transfer model, whereas Par6 mRNA expression was only elevated at the acute phase of DSS-induced colitis (FIG. 10A). Regarding the subunits of the Crumbs polarity complex as shown in FIG. 10B, Patj mRNA expression tended to be decreased at all DSS cycles, whereas its expression was upregulated at week 1 post-transfer. Also mRNA expression of Pals1 (Mpp5) was upregulated at the first time-point of the T cell transfer model (FIG. 10B). No significant alterations in Crb3 expression were observed in either colitis models (FIG. 10B). Interestingly, Scrib expression, which is known to be a negative regulator of the PAR complex, was increased at 1 week post-transfer and after the first DSS cycle (FIG. 10C). Although expression of Dlg1 and Llgl1 was altered in the T cell transfer model at 1 and 2 weeks post-transfer, respectively, no changes in expression of these subunits were observed in the DSS-colitis model (FIG. 10C). The above results highlight that epithelial cell polarity is disturbed as a consequence of colitis induction, both in the acute and chronic stages.

Figure 12:
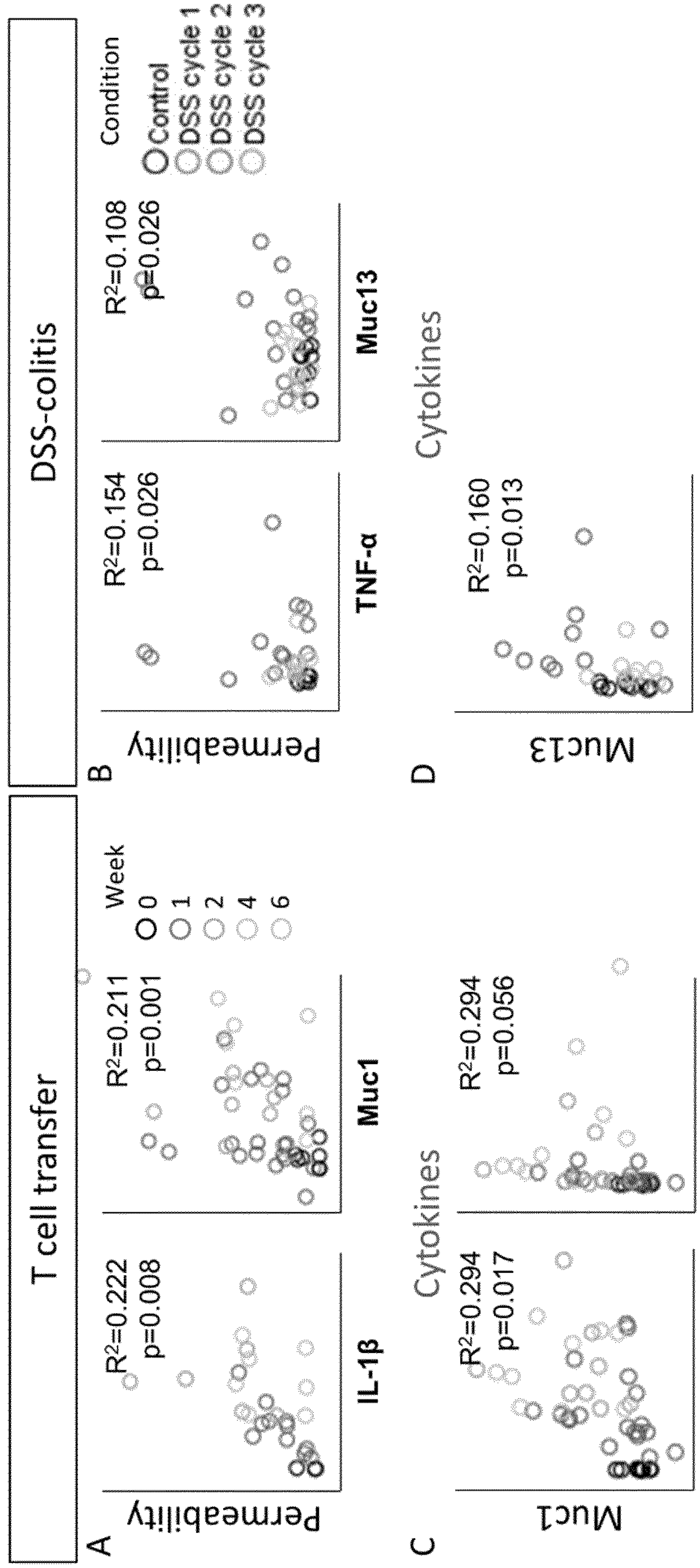
FIG. 12. Scatter plots of correlated data for the T cell transfer model and the DSS colitis model. T cell transfer model: (A) Correlation of intestinal permeability with IL-1β protein and Muc1 mRNA expression levels. (C) Correlation of Muc1 expression with IL-1β and IL-6 protein expression. (E) Correlation of Muc1 mRNA expression with the expression levels of the intercellular junctions Cldn1 and Ocln. (G) Correlation of Muc1 mRNA expression with the expression levels of the cell polarity complex subunits Par3 and aPKCζ. DSS colitis model: (B) Correlation of intestinal permeability with TNF-α protein and Muc13 mRNA expression levels. (D) Correlation of Muc13 mRNA expression with TNF-α protein expression. (F) Correlation of Muc13 mRNA expression with the expression levels of the intercellular junctions Cldn1, Jam2 and Tjp2. (H) Correlation of Muc13 mRNA expression with the expression levels of the cell polarity complex subunits aPKCζ, Crb3 and Scrib. The correlations were selected based on the results of a multiple linear regression analysis. The corresponding adjusted $R^2$-values and p-values of the regression model are shown.

3.4. Aberrant Mucin Expression Associated with Loss of Barrier Integrity Upon Inflammation It has been suggested that overexpression of transmembrane mucins in many cancer types can contribute to loss of epithelial barrier integrity by mediating junctional and cell polarity dysfunction. To elucidate the involvement of aberrantly expressed transmembrane mucins as potential mediators in intestinal mucosal barrier disruption upon inflammation-induced colitis, the mucin mRNA expression data were used to perform a discriminant analysis on both models and to correlate the changes in intestinal permeability and colonic inflammation (FIGS. 11 & 12).

In the T cell transfer model, Muc1 and Muc13 expression were the best factors to discriminate whether mice developed colitis by the adoptive transfer of T cells or were controls (FIG. 11A). In the DSS colitis model, Muc2 expression was found to be the major determinant for identifying mice receiving a DSS treatment, followed by expression of Muc1 and Muc13 (FIG. 11B). Interestingly, increased Muc1 expression correlated significantly with increased intestinal permeability (based on FITC dextran levels in sera) in the T cell transfer model (FIG. 12A), whereas a positive significant correlation between aberrant Muc13 expression and increased intestinal permeability was seen in the DSS model (FIG. 12B). Furthermore, whereas IL-1β was associated with increased permeability and aberrant Muc1 expression in T cell transfer colitis (FIGS. 12A&C), TNF-α positively correlated with intestinal permeability and increased Muc13 expression in DSS-induced colitis (FIGS. 12B&D). Besides, the expression levels of Muc13 also correlated with Muc1 ($p=0.013$) and Muc2 ($p=0.026$) expression in the DSS model (data not shown).

Figure 13:
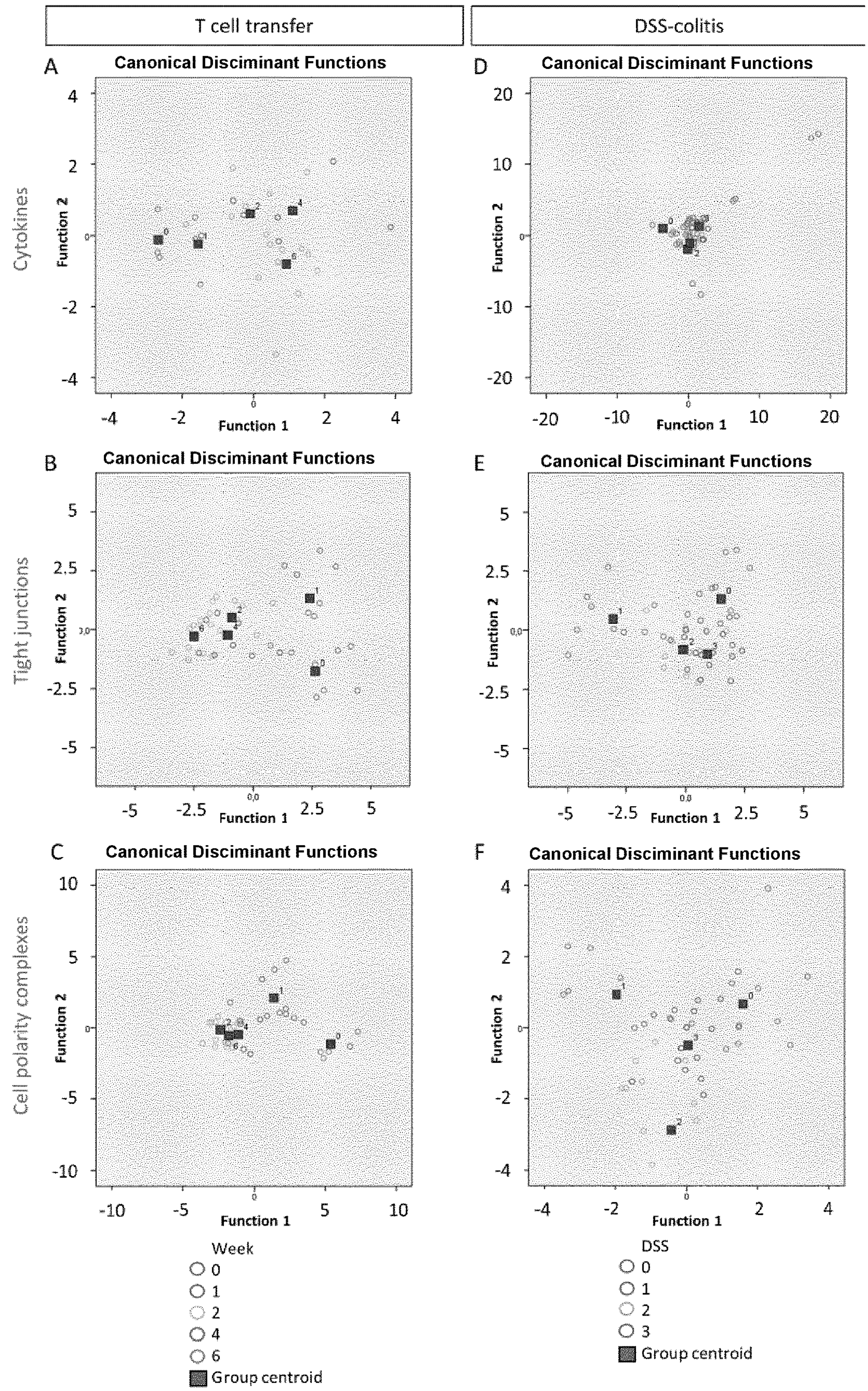
FIG. 13. Discriminant analysis with the expression levels of cytokines, tight junctions and polarity complexes as predictors. A discriminant analysis was performed to predict healthy controls and colitis groups (weeks after T cell transfer/cycles of DSS administration) based on the expression of cytokines (protein), tight junctions (mRNA) and cell polarity proteins (mRNA) in the T cell transfer (A-C) and DSS (D-F) colitis model. The main predictor variables for each function are stated in the legend (Pooled within-groups correlations not shown). Overall, mice sacrificed 1 week after T cell transfer and after DSS cycle 1 could be clearly discriminated from control mice and the other experimental groups. (A) 72,4% of cases were correctly classified based on cytokine expression and was mainly determined by the expression of IL-1β (function 1), TNF-α and IL-6 (function 2). (B) 72.1% of cases were correctly classified based on tight junction expression and was mainly determined by the expression of Ocln (function 1) and Cldn2, Cldn1, Tjp2, Jam2 and Jam2 (function 2). (C) 84,1% of cases were correctly classified based on the expression of cell polarity proteins and was mainly determined by the expression of Par3 (function 1) and Dlg, Patj, Scrib, Llgl1 and Pals1 (function 2). (D) 37.3% of cases were correctly classified based on cytokine expression and was mainly determined by the expression of IL-1β and IL-10 (function 1) and TNF-α (function 2). In this analysis, missing values were converted to mean values, potentially explaining the bad prediction. (E) 76.5% of cases were correctly classified based on tight junction expression and was mainly determined by the expression of Jam2, Cldn2, Jam3, Cldn15, Cldn5, Tjp1 and Cldn1 (function 1) and Tjp3, Ocln and Jam1 (function 2). (F) 64.7% of cases were correctly classified based on the expression of cell polarity subunits and was mainly determined by the expression of Par3 (function 1).

In both colitis models, altered expression of several junctional and polarity proteins correlated significantly with each other (data not shown), further indicating mutual dependence and their involvement in regulating barrier integrity. Moreover, their expression levels could also be used to discriminate between colitis mice and controls (FIG. 13). Furthermore, significant associations 5 between aberrant Muc1, Cldn1, Ocln, Par3 and aPKCζ expression in the T cell transfer model (FIGS. 12E&G) and between aberrant Muc13, Cldn1, Jam2, Tjp2, aPkcç, Crb3 and Scrib expression in the DSS model (FIGS. 12F&H) further suggested a potential role for Muc1 and Muc13 in intestinal mucosal barrier dysfunction.

4. Discussion

The intestinal mucosal barrier plays a critical role in gut health and function. Not only is it a physical barrier between the microbiome, toxins and food antigens in the lumen and the internal host tissues, it also is a dynamic barrier that regulates inflammatory responses. Loss of barrier integrity is generally accepted as a major hallmark in the pathophysiology of IBD. However, whether intestinal barrier dysfunction is a primary contributor to or rather a consequence of intestinal inflammation has not yet been fully elucidated. In this study, we investigated intestinal barrier integrity and inflammation during the course of colitis using the T cell transfer and DSS mouse models. These two models have a different mechanism of initiation of colitis and both are standard IBD models. In both models, increased intestinal permeability in association with an innate inflammatory response, as characterized by increased expression of the pro-inflammatory cytokines TNF-α and IL-1β and decreased expression of the anti-inflammatory cytokine IL-10, was already seen at 1 week post-transfer and after the first DSS administration, and was maintained during the course of disease. Excessive production of TNF-α and IL-1β has been described in IBD patients and these harmful cytokines, produced by T cells, macrophages and neutrophils, are likely to affect intestinal homeostasis leading to further aggravation of inflammation. In our study, increased expression of IL-6 appeared only in later stages of colitis progression. This pro-inflammatory cytokine has been shown to be an important mediator of Th17 cell differentiation, further promoting intestinal inflammation in IBD and modulating intestinal epithelial cells. Also IL-22 was increasingly expressed at the beginning of colitis induction and even at week 6 post-transfer and after the last DSS cycle. This cytokine is normally able to promote mucosal healing in the intestine, but when uncontrolled, it can lead to intestinal inflammation. Based on the above findings, we cannot clearly substantiate whether loss of barrier integrity precedes intestinal inflammation as suggested by several studies, that showed that increased intestinal permeability was present in first-degree relatives of IBD patients before intestinal inflammation occurred. However, expression analysis of junctional proteins and polarity complexes in both our models revealed that most changes already occurred at the beginning of colitis development. This would suggest that loss of barrier integrity is not only a result of an innate inflammatory response but might also be a primary contributor in the pathophysiology of IBD.

The key mediators underlying mucosal barrier dysfunction upon inflammation in IBD still remain to be further elucidated. Often overlooked in intestinal barrier research are the mucins. These heavily glycosylated proteins make up the first part of the barrier, the mucus layer, which is four times thicker than the actual epithelial cell layer and plays an important role in limiting contact between the host and the luminal content. MUC2 is the main component of the secreted mucus layer and provides the first line of defence against invading pathogens and toxins in the intestines. In IBD, this secretory mucin is critical for colonic protection since it has been shown that $Muc2^{-/-}$ mice spontaneously develop colitis. The gradual increase in Muc2 expression seen during the course of colitis in the DSS model can thus be assigned to the host defence to overcome the toxic effects of DSS on the colonic epithelium. Furthermore, this mucin is downregulated in the intestinal mucosae of IBD patients.

Since transmembrane mucins are increasingly expressed in IBD and given their role in signalling pathways involved in cell-cell adhesion and cell differentiation, they are excellent candidates to be involved in the regulation of the barrier function. In our study, expression of the transmembrane Muc1 and Muc13 mucins was increased during colitis progression in both models, whereas Muc4 showed variable expression patterns in the inflamed colon. Variable MUC4 expression has also been reported in IBD patients and increased MUC4 expression was mainly observed in UC patients with neoplastic conditions. Altered expression of MUC1 and MUC13 has been shown in the inflamed mucosa of IBD patients and such inappropriate overexpression induced by pro-inflammatory cytokines could lead to aberrant modulation of mucosal epithelial cell inflammatory signalling, which in turn could lead to pathological inflammation. Furthermore, acute DSS studies with knockout animals showed that $Muc1^{-/-}$ mice were resistant to inflammation-induced colitis whereas $Muc13^{-/-}$ mice developed more inflammation compared to wildtype animals. In our DSS model, Muc13 expression was altered in both the acute and chronic phases of DSS-induced colitis. This increase in expression in the more chronic stage of colitis was also confirmed in the T cell transfer model. Unlike MUC1, MUC13 is highly expressed by the intestinal epithelium playing at first a protective role against cytotoxic agents. Furthermore, Sheng and colleagues (Sheng et al., 2012) demonstrated that MUC13 has a pro-inflammatory activity in the intestinal epithelium modulating inflammatory responses induced by TNF-α. Also, in our DSS models, increased TNF-α expression was significantly associated with altered Muc13 expression, further suggesting that expression of this mucin is regulated by TNF-α upon inflammation and thus, the role of this mucin upon chronic colitis should be further investigated. In addition, we were able to correctly annotate individual mice to their experimental group (i.e. control or different time points of colitis) based on Muc1 and Muc13 expression (FIG. 11). Interestingly, three main clusters could be distinguished in both colitis models. In particular, mice that were sacrificed during the initial stages of colitis (after 1 cycle of DSS administration and after 1 week of T cell transfer) were separated from both the control mice and the other experimental groups. Mice that were sacrificed at later time points could clearly be distinguished from control mice yet were more closely associated. These results further indicate the importance of Muc1 and Muc13 during the course of colitis.

To the best of our knowledge, a clear association between increased expression of transmembrane mucins and barrier dysfunction in IBD, has so far never been reported. Here, we found a positive correlation between increased Muc1 and Muc13 expression and increased in vivo intestinal barrier permeability during colitis progression, which was further substantiated by a strong correlation between expression of these mucins and altered expression of barrier mediators, including junctional and polarity proteins. Also observed was a model-specific response for both mucins, which could be explained by the different mechanisms of colitis induction. Whereas colitis in the T cell transfer model is induced by disrupting systemic T cell homeostasis, DSS is toxic to the intestinal epithelium leading to the penetration of luminal bacteria and antigens through the intestinal barrier resulting in a strong innate inflammatory response. Since MUC13 is highly expressed at the healthy intestinal epithelium, its role in modulating the integrity of the intestinal barrier could be related to immediate threats from the external environment. MUC1, on the other hand, is expressed at low levels in the healthy intestine and thus its involvement in barrier dysfunction could be dependent on the infiltration of T lymphocytes upon an inflammatory stimulus. Another possibility is that subtle differences in cytokine secretion could induce specific changes in mucin expression in both models. Although similar cytokine profiles were associated with disease activity in both models, IL-1β was correlated to increased Muc1 expression and in vivo intestinal permeability in the T cell transfer model and TNF-α to increased Muc13 expression and in vivo intestinal permeability in the DSS-induced colitis model. Nevertheless, based on the above findings, we can conclude that aberrantly expressed Muc1 and Muc13 could play a role in modulating intestinal barrier dysfunction during the course of colitis. Overexpression of transmembrane mucins can result in a repositioning over the whole cell membrane, causing physical hindrance of neighbouring cells to make cell contact[6]. In our control animals, Muc1 and Muc13 were expressed at the apical side of the epithelial membrane, whereas they became generally visible throughout the cell during colitis progression. Transmembrane mucins can affect cell-cell interactions, and thus barrier functionality, in multiple ways. First, via extracellular EGF-like domains and intracellular phosphorylation sites, they can interact with receptor tyrosine kinases, such as ERBB2. Activation of this membrane-bound receptor can then result in a disruption of the PAR polarity complex and subsequent tight junction dysfunction by associating with Par6 and aPKC and blocking the interaction with Par3. In our colitis models, a correlation between increased Muc1 expression and decreased Par3 expression was found suggesting that loss of barrier integrity mediated by Muc1 might be caused by sequestering with ERBB2 and subsequent dissociation of the PAR complex. Interaction of MUC1, but also MUC4 and MUC13, with ERBB2 has been described in many cancer types and the role of ERBB2 in barrier functionality in IBD remains to be further investigated. Second, the cytoplasmic domain of transmembrane mucins can be transported into the nucleus and suppress transcription of crumbs and scribble polarity genes, via interaction with a transcription factor on the promoter of these polarity genes. In this way, loss of cell polarity and tight junction dysfunction can be induced as well. Here, we found a correlation between the expression levels of Muc13, Crb3 and Scrib in the DSS model, highlighting that these mucins could probably also act according to the mechanism described above. Additionally, it has also been described that MUC1 can intracellularly interact with β-catenin, which results in the disruption of the E-cadherin/β-catenin complex and eventually leads to loss of adherens junction stability. In our colitis models, however, increased Muc1 and Muc13 expression was not associated with altered Cdh1 (E-cadherin) expression.

Taken together, the results from our study clearly show the association of aberrant Muc1 and Muc13 expression with intestinal mucosal barrier dysfunction during the course of colitis. A model-specific response was observed, indicating a complex transcriptional regulation of mucin expression that results from the combined effects of the host inflammatory response, the microbiome and the type and course of disease. Nevertheless, the exact mechanisms by which these mucins affect barrier integrity and to prove their functional role in barrier integrity in IBD require further investigation. Most available therapies in IBD are directed against the inflammatory response. Due to the clinical heterogeneity of these diseases, biologicals are limited in efficacy and safety and still a substantial number of patients fail to respond or obtain full remission. Targeting the barrier, and particularly MUC1 and MUC13, could also have therapeutic potential. These transmembrane mucins have already shown their potential in antibody-based therapy in different cancer types, including colon cancer, making them valuable therapeutic targets in medicine. Furthermore, mucins are highly polymorphic and gene polymorphisms affecting mucin expression have been reported to influence susceptibility towards disease. The presence of genetic differences in mucin genes can result in different mRNA isoforms (i.e. splice variants via alternative splicing) produced from the same mucin gene locus. While most isoforms encode similar biological functions, others have the potential to alter the protein function resulting in progression toward disease[16]. So far, only the MUC13-R502S polymorphism has been related to UC and the MUC1-rs3180018 to CD but the MUC1 and MUC13 isoforms associated with IBD remain unknown as well. Inhibiting inflammation-induced MUC1 and MUC13 isoforms to restore intestinal barrier integrity may thus achieve greater efficacy with fewer side effects.

Overall, it is highlighted here that aberrantly expressed Muc1 and Muc13 might be involved in intestinal mucosal barrier dysfunction upon inflammation by affecting tight junction and cell polarity proteins and that they can act as possible targets for novel therapeutic interventions.

Example 2: Targeted PacBio Isoform Sequencing to Analyze Isoform Expression of MUC1 and MUC13 in Colonic Biopsies from IBD Patients

1. Background to the Invention

Here, we analyzed the expression of MUC1 and MUC13 isoforms in inflamed and non-inflamed colonic tissue from patients with active IBD to improve our understanding of mucin signaling during chronic inflammation.

2. Methods

2.1. IBD Patients and Clinical Specimens

IBD patients that underwent an endoscopy for clinical reasons (i.e. the presence of an acute flare), were recruited via the policlinic of the University Hospital of Antwerp (UZA), Belgium. Colonic biopsies were collected from 3 patients with active disease (1 Crohn's disease, 2 ulcerative colitis) and stored in RNA later at −80° C. until further use. All patients were previously diagnosed with IBD based on bowel complaints, blood and stool tests, radiography, endoscopy and histology. Disease activity was mainly based on the presence of active symptoms and endoscopic and microscopic evaluation of the colon. Prior to endoscopy, informed consent from each patient was obtained. This study was approved by the Ethical Committee of the UZA (Belgian Registration number B300201733423).

2.2. RNA Isolation and Quality Control

Total RNA from human colonic tissue stored in RNA later, was extracted using the NucleoSpin® RNA plus kit (Macherey-Nagel) following the manufacturer's instructions. The concentration and purity of the RNA were evaluated using the NanoDrop® ND-1000 UV-Vis Spectrophotometer (Thermo Fisher Scientific) and Qubit Fluorometer (Qubit Broad Range RNA kit, Thermo Fisher Scientific). Quality control of the RNA was performed by capillary electrophoresis using an Agilent 2100 Fragment Analyzer (Agilent).

2.3. cDNA Library Preparation and Multiplexing

Initially, 1600-2000 ng of input RNA per sample was used. The reactions from each sample were first labeled with a barcoded oligo dT nucleotide for multiplexing purposes as shown in Table 1. Subsequently, first-strand cDNA synthesis was performed using the SMARTer PCR cDNA synthesis kit (Takara Bio) according to the manufacturer's instructions. The reactions were then diluted 1:10 in Elution Buffer (PacBio) and large-scale amplification was performed using 16 reactions per sample. Each reaction of 50 μL consisted of 10 μL of the diluted cDNA sample, 10 μL 5×PrimeSTAR GXL buffer (Takara Bio), 4 μL dNTP Mix (2.5 mM each), 1 μL 5' PCR Primer IIA (12 μM), 1 μL PrimeSTAR GXL DNA Polymerase (1.25 U/μL, Takara Bio) and 24 μL nuclease-free water. The samples were then incubated in a thermocyler using the following program: an initial denaturation step at 98° C. for 30 s, followed by 14 cycles of amplification at 98° C. for 10 s, 65° C. for 15 s and 68° C. for 10 min, and a final extension step at 68° C. for 5 min. From these PCR products, two fractions were purified using AMPure magnetic purification beads. After equimolar pooling of both fractions, the samples were finally pooled and the DNA concentration and fragment length evaluated using a Qubit fluorometer (Qubit dsDNA HS kit, ThermoFisher) and an Agilent 2100 Bioanalyzer.

TABLE 1

Barcoded primers used for multiplexing purposes.

| Sample | Barcode | SEQ ID N | Sequence |
|---|---|---|---|
| P1 colon non-inflamed | dT_BC1001_PB | 61 | AAGCAGTGGTATCAACGCAGAGTACCACATATCAG AGTGCGTTTTTTTTTTTTTTTTTTTTTTTTTTTTVN |
| P1 colon inflamed | dT_BC1002_PB | 62 | AAGCAGTGGTATCAACGCAGAGTACACACACAGAC TGTGAGTTTTTTTTTTTTTTTTTTTTTTTTTTTTVN |
| P2 colon non-inflamed | dT_BC1003_PB | 63 | AAGCAGTGGTATCAACGCAGAGTACACACATCTCG TGAGAGTTTTTTTTTTTTTTTTTTTTTTTTTTTTVN |
| P2 colon inflamed | dT_BC1004_PB | 64 | AAGCAGTGGTATCAACGCAGAGTACCACGCACACA CGCGCGTTTTTTTTTTTTTTTTTTTTTTTTTTTTVN |
| P3 colon non-inflamed | dT_BC1005_PB | 65 | AAGCAGTGGTATCAACGCAGAGTACCACTCGACTC TCGCGTTTTTTTTTTTTTTTTTTTTTTTTTTTTTVN |
| P3 colon inflamed | dT_BC1006_PB | 66 | AAGCAGTGGTATCAACGCAGAGTACCATATATATCA GCTGTTTTTTTTTTTTTTTTTTTTTTTTTTTTVN |

*In accordance with the IUPAC nucleotide code, N is meant to be any base (A, G, T or C) and V is meant to be A, C or G.

2.4. CDNA Capture Using SeqCap EZ Probes

Initially, 1 μL of SMARTer PCR oligo (1000 μM) and 1 μL PolyT blocker (1000 μM) were added to 1.5 μg cDNA and subsequently dried for 1 hour in a DNA vacuum-concentrator. The cDNA was then hybridized with pre-designed SeqCap EZ probes targeting several mucin coding regions (Table 2 & 3) for 16 hours at 47° C. The captured cDNA was purified using Dynabeads M-270 (Thermo Fisher Scientific) according to the manufacturer's instructions and amplified by preparing a mixture containing 20 μl 10×LA PCR Buffer, 16 μl 2.5 mM dNTP's, 8.3 SMARTer PCR Oligos (12 μM each), 1.2 μl Takara LA Taq DNA polymerase, 50 μl cDNA supplemented with nuclease-free water to an end volume of 200 μl. For the actual PCR, the following program was ran on a thermocycler: an initial denaturation step at 95° C. for 2 min, followed by 11 cycles of amplification at 95° C. for 20 s and 68° C. for 10 min, and a final extension step at 72° C. for 10 min. A final clean-up of the amplified captured cDNA was performed using AMPure purification beads. The DNA concentration and fragment length were evaluated using a Qubit fluorometer (Qubit dsDNA HS kit, ThermoFisher) and an Agilent 2100 Bioanalyzer for subsequent SMRTbell library construction.

TABLE 2

Genomic regions targeted with SeqCap EZ probes.

| Mucin | Chromosome | Chromosomal location (GRCh38/hg38 genome annotation) |
|---|---|---|
| MUC1 | Chr 1 | 155,185,324-155,193,416 |
| MUC2 | Chr11 | 1,074,375-1,111,008 |
| MUC3-MUC12-MUC17 | Chr7 | 100,944,420-101,074,859 |
| MUC4 | Chr3 | 195,746,558-195,826,889 |
| MUC5AC-MUC5B | Chr11 | 1,146,953-1,272,672 |
| MUC6 | Chr11 | 1,012,323-1,037,218 |
| MUC13 | Chr3 | 124,905,442-124,940,751 |
| MUC15 | Chr11 | 26,558,532-26,572,763 |
| MUC16 | Chr19 | 8,848,344-9,001,342 |
| MUC20 | Chr3 | 195,720,384-195,738,123 |

TABLE 3

SeqCap EZ probe coverage of targeted mucin regions.

| | Probe coverage | Estimated coverage |
|---|---|---|
| Target Bases Covered | 493.161 (78.7%) | 561.699 (89.7%) |
| Target Bases Not Covered | 133.225 (21.3%) | 64.687 (10.3%) |

2.5. SMRTbell Library Construction and Sequencing on the PacBio Sequel System

Using the SMRTbell template prep kit (PacBio), 5 μg of captured cDNA was used for SMRTbell library construction. According to the manufacturer's instructions, the following steps were performed in chronological order: DNA damage repair, end repair, ligation of blunt adapters, Exo III and Exo VII treatment. One intermediate and two final purification steps were performed using AMPure purification beads. The DNA concentration and fragment length were evaluated using a Qubit fluorometer (Qubit dsDNA HS kit, ThermoFisher) and an Agilent 2100 Bioanalyzer for subsequent SMRTbell library construction. Following the instructions on SMRTlink, the Sequel Binding kit (PacBio) and Sequel Sequencing kit (PacBio) were used to dilute the DNA and internal control complexes, anneal the sequencing primer and bind the sequencing polymerase to the SMRTbell templates. Finally, the sample was loaded on a 1M v3 SMRT cell.

2.6. Data Analysis

Highly accurate (>99%) polished circular consensus sequencing (ccs) reads were used as initial input for data processing using the command line interface. The lima tool v1.10.0 was used for demultiplexing and primer removal. Subsequently, the isoseq3 v3.2.2 package was used for further read processing to generate high quality mRNA transcripts. First, the refine tool was used for trimming of Poly(A) tails and identification and removal of concatemers. The data of the individual samples were then pooled together according to the condition (i.e. 3 samples from non-inflamed tissue, 3 samples from inflamed tissue or all samples together) and analyzed in parallel. The isoseq3 cluster algorithm was used for transcript clustering. Minimap2 was used for the alignment of the processed reads to the human reference genome (GRCh38). After mapping, ToFU scripts from the cDNA_Cupcake GitHub repository were used to collapse redundant isoforms (minimal alignment coverage and minimal alignment identity set at 0.95), identify associated count information and filter away 5' degraded isoforms. Finally, the SQANTI2 tool was used for extensive characterization of MUC1 and MUC13 mRNA isoforms. The eventual isoforms were then further inspected by visualization in the Integrative Genomics Viewer (IGV) version 2.8.0 and by the analysis of the classification and junction files in Excel.

3. Results 3.1. Patient and Sample Characteristics

The samples were collected from the colon of 3 patients with known and active IBD, of which two were diagnosed with ulcerative colitis and one with Crohn's disease. Year of diagnosis and medication use was different for all patients. During endoscopy, the samples were collected from a macroscopically inflamed region in the colon and from an adjacent macroscopically non-inflamed region. A detailed overview of the patient characteristics as well as the location of the colon biopsies is shown in table 4.

TABLE 4

Summary of patient characteristics and primary disease location from which biopsies were collected.

| Patient | Sex | Age | Diagnosis | Years since diagnosis | Primary medication use | Primary disease location |
|---|---|---|---|---|---|---|
| Patient 1 | Female | 34 | Crohn's disease | 20 | Remicade | Rectum |
| Patient 2 | Female | 36 | Ulcerative colitis | 10 | No | Rectum/anus |
| Patient 3 | Female | 45 | Ulcerative colitis | 3 | Mesalamine | Sigmoid and descending colon |

3.2. General Features of Sequencing Run

Sequencing of all samples initially generated 103 699 ccs reads. Sequencing yield and read quality was high and comparable across all samples. The average read length was 2082 bp. 24592 (24%) reads were lost during primer removal and demultiplexing as a consequence of undesired barcoded primer combinations. After clustering, 55312 reads were remained corresponding to 6617 different transcripts. As visual analysis of targeted mucin regions in IGV showed complete and dense coverage of the full genomic region of only MUC1 and MUC13, further analysis was limited to these two mucin glycoproteins.

3.3. MUC1 Isoforms

Figure 14:
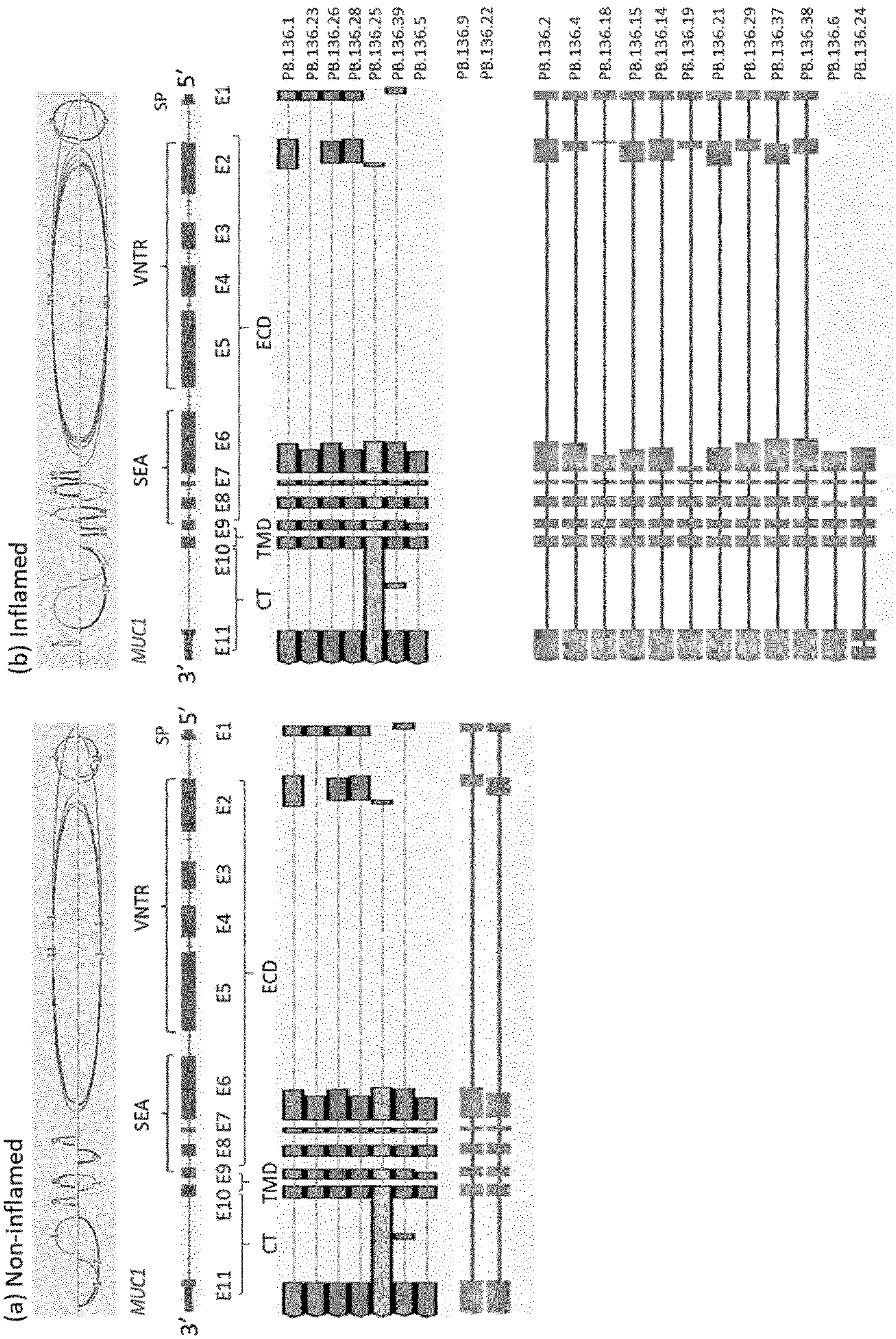
FIG. 14: Alternative mRNA transcripts of MUC1 in (a) non-inflamed and (b) inflamed colonic tissue from IBD patients. The upper panel indicates a Sashimi plot to summarize the splice junctions in the alternative mRNA transcripts. The gene structure highlighted in blue illustrates the overall exonic structure of MUC1 with the corresponding exon numbers and coding domains (CT=cytoplasmic tail; TMD=transmembrane domain; ECD=extracellular domain; EGF=epidermal growth factor; SEA=sea urchin sperm protein, enterokinase and agrin; VNTR=variable number tandem repeat; SP=signal peptide). The coloured transcripts are found in both non-inflamed and inflamed intestinal tissue. The gray mRNA transcripts highlight transcripts that are found in only one condition (i.e. inflamed or non-inflamed). On the right panel, the isoform identity number can be found of which the details are shown in table 5 (n=3 paired samples).

Targeted PacBio isoform sequencing revealed the identification of both known and novel MUC1 isoforms in colonic tissue from IBD patients that were all found to be coding transcripts (FIG. 14 & Table 5). In particular, 7 alternative mRNA transcripts (=isoforms) were found in both non-inflamed and inflamed colonic tissue, of which 1 (PB.136.39) matched to a known isoform (ENST00000462317.5) and 6 had not been described elsewhere. Interestingly, from these alternative transcripts, 3 were increased in expression based on the read counts in the inflamed tissue as compared to the non-inflamed tissue (PB.136.1, PB.136.25, PB.136.28). Additionally, 2 other novel isoforms were found which were only reported in non-inflamed colonic tissue, whereas in the inflamed colonic tissue, 1 known (PB.136.19, ENST00000368390.7) and 11 novel alternative transcripts were found. Interestingly, 2 newly identified isoforms showed dominant expression in the inflamed tissue (PB.136.2, PB.136.15). Concerning the overall exonic structure of the alternative transcripts, no transcripts were found that contained exon 3 to 5 (VNTR). Exon 2 (VNTR) and exon 6 (SEA domain) were most prone to alternative splicing in both non-inflamed and inflamed colonic tissue (FIG. 14 & Table 5). All novel alternative transcripts found resulted from the partial retention of intronic regions (Table 5). A detailed overview of splice junctions can be found in supplementary table S2.

The results of these limited number of samples clearly shows that different alternative transcripts of MUC1 are formed in the colon and that inflammation stimulates alternative splicing as well as increasing the expression of particular transcripts. This is the first study that highlights the potential importance of MUC1 isoforms in IBD. Only in cancer research, a few papers investigating the pathogenic significance of MUC1 splice variants are available. More specifically, it has been shown that different MUC1 isoforms might interact together to form a ligand-receptor complex, associate with other host receptors or influence cytokine expression mediating inflammatory signaling pathways (Zaretsky et al., 2006). Alternative splicing of MUC1 isoforms was also shown to be cancer-type dependent and able to distinguish cancer samples from benign samples (Obermair et al., 2002). In breast cancer, for instance, it has been described that a shorter MUC1 isoform was specifically expressed in tumor tissue but not in the adjacent healthy tissue (Zrihan-Licht et al., 1994), whereas estrogen treatment induced the expression of another variant (Zartesky et al., 2006). All this highlight the intriguing complexity and biological role of alternative splicing.

TABLE 5

Detailed overview of characteristics of MUC1 mRNA isoforms in colonic biopsies from IBD patients

| Isoform ID | Chrom | Length (bp) | Exons | Coding | Transcript | Main mechanism of alternative splicing | Counts |
|---|---|---|---|---|---|---|---|
| **Both conditions** | | | | | | | |
| PB.136.1 | chr1 | 1712 | 8 | Coding | Novel | Intron retention | NI: 3<br>I: 11 |
| PB.136.23 | chr1 | 1257 | 7 | Coding | Novel | Intron retention | NI: 8<br>I: 9 |
| PB.136.26 | chr1 | 1619 | 8 | Coding | Novel | Intron retention | NI: 2<br>I: 5 |
| PB.136.28 | chr1 | 1551 | 8 | Coding | Novel | Intron retention | NI: 8<br>I: 21 |
| PB.136.25 | chr1 | 2306 | 6 | Coding | Novel | Intron retention | NI: 5<br>I: 15 |
| PB.136.39 | chr1 | 1377 | 8 | Coding | ENST00000462317.5 | Multi-exon | NI: 3<br>I: 3 |
| PB.136.5 | chr1 | 1090 | 6 | Coding | Novel | Intron retention | NI: 2<br>I: 3 |
| **Non-inflamed** | | | | | | | |
| Isoform ID | Chrom | Length (bp) | Exons | Coding | Transcript | subcategory | Counts |
| PB.136.9 | chr1 | 1497 | 8 | Coding | Novel | Intron retention | 7 |
| PB.136.22 | chr1 | 1493 | 8 | Coding | Novel | Intron retention | 2 |
| **Inflamed** | | | | | | | |
| Isoform ID | Chrom | Length (bp) | Exons | Coding | Transcript | subcategory | Counts |
| PB.136.2 | chr1 | 1652 | 8 | Coding | Novel | Intron retention | 30 |
| PB.136.4 | chr1 | 1470 | 8 | Coding | Novel | Intron retention | 2 |
| PB.136.18 | chr1 | 1233 | 8 | Coding | Novel | Intron retention | 2 |
| PB.136.15 | chr1 | 1526 | 8 | Coding | Novel | Intron retention | 24 |
| PB.136.14 | chr1 | 1564 | 8 | Coding | Novel | Intron retention | 3 |
| PB.136.19 | chr1 | 1141 | 8 | Coding | ENST00000368390.7 | Multi-exon | 3 |
| PB.136.21 | chr1 | 1590 | 8 | Coding | Novel | Intron retention | 3 |

TABLE 5-continued

| Detailed overview of characteristics of MUC1 mRNA isoforms in colonic biopsies from IBD patients | | | | | | | |
|---|---|---|---|---|---|---|---|
| PB.136.29 | chr1 | 1493 | 8 | Coding | Novel | Intron retention | 2 |
| PB.136.37 | chr1 | 1640 | 8 | Coding | Novel | Intron retention | 2 |
| PB.136.38 | chr1 | 1583 | 8 | Coding | Novel | Intron retention | 5 |
| PB.136.6 | chr1 | 1055 | 6 | Coding | Novel | Intron retention | 3 |
| PB.136.24 | chr1 | 1088 | 7 | Coding | Novel | Intron retention | 2 |

3.4. MUC13 Isoforms

Figure 15:
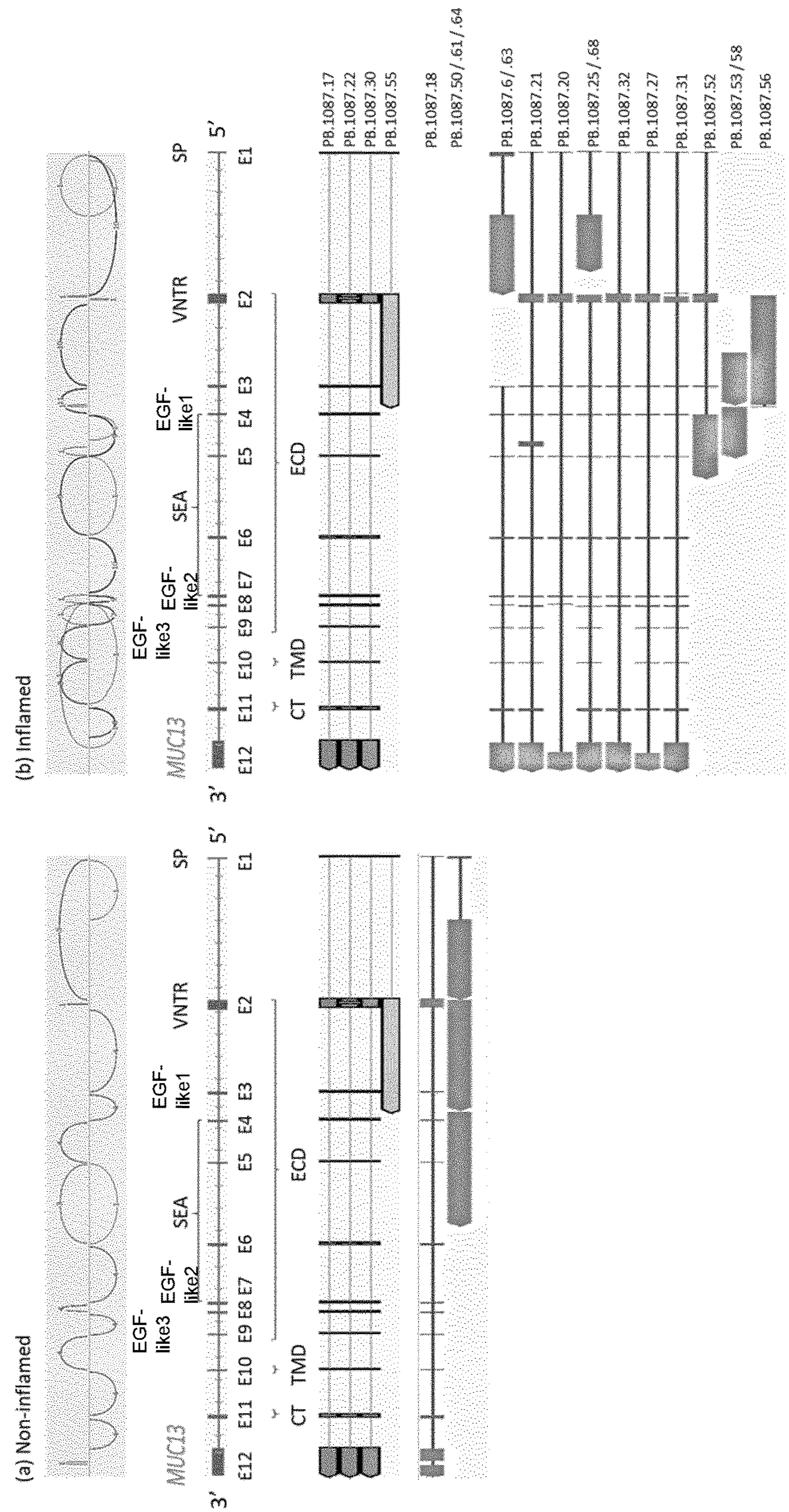
FIG. 15: Alternative mRNA transcripts of MUC13 in (a) non-inflamed and (b) inflamed colonic tissue from IBD patients. The upper panel indicates a Sashimi plot to summarize the splice junctions in the alternative mRNA transcripts. The gene structure highlighted in blue illustrates the overall exonic structure of MUC13 with the corresponding exon numbers and coding domains (CT=cytoplasmic tail; TMD=transmembrane domain; ECD=extracellular domain; EGF=epidermal growth factor; SEA=sea urchin sperm protein, enterokinase and agrin; VNTR=variable number tandem repeat; SP=signal peptide). The coloured transcripts are found in both non-inflamed and inflamed intestinal tissue.

Twenty-one alternative MUC13 mRNA transcripts were found in colonic tissue from IBD patients (FIG. 15 & Table 6). Of these, 17 transcripts were identified as being coding isoforms and 4 as non-coding splice variants. Such long untranslated mucin isoforms can function similar to long noncoding RNA and act as a scaffold for assembly of multimeric protein complexes involved in the regulation of cellular processes. Importantly, the full-length known isoform (ENST00000616727.4) was present in both conditions but was highly upregulated in the inflamed colonic tissue (Table 6).

In both conditions, 3 additional isoforms were found that had not been reported previously. Other isoforms showed a condition-specific expression pattern. More specifically, 4 mRNA isoforms were uniquely found in the non-inflamed tissue, whereas 13 mRNA isoforms were only reported in the inflamed colonic tissue. Several mechanisms of alternative splicing were identified concerning MUC13 isoforms. Exon skipping was observed in two alternative transcripts in the inflamed colon (i.e. exon 9 (EGF-like) and 10 (TMD) in PB.1087.32; exon 9 (EGF-like), 10 (TMD) and 11 (CT) in PB.1087.20). Some mono-exonic transcripts were found that resulted from intron retention in the genomic region coding for the ECD (i.e. PB.1087.50, PB.1087.53, PB.1087.58, PB.1087.61). The other isoforms resulted from more subtle recombinations using both known and novel splice sites mainly in the ECD-coding regions of MUC13 (FIG. 15 & Table 6). A detailed overview of all splice junctions can be found in Supplementary table S3.

To our knowledge, the heterogeneity of MUC13 isoform expression during inflammation and cancer has not been studied in much detail before. Here, evidence is provided that MUC13 is alternatively spliced in both non-inflamed and inflamed colonic tissue from IBD patients.

TABLE 6

Detailed overview of characteristics of MUC13 mRNA isoforms in colonic biopsies from IBD patients

| Isoform ID | Chrom | Strand | Length (bp) | Exons | Coding | Transcript | Main mechanism of alternative splicing | Counts |
|---|---|---|---|---|---|---|---|---|
| Both conditions | | | | | | | | |
| PB.1087.17 | chr3 | — | 2878 | 12 | Coding | ENST00000616727.4 | Constitutive | NI: 518<br>I: 936 |
| PB.1087.22 | chr3 | — | 2830 | 13 | Coding | Novel | At least one novel splicesite | NI: 3<br>I: 7 |
| PB.1087.30 | chr3 | — | 2859 | 12 | Coding | Novel | At least one novel splicesite | NI: 2<br>I: 2 |
| PB.1087.55 | chr3 | — | 5414 | 3 | Coding | Novel | Intron retention | NI: 2<br>I: 4 |
| Non-inflamed | | | | | | | | |
| PB.1087.18 | chr3 | — | 2725 | 13 | Coding | Novel | At least one novel splicesite | 2 |
| PB.1087.50 | chr3 | — | 5304 | 1 | Non-coding | Novel | Mono-exon/intron retention | 2 |
| PB.1087.61 | chr3 | — | 5106 | 1 | Coding | Nove | Mono-exon/intron retention | 2 |
| PB.1087.64 | chr3 | — | 3860 | 2 | Coding | Novel | At least one novel splicesite | 3 |
| Inflamed | | | | | | | | |
| PB.1087.6 | chr3 | — | 2243 | 10 | Coding | Novel | At least one novel splicesite | 2 |
| PB.1087.63 | chr3 | — | 3962 | 2 | Coding | Novel | At least one novel splicesite | 2 |
| PB.1087.21 | chr3 | — | 3195 | 13 | Coding | Novel | At least one novel splicesite | 2 |
| PB.1087.20 | chr3 | — | 1979 | 9 | Coding | Novel | At least one novel splicesite | 2 |
| PB.1087.25 | chr3 | — | 2671 | 11 | Coding | Novel | At least one novel splicesite | 2 |
| PB.1087.68 | chr3 | — | 2643 | 2 | Coding | Novel | At least one novel splicesite | 2 |
| PB.1087.32 | chr3 | — | 2754 | 10 | Coding | Novel | Novel combination of known splicesites | 8 |

TABLE 6-continued

| Detailed overview of characteristics of MUC13 mRNA isoforms in colonic biopsies from IBD patients | | | | | | | | |
|---|---|---|---|---|---|---|---|---|
| Isoform ID | Chrom | Strand | Length (bp) | Exons | Coding | Transcript | Main mechanism of alternative splicing | Counts |
| PB.1087.27 | chr3 | | 2328 | 12 | Coding | Novel | At least one novel splicesite | 2 |
| PB.1087.31 | chr3 | — | 2795 | 13 | Coding | Novel | At least one novel splicesite | 2 |
| PB.1087.52 | chr3 | — | 3622 | 4 | Coding | Novel | Intron retention | 2 |
| PB.1087.53 | chr3 | — | 2303 | 1 | Non-coding | Novel | Mono-exon/intron retention | 2 |
| PB.1087.58 | chr3 | — | 2362 | 1 | Non-coding | Novel | Mono-exon/intron retention | 4 |
| PB.1087.56 | chr3 | — | 5246 | 2 | Coding | Novel | Intron retention | 3 |

4. Concluding Remarks

Based on the PacBio isoform sequencing data gathered from a limited number of samples, we were able to identify both known and novel mRNA isoforms of MUC1 and MUC13 in non-inflamed and inflamed colonic tissue from IBD patients. Alternative splicing of MUC1 and MUC13 mucin genes was clearly increased upon inflammation. Although some isoforms were found in both inflamed and non-inflamed tissue, several other isoforms were uniquely attributed to inflammation.

In conclusion, mucin isoform expression is altered upon inflammation in IBD patients, highlighting its potential for disease surveillance or treatment. Moreover, these novel insights could be extrapolated to other inflammatory diseases and cancer that involve a dysfunctional mucosal epithelial barrier. The unexplored world of mucin isoforms provides thus a unique opportunity to understand their biological significance, utility as biomarker and pathology-specific targeting.

| Supplementary table S2: Detailed overview of splice junctions of MUC1 alternative mRNA transcripts | | | | | | | | |
|---|---|---|---|---|---|---|---|---|
| isoform | Chrom. | strand | junction_number | genomic_start_coord | genomic_end_coord | junction_category | splice_site | canonical |
| Both conditions | | | | | | | | |
| PB.136.1 | chr1 | — | junction_1 | 155186210 | 155187224 | known | GTAG | canonical |
| PB.136.1 | chr1 | — | junction_2 | 155187375 | 155187454 | known | GTAG | canonical |
| PB.136.1 | chr1 | — | junction_3 | 155187577 | 155187721 | known | GTAG | canonical |
| PB.136.1 | chr1 | — | junction_4 | 155187859 | 155188007 | known | GTAG | canonical |
| PB.136.1 | chr1 | — | junction_5 | 155188064 | 155188162 | known | GTAG | canonical |
| PB.136.1 | chr1 | — | junction_6 | 155188528 | 155191938 | novel | CCAG | non_canonical |
| PB.136.1 | chr1 | — | junction_7 | 155192311 | 155192785 | known | GTAG | canonical |
| PB.136.23 | chr1 | — | junction_1 | 155186210 | 155187224 | known | GTAG | canonical |
| PB.136.23 | chr1 | — | junction_2 | 155187375 | 155187454 | known | GTAG | canonical |
| PB.136.23 | chr1 | — | junction_3 | 155187577 | 155187721 | known | GTAG | canonical |
| PB.136.23 | chr1 | — | junction_4 | 155187859 | 155188007 | known | GTAG | canonical |
| PB.136.23 | chr1 | — | junction_5 | 155188064 | 155188162 | known | GTAG | canonical |
| PB.136.23 | chr1 | — | junction_6 | 155188452 | 155192787 | novel | AGAG | non_canonical |
| PB.136.26 | chr1 | — | junction_2 | 155187375 | 155187454 | known | GTAG | canonical |
| PB.136.26 | chr1 | — | junction_3 | 155187577 | 155187721 | known | GTAG | canonical |
| PB.136.26 | chr1 | — | junction_4 | 155187859 | 155188007 | known | GTAG | canonical |
| PB.136.26 | chr1 | — | junction_5 | 155188064 | 155188162 | known | GTAG | canonical |
| PB.136.26 | chr1 | — | junction_6 | 155188538 | 155192008 | novel | ACCC | non_canonical |
| PB.136.26 | chr1 | — | junction_7 | 155192284 | 155192785 | known | GTAG | canonical |
| PB.136.28 | chr1 | — | junction_1 | 155186210 | 155187224 | known | GTAG | canonical |
| PB.136.28 | chr1 | — | junction_2 | 155187375 | 155187454 | known | GTAG | canonical |
| PB.136.28 | chr1 | — | junction_3 | 155187577 | 155187721 | known | GTAG | canonical |
| PB.136.28 | chr1 | — | junction_4 | 155187859 | 155188007 | known | GTAG | canonical |
| PB.136.28 | chr1 | — | junction_5 | 155188064 | 155188162 | known | GTAG | canonical |
| PB.136.28 | chr1 | — | junction_6 | 155188452 | 155192017 | novel | GGAG | non_canonical |
| PB.136.28 | chr1 | — | junction_7 | 155192311 | 155192785 | known | GTAG | canonical |
| PB.136.25 | chr1 | — | junction_1 | 155187375 | 155187454 | known | GTAG | canonical |
| PB.136.25 | chr1 | — | junction_2 | 155187577 | 155187721 | known | GTAG | canonical |
| PB.136.25 | chr1 | — | junction_3 | 155187859 | 155188007 | known | GTAG | canonical |
| PB.136.25 | chr1 | — | junction_4 | 155188064 | 155188162 | known | GTAG | canonical |
| PB.136.25 | chr1 | — | junction_5 | 155188557 | 155191967 | novel | GCAG | canonical |
| PB.136.39 | chr1 | — | junction_1 | 155186210 | 155186729 | known | GTAG | canonical |
| PB.136.39 | chr1 | — | junction_2 | 155186805 | 155187224 | known | GTAG | canonical |
| PB.136.39 | chr1 | — | junction_3 | 155187375 | 155187454 | known | GTAG | canonical |
| PB.136.39 | chr1 | — | junction_4 | 155187577 | 155187721 | known | GTAG | canonical |
| PB.136.39 | chr1 | — | junction_5 | 155187859 | 155188007 | known | GTAG | canonical |
| PB.136.39 | chr1 | — | junction_6 | 155188064 | 155188162 | known | GTAG | canonical |
| PB.136.39 | chr1 | — | junction_7 | 155188541 | 155192863 | novel | CCCC | non_canonical |

-continued

Supplementary table S2: Detailed overview of splice junctions of MUC1 alternative mRNA transcripts

| isoform | Chrom. | strand | junction_ number | genomic_ start_coord | genomic_ end_coord | junction_ category | splice_ site | canonical |
|---|---|---|---|---|---|---|---|---|
| PB.136.5 | chr1 | — | junction_1 | 155186210 | 155187224 | known | GTAG | canonical |
| PB.136.5 | chr1 | — | junction_2 | 155187375 | 155187454 | known | GTAG | canonical |
| PB.136.5 | chr1 | — | junction_3 | 155187545 | 155187721 | known | GTAG | canonical |
| PB.136.5 | chr1 | — | junction_4 | 155187859 | 155188007 | known | GTAG | canonical |
| PB.136.5 | chr1 | — | junction_5 | 155188064 | 155188162 | known | GTAG | canonical |
| Non-inflamed | | | | | | | | |
| PB.136.9 | chr1 | — | junction_1 | 155186210 | 155187224 | known | GTAG | canonical |
| PB.136.9 | chr1 | — | junction_2 | 155187375 | 155187454 | known | GTAG | canonical |
| PB.136.9 | chr1 | — | junction_3 | 155187577 | 155187721 | known | GTAG | canonical |
| PB.136.9 | chr1 | — | junction_4 | 155187859 | 155188007 | known | GTAG | canonical |
| PB.136.9 | chr1 | — | junction_5 | 155188064 | 155188162 | known | GTAG | canonical |
| PB.136.9 | chr1 | — | junction_6 | 155188533 | 155192128 | novel | ACCC | non_canonical |
| PB.136.9 | chr1 | — | junction_7 | 155192284 | 155192785 | known | GTAG | canonical |
| PB.136.22 | chr1 | — | junction_1 | 155186210 | 155187224 | known | GTAG | canonical |
| PB.136.22 | chr1 | — | junction_2 | 155187375 | 155187454 | known | GTAG | canonical |
| PB.136.22 | chr1 | — | junction_3 | 155187577 | 155187721 | known | GTAG | canonical |
| PB.136.22 | chr1 | — | junction_4 | 155187859 | 155188007 | known | GTAG | canonical |
| PB.136.22 | chr1 | — | junction_5 | 155188064 | 155188162 | known | GTAG | canonical |
| PB.136.22 | chr1 | — | junction_6 | 155188467 | 155192028 | novel | GGAA | non_canonical |
| PB.136.22 | chr1 | — | junction_7 | 155192248 | 155192785 | novel | GTAG | canonical |
| Inflamed | | | | | | | | |
| PB.136.2 | chr1 | — | junction_1 | 155186210 | 155187224 | known | GTAG | canonical |
| PB.136.2 | chr1 | — | junction_2 | 155187375 | 155187454 | known | GTAG | canonical |
| PB.136.2 | chr1 | — | junction_3 | 155187577 | 155187721 | known | GTAG | canonical |
| PB.136.2 | chr1 | — | junction_4 | 155187859 | 155188007 | known | GTAG | canonical |
| PB.136.2 | chr1 | — | junction_5 | 155188064 | 155188162 | known | GTAG | canonical |
| PB.136.2 | chr1 | — | junction_6 | 155188538 | 155192008 | novel | ACCC | non_canonical |
| PB.136.2 | chr1 | — | junction_7 | 155192311 | 155192785 | known | GTAG | canonical |
| PB.136.4 | chr1 | — | junction_1 | 155186210 | 155187224 | known | GTAG | canonical |
| PB.136.4 | chr1 | — | junction_2 | 155187375 | 155187454 | known | GTAG | canonical |
| PB.136.4 | chr1 | — | junction_3 | 155187577 | 155187721 | known | GTAG | canonical |
| PB.136.4 | chr1 | — | junction_4 | 155187859 | 155188007 | known | GTAG | canonical |
| PB.136.4 | chr1 | — | junction_5 | 155188064 | 155188162 | known | GTAG | canonical |
| PB.136.4 | chr1 | — | junction_6 | 155188528 | 155192153 | novel | CCAG | non_canonical |
| PB.136.4 | chr1 | — | junction_7 | 155192284 | 155192785 | known | GTAG | canonical |
| PB.136.18 | chr1 | — | junction_1 | 155186210 | 155187224 | known | GTAG | canonical |
| PB.136.18 | chr1 | — | junction_2 | 155187375 | 155187454 | known | GTAG | canonical |
| PB.136.18 | chr1 | — | junction_3 | 155187577 | 155187721 | known | GTAG | canonical |
| PB.136.18 | chr1 | — | junction_4 | 155187859 | 155188007 | known | GTAG | canonical |
| PB.136.18 | chr1 | — | junction_5 | 155188064 | 155188162 | known | GTAG | canonical |
| PB.136.18 | chr1 | — | junction_6 | 155188375 | 155192244 | novel | GATG | non_canonical |
| PB.136.18 | chr1 | — | junction_7 | 155192284 | 155192785 | known | GTAG | canonical |
| PB.136.15 | chr1 | — | junction_1 | 155186210 | 155187224 | known | GTAG | canonical |
| PB.136.15 | chr1 | — | junction_2 | 155187375 | 155187454 | known | GTAG | canonical |
| PB.136.15 | chr1 | — | junction_3 | 155187577 | 155187721 | known | GTAG | canonical |
| PB.136.15 | chr1 | — | junction_4 | 155187859 | 155188007 | known | GTAG | canonical |
| PB.136.15 | chr1 | — | junction_5 | 155188064 | 155188162 | known | GTAG | canonical |
| PB.136.15 | chr1 | — | junction_6 | 155188452 | 155192017 | novel | GGAG | non_canonical |
| PB.136.15 | chr1 | — | junction_7 | 155192284 | 155192785 | known | GTAG | canonical |
| PB.136.14 | chr1 | — | junction_1 | 155186210 | 155187224 | known | GTAG | canonical |
| PB.136.14 | chr1 | — | junction_2 | 155187375 | 155187454 | known | GTAG | canonical |
| PB.136.14 | chr1 | — | junction_3 | 155187577 | 155187721 | known | GTAG | canonical |
| PB.136.14 | chr1 | — | junction_4 | 155187859 | 155188007 | known | GTAG | canonical |
| PB.136.14 | chr1 | — | junction_5 | 155188064 | 155188162 | known | GTAG | canonical |
| PB.136.14 | chr1 | — | junction_6 | 155188471 | 155192025 | novel | CAGC | non_canonical |
| PB.136.14 | chr1 | — | junction_7 | 155192311 | 155192785 | known | GTAG | canonical |
| PB.136.19 | chr1 | — | junction_1 | 155186210 | 155187224 | known | GTAG | canonical |
| PB.136.19 | chr1 | — | junction_2 | 155187375 | 155187454 | known | GTAG | canonical |
| PB.136.19 | chr1 | — | junction_3 | 155187577 | 155187721 | known | GTAG | canonical |
| PB.136.19 | chr1 | — | junction_4 | 155187859 | 155188007 | known | GTAG | canonical |
| PB.136.19 | chr1 | — | junction_5 | 155188064 | 155188162 | known | GTAG | canonical |
| PB.136.19 | chr1 | — | junction_6 | 155188232 | 155192182 | known | GTAG | canonical |
| PB.136.19 | chr1 | — | junction_7 | 155192284 | 155192785 | known | GTAG | canonical |
| PB.136.21 | chr1 | — | junction_1 | 155186210 | 155187224 | known | GTAG | canonical |
| PB.136.21 | chr1 | — | junction_2 | 155187375 | 155187454 | known | GTAG | canonical |
| PB.136.21 | chr1 | — | junction_3 | 155187577 | 155187721 | known | GTAG | canonical |
| PB.136.21 | chr1 | — | junction_4 | 155187859 | 155188007 | known | GTAG | canonical |
| PB.136.21 | chr1 | — | junction_5 | 155188064 | 155188162 | known | GTAG | canonical |
| PB.136.21 | chr1 | — | junction_6 | 155188467 | 155191967 | novel | GCAA | non_canonical |
| PB.136.21 | chr1 | — | junction_7 | 155192284 | 155192785 | known | GTAG | canonical |
| PB.136.29 | chr1 | — | junction_1 | 155186210 | 155187224 | known | GTAG | canonical |

-continued

Supplementary table S2: Detailed overview of splice junctions of MUC1 alternative mRNA transcripts

| isoform | Chrom. | strand | junction_ number | genomic_ start_coord | genomic_ end_coord | junction_ category | splice_ site | canonical |
|---|---|---|---|---|---|---|---|---|
| PB.136.29 | chr1 | — | junction_2 | 155187375 | 155187454 | known | GTAG | canonical |
| PB.136.29 | chr1 | — | junction_3 | 155187577 | 155187721 | known | GTAG | canonical |
| PB.136.29 | chr1 | — | junction_4 | 155187859 | 155188007 | known | GTAG | canonical |
| PB.136.29 | chr1 | — | junction_5 | 155188064 | 155188162 | known | GTAG | canonical |
| PB.136.29 | chr1 | — | junction_6 | 155188528 | 155192153 | novel | CCAG | non_canonical |
| PB.136.29 | chr1 | — | junction_7 | 155192311 | 155192785 | known | GTAG | canonical |
| PB.136.37 | chr1 | — | junction_1 | 155186210 | 155187224 | known | GTAG | canonical |
| PB.136.37 | chr1 | — | junction_2 | 155187375 | 155187454 | known | GTAG | canonical |
| PB.136.37 | chr1 | — | junction_3 | 155187577 | 155187721 | known | GTAG | canonical |
| PB.136.37 | chr1 | — | junction_4 | 155187859 | 155188007 | known | GTAG | canonical |
| PB.136.37 | chr1 | — | junction_5 | 155188064 | 155188162 | known | GTAG | canonical |
| PB.136.37 | chr1 | — | junction_6 | 155188580 | 155191990 | novel | GTGT | non_canonical |
| PB.136.37 | chr1 | — | junction_7 | 155192248 | 155192785 | novel | GTAG | canonical |
| PB.136.38 | chr1 | — | junction_1 | 155186210 | 155187224 | known | GTAG | canonical |
| PB.136.38 | chr1 | — | junction_2 | 155187375 | 155187454 | known | GTAG | canonical |
| PB.136.38 | chr1 | — | junction_3 | 155187577 | 155187721 | known | GTAG | canonical |
| PB.136.38 | chr1 | — | junction_4 | 155187859 | 155188007 | known | GTAG | canonical |
| PB.136.38 | chr1 | — | junction_5 | 155188064 | 155188162 | known | GTAG | canonical |
| PB.136.38 | chr1 | — | junction_6 | 155188580 | 155192110 | novel | GTGT | non_canonical |
| PB.136.38 | chr1 | — | junction_7 | 155192311 | 155192785 | known | GTAG | canonical |
| PB.136.6 | chr1 | — | junction_1 | 155186210 | 155187224 | known | GTAG | canonical |
| PB.136.6 | chr1 | — | junction_2 | 155187375 | 155187454 | known | GTAG | canonical |
| PB.136.6 | chr1 | — | junction_3 | 155187577 | 155187721 | known | GTAG | canonical |
| PB.136.6 | chr1 | — | junction_4 | 155187804 | 155188007 | novel | GTAT | non_canonical |
| PB.136.6 | chr1 | — | junction_5 | 155188064 | 155188162 | known | GTAG | canonical |
| PB.136.24 | chr1 | — | junction_1 | 155185989 | 155186052 | novel | CTCC | non_canonical |
| PB.136.24 | chr1 | — | junction_2 | 155186210 | 155187224 | known | GTAG | canonical |
| PB.136.24 | chr1 | — | junction_3 | 155187375 | 155187454 | known | GTAG | canonical |
| PB.136.24 | chr1 | — | junction_4 | 155187577 | 155187721 | known | GTAG | canonical |
| PB.136.24 | chr1 | — | junction_5 | 155187859 | 155188007 | known | GTAG | canonical |
| PB.136.24 | chr1 | — | junction_6 | 155188064 | 155188162 | known | GTAG | canonical |

Supplementary table S3: Detailed overview of splice junctions of MUC13 alternative mRNA transcripts Both conditions

| Iso-form | chromo-some | strand | junction_ number | genomic_ start_coord | genomic_ end_coord | junction_ category | splice_ site | Canonical |
|---|---|---|---|---|---|---|---|---|
| PB.1087.17 | chr3 | — | junction_1 | 124906743 | 124908146 | known | GTAG | canonical |
| PB.1087.17 | chr3 | — | junction_2 | 124908349 | 124910414 | known | GTAG | canonical |
| PB.1087.17 | chr3 | — | junction_3 | 124910500 | 124912103 | known | GTAG | canonical |
| PB.1087.17 | chr3 | — | junction_4 | 124912142 | 124913110 | known | GTAG | canonical |
| PB.1087.17 | chr3 | — | junction_5 | 124913241 | 124913561 | known | GTAG | canonical |
| PB.1087.17 | chr3 | — | junction_6 | 124913682 | 124916316 | known | GTAG | canonical |
| PB.1087.17 | chr3 | — | junction_7 | 124916481 | 124920233 | known | GTAG | canonical |
| PB.1087.17 | chr3 | — | junction_8 | 124920290 | 124922196 | known | GTAG | canonical |
| PB.1087.17 | chr3 | — | junction_9 | 124922304 | 124923526 | known | GTAG | canonical |
| PB.1087.17 | chr3 | — | junction_10 | 124923650 | 124927531 | known | GTAG | canonical |
| PB.1087.17 | chr3 | — | junction_11 | 124927994 | 124934660 | known | GTAG | canonical |
| PB.1087.22 | chr3 | — | junction_1 | 124906743 | 124908146 | known | GTAG | canonical |
| PB.1087.22 | chr3 | — | junction_2 | 124908349 | 124910414 | known | GTAG | canonical |
| PB.1087.22 | chr3 | — | junction_3 | 124910500 | 124912103 | known | GTAG | canonical |
| PB.1087.22 | chr3 | — | junction_4 | 124912142 | 124913110 | known | GTAG | canonical |
| PB.1087.22 | chr3 | — | junction_5 | 124913241 | 124913561 | known | GTAG | canonical |
| PB.1087.22 | chr3 | — | junction_6 | 124913682 | 124916316 | known | GTAG | canonical |
| PB.1087.22 | chr3 | — | junction_7 | 124916481 | 124920233 | known | GTAG | canonical |
| PB.1087.22 | chr3 | — | junction_8 | 124920290 | 124922196 | known | GTAG | canonical |
| PB.1087.22 | chr3 | — | junction_9 | 124922304 | 124923526 | known | GTAG | canonical |
| PB.1087.22 | chr3 | — | junction_10 | 124923650 | 124927531 | known | GTAG | canonical |
| PB.1087.22 | chr3 | — | junction_11 | 124927748 | 124927795 | novel | CATA | non_canonical |
| PB.1087.22 | chr3 | — | junction_12 | 124927994 | 124934660 | known | GTAG | canonical |
| PB.1087.30 | chr3 | — | junction_1 | 124906743 | 124908146 | known | GTAG | canonical |
| PB.1087.30 | chr3 | — | junction_2 | 124908349 | 124910414 | known | GTAG | canonical |
| PB.1087.30 | chr3 | — | junction_3 | 124910500 | 124912103 | known | GTAG | canonical |
| PB.1087.30 | chr3 | — | junction_4 | 124912142 | 124913110 | known | GTAG | canonical |
| PB.1087.30 | chr3 | — | junction_5 | 124913241 | 124913561 | known | GTAG | canonical |
| PB.1087.30 | chr3 | — | junction_6 | 124913682 | 124916316 | known | GTAG | canonical |
| PB.1087.30 | chr3 | — | junction_7 | 124916463 | 124920233 | novel | GTAG | canonical |

-continued

Supplementary table S3: Detailed overview of splice junctions of MUC13 alternative mRNA transcripts

| | | | | | | | | |
|---|---|---|---|---|---|---|---|---|
| PB.1087.30 | chr3 | — | junction_8 | 124920290 | 124922196 | known | GTAG | canonical |
| PB.1087.30 | chr3 | — | junction_9 | 124922304 | 124923526 | known | GTAG | canonical |
| PB.1087.30 | chr3 | — | junction_10 | 124923650 | 124927531 | known | GTAG | canonical |
| PB.1087.30 | chr3 | — | junction_11 | 124927994 | 124934660 | known | GTAG | canonical |
| PB.1087.55 | chr3 | — | junction_1 | 124922615 | 124922693 | novel | GTTC | non_canonical |
| PB.1087.55 | chr3 | — | junction_2 | 124927994 | 124934660 | known | GTAG | canonical |

Non-inflamed

| isoform | chromo-some | strand | junction_number | genomic_start_coord | genomic_end_coord | junction_category | splice_site | canonical |
|---|---|---|---|---|---|---|---|---|
| PB.1087.18 | chr3 | — | junction_1 | 124905998 | 124906137 | novel | AGAG | non_canonical |
| PB.1087.18 | chr3 | — | junction_2 | 124906743 | 124908146 | known | GTAG | canonical |
| PB.1087.18 | chr3 | — | junction_3 | 124908349 | 124910414 | known | GTAG | canonical |
| PB.1087.18 | chr3 | — | junction_4 | 124910500 | 124912103 | known | GTAG | canonical |
| PB.1087.18 | chr3 | — | junction_5 | 124912142 | 124913110 | known | GTAG | canonical |
| PB.1087.18 | chr3 | — | junction_6 | 124913241 | 124913561 | known | GTAG | canonical |
| PB.1087.18 | chr3 | — | junction_7 | 124913682 | 124916316 | known | GTAG | canonical |
| PB.1087.18 | chr3 | — | junction_8 | 124916481 | 124920233 | known | GTAG | canonical |
| PB.1087.18 | chr3 | — | junction_9 | 124920290 | 124922196 | known | GTAG | canonical |
| PB.1087.18 | chr3 | — | junction_10 | 124922304 | 124923526 | known | GTAG | canonical |
| PB.1087.18 | chr3 | — | junction_11 | 124923650 | 124927531 | known | GTAG | canonical |
| PB.1087.18 | chr3 | — | junction_12 | 124927994 | 124934660 | known | GTAG | canonical |
| PB.1087.64 | chr3 | — | junction_1 | 124931778 | 124934586 | novel | CTAG | non_canonical |

Inflamed

| isoform | chromo-some | strand | junction_number | genomic_start_coord | genomic_end_coord | junction_category | splice_site | canonical |
|---|---|---|---|---|---|---|---|---|
| PB.1087.6 | chr3 | — | junction_1 | 124906743 | 124908146 | known | GTAG | canonical |
| PB.1087.6 | chr3 | — | junction_2 | 124908349 | 124910414 | known | GTAG | canonical |
| PB.1087.6 | chr3 | — | junction_3 | 124910500 | 124912103 | known | GTAG | canonical |
| PB.1087.6 | chr3 | — | junction_4 | 124912142 | 124913161 | novel | GTAG | canonical |
| PB.1087.6 | chr3 | — | junction_5 | 124913241 | 124913561 | known | GTAG | canonical |
| PB.1087.6 | chr3 | — | junction_6 | 124913682 | 124916316 | known | GTAG | canonical |
| PB.1087.6 | chr3 | — | junction_7 | 124916481 | 124920233 | known | GTAG | canonical |
| PB.1087.6 | chr3 | — | junction_8 | 124920290 | 124922196 | known | GTAG | canonical |
| PB.1087.6 | chr3 | — | junction_9 | 124922304 | 124923526 | known | GTAG | canonical |
| PB.1087.63 | chr3 | — | junction_1 | 124931778 | 124934480 | novel | CAAG | non_canonical |
| PB.1087.21 | chr3 | — | junction_1 | 124906743 | 124908146 | known | GTAG | canonical |
| PB.1087.21 | chr3 | — | junction_2 | 124908349 | 124910414 | known | GTAG | canonical |
| PB.1087.21 | chr3 | — | junction_3 | 124910500 | 124912103 | known | GTAG | canonical |
| PB.1087.21 | chr3 | — | junction_4 | 124912142 | 124913110 | known | GTAG | canonical |
| PB.1087.21 | chr3 | — | junction_5 | 124913241 | 124913561 | known | GTAG | canonical |
| PB.1087.21 | chr3 | — | junction_6 | 124913682 | 124916316 | known | GTAG | canonical |
| PB.1087.21 | chr3 | — | junction_7 | 124916481 | 124920233 | known | GTAG | canonical |
| PB.1087.21 | chr3 | — | junction_8 | 124920290 | 124920708 | novel | GTAG | canonical |
| PB.1087.21 | chr3 | — | junction_9 | 124921025 | 124922196 | novel | GTAG | canonical |
| PB.1087.21 | chr3 | — | junction_10 | 124922304 | 124923526 | known | GTAG | canonical |
| PB.1087.21 | chr3 | — | junction_11 | 124923650 | 124927531 | known | GTAG | canonical |
| PB.1087.21 | chr3 | — | junction_12 | 124927994 | 124934660 | known | GTAG | canonical |
| PB.1087.20 | chr3 | — | junction_1 | 124906256 | 124913196 | novel | CAAG | non_canonical |
| PB.1087.20 | chr3 | — | junction_2 | 124913241 | 124913561 | known | GTAG | canonical |
| PB.1087.20 | chr3 | — | junction_3 | 124913682 | 124916316 | known | GTAG | canonical |
| PB.1087.20 | chr3 | — | junction_4 | 124916481 | 124920233 | known | GTAG | canonical |
| PB.1087.20 | chr3 | — | junction_5 | 124920290 | 124922196 | known | GTAG | canonical |
| PB.1087.20 | chr3 | — | junction_6 | 124922304 | 124923526 | known | GTAG | canonical |
| PB.1087.20 | chr3 | — | junction_7 | 124923650 | 124927531 | known | GTAG | canonical |
| PB.1087.20 | chr3 | — | junction_8 | 124927994 | 124934660 | known | GTAG | canonical |
| PB.1087.25 | chr3 | — | junction_1 | 124906743 | 124908146 | known | GTAG | canonical |
| PB.1087.25 | chr3 | — | junction_2 | 124908349 | 124910414 | known | GTAG | canonical |
| PB.1087.25 | chr3 | — | junction_3 | 124910500 | 124912103 | known | GTAG | canonical |
| PB.1087.25 | chr3 | — | junction_4 | 124912142 | 124913110 | known | GTAG | canonical |
| PB.1087.25 | chr3 | — | junction_5 | 124913203 | 124913577 | novel | AGAG | non_canonical |
| PB.1087.25 | chr3 | — | junction_6 | 124913682 | 124916316 | known | GTAG | canonical |
| PB.1087.25 | chr3 | — | junction_7 | 124916481 | 124920233 | known | GTAG | canonical |
| PB.1087.25 | chr3 | — | junction_8 | 124920290 | 124922196 | known | GTAG | canonical |
| PB.1087.25 | chr3 | — | junction_9 | 124922304 | 124923526 | known | GTAG | canonical |
| PB.1087.68 | chr3 | — | junction_1 | 124931778 | 124934705 | novel | CCAG | non_canonical |
| PB.1087.32 | chr3 | — | junction_1 | 124906743 | 124908146 | known | GTAG | canonical |
| PB.1087.32 | chr3 | — | junction_2 | 124908349 | 124913110 | novel | GTAG | canonical |
| PB.1087.32 | chr3 | — | junction_3 | 124913241 | 124913561 | known | GTAG | canonical |

-continued

Supplementary table S3: Detailed overview of splice junctions of MUC13 alternative mRNA transcripts

| | | | | | | | | |
|---|---|---|---|---|---|---|---|---|
| PB.1087.32 | chr3 | — | junction_4 | 124913682 | 124916316 | known | GTAG | canonical |
| PB.1087.32 | chr3 | — | junction_5 | 124916481 | 124920233 | known | GTAG | canonical |
| PB.1087.32 | chr3 | — | junction_6 | 124920290 | 124922196 | known | GTAG | canonical |
| PB.1087.32 | chr3 | — | junction_7 | 124922304 | 124923526 | known | GTAG | canonical |
| PB.1087.32 | chr3 | — | junction_8 | 124923650 | 124927531 | known | GTAG | canonical |
| PB.1087.32 | chr3 | — | junction_9 | 124927994 | 124934660 | known | GTAG | canonical |
| PB.1087.27 | chr3 | — | junction_1 | 124906225 | 124908173 | novel | AGAC | non_canonical |
| PB.1087.27 | chr3 | — | junction_2 | 124908349 | 124910414 | known | GTAG | canonical |
| PB.1087.27 | chr3 | — | junction_3 | 124910500 | 124912103 | known | GTAG | canonical |
| PB.1087.27 | chr3 | — | junction_4 | 124912142 | 124913110 | known | GTAG | canonical |
| PB.1087.27 | chr3 | — | junction_5 | 124913241 | 124913561 | known | GTAG | canonical |
| PB.1087.27 | chr3 | — | junction_6 | 124913682 | 124916316 | known | GTAG | canonical |
| PB.1087.27 | chr3 | — | junction_7 | 124916481 | 124920233 | known | GTAG | canonical |
| PB.1087.27 | chr3 | — | junction_8 | 124920290 | 124922196 | known | GTAG | canonical |
| PB.1087.27 | chr3 | — | junction_9 | 124922304 | 124923526 | known | GTAG | canonical |
| PB.1087.27 | chr3 | — | junction_10 | 124923650 | 124927531 | known | GTAG | canonical |
| PB.1087.27 | chr3 | — | junction_11 | 124927994 | 124934660 | known | GTAG | canonical |
| PB.1087.31 | chr3 | — | junction_1 | 124906743 | 124908146 | known | GTAG | canonical |
| PB.1087.31 | chr3 | — | junction_2 | 124908349 | 124910414 | known | GTAG | canonical |
| PB.1087.31 | chr3 | — | junction_3 | 124910500 | 124912103 | known | GTAG | canonical |
| PB.1087.31 | chr3 | — | junction_4 | 124912142 | 124913110 | known | GTAG | canonical |
| PB.1087.31 | chr3 | — | junction_5 | 124913241 | 124913561 | known | GTAG | canonical |
| PB.1087.31 | chr3 | — | junction_6 | 124913682 | 124916316 | known | GTAG | canonical |
| PB.1087.31 | chr3 | — | junction_7 | 124916481 | 124920233 | known | GTAG | canonical |
| PB.1087.31 | chr3 | — | junction_8 | 124920290 | 124922196 | known | GTAG | canonical |
| PB.1087.31 | chr3 | — | junction_9 | 124922304 | 124923526 | known | GTAG | canonical |
| PB.1087.31 | chr3 | — | junction_10 | 124923650 | 124927531 | known | GTAG | canonical |
| PB.1087.31 | chr3 | — | junction_11 | 124927874 | 124927951 | novel | AAAG | non_canonical |
| PB.1087.31 | chr3 | — | junction_12 | 124927994 | 124934660 | known | GTAG | canonical |
| PB.1087.52 | chr3 | — | junction_1 | 124922304 | 124923526 | known | GTAG | canonical |
| PB.1087.52 | chr3 | — | junction_2 | 124923650 | 124927531 | known | GTAG | canonical |
| PB.1087.52 | chr3 | — | junction_3 | 124927994 | 124934660 | known | GTAG | canonical |
| PB.1087.56 | chr3 | — | junction_1 | 124922624 | 124922693 | novel | GTGT | non_canonical |

Example 3: Aberrant Mucin Expression in Association with Tight Junction Dysfunction in the Respiratory and Intestinal Epithelium During SARS-CoV-2 Infection

1. Background to the Invention

Severe acute respiratory syndrome coronavirus 2 (SARS-CoV-2), causing coronavirus disease 2019 (COVID-19), emerged in Wuhan, China, in December 2019. An initial cluster of infections was linked to the Huanan seafood market, potentially due to animal contact. SARS-CoV-2 is closely related to SARS-CoV, responsible for the SARS outbreak 18 years ago (Zhou et al., 2020), and has now spread rapidly worldwide. On Mar. 11, 2020, the World Health Organization (WHO) declared COVID-19 a pandemic. Common symptoms reported in adults are fever, dry cough, fatigue and shortness of breath. While most COVID-19 patients (ca. 80%) remain asymptomatic or have mild to less severe respiratory complaints, some (ca. 15-20%) are hospitalised of which a minority develops a frequently lethal acute respiratory distress syndrome (ARDS). This results in mucus exudation, pulmonary oedema, hypoxia and lung failure in association with a cytokine storm characterized by amongst others Th17 immune profiles. Besides elderly or those with chronic underlying diseases, also young, healthy individuals die of COVID-19.

SARS-CoV-2 is a positive-sense single stranded RNA virus having 4 structural proteins, known as the S (spike), E (envelope), M (membrane) and N (nucleocapsid) proteins. The N protein holds the RNA genome, and the S, E and M proteins create the viral envelope. The S protein of coronaviruses regulates viral entry into target cells, i.e. ciliated epithelial cells. Entry depends on binding of the subunit S1 to a cellular receptor, which facilitates viral attachment to the surface of target cells. Entry also requires S protein priming by cellular proteases, which cleave the S protein at its S1/S2 site allowing fusion of viral and cellular membranes, a process driven by the S2 subunit. Similar to SARS-CoV, the angiotensin-converting enzyme 2 (ACE2) is the entry receptor for SARS-CoV-2 and the cellular serine protease TMPRSS2 is essential for priming the S protein. ACE2 and TMPRSS2 expression is not only limited to the respiratory tract and extrapulmonary spread of SARS-COV-2 should therefore not be neglected. Indeed, a subset (ca. 30-35%) of COVID-19-positive patients (both ambulatory and hospitalised) showed gastrointestinal symptoms, including diarrhoea, abdominal pain, loss of appetite and nausea, and associated with a more indolent form of COVID-19 compared to patients with respiratory symptoms. Live SARS-CoV-2 was even successfully isolated from the stool of patients. This indicates that the intestinal epithelium is also susceptible to infection and recent work even provided evidence for an additional serine protease TMPRSS4 in priming the SARS-CoV-2S protein.

Furthermore, it has been suggested that the modest ACE2 expression in the upper respiratory tract has limited SARS-CoV transmissibility in the past. This is in large contrast to the currently reported SARS-CoV-2 infected cases which clearly surpassed that of SARS-CoV. In light of this increased transmissibility, we can speculate that this new coronavirus utilizes additional cellular attachment-promoting co-factors to ensure robust infection of ACE2+ cells in the respiratory tract. This could comprise binding to cellular glycans, as shown for other coronaviruses. Interestingly, mucus hyperproduction in the bronchioles and alveoli from severely ill COVID-19 patients has been reported (Guan et al., 2020; own observations ICU UZA), complicating the ICU stay and recovery. Secreted and transmembrane mucins are O-linked glycans produced by goblet and ciliated cells, respectively, and are the major components of the mucus layer covering the epithelial cells. Both mucus and epithelium constitute the mucosal barrier. Besides having a protective function, transmembrane mucins also participate in intracellular signal transduction and thus play an important role in mucosal homeostasis by establishing a delicate balance with tight junctions to maintain barrier integrity. Transmembrane mucins, particularly MUC13, might thus act as additional host factors enabling the virus to spread faster and cause tissue damage. In this study, we therefore investigated the expression patterns of ACE2, TMPRSS2/TMPRSS4, mucins and junctional proteins during SARS-CoV-2 infection in the respiratory and intestinal epithelium. Furthermore, the interplay between MUC13 and ACE2 expression upon viral infection was also studied.

2. Material and Methods

2.1. Viruses and Biosafety

The SARS-CoV-2 isolate 2019-nCoV/Italy-INM11, available at the European Virus Archive-Global (EVAg) database, was used throughout the study. SARS-CoV-2 was subjected to passages in Vero E6 cells (green monkey kidney; ATCC CRL-1586), grown in Dulbecco's modified Eagle's minimal essential medium (DMEM; Gibco) supplemented with 10% heat-inactivated fetal calf serum (FCS), before usage in the cell culture experiments. The infectious viral titers in the cell-free supernatant were determined by a standard $TCID_{50}$ assay. All experiments entailing live SARS-CoV-2 were conducted in the biosafety level 3 facility at the Institute for Tropical Medicine, Antwerp, Belgium.

2.2. Cell Culture and Virus Infection

LS513 (human colorectal carcinoma (ATCC CRL-2134TM)) and Caco-2 (human colorectal carcinoma ATCC HTB-37) cells were grown in Roswell Park Memorial Institute (RPMI)-1640 medium (Life Technologies) supplemented with 10% heat-inactivated FCS, 100 U $ml^{-1}$ penicillin, 100 μg $ml^{-1}$ streptomycin, and 2 mM L-glutamine. Calu3 (lung adenocarcinoma ATCC HBT-55) cells were grown in Minimal Essential Medium (MEM; Gibco) supplemented with 10% heat-inactivated FCS, 100 U $ml^{-1}$ penicillin, 100 μg $ml^{-1}$ streptomycin, 1×MEM Non-essential Amino Acids and 1 mM sodium pyruvate. For viral infection, all cells were seeded in 6 well-plates: $1\times10^6$ cells/ml (LS513); $5\times10^5$ cells/ml (Caco-2 and Calu3). After reaching confluence, the cells were inoculated with SARS-CoV-2 at a multiplicity of infection (MOI) of 0.1 for 24 h and 48 h at 37° C. (5% $CO_2$). Cells treated with the growth medium of the virus were included as controls. All experiments were performed containing 6 technical replicates for each time-point and cell line.

2.3. Small Interfering RNA (siRNA) Transfection Assays

At the start of the transfection experiments, cells were seeded and grown in 6 well-plates (LS513: $1\times10^6$ cells/ml; Caco-2 and Calu-3: $3\times10^5$ cells/ml). After 24 hours, the cells were transfected with 75 pmol Silencer Select siRNA targeting MUC13 (s32232, ThermoFisher Scientific) or with 75 pmol Silencer Select Negative Control siRNA (4390843, ThermoFisher Scientific) using Lipofectamine RNAiMAX transfection reagent (7.5 μl/well, Invitrogen). Forty-eight hours post-transfection, cells were extensively washed and infected with SARS-CoV-2 at a MOI of 0.1 for 48 hours. Cells treated with the growth medium of the virus were included as controls. All transfection experiments were performed containing 6 technical replicates per cell line.

2.4. RNA Extraction and Quantitative RT-PCR

Cells and supernatants were harvested at 24 hpi (hours post infection) and 48 hpi for quantitative RT-PCR analysis of host gene expression and virus replication, as previously described (Corman et al., 2020; Breugelmans et al., 2020). Briefly, total RNA from lysed cells and supernatants (100 μl) was extracted using the Nucleospin RNA plus kit (Macherey-Nagel) and QIAamp viral RNA kit (Qiagen), respectively, following the manufacturer's instructions. The concentration and quality of the RNA were evaluated using the Nanodrop ND-1000 UV-Vis Spectrophotometer (Thermo Fisher Scientific). For gene expression analysis, 1 μg RNA extracted from transfected and non-transfected cells was subsequently converted to cDNA by reverse transcription using the SensiFast™ cDNA synthesis kit (Bioline). Relative gene (i.e. ACE2, TMPRSS2, TMPRSS4, mucins and tight junctions) expression was then determined by SYBR Green RT-qPCR using the GoTaq qPCR master mix (Promega) on a QuantStudio 3 Real-Time PCR instrument (Thermo Fisher Scientific). Following quantitect primer assays (Qiagen) were used: Hs_GAPDH (QT00079247), Hs_ACTB (QT00095431), Hs_TMPRSS2 (QT00058156), Hs_TMPRSS4 (QT00033775), Hs_ACE2 (QT00034055), Hs_MUC1 (QT00015379), Hs_MUC2 (QT01004675), Hs_MUC4 (QT00045479), Hs_MUC5AC (QT00088991), Hs_MUC5B (QT01322818), Hs_MUC6 (QT00237839), Hs_MUC13 (QT00002478), Hs_CLDN1 (QT00225764), Hs_CLDN2 (QT00089481), Hs_CLDN3 (QT00201376), Hs_CLDN4 (QT00241073), Hs_CLDN7 (QT00236061), Hs_CLDN12 (QT01012186), Hs_CLDN15 (QT00202048), Hs_CLDN18 (QT00039550), Hs_CDH1 (QT00080143), Hs_OCLN (QT00081844), Hs_ZO-1 (QT00077308), Hs_ZO-2 (QT00010290).

All RT-qPCR reactions were performed in duplicate and involved an initial DNA polymerase activation step for 2 min at 95° C., followed by 40 cycles of denaturation at 95° C. for 15 sec and annealing/extension for 1 min at 60° C. Analysis and quality control were performed using qbase+ software (Biogazelle). Relative expression of the target genes was normalized to the expression of the housekeeping genes ACTB and GAPDH. To quantify viral RNA in the transfected and non-transfected cells and supernatants, the iTaq Universal Probes One-Step kit (BioRad) was used on a LightCycler 480 Real-Time PCR System (Roche). A 25 μl reaction contained 1 μl RNA, 12.5 μl of 2×reaction buffer provided with the kit, 0.625 μl of iScript reverse transcriptase from the kit, 0.4 μl forward primer (25 μM), 0.4 μl reverse primer (25 μM), 0.5 μl probe (10 μM) targeting the SARS-CoV-2 E gene and 9.575 μl $H_2O$. We incubated the reactions at 50° C. for 10 min for reverse transcription, 95° C. for 5 min for denaturation, followed by 50 cycles of 95° C. for 10 s and 58° C. for 30 s. Analysis was performed using qbase+ software to determine cycle thresholds (Ct).

2.5. Statistical Analysis

Statistical analysis using the GraphPad Prism 8.00 software (license DFG170003) was performed to determine significant differences between SARS-CoV-2 infected and uninfected cells and between MUC13 siRNA and ctrl siRNA transfected cells infected or not with SARS-CoV-2. Data were analysed by the Analysis of Variance (ANOVA) test and are presented as means±standard error of mean (SEM). Significance levels are indicated on the graphs and were corrected for multiple testing using the Tukey-Kramer's and Dunn's post-hoc multiple comparisons tests.

3. Results and Discussion

All cell lines tested here were susceptible for SARS-CoV-2 infection as shown by virus replication over a period of 48 h (data not shown). Virus production was significantly higher in the supernatant of Caco-2 and Calu3 cells compared to LS513 (p=0.0004; FIG. 16). This is in agreement with a recent study that described a robust replication of SARS-CoV-2 in both Caco-2 and Calu3 cells. Cell damage induced by SARS-CoV-2 was also assessed microscopically. No cytopathic effects, as typically described in Vero E6 cells, was noted in LS513 and Caco-2 cells. Interestingly, a substantial cell damage was noted in transfected Calu3 cells (30% viability at 48 hpi; p<0.001) but not in non-transfected cells. The induction of cell damage in Calu3 cells caused by corona viruses still remains controversial. A recent study described no cell death in SARS-CoV- and SARS-CoV-2-infected Calu3 cells, whereas earlier studies reported that SARS-CoV infection induced cytopathic effects in Calu3. A reason for these discrepancies is currently unknown, but it cannot be excluded that in our study transfection with siRNA made the cells more susceptible for viral cytopathic effects.

As SARS-CoV-2 uses the receptor ACE2 for entry and the serine proteases TMPRSS2 and TMPRSS4 for S protein priming, expression of these host factors was investigated. In our study, ACE2 mRNA expression was significantly reduced in Caco-2 cells at 24 hpi (p=0.0001) and 48 hpi (p=0.0008) and in Calu3 cells at 24 hpi only (p=0.0004) (FIG. 17). No changes in ACE2 expression were noted in LS513 which could explain the significant lower virus production compared to Caco-2 and Calu3 (FIGS. 16 & 17). ACE2 is an important component of the renin-angiotensin pathway and counterbalances the effects of AT1 activation by angiotensin II. In the lungs, ACE2 has an anti-inflammatory role protecting the respiratory tract from injury, whereas it maintains mucosal barrier homeostasis in the intestines by regulating expression of antimicrobial peptides (AMPs) and the ecology of the gut microbiome. Downregulation of this receptor upon SARS-CoV-2 infection could thus exaggerate acute lung and intestinal injury because of the imbalance in angiotensin II or AT1 signalling. On the contrary, expression of TMPRSS2 was significantly increased in all cell types at 48 hpi (TMPRSS2: p=0.0433 (LS513), p=0.0057 (Caco-2), p=0.0001 (Calu3); FIG. 17) compared to uninfected controls whereas upregulation of TMPRSS4 was remarkably only seen in Calu3 cells (p=0.0152). The abundancy of TMPRSS2 and to a lesser extend TMPRSS4 is thus essential for promoting viral entry into host cells. In addition, TMPRSS2 is also an important mediator of mucosal barrier dysfunction and linked to aberrant mucin expression. We therefore also investigated the impact of SARS-CoV-2 infection on mucin and tight junction expression. In our study, significant changes in mucin expression were mainly seen at 48 hpi. More specifically, the transmembrane MUC1, MUC13 and MUC4 mucins were strongly upregulated in both intestinal and pulmonary SARS-CoV-2-infected epithelial cells (MUC1: p=0.0022 (LS513); p=(Calu3); MUC4: p=0.0022 (LS513); p=0.0022 (Calu3); MUC13: p=0.0022 (LS513); p=0.0022 (Caco-2); p=0.0022 (Calu3); FIG. 18), whereas the secreted mucins (particularly MUC2 (p=0.058 (LS513); p=(Caco, 24 hpi); p=(Caco-2; 48 hpi)), MUC5AC (p=0.0012 (LS513)) and MUC6 (p=0.0022 (LS513)), which are at the frontline of mucosal defence (Linden et al., 2007), were significantly downregulated with the exception of MUC2 (p=0.0001) and MUC5AB (p=0.0001) expression in Calu3 cells (FIG. 19). As own data showed a functional link between MUC13 and ACE2, we further investigated whether ACE2 downregulation upon viral infection is mediated by MUC13 using siRNA transfection assays. Knockdown of MUC13 was successful in all three cell lines in which a reduction in MUC13 expression of approximately 70-80% was maintained during infection (FIG. 5). In ctrl siRNA transfected Caco-2 and Calu-3 cells, MUC13 expression significantly increased upon SARS-CoV-2 infection whereas ACE2 expression significantly decreased (FIG. 20). This is in agreement to what is seen in wildtype SARS-CoV-2-infected Caco-2 and Calu3 cells (FIG. 18). Interestingly, knockdown of MUC13 decreased ACE2 expression in Caco-2 and Calu3 control cells (p=0.0004 (Caco-2); p=0,09 (Calu3)) and its expression further declined upon SARS-CoV-2 infection although not significant (FIG. 20). This strengthens the evidence that ACE2 expression is mediated by MUC13. In addition, MUC13 expression was not altered in ctrl siRNA transfected LS513 cells upon infection (FIG. 20) which is in contrast to what is seen in wildtype SARS-CoV-2-infected LS513 cells (FIG. 18). ACE2 expression remained unchanged (FIG. 20) and lower virus production in the supernatants was noted (FIG. 16). This further highlights the importance of increased MUC13 expression mediating ACE2 signalling for optimal virus production.

Furthermore, inappropriate overexpression of MUC13 can also affect barrier integrity by disrupting cell polarity and cell-cell interactions resulting in tight junction dysfunction, as recently shown. In our study, a significant increase in gene expression of several junctional proteins was noted at 48 hpi (FIG. 21), suggesting the ability of SARS-CoV-2 to alter epithelial barrier integrity, as described for SARS-CoV. Most alterations in expression were seen in LS513 and Calu3 cells, i.e.: CLDN1 (p=0.0022 5LS513); p=0.0001 (Calu3)), CLDN2 (p=0.0007 (Caco-2)), CLDN3 (p=0.075 (LS513); p=0.0001 (Calu3)), CLDN4 (p=0.01 (LS513); p=0.0001 (Calu3)), CLDN7 (p=0.0085 (LS513); p=0.0001 (Calu3)), CLDN12 (p=0.031 (Calu3)), CLDN15 (p=0.0139 (Caco-2); P=0.0004 (Calu3)), CDH1 (p=0.003 (Caco-2); p=0.0013 (Calu3)), OCLN (p=0.0335 (LS513); p=0.0004 (Caco-2); p=0.0002 (Calu3)), ZO-1 (p=0.034 (Caco-2); p=0.0001 (Calu3)) and ZO-2 (p=0.0005 (Caco-2)).

Taken together, the results from this study further underline the tropism of SARS-CoV-2 for both the respiratory and intestinal epithelium and demonstrate that this novel coronavirus strongly affects the mucosal barrier integrity upon infection by inducing aberrant mucin expression and tight junction dysfunction. Furthermore, a role for transmembrane mucins, particularly MUC13, in contributing to the infection of SARS-CoV-2 is also suggested.

Example 4: Mucin mRNA Isoforms for Diagnosis and Monitoring Coronaviral Infections 1. Background of the Invention A novel coronavirus, SARS-CoV-2 causing coronavirus disease 2019 (COVID-19), emerged in Wuhan, China, in December 2019 and has since then disseminated globally. Common symptoms are fever, dry cough, fatigue, shortness of breath and changes in smell or taste whereas gastrointestinal symptoms, such diarrhoea, abdominal pain, loss of appetite and nausea can also occur.

Patients with COVID-19 exhibit a broad spectrum of disease severity with 80% showing mild, moderate or no symptoms; 15% showing severe symptoms; and 5% developing acute lung injury with the potential progression towards a lethal acute respiratory distress syndrome. Besides elderly or those with chronic underlying diseases, also young, healthy individuals and even children die of COVID-19 (Huang et al., 2020; Ruan, 2020). This underscores the urgent need to unravel molecular factors that shape the course of COVID-19 and identify "at risk" patients for progressing to severe disease.

Respiratory ciliated epithelial cells are the primary targets of SARS-CoV-2 and viral entry requires binding to the ACE2 receptor and subsequent priming by TMPRSS2. Interestingly, ACE2 expression increases with age and variation in ACE2 expression between children with high and low viral loads was recently described (Hoffmann et al., 2020). However, as other coronaviruses with markedly milder pathogenicity also use ACE2 for initial cellular entry (Hoffmann et al., 2020), we can then speculate that SARS-CoV-2 uses additional factors mediating infection of ACE2+ cells and subsequent tissue damage.

Figure 22C:
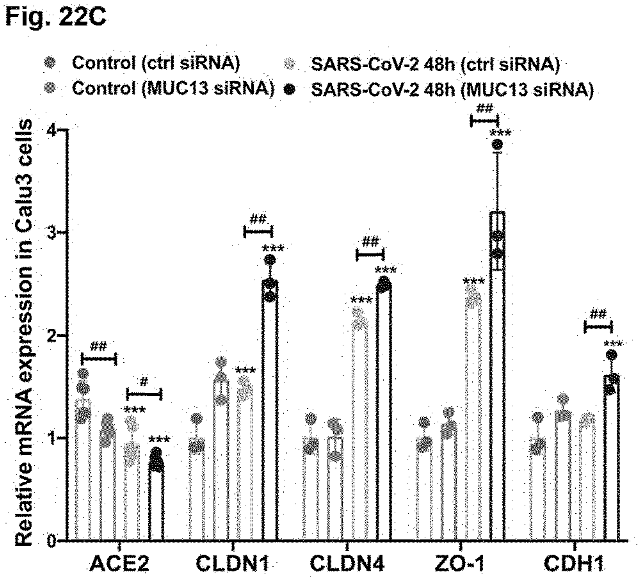

Secreted and transmembrane mucins (MUCs), produced by goblet and ciliated cells, respectively, are the gatekeepers of the mucus layer protecting the respiratory barrier function against inhaled injurious substances. Upon disease, however, aberrant mucin expression forms a dysfunctional mucus barrier and becomes pathologic (Breugelmans et al., 2020). Indeed, mucin hypersecretion is a major clinical feature seen in severely ill COVID-19 patients with mucus accumulating in the airways obstructing the respiratory tract and complicating breathing and recovery (Wenju et al., 2020). These observations prompted us to hypothesize that SARS-CoV-2 infection stimulates mucin overexpression, further promoting disease severity. Own recent unpublished data showed that the excessive mucus production seen in the lungs of COVID-19 patients is characterized by the presence of several mucins including not only MUC1 and MUC5AC as shown before (Wenju et al., 2020), but also MUC2, MUC4, MU5B, MUC13, MUC16 and MUC21 (FIG. 22A), which are triggered by SARS-CoV-2 (FIGS. 19 and 22B), and we have also evidence for a functional link between increased MUC13 expression, ACE2 downregulation and lung barrier dysfunction (characterized by aberrant tight junction expression) upon viral infection (FIG. 22C).

Furthermore, mucins are highly polymorphic, and the presence of genetic differences can alter gene expression resulting in several mRNA isoforms via alternative splicing. While most mRNA isoforms encode similar biological functions, some alter protein function resulting in progression towards disease (Moehle et al., 2006). Such disease-associated mucin mRNA isoforms might thus contribute to COVID-19 severity and treatment to reduce mucin hyperproduction can be of utmost clinical importance (d'Alessandro et al., 2020).

In this study, we first analysed the mRNA expression levels of mucins in the blood of hospitalized COVID-19 patients with severe disease, ambulatory COVID-19 and non-COVID-19 patients with mild disease and healthy controls and correlated aberrantly expressed mucins with COVID-19 positivity and severity. Thereafter, we investigated the effect of treatment with FDA approved drugs for COVID-9 on mucin expression in pulmonary epithelial cells. Finally, we unraveled the mucin mRNA isoforms that were aberrantly expressed in COVID-19 patients and associated with COVID-19 positivity and severity.

2. Material and Methods

2.1. Patient Cohorts, Clinical Characteristics and Sample Collection

Critical COVID-19 patients hospitalized at the tertiary intensive care unit (ICU) of the University hospital Antwerp, Belgium (Table 7; N=15) and ambulatory COVID-19 patients (Table 7; N=10) with mild symptoms (Table 8) recruited at general practitioner practices, were enrolled for this study. Ambulatory patients with mild common cold symptoms but negative for COVID-19 (Table 7; N=4) and healthy controls (Table 7; N=4) were included as control groups.

Regarding the hospitalized patients with severe COVID-19, the median duration from symptom onset until hospital admission was 6 days, with a total median hospital duration of 29 days of which ca. 18 days at the ICU. Most of these ICU patients required invasive ventilation with a median length of 13.8 days of which 50% also needed a replacement of the endotracheal tube due to mucus obstruction (Table 9). Other clinical characteristics, including co-morbidities, hospitalization, organ failure and mortality, are also shown in Table 9.

TABLE 7

Demographics of the different patient groups

| Demographics | COVID-19 (severe, ICU) | COVID-19 (mild, ambulatory) | Non-COVID-19 (mild, ambulatory) | Non-COVID-19 (healthy) |
|---|---|---|---|---|
| Number | 15 | 10 | 4 | 4 |
| Age, years (median, range) | 57.33 (27-82) | 30 (17-57) | 40 (32-48) | 36 (25-52) |
| Sex (male, female) | 9/15 (male) 6/15 (female) | 5/10 (male) 5/10 (female) | 3/4 (male) 1/4 (female) | 2/4 (male) 2/4 (female) |
| BMI, kg/m$^2$ (median, range) | 29.02 (21.2-43) | — | — | — |

TABLE 8

Overview of the symptoms among mild COVID-19 patients (N = 10)

| Symptoms | Loss of smell and taste | Rhinitis | Fever | Myalgia | Malaise | Cough | Headache | Gastro-intestinal symptoms |
|---|---|---|---|---|---|---|---|---|
| Number of patients (%) | 9/10 (90%) | 6/10 (60%) | 3/10 (30%) | 2/10 (20%) | 2/10 (20%) | 1/10 (10%) | 3/10 (30%) | 1/10 (10%) |

TABLE 9 clinical data of critically ill COVID-19 patients hospitalized at the ICU (N = 15)

| Co-morbidities | Number of patients (%) | Hospitalization | Mean (range) | Organ failure | Number of patients (%) |
|---|---|---|---|---|---|
| Diabetes | 5/15 (33%) | Symptom onset until hospital admission (days) | 6.08 (3-10) | ARDS | 3/15 (20%) |
| Lung disease | 5/15 (33%) | SOFA/$SOFA_{max}$ scores* | 8 (2-18)/12 (3-21) | Renal failure | 4/15 (27%) |
| Heart failure | 1/15 (7%) | Hospitalisation ICU (days) | 17.93 (6-65) | Need vasopressors | 11/15 (73%) |
| Hypertension | 6/15 (40%) | Total hospitalisation (days) | 29.47 (15-77) | Bacterial co-infection | 7/15 (47%) |
| Renal insufficiency | 4/15 (27%) | Invasive ventilation (Y/N) | 0.8 (0-1) | Fungal co-infection | 7/15 (47%) |
| Malignancy | 6/15 (40%) | Duration invasive ventilation (days) | 13.8 (0-65) | Cardiac complications | 3/15 (20%) |
| Lymphoproliferative disease | 3/15 (20%) | $P_aO_2/F_iO_2$ ratio | 97.57 (44-231) | Neurological complications | 4/15 (27%) |
| Auto-immune diseases | 3/15 (20%) | Replacement endotracheal tubes (ETT) (Y/N) | 0.5 (0-1) | mortality | 4/15 (27%) |

*sequential organ failure assessment scores (SOFA)

From all patients, blood samples were collected in PAXgene RNA blood tubes (PreAnalytiX) for RNA extraction purposes and subsequent gene expression and iso-sequencing approaches (see further). This study was approved by the Ethical Committee of the UZA (20/14/176 and 20/43/555) and signed informed consent was obtained.

2.2. Screening the Ability of Different Therapies for COVID-19 to Reduce Mucin Hypersecretion Calu3 (lung adenocarcinoma ATCC HBT-55) cells were grown in Minimal Essential Medium (MEM; Gibco) supplemented with 10% heat-inactivated FCS, 100 U $ml^{-1}$ penicillin, 100 μg $ml^{-1}$ streptomycin, 1×MEM Non-essential Amino Acids and 1 mM sodium pyruvate. For viral infection, all cells were seeded in 6 well-plates at a concentration of $5\times10^5$ cells/ml. After reaching confluence, the cells were inoculated with SARS-CoV-2 at MOI of 0.1 for 2 h, thereafter washed and treated with a drug at different concentrations for 48 h. These include the following drugs approved by the FDA to treat COVID-19: Remdesivir (antiviral; 3.7 μM); favipiravir (antiviral; 1 mM), (Hydroxy)chloroquine (10 μM); Dexamethasone (corticosteroid able to reduce mucin expression; 1-5-10 μM); Tocilizumab (anti-IL6; 10-100-1000 ng/ml); Anakinra (anti-IL1; 50-500 ng/ml, 10 μg/ml); and Baricitinib (JAK1/2 inhibitor; 0.3-1-5 μM). Untreated cells infected with SARS-CoV-2 were also included as control group. After the treatment, cells were lysed for RNA and RT-qPCR extraction purposes.

2.3. RNA Isolation and Quality Control

Total RNA was extracted from the collected blood samples using the PAXgene RNA blood kit (PreAnalytiX) and from the lysed cells using the Nucleospin RNA plus kit, following the manufacturer's instructions. The concentration and purity of the RNA were evaluated using the NanoDrop® ND-1000 UV-Vis Spectrophotometer (Thermo Fisher Scientific) and Qubit Fluorometer (Qubit Broad Range RNA kit, Thermo Fisher Scientific). Quality control of the RNA was performed by capillary electrophoresis using an Agilent 2100 Fragment Analyzer (Agilent).

2.4. Mucin mRNA Expression by RT-qPCR

One μg RNA was converted to cDNA by reverse transcription using the SensiFast™ cDNA synthesis kit (Bioline). Relative mucin gene expression was then determined by SYBR Green RT-qPCR using the GoTaq qPCR master mix (Promega) on a QuantStudio 3 Real-Time PCR instrument (Thermo Fisher Scientific). Standard validated QuantiTect primers available from Qiagen were used for GAPDH (QT00079247), ACTB (QT00095431), MUC4 (QT00045479), MUC5AC (QT00088991) and MUC5B (QT01322818), MUC2 (QT01004675), MUC13 (QT00002478), MUC16 (QT01192996), MUC20 (QT00012068), MUC21 (QT01159060) and MUC1 (QT00015379). All RT-qPCR reactions were performed in duplicate and involved an initial DNA polymerase activation step for 2 min at 95° C., followed by 40 cycles of denaturation at 95° C. for 15 sec and annealing/extension for 1 min at 60° C. Analysis and quality control were performed using qbase+ software (Biogazelle). Relative expression of the target genes was normalized to the expression of the housekeeping genes ACTB and GAPDH.

2.5. cDNA Library Preparation and Multiplexing

Initially, 1600-2000 ng of input RNA per sample was used. The reactions from each sample were first labeled with a barcoded oligo dT nucleotide for multiplexing purposes as shown in Table 10. Subsequently, first-strand cDNA synthesis was performed using the SMARTer PCR cDNA synthesis kit (Takara Bio) according to the manufacturer's instructions. The reactions were then diluted 1:10 in Elution Buffer (PacBio) and large-scale amplification was performed using 16 reactions per sample. Each reaction of 50 μL consisted of 10 μL of the diluted cDNA sample, 10 μL 5×PrimeSTAR GXL buffer (Takara Bio), 4 μL dNTP Mix (2.5 mM each), 1 μL 5' PCR Primer IIA (12 μM), 1 μL PrimeSTAR GXL DNA Polymerase (1.25 U/μL, Takara Bio) and 24 μL nuclease-free water. The samples were then incubated in a thermocyler using the following program: an initial denaturation step at 98° C. for 30 s, followed by 20 cycles of amplification at 98° C. for 10 s, 65° C. for 15 s and 68° C. for 10 min, and a final extension step at 68° C. for 5 min. From these PCR products, two fractions were purified using AMPure magnetic purification beads. After equimolar pooling of both fractions, two pools of 6 samples were generated by equimolar pooling of the samples based on the individual DNA concentration and fragment length which were evaluated using a Qubit fluorometer (Qubit dsDNA HS kit, ThermoFisher) and an Agilent 2100 Bioanalyzer. Hereafter, samples (pool 1 and pool 2) were ready for cDNA capture.

TABLE 10

Barcoded primers used for multiplexing purposes.

| Patient | Condition | SEQ ID No | Barcode | Sequence |
|---|---|---|---|---|
| P01 | NON-COVID-19 (mild, ambulatory) | 67 | dT_BC1001_PB | AAGCAGTGGTATCAACGCAGAGTACCACATATCAGAG TGCGTTTTTTTTTTTTTTTTTTTTTTTTTTTTTTVN |
| P02 | COVID-19 (mild, ambulatory) | 68 | dT_BC1002_PB | AAGCAGTGGTATCAACGCAGAGTACACACACAGACTG TGAGTTTTTTTTTTTTTTTTTTTTTTTTTTTTTTVN |
| P03 | COVID-19 (mild, ambulatory) | 69 | dT_BC1003_PB | AAGCAGTGGTATCAACGCAGAGTACACACATCTCGTG AGAGTTTTTTTTTTTTTTTTTTTTTTTTTTTTTTVN |
| P04 | COVID-19 (severe, ICU) | 70 | dT_BC1004_PB | AAGCAGTGGTATCAACGCAGAGTACCACGCACACACG CGCGTTTTTTTTTTTTTTTTTTTTTTTTTTTTTTVN |
| P05 | COVID-19 (mild, ambulatory) | 71 | dT_BC1005_PB | AAGCAGTGGTATCAACGCAGAGTACCACTCGACTCTC GCGTTTTTTTTTTTTTTTTTTTTTTTTTTTTTTVN |
| P06 | COVID-19 (severe, ICU) | 72 | dT_BC1006_PB | AAGCAGTGGTATCAACGCAGAGTACCATATATATCAG CTGTTTTTTTTTTTTTTTTTTTTTTTTTTTTTTTVN |
| P07 | NON-COVID-19 (mild, ambulatory) | 73 | dT_BC1007_PB | AAGCAGTGGTATCAACGCAGAGTACTCTGTATCTCTAT GTGTTTTTTTTTTTTTTTTTTTTTTTTTTTTTTVN |
| P08 | COVID-19 (mild, ambulatory) | 74 | dT_BC1008_PB | AAGCAGTGGTATCAACGCAGAGTACACAGTCGAGCGC TGCGTTTTTTTTTTTTTTTTTTTTTTTTTTTTTTTVN |
| P09 | COVID-19 (severe, ICU) | 75 | dT_BC1009_PB | AAGCAGTGGTATCAACGCAGAGTACACACACGCGAGA CAGATTTTTTTTTTTTTTTTTTTTTTTTTTTTTTTVN |
| P10 | COVID-19 (severe, ICU) | 76 | dT_BC1010_PB | AAGCAGTGGTATCAACGCAGAGTACACGCGCTATCTC AGAGTTTTTTTTTTTTTTTTTTTTTTTTTTTTTTTVN |
| P11 | COVID-19 (mild, ambulatory) | 77 | dT_BC1011_PB | AAGCAGTGGTATCAACGCAGAGTACCTATACGTATAT CTATTTTTTTTTTTTTTTTTTTTTTTTTTTTTTTVN |
| P12 | COVID-19 (severe, ICU) | 78 | dT_BC1012_PB | AAGCAGTGGTATCAACGCAGAGTACACACTAGATCGC GTGTTTTTTTTTTTTTTTTTTTTTTTTTTTTTTTVN |

2.6. CDNA Capture Using SeqCap EZ Probes

Initially, 1 μL of SMARTer PCR oligo (1000 μM) and 1 μL PolyT blocker (1000 μM) were added to 1.5 μg cDNA of pool 1 and pool 2 and subsequently dried for approximately 40 minutes in a DNA vacuum-concentrator. The cDNA was then hybridized with pre-designed SeqCap EZ probes targeting several mucin coding regions (Table 2 & 3) for 20 hours at 47° C. The captured cDNA was purified using Dynabeads M-270 (Thermo Fisher Scientific) according to the manufacturer's instructions and amplified by preparing a mixture containing 20 μl 10×LA PCR Buffer, 16 μl 2.5 mM dNTP's, 8.3 μL SMARTer PCR Oligos (12 μM each), 1.2 μl Takara LA Taq DNA polymerase and 50 μl cDNA supplemented with nuclease-free water to an end volume of 200 μl. For the actual PCR, the following program was ran on a thermocycler: an initial denaturation step at 95° C. for 2 min, followed by 11 cycles of amplification at 95° C. for 20 s and 68° C. for 10 min, and a final extension step at 72° C. for 10 min. A final clean-up of the amplified captured cDNA was performed using AMPure purification beads. The DNA concentration and fragment length were evaluated using a Qubit fluorometer (Qubit dsDNA HS kit, ThermoFisher) and an Agilent 2100 Bioanalyzer, after which the samples were equimolary pooled. The resulting cDNA library was then ready for SMRTbell library construction.

2.7. SMRTbell Library Construction and Sequencing on the PacBio Sequel System

Using the SMRTbell template prep kit (PacBio), 3 μg of captured cDNA was used for SMRTbell library construction. According to the manufacturer's instructions, the following steps were performed in chronological order: DNA damage repair, end repair, ligation of blunt adapters, Exo III and Exo VII treatment. One intermediate and two final purification steps were performed using AMPure purification beads. The DNA concentration and fragment length were evaluated using a Qubit fluorometer (Qubit dsDNA HS kit, ThermoFisher) and an Agilent 2100 Bioanalyzer for subsequent SMRTbell library construction. Following the instructions on SMRTlink, the Sequel Binding kit (PacBio) and Sequel Sequencing kit (PacBio) were used to dilute the DNA and internal control complexes, anneal the sequencing primer and bind the sequencing polymerase to the SMRTbell templates. Finally, 12 μM of the SMRTbell library was loaded on a 1M v3 SMRT cell.

2.8. Data Analysis

Statistical analysis using the GraphPad Prism 8.00 software (license DFG170003) was performed to determine significant differences in mucin mRNA expression between COVID-19 patients with severe and mild disease, non-COVID-19 patients with mild disease and healthy controls. Data were analysed by the Analysis of Variance (ANOVA) test and are presented as means±standard error of mean (SEM). Significance levels are indicated on the graphs and were corrected for multiple testing using the Tukey-Kramer's and Dunn's post-hoc multiple comparisons tests.

A discriminant function analysis was performed to determine COVID-19 severity and positivity based on a set of predictor variables [i.e. the mRNA expression of mucins]. The results are depicted as scatter plots showing the two main discriminant functions [i.e. function 1 (i.e. COVID-19 severity) and function 2 (i.e. COVID-19 positivity)] with the relevant main predictor variables summarized in a table. Furthermore, a multiple linear regression analysis was carried out to investigate associations [1] among mucin mRNA expression of the different patient groups (severe COVID-19, mild COVID-19 and mild non-COVID-19) and [2] between mucin expression and the clinical patient data. Correlation plots display results from Spearman correlation tests as well as a linear regression line with 95% confidence interval. A p-value below 0.05 was considered statistically significant. These analyses were performed using IBM SPSS Statistics 24 software.

Regarding analysis of isoform sequencing data, the raw subreads from single Zero Mode Waveguides (ZMWs) were initially aligned resulting in highly accurate polished circular consensus sequencing (ccs) reads (read accuracy set at 80% and minimum of 1 full pass for the ZMW) which were further processed using the command line interface. The lima tool v1.10.0 was used for demultiplexing and primer removal. Subsequently, the isoseq3 v3.2.2 package was used for further read processing to generate high quality mRNA transcripts. First, the refine tool was used for trimming of Poly(A) tails and identification and removal of concatemers. The data of the individual samples were then pooled together according to the condition (i.e. 2 samples from non-COVID patients with mild symptoms, 5 samples from COVID patients with mild symptoms and 5 samples from patients with severe symptoms) and analyzed in parallel. The isoseq3 cluster algorithm was used for transcript clustering. Minimap2 was used for the alignment of the processed reads to the human reference genome (GRCh38). After mapping, ToFU scripts from the cDNA_Cupcake GitHub repository were used to collapse redundant isoforms (minimal alignment coverage and minimal alignment identity set at 0.90) and identify associated count information. Finally, the SQANTI2 tool was used for extensive characterization of mucin mRNA isoforms. The eventual isoforms were then further inspected by visualization in the Integrative Genomics Viewer (IGV) version 2.8.0 and by the analysis of the classification and junction files in Excel.

3. Results 3.1. Aberrant Mucin mRNA Expression Associated with COVID-19 Positivity and Severity Here, we first investigated mucin mRNA expression levels in the blood of the different patient groups by RT-qPCR. Compared to healthy controls, expression of MUC13 and MUC21 mRNA was significantly altered in COVID-19 patients with severe and mild disease, with a higher trend of expression seen in the COVID-19 patient group with mild symptoms. MUC1 mRNA expression was significantly increased in critical severely ill COVID-19 patients compared to COVID-19 and non-COVID-19 patients with mild symptoms and healthy controls (FIG. 23). On the contrary, mRNA levels of MUC16 was significantly increased in the ambulatory patients with mild symptoms, irrespective of COVID-19 positivity, and remained low in the severe COVID-19 group (FIG. 23), whereas expression of MUC2 and MUC5B mRNA was significantly increased in all patient groups compared to healthy controls with a higher trend of expression seen in the COVID-19 mild patient group (FIG. 23). MUC4 mRNA expression was only significantly increased in the mild COVID-19 patient group compared the healthy controls (FIG. 23). MUC5AC mRNA expression was not significantly altered, although a decreasing trend in expression was seen in the severe COVID-19 patient group (FIG. 23).

To elucidate which of the aberrantly expressed mucins can predict COVID-19 positivity and severity, the mucin mRNA expression data were used to perform a discriminant analysis. MUC1 mRNA expression is the major determinant for identifying COVID-19 severity, followed by expression of MUC13 and MUC21 mRNA which are the best factors to discriminate between mild COVID-19 and mild non-COVID-19 (FIG. 24A; 84% of original grouped cases classified correctly). Interestingly, when MUC16 mRNA expression was added to the analysis, correct classification of the original grouped cases even increased to 94.4% with MUC1 and MUC16 mRNA expression now being the best factors to discriminate for COVID-19 severity (FIG. 24B). MUC13 and MUC21 mRNA expression (and to a lesser extend MUC2, MUC5AC and MUC5B mRNA expression) remained the best factors to discriminate between mild COVID-19 and mild non-COVID-19 (FIG. 24B). Subsequently, a stepwise linear regression analysis on the mucin expression data of the different patient groups (severe COVID-19, mild COVID-19 and mild non-COVID-19), further confirmed MUC16 (β-coefficient=−0.447; p=0.025) and MUC1 (β-coefficient=0.657; p=0.003) mRNA expression as major determinants for COVID-19 severity. To further investigate associations between MUC16 and MUC1 mRNA expression and the clinical data of the severe COVID-19 patient group, a backward linear regression analysis was performed. Interestingly, increased MUC1 mRNA expression strongly associated with fungal co-infection (β-coefficient=0.759; p=0.001). On its turn, the presence of fungal co-infection associated with mortality (β-coefficient=0.645; p=0.009).

Furthermore, we also verified collinearity among the mucin mRNA expression data of the different patient groups (severe COVID-19, mild COVID-19 and mild non-COVID-19) and between mucin mRNA expression and the clinical patient data using Spearman correlation tests. Among the different patient groups, MUC16 and MUC1 mRNA expression strongly correlated with COVID-19 severity (FIG. 25A) with a significant negative correlation seen between MUC16 and MUC1 mRNA expression (FIG. 25B). While increased MUC13 mRNA expression was associated with increased MUC2 and MUC21 mRNA expression (FIG. 25C-E), MUC21 mRNA expression also positively correlated with MUC5B mRNA expression (FIG. 25F) and MUC2 mRNA expression strongly correlated with MUC4 mRNA expression (FIG. 25G).

Finally, the mRNA expression levels of MUC1 and MUC13 also significantly correlated with fungal co-infection and the SOFA score, respectively (FIG. 26).

In addition, also other correlations among the clinical variables were found within the severe COVID-19 patient group. These include associations between age and BMI (r=−0.677, p=0.007), age and diabetes (r=−0.594, p=0.020), diabetes and renal insufficiency (r=0.533, p=0.041), sex and lung disease (r=0.661, p=0.007), symptom onset between hospital admission and SOFA score (r=0.598, p=0.031), ICU/total hospitalization and duration ventilation (r=0.985/0.889, p=0.0001), replacement ETT and ICU hospitalization (r=0.640, p=0.010), replacement ETT and duration ventilation (r=0.639, p=0.010), replacement ETT and $P_aO_2/F_iO_2$ ratio (r=−0.537, p=0.048), replacement ETT and $SOFA_{max}$ (r=0.569, p=0.027), replacement ETT and fungal co-infection (r=0.600, p=0.018) and fungal co-infection and $P_aO_2/F_iO_2$ ratio (r=−0.595, p=0.025).

3.2. Remdesivir, Favipiravir and Baricitinib are Able to Reduce Aberrant Mucin Expression Induced by SARS-CoV-2 Infection in Pulmonary Epithelial Cells Subsequently, we investigated the ability of potential COVID-19 treatments to reduce aberrant mucin expression triggered by SARS-CoV-2. In vitro stimulation of pulmonary epithelial Calu3 cells with several therapeutic drugs at certain doses, showed that remdesivir and baricitinib were able to significantly reduce MUC1, MUC4, MUC5AC, MUC5B, MUC13 and MUC21 mRNA expression (FIG. 27). Also, favipiravir (another antiviral agent) was able to decrease MUC4, MUC5AC, MUC5B, MUC13 and MUC21 mRNA expression and to increase MUC1 mRNA expression (FIG. 27). MUC1 and MUC21 mRNA expression were also significantly increased upon dexamethasone treatment whereas toculizumab was able to significantly reduce MUC1, MUC4 and MUC21 mRNA expression (FIG. 27).

3.3. Mucin mRNA Isoforms Associated with COVID-19 Positivity and Severity 3.3.1. General Features of the Sequencing Run Long-read RNA sequencing of all samples initially generated a total of $10.59\times10^9$ bases after a movie time of 20 hours. Sequencing yield and read quality was high and comparable across all samples. The average read length was 2561 bp. Initially, 77547 ccs reads were generated from the alignment of subreads taken from a single ZMW. 28439 (37%) reads were lost during primer removal and demultiplexing as a consequence of undesired barcoded primer combinations. After clustering, 24661 reads were remained corresponding to 4939 different transcripts. As visual analysis of targeted mucin regions in IGV showed dense coverage of the genomic regions of MUC1, MUC2, MUC12, MUC13, MUC16 and MUC17, further analysis was limited to these mucin glycoproteins.

3.3.2. MUC1 mRNA Isoforms

Targeted PacBio isoform sequencing revealed the identification of novel MUC1 mRNA isoforms (FIG. 28 & Table 11) which had not been previously characterized. Interestingly, whereas no mRNA isoforms were identified using PacBio sequencing in the blood from non-COVID19 patients and COVID-19 patients with mild symptoms, 2 mono-exonic alternative transcripts were identified in the blood from COVID19 patients with severe symptoms that resulted from intron retention upstream of exon 11 (which is coding for the intracellular mucin domain (CT)). The results of these limited number of samples show that different alternative transcripts of MUC1 can be identified in the blood of COVID19 patients which are associated with severe disease.

3.3.3. MUC2 mRNA Isoforms

Targeted PacBio isoform sequencing revealed the identification of novel MUC2 mRNA isoforms in the blood from COVID19 and non-COVID19 patients (FIG. 29 & Table 11). In general, 3 alternative mRNA transcripts were found in mRNA isolated from blood which had not been previously characterized. Two alternative transcripts were found in non-COVID19 patients and one was found in COVID-19 patients with mild disease, which were all transcripts coding for the VNTR region of the MUC2 gene. No alternative transcripts were identified in the blood of COVID-19 patients with severe disease. Nevertheless, targeted PacBio isoform sequencing suggests a distinct expression pattern of MUC2 mRNA isoforms in the blood of COVID19 and non-COVID19 patients.

3.3.4. MUC13 mRNA Isoforms

Five smaller alternative MUC13 mRNA transcripts were identified in the blood from COVID19 patients, of which four were found in patients with mild disease and one in patients with severe disease (FIG. 30 & Table 11). No mRNA isoforms could be characterized in the blood from non-COVID19 patients with the targeted PacBio isoform sequencing approach (FIG. 30 & Table 11). All mRNA isoforms found had not been identified previously and mainly resulted from intron retention. Of these expressed in the blood from patients with mild symptoms, two transcripts were coding for EGF-like domains (PB.3.2 and PB.3.4) and one transcript for the TM domain (PB.3.1).

3.3.5. MUC16 mRNA Isoforms

Targeted PacBio isoform sequencing revealed the identification of many small novel MUC16 mRNA isoforms in the blood from COVID19 and non-COVID19 (FIG. 31 & Table 11). In general, 20 alternative mRNA transcripts (=isoforms) were found in mRNA isolated from blood which had not been previously characterized. All novel isoforms mapped to the extracellular domain of the MUC16 gene. One multi-exonic mRNA isoform was identified in non-COVID19 patients (PB.4.1), which was also found in COVID19 patients. In addition, several other small MUC16 mRNA isoforms were found, of which 14 were identified in patients with mild disease and five in patients with severe COVID-9. Hence, the expression of MUC16 mRNA isoforms was associated with disease severity in COVID19 patients. Most mRNA isoforms were mono-exonic and resulted from intron retention. A detailed overview of all alternative transcripts can be found in Table 11.

TABLE 11

Detailed overview of characteristics of mucin mRNA isoforms in blood samples from COVID-19 patients and non-COVID19 controls.

| Isoform ID | Chrom | Gene | Length (bp) | Exons | Transcript | Sub-category |
|---|---|---|---|---|---|---|
| Ambulatory non-COVID19 patients with mild common cold symptoms | | | | | | |
| PB.2.1 | chr11 | MUC2 | 870 | 1 | Novel | Mono-exon |
| PB.2.2 | chr11 | MUC2 | 1765 | 11 | Novel | Intron retention |
| PB.4.1 | chr19 | MUC16 | 2263 | 2 | Novel | Multi-exon |
| ambulatory COVID-19 patients with mild symptoms | | | | | | |
| PB.2.3 | chr11 | MUC2 | 271 | 1 | Novel | Mono-exon |
| PB.3.1 | chr3 | MUC13 | 2538 | 2 | Novel | Intron retention |
| PB.3.2 | chr3 | MUC13 | 1442 | 1 | Novel | Intron retention |
| PB.3.3 | chr3 | MUC13 | 712 | 1 | Novel | Intron retention |

TABLE 11-continued

Detailed overview of characteristics of mucin mRNA isoforms in blood samples from COVID-19 patients and non-COVID19 controls.

| Isoform ID | Chrom | Gene | Length (bp) | Exons | Transcript | Sub-category |
|---|---|---|---|---|---|---|
| PB.3.4 | chr3 | MUC13 | 2538 | 2 | Novel | Intron retention |
| PB.4.1 | chr19 | MUC16 | 2263 | 2 | Novel | Multi-exon |
| PB.4.2 | chr19 | MUC16 | 2540 | 2 | Novel | Multi-exon |
| PB.4.3 | chr19 | MUC16 | 3017 | 1 | Novel | Intron retention |
| PB.4.4 | chr19 | MUC16 | 1807 | 1 | Novel | Intron retention |
| PB.4.5 | chr19 | MUC16 | 1808 | 1 | Novel | Intron retention |
| PB.4.6 | chr19 | MUC16 | 207 | 1 | Novel | Intron retention |
| PB.4.7 | chr19 | MUC16 | 2795 | 1 | Novel | Intron retention |
| PB.4.8 | chr19 | MUC16 | 984 | 1 | Novel | Intron retention |
| PB.4.9 | chr19 | MUC16 | 1438 | 1 | Novel | Intron retention |
| PB.4.10 | chr19 | MUC16 | 2239 | 1 | Novel | Intron retention |
| PB.4.11 | chr19 | MUC16 | 2364 | 1 | Novel | Intron retention |
| PB.4.12 | chr19 | MUC16 | 2309 | 1 | Novel | Intron retention |
| PB.4.13 | chr19 | MUC16 | 2241 | 1 | Novel | Intron retention |
| PB.4.14 | chr19 | MUC16 | 2223 | 1 | Novel | Intron retention |
| PB.4.15 | chr19 | MUC16 | 2200 | 1 | Novel | Intron retention |
| COVID19 patients with severe symptoms and hospitalized at the ICU | | | | | | |
| PB.1.1 | chr1 | MUC1 | 694 | 1 | Novel | Intron retention |
| PB.1.2 | chr1 | MUC1 | 1269 | 1 | Novel | Intron retention |
| PB.3.5 | chr3 | MUC13 | 494 | 1 | Novel | Intron retention |
| PB.4.1 | chr19 | MUC16 | 2266 | 2 | Novel | Multi-exon |
| PB.4.16 | chr19 | MUC16 | 2546 | 6 | Novel | Multi-exon |
| PB.4.17 | chr19 | MUC16 | 1488 | 1 | Novel | Intron retention |
| PB.4.18 | chr19 | MUC16 | 2224 | 1 | Novel | Intron retention |
| PB.4.19 | chr19 | MUC16 | 1457 | 1 | Novel | Intron retention |
| PB.4.20 | chr19 | MUC16 | 2155 | 1 | Novel | Intron retention |

4. Concluding Remarks

Based on the mucin mRNA expression data measured in the blood of COVID-19 patients with a varying degree of disease severity, non-COVID-19 patients with common cold like symptoms and healthy controls, a specific mucin signature for COVID-19 could be identified with a central role for MUC1 and MUC16 mRNA expression in predicting disease severity and MUC13 and MUC21 mRNA expression in predicting COVID-19 positivity. Furthermore, several COVID-19 treatments, such as baricitinib, favipiravir and remdesivir, which have shown promising results in clinical trials, were able to suppress mucin hypersecretion and more specifically the mucins defining the mucin mRNA signature for COVID-19 disease severity and positivity, i.e. MUC13, MUC21, MUC16 and MUC1. This highlights the potential of these mucins in disease surveillance as well.

Subsequently, based on the PacBio isoform sequencing data gathered from a limited number of blood samples, we were able to identify unique and novel MUC1 mRNA isoforms associated with severe COVID-19 and unique and novel MUC2 mRNA isoforms, MUC13 mRNA isoforms and MUC16 mRNA isoforms associated with mild COVID-19 and COVID-19 positivity.

In conclusion, altered mRNA expression of MUC1, MUC2, MUC5AC, MUC5B, MUC13, MUC16 and MUC21 mucins as well as alternative mRNA isoforms of MUC1, MUC2, MUC13 and MUC16 could be associated with COVID-19 severity and positivity, highlighting their potential for COVID-19 diagnosis, prognosis, disease surveillance and treatment.

Example 5: A Dynamic COVID-19 Mucin mRNA Signature Associates with Disease Presentation and Prognosis

1. Background of the Invention

In this work, we show a dynamic COVID-19 mucin mRNA blood signature associated with disease presentation and severity.

2. Material and Methods

Patient cohorts and sample collection. Between 20 Aug. 2020 and 6 Jan. 2021, 40 severely ill COVID-19 patients hospitalized at the tertiary ICU of the Antwerp University Hospital, Belgium and 32 ambulatory COVID-19 patients with mild-moderate symptoms, were enrolled for this study. The severity of the disease was classified in line with the WHO scale as: (i) mild; (ii) moderate (symptoms such as fever, cough, dyspnea, but no signs of severe pneumonia); (iii) severe: clinical signs of pneumonia (fever, cough, dyspnea, fast breathing) plus the need for respiratory support (high flow oxygen and/or mechanical ventilation); (iv) critical: presence of Acute Respiratory Distress Syndrome (ARDS), and/or sepsis or multiple organ failure (septic shock).

Ambulatory patients with mild common cold symptoms (n=30) and healthy controls (n=6), which are all negative for COVID-19 as confirmed by viral PCR, were included as control groups. The ambulatory COVID-19 positive and negative patient groups and healthy controls were recruited at 5 different general practitioner practices and one triage station in Antwerp, Belgium.

The recorded data for the ICU patients, all presenting with the hallmarks of the acute respiratory distress syndrome (ARDS), the most severe form of lung injury, includes: 1) demographic and anthropometric data; 2) several markers of severity of pulmonary involvement (i.e. necessity for invasive ventilation, duration of invasive ventilation, unforeseen replacement of endotracheal tubes (ETT) due to mucus impaction, lowest $P_aO_2/F_iO_2$ ratio during ICU stay); 3) assessment of severity of disease (i.e. duration of hospitalization, renal failure necessitating dialysis, occurrence of secondary bacterial or fungal infection during ICU stay, routine measurements of IL-6 (μg/ml; Elecsys IL-6 assay (Roche)) and ferritin (μg/l; Atellica IM Fer assay (Siemens Healthineers)) serum levels at admission onset and their maximum serum levels during ICU stay, cardiac/neurologic/thromboembolic complications, the highest sequential organ failure assessment (SOFA) score[31] and in-hospital mortality). These data were retrieved from the patient data management system (Metavision, IMD software).

Blood sampling for unravelling the peripheral blood mucin mRNA landscape was performed upon admission at the ICU for the severely ill COVID-19 patients or, in case of the ambulatory patients and healthy controls, at the same time of their COVID-19 PCR test in order to recruit both COVID-19 positive and negative patients. All blood samples were stored in PAXgene RNA blood tubes (PreAnalytiX) at −80° C. until RNA extraction and subsequent mucin gene expression analyses (see further). This study was approved by the Ethical Committee of the UZA (20/14/176 (B3002020000059) and 20/43/555 (B3002020000193)) and signed informed consent was obtained from the healthy controls, the patients or in case of intubated ICU patients by their closest relative. Samples were registered and stored until analysis in the Antwerp University Hospital Biobank, Antwerp, Belgium (ID: 71030031000).

RNA Isolation and Quality Control: See Example 4

Mucin mRNA expression by RT-PCR. One μg RNA was converted to cDNA by reverse transcription using the SensiFast™ cDNA synthesis kit (Bioline). Relative mucin gene expression was then determined by SYBR Green RT-qPCR using the GoTaq qPCR master mix (Promega) on a QuantStudio 3 Real-Time PCR instrument (Thermo Fisher Scientific). Standard validated QuantiTect primers available from Qiagen were used for GAPDH (QT00079247), ACTB (QT00095431), MUC1 (QT00015379), MUC2 (QT01004675), MUC4 (QT00045479), MUC5AC (QT00088991) and MUC5B (QT01322818), MUC6 (QT00237839), MUC13 (QT00002478), MUC16 (QT01192996), MUC20 (QT00012068) and MUC21 (QT01159060). All RT-qPCR reactions were performed in duplicate and involved an initial DNA polymerase activation step for 2 min at 95° C., followed by 40 cycles of denaturation at 95° C. for 15 sec and annealing/extension for 1 min at 60° C. Analysis and quality control were performed using qbase+ software (Biogazelle). Relative expression of the target genes was normalized to the expression of the housekeeping genes ACTB and GAPDH. In the blood, mucin expression values are expressed as fold change using the delta delta Ct method.

Data analysis. Statistical analysis using the GraphPad Prism 8.00 software (license DFG170003) was performed to determine significant differences in 1) age and gender distribution among the different patient groups (severe COVID-19; mild COVID-19, mild non-COVID-19 and healthy controls) and 2) mucin mRNA expression between COVID-19 patients with severe and mild disease, non-COVID-19 patients with mild disease and healthy controls. Data were analysed by the Analysis of Variance (ANOVA) test and are presented as means±standard error of mean (SEM). Significance levels are indicated on the graphs and were corrected for multiple testing using the Tukey-Kramer's and Dunn's post-hoc multiple comparisons tests.

A linear regression analysis was carried out to investigate associations between mucin mRNA expression and the clinical data (i.e. age and gender) of the different patient groups (severe COVID-19, mild COVID-19 and mild non-COVID-19). A discriminant function analysis was then performed to determine COVID-19 severity based on a set of predictor variables [i.e. the mRNA expression of mucins]. The results are depicted as a scatter plot showing the two main discriminant functions [i.e. function 1 (i.e. severe COVID-19) and function 2 (i.e. mild COVID-19)] with the relevant main predictor variables summarized in a table. Subsequently, a least absolute shrinkage and selection operator (Lasso) regression with leave-one-out cross validation and ROC analysis was also carried out to investigate which mucin mRNA expression profiles are the most accurate predictors for COVID-19 severity and presentation. In addition, Spearman correlations between mucin mRNA expression and the clinical data (i.e. COVID-19 severity and symptoms) were identified among the different patient cohorts and between mucin mRNA expression and the clinical patient data separately in the severe COVID-19 group. Correlation plots display results from Spearman correlation tests as well as a linear regression line with 95% confidence interval. Correlations with $r>0.3$, $r<-0.3$ and a p-value below 0.05 were considered statistically significant. These analyses were performed using IBM SPSS Statistics 24 and R software (gplots, ggplot2, tidyverse, RColorBrewer, dplyr, glmnet and ROCR packages).

3. Results

Patient demographics and clinical characteristics. In total, we included 108 individuals which were divided in 4 patient groups. Seventy-two had confirmed COVID-19 infection: i.e. the severe COVID-19 group consisting of 40 critically ill patients with severe symptoms (severe hypoxemia, ARDS) necessitating intensive care unit (ICU) admission; the mild COVID-19 group consisting of 32 ambulatory patients with moderate (n=4) to mild (n=28) symptoms. Thirty ambulatory patients, designated as the non-COVID-19 patient group, had mild common cold-like symptoms and were screened negative for COVID-19. Six patients were COVID-19 negative confirmed cases and assigned to the healthy control group.

In the severe COVID-19 patient group, significantly more males than females were recruited in the severe COVID-19 group with a median age of 63 years (Table 12) and BMI of 28.15 kg/m$^2$ (interquartile range (IQR)=23.53-31.05 kg/m$^2$), whereas the ambulatory mild COVID-19 and non-COVID-19 patient groups comprised significant more females than males with a median age of 35 and 36 years, respectively (Table 12). The healthy controls had a similar median age as the ambulatory patient groups and an equal gender distribution (Table 12). A linear regression analysis further showed that COVID-19 severity increased with age (β-coefficient=−0.431; p=0.0001). Information on symptoms upon emergency admission (severe COVID-19 group) or PCR testing (ambulatory patient groups) was also available. Overall, symptoms described by severe COVID-19 patients include cough (46%), dyspnea (77%), fever (42%), gastrointestinal complaints (46%) and malaise (42%). On the contrary, the majority of the ambulatory COVID-19 patients experienced loss of smell and taste (i.e. anosmia/ageusia; 50%), cough (41%), fever (37.5%), headache (41%) and rhinitis (41%). Similar symptoms were also described in the ambulatory COVID-19 negative group with the exception of loss of smell and taste (0%).

TABLE 12

Age and gender distribution among the different patient groups (n = 108)

| | severe COVID-19 | mild COVID-19 | mild non-COVID-19 | healthy controls | p-value |
|---|---|---|---|---|---|
| male/female sex ratio | 3 (30/10) | 0.60 (12/20) | 0.43 (9/21) | 1 (3/3) | 0.0014 |
| age (median, IQR) | | | | | |

TABLE 12-continued

Age and gender distribution among the different patient groups (n = 108)

| | severe COVID-19 | mild COVID-19 | mild non-COVID-19 | healthy controls | p-value |
|---|---|---|---|---|---|
| male | 67 (56.25-73.25) | 36.5 (25.25-57.75) | 54 (28-57) | 31 (26-31) | 0.0043 |
| female | 54 (29-64) | 35 (25.75-44.5) | 32 (25.5-42) | 39 (38-39) | 0.0461 |
| total | 63 (52.25-71.5) | 35 (25.75-49) | 36 (25.75-54.5) | 38.5 (29.75-50) | 0.0043 |

severe COVID-19 (n = 40); mild COVID-19 (n = 32); mild non-COVID-19 (n = 30); healthy controls (n = 6).
p-value: significance compared to the severe COVID-19 group Regarding hospitalization of the ICU COVID-19 patients, the median duration from symptom onset until hospital admission was 6 days (IQR=4-7 days), with a total median hospitalization of 25 days (IQR=16-36.5 days) of which ca. 15 days (IQR=9-28) at the ICU (Extended data FIG. 2*a*). All patients received respiratory support as the median ratio of minimal partial pressure of arterial oxygen to fractional concentration of oxygen inspired ($P_aO_2/F_iO_2$) was 77 mmHg (IQR=53-107). Seventy-five percent of the ICU patients (30/40) even required invasive ventilation with a median length of 11 days (IQR=0.25-22) of which 50% (15/30) also needed a replacement of the endotracheal tube (ETT) due to, amongst others, mucus obstruction. Furthermore, the maximal sequential organ failure assessment (SOFA) score and maximal IL-6 and ferritin serum levels were 12 (IQR=7.75-14), 102 μg/ml (IQR=36.25-377 μg/ml) and 1628 μg/l (IQR=904.75-2892 μg/l), respectively. A Spearman correlation assay further highlighted several positive and negative correlations between the clinical characteristics of severe COVID-19 patients, such as associations between age and gender, age and BMI, age and mortality, mortality and the necessity for invasive ventilation, mortality and occurrence of bacterial/fungal co-infections and $ferritin_{max}/IL6_{max}$ levels and occurrence of fungal co-infections.

A COVID-19 mucin mRNA signature. First, we tested the blood samples from the different patient groups to measure mucin mRNA expression using validated RT-PCR assays. MUC1 mRNA expression was significantly higher in the severe and mild COVID-19 patients compared to healthy controls (FIG. 32*a,k*). A significant difference in MUC1 mRNA expression was also seen between the severe COVID-19 patients and the mild non-COVID-19 patient group (FIG. 32*a,k*). Compared to healthy controls, expression of MUC2 mRNA was significantly altered in severe COVID-19, mild COVID-19 and mild non-COVID-19 patients with a significant higher expression level in the COVID-19 patient groups compared to the mild non-COVID-19 group (FIG. 32*b,k*). Both mRNA expression of MUC13 and MUC21 was only significantly increased in COVID-19 patients compared to healthy controls (FIG. 32*g,j,k*) with their highest level expression seen in the mild COVID-19 patient group (FIG. 32*g,k*). On the contrary, mRNA levels of MUC16 and MUC20 were significantly increased in the mild non-COVID-19 group (FIG. 32*h,l,k*) and of MUC20 also in the mild COVID-19 group (FIG. 32*i,k*). Expressions of both mucins remained however unchanged in the severe COVID-19 group compared to healthy controls and were significantly lower compared to the mild non-COVID-19 group (FIG. 32*h,l,k*). Whereas expression of MUC5B mRNA was significantly increased in all patient groups compared to healthy controls with a higher trend of expression seen in severe COVID-19 patients (FIG. 32*e,k*), no significant alterations in mRNA expression were identified for MUC4, MUC5AC and MUC6 (FIG. 32*c,d,f,k*). Although, expression of MUC4 mRNA was significantly lower in the severe COVID-19 group compared to the non-COVID-19 patient group (FIG. 32*c*).

To elucidate which of the aberrantly expressed mucins can predict COVID-19 severity, the mucin mRNA expression data were first used to perform a discriminant analysis. Systemic MUC1 and MUC16 mRNA expression are the major determinants for identifying severe COVID-19 patients, followed by expression of MUC2, MUC13, MUC20 and MUC21 mRNA, which are the best factors to discriminate mild COVID-19 patients from patients with severe COVID-19 and mild non-COVID-19 patients (FIG. 33*a;* 82.8% of original grouped cases classified correctly). Interestingly, when leaving out single mucins or combination of mucins from the analysis, correct classification of the original grouped cases decreased (data not shown). Subsequently, a Lasso regression with leave-one-out cross validation and receiver operating characteristic (ROC) analysis further validated the results of the discriminant analysis in which mRNA expression of MUC1, MUC5B, MUC13, MUC16 and MUC20 are the discriminative variables for COVID-19 severity (i.e. severe or mild COVID-19), with an $AUC_{ROC}$ of 81.7% and a sensitivity and specificity of 75.0% and 84.4%, respectively (FIG. 33*b*). By using the same approach, we also showed that mRNA expression of MUC1, MUC2, MUC16 and MUC20 are the most accurate variables to predict the presence of COVID-19 among symptomatic patients (FIG. 33*c*; $AUC_{ROC}$=93.2%; sensitivity: 88.9%; specificity: 83.3%).

Furthermore, we also verified collinearity between the mucin mRNA expression data and disease severity (severe COVID-19, mild COVID-19 and mild non-COVID-19) and between mucin mRNA expression and the clinical patient data using Spearman correlation tests. MUC1, MUC2, MUC16 and MUC20 mRNA expression strongly correlated with COVID-19 severity (FIG. 34*a-d*). Although MUC4 mRNA expression did not alter significantly among the different patient groups and compared to healthy controls, its expression level showed a weak but significant negative correlation with COVID-19 severity (r=−0.223; p=0.029). A significant positive correlation was also seen between MUC1 and MUC2 mRNA expression (FIG. 34*e*) and between MUC16 and MUC20 mRNA expression (FIG. 34*f*). While increased MUC13 mRNA expression was associated with increased MUC2 (FIG. 34*g*) and MUC21 (FIG. 34*h*) mRNA expression, MUC21 mRNA expression positively correlated with MUC2 (r=0.408; p=0.0001), MUC16 (r=0.259; p=0.01) and MUC20 (r=0.325; p=0.001) mRNA expression as well. Other significant relationships among mucin mRNA expression profiles were also found for MUC2, MUC5AC and MUC5B ($r_{MUC2\text{-}MUC5AC}$=0.373; p=0.0001; $r_{MUC2\text{-}MUC5B}$=0.287; p=0.003), MUC16, MUC4, MUC5AC, MUC5B and MUC6 ($r_{MUC4\text{-}MUC16}$=0.273; p=0.0007, $r_{MUC5AC\text{-}MUC16}$=0.256; p=0.010, $r_{MUC5B\text{-}MUC16}$=0.243, p=0.014, $r_{MUC6\text{-}MUC16}$=0.362; p=0.0001) and MUC20, MUC4, MUC5AC, MUC5B and MUC6 ($r_{MUC4\text{-}MUC20}$=0.277; p=0.006, $r_{MUC5AC\text{-}MUC20}$=0.353; p=0.0001, $r_{MUC5B\text{-}MUC20}$=0.316; p=0.001, $r_{MUC6\text{-}MUC20}$=0.507; p=0.0001). In addition, MUC1 mRNA expression positively correlated with age (FIG. 35*a*) and MUC4 mRNA expression with gender (i.e. higher MUC4 expression was noted in females; r=0.215; p=0.036). Associations between mucin mRNA expression, the clinical characteristics of the ICU severe COVID-19 patients and the symptoms described in the different patient cohorts were also found. Within the severe COVID-19 patient group, MUC1 mRNA expression significantly correlated with the $P_aO_2/F_iO_2$ ratio (FIG. 35*b*) and mortality (FIG. 35*c*) and MUC16 mRNA expression with the need for invasive ventilation (FIG. 35*d*). The association between MUC1 expression and mortality is also shown in FIG. 32*a* were high MUC1 expression was mostly seen in deceased COVID-19 ICU patients (marked as filled blue bullets with a cross). Furthermore, the occurrence of pulmonary fungal co-infection positively correlated with MUC1 mRNA expression (FIG. 35*e*) but negatively with MUC2 (FIG. 35*f*), MUC16 (FIG. 35*g*) and MUC20 (FIG. 35*h*) mRNA expression. As the occurrence of fungal co-infections correlated strongly with $ferritin_{max}$ and IL-$6_{max}$ serum levels, negative correlations were also identified for these clinical outcome parameters and MUC2, MUC13, MUC20 (FIG. 35*i*-1) and MUC21 (r=−0.392; p=0.012) mRNA expression. Interestingly, no significant associations between mucin expression and the presence of a co-morbidity were found further confirming that the changes in mucin expression could be attributed to COVID-19. Finally, MUC13 and MUC2 mRNA expression strongly associated with the loss of smell and taste (FIG. 35*m,n*), whereas MUC16 and MUC20 mRNA expression positively correlated with sore throat (FIG. 35*o,p*), MUC1 mRNA expression with dyspnea (FIG. 35*q*) and MUC2 mRNA expression with both dyspnea (FIG. 4*r*) and gastrointestinal symptoms (r=0.221; p=0.040).

4. Conclusions

In summary, the multifaceted mucin mRNA signature identifies COVID-19 presentation in symptomatic patients with high sensitivity and specificity, serves as prognostic biomarker for COVID-19 patient severity stratification and may collectively and individually guide treatment options (FIG. 36). It also provides a basis for addressing many clinical and research questions, including whether or not specific mucin traits are causes or consequences of disease progression and which mucin mRNA isoforms are associated with COVID-19 severity allowing to identify high-risk and low-risk patients. Mucins are highly polymorphic, and the presence of genetic differences can alter gene expression resulting in several mRNA isoforms via alternative splicing. While most isoforms encode similar biological functions, some alter protein function resulting in progression towards disease. Nevertheless, the identified dynamic mucin mRNA signature has great potential to improve COVID-19 management thereby diminishing the life-threatening potential of SARS-CoV-2 infection and independent validation (i.e. mucin mRNA measurements at baseline and during infection) in other COVID-19 cohorts is recommended.

Example 6: a Dynamic COVID-19 Mucin mRNA Signature Associates with Disease Presentation and Prognosis (Amendment of Example 5)

1. Background of the Invention

In this work, we show a dynamic COVID-19 mucin mRNA blood signature associated with disease presentation and severity. This example is an extension of example 4 in which added additional patients to each group and included age and gender as additional variables in the statistical analysis to define the mucin mRNA signature specific for COVID-19 severity and presentation.

2. Material and Methods

Patient cohorts and sample collection. Between 20 Aug. 2020 and 6 Apr. 2021, 50 critically ill COVID-19 patients hospitalized at the tertiary ICU of the Antwerp University Hospital, Belgium and 35 ambulatory COVID-19 patients with no or mild-moderate symptoms, were enrolled for this study (Table 13). The severity of the disease was classified in line with the WHO scale as: (i) mild; (ii) moderate (symptoms such as fever, cough, dyspnea, but no signs of severe pneumonia); (iii) severe: clinical signs of pneumonia plus the need for respiratory support (high flow oxygen and/or mechanical ventilation); (iv) critical: presence of Acute Respiratory Distress Syndrome (ARDS), and/or sepsis or multiple organ failure (septic shock)

Ambulatory patients with mild common cold symptoms (n=30) and healthy controls (n=20), which are all negative for COVID-19 as confirmed by viral PCR, were included as control groups (Table 13). The ambulatory COVID-19 positive and negative patient groups and healthy controls were recruited at 5 different general practitioner practices and one triage station in Antwerp, Belgium.

TABLE 13

Demographics of the different patient cohorts

| | Critically ill COVID-19 (n = 50) | Mild COVID-19 (n = 35) | Mild non-COVID-19 (n = 30) | Healthy controls (n = 20) | P value |
|---|---|---|---|---|---|
| Demographics | | | | | |
| Sex, male, n (%) | 33 (66) | 12 (34) | 9 (30) | 12 (60) | 0.003 |
| Age_all (yrs), median (IQR) | 63 (50-70) | 34 (26-49) | 36 (25.75-54.5) | 56 (38.25-83) | <0.0001 |
| Age_male (yrs), median (IQR) | 65 (53.5-72.5) | 36.5 (25.25-57.75) | 54 (28-57) | 56 (31-85.75) | 0.0006 |
| Age_female (yrs) median (IQR) | 56 (31.5-63.5) | 34 (26-43) | 32 (25.5-42) | 56 (39-75.75) | 0.0003 |

Blood sampling for unravelling the peripheral blood mucin mRNA landscape was performed upon admission at the ICU for the severely ill COVID-19 patients or, in case of the ambulatory patients and healthy controls, at the same time of their COVID-19 PCR test in order to recruit both COVID-19 positive and negative patients. Blood sampling for unravelling the peripheral blood mucin mRNA landscape was performed upon admission at the ICU for the severely ill COVID-19 patients or, in case of the ambulatory patients and healthy controls, at the same time of their COVID-19 PCR test in order to recruit both COVID-19 positive and negative patients. All blood samples were immediately stored in PAXgene RNA blood tubes (PreAnalytiX) at −80° C. until RNA extraction and subsequent mucin gene expression analyses.

RNA Isolation and Quality Control: See Example 4

Mucin mRNA Expression by RT-PCR: See Example 5

Data analysis. A principal component analysis (PCA; unsupervised method) and a Sparse Partial Least Square Discriminant Analysis (sPLS-DA; supervised method) were performed to determine COVID-19 severity based on a set of predictor variables [i.e. the peripheral mRNA expression levels of mucins, age and sex]. PCA was carried out using the R (v3·6·1) packages pca3d (v0·10·2), rgl (v0·106·8), Factoextra (v1·0·7), FactoMineR (v2·3) and devtools (v2·4·1) in Rstudio (1·1·456), whereas sPLS-DA was done using the Github package Mixomics including 12 variables in the first component. Subsequently, a least absolute shrinkage and selection operator (Lasso) regression with leave-one-out cross validation and ROC analysis was also carried out to investigate which variables (peripheral mucin expression levels, age and sex) are the most accurate predictors for COVID-19 severity and presentation. These analyses were performed using the R packages glmnet (v4·1·1), gplots (v3·1·1), ROCR (v1·0·11), foreign (v0·8·81), propCls (v0·3·0)) in Rstudio.

3. Results

Mucin mRNA expression results in blood samples from critically ill COVID-19, mild COVID-19 and mild non-COVID-19 patients: see FIG. 37A. To test the hypothesis that patients with COVID-19 display an aberrant peripheral blood mucin mRNA signature, a principal component analysis (PCA) based on the mucin expression data was first undertaken. As the different patient groups were not age and sex matched, these 2 clinical parameters were also taken into account. Strikingly, these variables (i.e. mucin mRNA expression levels, age and sex) segregated patients with critical COVID-19, mild COVID-19 and mild non-COVID-19 (FIG. 37B) making them appropriate for further testing. To identify which of these variables are the major discriminators for disease severity (i.e. critical COVID-19, mild COVID-19 and mild non-COVID-19), a sparse partial least square discriminant analysis (sPLS-DA) was then carried out. The sPLA-DA plot showed again a clear discrimination among the different patient groups (FIG. 37C) with MUC1 mRNA expression and age as major determinants for critically ill COVID-19 patients, whereas expression of MUC2, MUC5AC, MUC5B, MUC13, MUC20 and MUC21 mRNA are the best factors to identify mild COVID-19 patients and sex, MUC4, MUC6 and MUC16 mRNA expression are the best predictors for mild non-COVID-19 patients (FIG. 37D). Thereafter, a Lasso Regression with internal leave-one-out cross validation and receiver operating characteristic (ROC) analysis further strengthened the results of the sPLS-DA in which mRNA expression of MUC16, MUC20 and MUC21 were included as additional discriminative variables, besides age, for COVID-19 severity (i.e. critically ill or mild COVID-19), with an area under the ROC-curve ($AUC_{ROC}$) of 89.1% and a sensitivity and specificity of 90.0% and 85.7%, respectively (FIG. 37E). By using the same approach, we also showed that age and mRNA expression of MUC1, MUC2, MUC4, MUC6, MUC13, MUC16 and MUC20 are the most accurate variables to predict the presence of COVID-19 among symptomatic patients (FIG. 37F; $AUC_{ROC}$=91.8%; sensitivity: 90.6%; specificity: 93.3%).

4. Conclusion

In summary, the multifaceted mucin mRNA signature identifies COVID-19 presentation in symptomatic patients with high sensitivity and specificity and might serve as prognostic biomarker for COVID-19 patient severity stratification.

Example 7: Specific Peripheral Mucin mRNA Isoforms Associate with COVID-19 Presentation and Severity 1. Background of the Invention In this work, we show the presence of specific mucin mRNA isoforms in the blood and mucus of COVID-19 patients which associate with disease presentation and severity.

2. Material and Methods

Patient cohorts and sample collection. 16 critically ill COVID-19 patients hospitalized at the tertiary ICU of the Antwerp University Hospital, Belgium and 12 ambulatory COVID-19 patients with mild-moderate symptoms, were enrolled for this study. The severity of the disease was classified in line with the WHO scale as: (i) mild; (ii) moderate (symptoms such as fever, cough, dyspnea, but no signs of severe pneumonia); (iii) severe: clinical signs of pneumonia (fever, cough, dyspnea, fast breathing) plus the need for respiratory support (high flow oxygen and/or mechanical ventilation); (iv) critical: presence of Acute Respiratory Distress Syndrome (ARDS), and/or sepsis or multiple organ failure (septic shock). Ambulatory patients with mild common cold symptoms (n=12) and healthy controls (i.e. post-COVID-19 assymptomatic patients; n=4), which are all negative for COVID-19 as confirmed by viral PCR, were included as control groups. The ambulatory COVID-19 positive and negative patient groups and healthy controls were recruited at 5 different general practitioner practices and one triage station in Antwerp, Belgium.

Blood sampling for unravelling the peripheral blood mucin mRNA isoform landscape was performed upon admission at the ICU for the severely ill COVID-19 patients or, in case of the ambulatory patients and healthy controls, at the same time of their COVID-19 PCR test in order to recruit both COVID-19 positive and negative patients. Additionally, endotracheal tubes (ETT) from mechanically ventilated ICU COVID-19 patients were collected upon ETT replacement due to mucus obstruction (n=4).

All blood and mucus samples were stored in PAXgene RNA blood tubes (PreAnalytiX) and Trizol™ reagent (Thermo Fisher Scientific), respectively, at −80° C. until RNA extraction and subsequent mucin mRNA isoform analyses (see below). This study was approved by the Ethical Committee of the UZA (20/14/176 (B3002020000059) and 20/43/555 (B3002020000193)) and signed informed consent was obtained from the healthy controls, the patients or in case of intubated ICU patients by their closest relative. Samples were registered and stored until analysis in the Antwerp University Hospital Biobank, Antwerp, Belgium (ID: 71030031000).

RNA Isolation and Quality Control: See Example 4

Targeted isoform long-read RNA sequencing pipeline using the PacBio SMRT technology. Briefly, blood samples collected from critically ill COVID-19 patients, mild COVID-19 patients, mild non-COVID-19 patients and controls as well as mucus from ET tubes from intubated critically ill COVID-19 patients will be processed to generate high-quality total RNA. Using the NEBNext Single Cell/Low Input cDNA Synthesis & Amplification Module (New England BioLabs), a cDNA library will be generated by reverse transcription of full-length mRNA transcripts. During this step, unique barcodes will be ligated to each sample for multiplexing purposes. After sample pooling (6 to 12 samples), hybrid capture of the cDNA will be performed using a custom NGS discovery pool (IDT). This pool consists of high-fidelity, individually-synthesized, 5'-biotinylated oligos targeting the exons and 5' and 3' UTR regions of our mucin panel (Table 14). The probe design was ran against the human genome assembly GRCh38 (hg38). Potential off-target effects of the probe sequences were evaluated by BLAST and Minimap alignment to the hg38 genome. After removal of the probes with high risk for off-target effects, a pool of 2056 probes (containing 1728 with low and 328 probes with moderate off-target risk) was generated with a complete capture of the target genes (Table 14).

TABLE 14

General characteristics of NGS discovery pool for hybrid capture of cDNA

| Mucin Gene | Chromosome | Strand | mRNA (bp) | Target start | Target stop | Target coverage (%) | Probes |
|---|---|---|---|---|---|---|---|
| MUC1 | chr1 | − | 1853 | 155185777 | 155192970 | 100 | 42 |
| MUC2 | chr11 | + | 16050 | 1074867 | 1110561 | 96.2 | 128 |
| MUC3A | chr7 | + | 11248 | 100949490 | 100968394 | 100 | 100 |
| MUC4 | chr3 | − | 16756 | 195746716 | 195811952 | 100 | 153 |
| MUC5AC | chr11 | + | 17448 | 1157893 | 1201148 | 99.99 | 175 |
| MUC5B | chr11 | + | 17911 | 1223010 | 1262200 | 100 | 166 |
| MUC6 | chr11 | − | 8016 | 1012808 | 1036720 | 100 | 85 |
| MUC7 | chr4 | + | 2541 | 70430470 | 70483038 | 100 | 25 |
| MUC8 | chr12 | − | 2205 | 132471557 | 132476658 | 100 | 24 |
| MUC12 | chr7 | + | 16366 | 100969507 | 101018945 | 100 | 143 |
| MUC13 | chr3 | − | 2879 | 124905433 | 124934765 | 100 | 30 |
| MUC15 | chr11 | − | 3387 | 26558989 | 26572271 | 100 | 31 |
| MUC16 | chr19 | − | 42900 | 8848815 | 9010449 | 100 | 421 |
| MUC17 | chr7 | + | 14352 | 101020029 | 101058910 | 100 | 127 |
| MUC19 | chr12 | + | 25332 | 40393387 | 40570790 | 100 | 302 |
| MUC20 | chr3 | + | 2493 | 195720971 | 195733590 | 100 | 22 |
| MUC21 | chr6 | + | 3651 | 30983700 | 30989911 | 93.4 | 31 |
| MUC22 | chr6 | + | 5970 | 31010664 | 31035457 | 97.0 | 51 |

After amplification of the captured DNA, SMRTbell libraries will then be constructed for loading onto SMRT cells using the SMRTbell Express Template Prep Kit 2.0. Subsequently, sequencing will be performed on the PacBio Sequel System providing ultra-long and accurate reads. Quality control and processing of sequence subreads will be performed using ccs (for the generation of highly accurate single-molecule consensus reads (HiFi Reads)), lima (for primer removal and demultiplexing) and isoseq3 (for trimming of Poly(A)-tails, removal of concatemers and clustering of transcripts by using a hierarchical alignment algorithm) tool packages on the command line to generate highly-accurate unique full-length transcripts. Subsequently, these will be mapped to the human reference genome (GRCh38.p12) using the Minimap2 alignment program. Eventually, the mucin mRNA isoforms and corresponding splicing events will be identified using Cupcake ToFU and SQANTI2 bioinformatics tools in combination with isoform visualization in the Integrative Genome Viewer (IGV). Differential isoform expression analysis of the identified mRNA isoforms, comparing critically ill COVID-19 patients to mild COVID-19 patients and comparing COVID-19 patients to non-COVID-19 patients and healthy controls, will be performed using the tappAS Java application. Finally, differential mucin isoform expression will be correlated to the disease severity (mild versus critically ill COVID-19) and disease presentation (COVID-19 vs non-COVID-19), using Pearson correlation and multiple linear regression analysis (R package). In addition, as epithelial cells can enter the bloodstream due to a dysfunctional mucosal barrier in COVID-19 patients, we also verified whether the peripheral mucin mRNA isoforms associated with critically ill COVID-19 patients can also be identified in mucus samples from these patients.

Data Analysis: See Example 4

3. Results

3.1. Mucin mRNA Isoforms Identified in Endotracheal Mucus of Critically Ill COVID-19 Patients

3.1.1. MUC1 mRNA Isoforms

A high number of transcripts mapped to 16 different known MUC1 mRNA isoforms (ENST00000337604.6 (full splice match (FSM)), ENST00000338684.9 (incomplete splice match (ISM)), ENST00000342482.8 (FSM), ENST00000343256.9 (FSM), ENST00000368390.7 (FSM), ENST00000368392.7 (FSM), ENST00000368393.7 (ISM), ENST00000438413.5 (FSM), ENST00000462317.5 (FSM), ENST00000467134.5 (ISM), ENST00000468978.2 (FSM), ENST00000485118.5 (ISM), ENST00000610359.4 (FSM), ENST00000612778.4 (FSM), ENST00000614519.4 (ISM), ENST00000620103.4 (ISM) (Table 15).

3.1.2. MUC2 mRNA Isoforms

A low number of multi-exonic transcripts incompletely mapped to the known MUC2 mRNA isoform (ENST00000361558.7 (ISM)) (Table 15).

3.1.3. MUC3A mRNA Isoforms

Transcripts mapped to three known MUC3A mRNA isoforms (ENST00000379458.9 (ISM), ENST00000483366.5 (ISM) & ENST00000614399.1 (FSM)).

3.1.4. MUC4 mRNA Isoforms

Nine known MUC4 mRNA isoforms were identified: ENST00000308466.12 (ISM), ENST00000346145.8 (ISM), ENST00000349607.8 (ISM), ENST00000448861.5 (ISM), ENST00000463781.8 (ISM), ENST00000464234.5 (FSM), ENST00000478156.5 (ISM), ENST00000478685.1 (FSM), ENST00000479406.5 (ISM) (Table 15).

3.1.5. MUC5AC mRNA Isoforms

Numerous multi-exonic transcripts showed incomplete mapping to the known MUC5AC mRNA isoform (ENST00000621226.2) (Table 15).

3.1.6. MUC5B mRNA Isoforms

Numerous multi-exonic transcripts showed incomplete mapping to the known MUC5B mRNA isoform (ENST00000525715.5) (Table 15).

3.1.7. MUC7 mRNA Isoforms

Full length mapping was identified to two known MUC7 mRNA isoforms (ENST00000304887.6 & ENST00000413702.5) (Table 15).

3.1.8. MUC12 mRNA Isoforms

One known MUC12 mRNA isoform was found (ENST00000474482.1) (Table 15).

3.1.9. MUC13 mRNA Isoforms

High numbers of transcripts mapping to the full-length mRNA isoform of MUC13 (ENST00000616727.4) were identified (Table 15).

3.1.10. MUC15 mRNA Isoforms

Transcripts mapped to four known MUC15 mRNA isoforms (ENST00000455601.6 (FSM), ENST00000527569.1 (FSM), ENST00000529533.6 (FSM) & ENST00000436318.6 (ISM)) (Table 15).

3.1.11. MUC16 mRNA Isoforms

Incomplete mapping was found to four known MUC16 mRNA isoforms (ENST00000397910.8, ENST00000596768.5, ENST00000599436.1 & ENST00000601404.5) (Table 15).

3.1.12. MUC20 mRNA Isoforms

Transcripts were identified mapping to two known MUC20 mRNA isoforms (ENST00000445522.6 & ENST00000498018.1) (Table 15).

3.1.13. MUC21 mRNA Isoforms

High numbers of incompletely mapping transcripts were found for two known MUC21 mRNA isoforms (ENST00000376296.3 & ENST00000486149.2) (Table 15).

3.1.14. MUC22 mRNA Isoforms

Transcripts mapping to the full-length mRNA isoform of MUC22 (ENST00000561890.1) were identified (Table 15).

3.2. Mucin mRNA Isoforms Identified in Critically Ill and Mild COVID-19 Patients.

3.2.1. MUC1 Isoforms

In total, 11 different MUC1 transcripts were found in the blood of mild COVID-19 patients. In the blood of critically ill COVID-19 patients, 13 different MUC1 transcripts were found (Table 16). In the blood of critically ill and mild COVID-19 patients, transcripts of seven known MUC1 isoforms were found (ENST00000337604.6 (FSM), ENST00000368390.7 (FSM), ENST00000368392.7 (FSM), ENST00000467134.5 (mild COVID-19: FSM; critically ill COVID-19: ISM), ENST00000468978.2 (FSM & ISM), ENST00000614519.4 (mild COVID-19: ISM; critically ill COVID-19: FSM) & ENST00000620103.4 (ISM) (Table 16). The analysis of transcript counts revealed a higher number of transcripts mapping to ENST00000337604.6 (108 vs 41), ENST00000368390.7 (199 vs 59), ENST00000468978.2 (99 vs 55) and ENST00000620103.4 (364 vs 127), and a lower number to ENST00000368392.7 (90 vs 98) and ENST00000467134.5 (7 vs 34) in critically ill COVID-19 patients as compared to mild COVID-19 patients (Table 16). Interestingly, four known MUC1 mRNA isoforms were uniquely found in mild COVID-19 patients (ENST00000338684.9 (ISM) & ENST00000610359.4 (ISM)) or in critically ill COVID-19 patients (ENST00000462215.5 (ISM) & ENST00000485118.5 (ISM)) (Table 16).

3.2.2. MUC12 mRNA Isoforms

In both mild and critically ill COVID-19 patients, transcripts were found mapping to a known splice variant of MUC12 (ENST00000474482.1) (Table 16). Moreover, a higher number of transcripts mapping to these mRNA isoforms were found in mild patients as compared to critically ill patients (49 vs 12) (Table 16).

3.2.3. MUC13 mRNA Isoforms

Multi-exonic transcripts were found in the blood of mild COVID-19 patients that were characterized as two known isoforms of MUC13 (ENST00000490147.1 & ENST00000616727.4) (Table 16). Interestingly, these were not found in critically ill COVID-19 patients.

3.2.4. MUC16 mRNA Isoforms

In both mild and critically ill COVID-19 patients, numerous multi-exonic and mono-exonic transcripts were found mapping to the main isoform of MUC16 (ENST00000397910.8 (ISM)) (Table 16). In addition, in mild COVID-19 patients, two other known isoforms of MUC16 (ENST00000596768.5 & ENST00000599436.1) were also identified, which were not found in critically ill COVID-19 patients (Table 16).

3.2.5. MUC19 mRNA Isoforms

In the blood of critically COVID-19 patients, transcripts were identified mapping to two known isoforms of MUC19 (ENST00000427572.2 & ENST00000454784.9), which were not found in the blood of mild COVID-19 patients (Table 16).

3.2.6. MUC20 mRNA Isoforms

Transcripts were found completely mapping to two known MUC20 mRNA isoforms in both mild and critically ill COVID-19 patients (ENST00000445522.6 (FSM) & ENST00000498018.1 (FSM)) (Table 16). Overall, a higher number of transcript counts were found in mild compared to critically ill patients (ENST00000445522.6 (428 vs 104), ENST00000498018.1 (132 vs 8) (Table 16).

3.3. Mucin Isoforms Identified in the Blood of Control Patients (Post Asymptomatic COVID-19 and Patients with Mild Symptoms but Negative for COVID-19)

3.3.1. MUC1 mRNA Isoforms

In the combined control group, 9 known MUC1 isoforms were characterized, of which 4 were found in both the post-COVID-19 and non-COVID-19 patients with mild symptoms (ENST00000337604.6 (FSM), ENST00000368390.7 (FSM), ENST00000368392.7 (FSM), ENST00000620103.4 (ISM)) (Table 17). Two additional known MUC1 isoforms were found in post-COVID-19 patients (ENST00000438413.5 (FSM), ENST00000467134.5 (ISM)) and three in mild non-COVID-19 patients (ENST00000462317.5 (ISM), ENST00000468978.2 (FSM) & ENST00000485118.5 (ISM)) (Table 17).

3.3.2. MUC12 mRNA Isoforms

In both post-COVID-19 and mild non-COVID-19 patients, transcripts were found mapping to a known non-coding splice variant of MUC12 (ENST00000474482.1 (FSM)) (Table 17). Moreover, another known non-coding isoform was also identified in mild non-COVID-19 patients (ENST00000473098.5 (FSM)) (Table 17).

3.3.3. MUC16 mRNA Isoforms

In both post-COVID-19 and mild non-COVID-19 patients, numerous transcripts were found mapping to the main isoform of MUC16 (ENST00000397910.8 (ISM)) (Table 17).

3.3.4. MUC19 mRNA Isoforms

In post-COVID-19 patients, transcripts were identified mapping to two known non-coding (ENST00000484665.2 (ISM) & ENST00000427572.2 (ISM)). In mild non-COVID-19 patients, another known non-coding MUC19 mRNA isoform was identified (ENST00000454784.9 (ISM)) (Table 17).

3.3.5. MUC20 mRNA Isoforms

In both post-COVID-19 and mild non-COVID-19 patients, a high number of transcripts was found mapping to a known MUC20 mRNA isoform (ENST00000445522.6 (FSM)). Moreover, in the blood of mild non-COVID-19 patients, also another known MUC20 mRNA isoform was identified (ENST00000498018.1 (FSM)) (Table 17).

3.4. Comparison Between Mucin mRNA Isoforms Identified in Mucus (from ET Tubes) and Blood of COVID-19 Patients (Mild and Critically Ill)

Many known mRNA isoforms of several mucin genes were found in the mucus samples which were not found in the blood of COVID-19 patients (i.e. MUC2, MUC3A, MUC4, MUC5AC, MUC5B, MUC7, MUC15, MUC21 & MUC22) (Table 18). Several other mucin mRNA isoforms were found in both the blood and endotracheal mucus. This was the case for transcript variants of (i) MUC1 (ENST00000337604.6, ENST00000338684.9, ENST00000368390.7, ENST00000368392.7, ENST00000467134.5, ENST00000468978.2, ENST00000485118.5 & ENST00000620103.4), (ii) MUC12 (ENST00000474482.1), (iii) MUC16 (ENST00000397910.8, ENST00000596768.5 & ENST00000599436.1) and (iiii) MUC20 (ENST00000445522.6 & ENST00000498018.1) (Table 18). Additionally, several mucin mRNA isoforms were only found in the blood of COVID-19 patients (i.e. ENST00000462215.5 (MUC1), ENST00000490147.1 (MUC13), ENST00000454784.9 (MUC19), ENST00000427572.2 (MUC19) & ENST00000546043.2 (MUC19)) (Table 18).

3.5. Comparison Between Mucin mRNA Isoforms Identified in the Blood of COVID-19 Patients and Controls Concerning MUC1 mRNA isoforms, the transcript variant ENST00000338684.9 was only found in mild COVID-19 patients and the variants ENST00000485118.5 and ENST00000462215.5 in critically ill COVID-19 patients, whereas ENST00000614519.4 was identified in both mild and critically ill COVID-19 patients but not in control patients (Table 18). On the contrary, ENST00000438413.5 was only characterized in post-COVID-19 patients and ENST00000462317.5 in mild non-COVID-19 patients (Table 18). Besides, an increased abundance in terms of transcript counts was noticed for ENST00000337604.6, ENST00000368390.7, ENST00000368392.7, ENST00000467134.5, ENST00000468978.2, ENST00000620103.4 in COVID-19 patients as compared to control patients (especially post-COVID-19 patients) (Table 18). Regarding MUC12, the splice variant ENST00000473098.5 was only found in the blood of mild non-COVID-19 patients but not in patients that were diagnosed with COVID-19 (both mild and critically ill) and post-COVID-19 patients (Table 18). Interestingly, two known transcript variants of MUC13 (ENST00000616727.4 & ENST00000490147.1) and MUC16 (ENST00000596768.5 & ENST00000599436.1) were only discovered in the blood of mild COVID-19 patients (Table 18). In addition, an increased abundance of the MUC16 mRNA isoform ENST00000397910.8 was observed in COVID-19 patients as compared to control patients (Table 18). Considering MUC19, the transcript variant ENST00000454784.9 was identified in both critically ill and mild non-COVID-19 patients. Similarly, MUC19 transcript variant ENST00000427572.2 was found in both critically ill COVID-19 and post-COVID-19 patients. Besides, whereas MUC19 transcript variant ENST00000484665.2 was only noticed in post-COVID-19 patients, MUC19 transcript variant ENST00000546043.2 was only characterized in severe COVID-19 patients (Table 18). For MUC20, the splice variant ENST00000445522.6 was found in the blood of all patient groups but had the highest abundance in mild COVID-19 patients. Likewise, MUC20 transcript variant ENST00000498018.1 showed high abundance in mild COVID-19 and mild non-COVID-19 patients but was low or absent in critically ill COVID-19 and post-COVID-19 patients, respectively (Table 18).

4. Conclusion

Based on the targeted mucin isoform sequencing data gathered from blood samples of COVID-patients with varying degree of disease severity, non-COVID-19 patients with mild symptoms and healthy controls (i.e. asymptomatic post-COVID-19), we were able to identify specific mucin mRNA isoforms associated with critical or mild COVID-19 as well as mucin mRNA isoforms associated with the presence of COVID-19.

TABLE 14

Classification of mucin mRNA isoforms in endotracheal mucus of COVID-19 patients with severe disease (critically ill COVID-19).

| PB_ isoform_ID | Length | Exons | Associated_ transcript | Structural_ category | Subcategory | Transcript_ count | Type of splice site | Coding? | CDS_ genomic_start | CDS_ genomic_end |
|---|---|---|---|---|---|---|---|---|---|---|
| MUC1 mRNA isoforms | | | | | | | | | | |
| PB.172.54 | 1194 | 8 | ENST00000337604.6 | full-splice_match | alternative_3end | 217 | canonical | non_coding | NA | NA |
| PB.172.47 | 847 | 5 | ENST00000338684.9 | incomplete-splice_match | 3prime_fragment | 101 | canonical | coding | 155187302 | 155186135 |
| PB.172.33 | 876 | 5 | ENST00000342482.8 | full-splice_match | alternative_3end | 8 | canonical | coding | 155192843 | 155186135 |
| PB.172.39 | 985 | 7 | ENST00000343256.9 | full-splice_match | alternative_3end | 4 | canonical | coding | 155192843 | 155186135 |
| PB.172.26 | 1596 | 8 | ENST00000368390.7 | full-splice_match | alternative_3end5end | 311 | canonical | coding | 155192843 | 155186135 |
| PB.172.55 | 1167 | 8 | ENST00000368392.7 | full-splice_match | alternative_3end | 17 | canonical | non_coding | NA | NA |
| PB.172.45 | 1029 | 5 | ENST00000368393.7 | incomplete-splice_match | 3prime_fragment | 4 | canonical | non_coding | NA | NA |
| PB.172.83 | 1059 | 7 | ENST00000438413.5 | full-splice_match | alternative_3end | 23 | canonical | coding | 155192843 | 155186135 |

TABLE 14-continued

Classification of mucin mRNA isoforms in endotracheal mucus of COVID-19 patients with severe disease (critically ill COVID-19).

| PB_ isoform_ID | Length | Exons | Associated_ transcript | Structural_ category | Subcategory | Transcript_ count | Type of splice site | Coding? | CDS_ genomic_start | CDS_ genomic_end |
|---|---|---|---|---|---|---|---|---|---|---|
| PB.172.29 | 1371 | 7 | ENST00000462317.5 | full-splice_match | alternative_5end | 8 | canonical | coding | 155188165 | 155186772 |
| PB.172.57 | 825 | 4 | ENST00000467134.5 | incomplete-splice_match | 3prime_fragment | 5 | canonical | non_coding | NA | NA |
| PB.172.91 | 2132 | 3 | ENST00000468978.2 | full-splice_match | alternative_3end5end | 8 | canonical | non_coding | NA | NA |
| PB.172.59 | 2213 | 2 | ENST00000468978.2 | incomplete-splice_match | intron_retention | 21 | canonical | non_coding | NA | NA |
| PB.172.9 | 1442 | 3 | ENST00000485118.5 | incomplete-splice_match | intron_retention | 19 | canonical | non_coding | NA | NA |
| PB.172.90 | 1692 | 2 | ENST00000485118.5 | incomplete-splice_match | intron_retention | 4 | canonical | coding | 155188165 | 155188127 |
| PB.172.44 | 1092 | 7 | ENST00000610359.4 | full-splice_match | reference_match | 2 | canonical | coding | 155192843 | 155186135 |
| PB.172.56 | 1095 | 5 | ENST00000610359.4 | incomplete-splice_match | 3prime_fragment | 6 | canonical | non_coding | NA | NA |
| PB.172.20 | 1832 | 8 | ENST00000612778.4 | full-splice_match | reference_match | 11 | canonical | coding | 155192176 | 155186135 |
| PB.172.13 | 1159 | 5 | ENST00000614519.4 | incomplete-splice_match | 3prime_fragment | 6 | canonical | coding | 155188165 | 155187570 |
| PB.172.15 | 771 | 4 | ENST00000620103.4 | incomplete-splice_match | 3prime_fragment | 133 | canonical | coding | 155187302 | 155186135 |
| PB.172.6 | 1589 | 6 | ENST00000620103.4 | incomplete-splice_match | 3prime_fragment | 1028 | canonical | coding | 155188165 | 155186135 |
| MUC2 mRNA isoforms | | | | | | | | | | |
| PB.329.1 | 2382 | 17 | ENST00000361558.7 | incomplete-splice_match | 3prime_fragment | 6 | canonical | coding | 1101852 | 1110355 |
| PB.329.2 | 2160 | 16 | ENST00000361558.7 | incomplete-splice_match | 3prime_fragment | 2 | canonical | coding | 1102644 | 1110355 |
| PB.329.4 | 1871 | 15 | ENST00000361558.7 | incomplete-splice_match | 3prime_fragment | 6 | canonical | coding | 1104806 | 1110355 |
| PB.329.5 | 1715 | 14 | ENST00000361558.7 | incomplete-splice_match | 3prime_fragment | 5 | canonical | coding | 1104806 | 1110355 |
| PB.329.6 | 1551 | 13 | ENST00000361558.7 | incomplete-splice_match | 3prime_fragment | 2 | canonical | coding | 1104806 | 1110355 |
| PB.329.7 | 967 | 8 | ENST00000361558.7 | incomplete-splice_match | 3prime_fragment | 6 | canonical | coding | 1108560 | 1110355 |
| PB.329.8 | 868 | 6 | ENST00000361558.7 | incomplete-splice_match | 3prime_fragment | 2 | canonical | coding | 1108560 | 1110355 |
| MUC3A mRNA isoforms | | | | | | | | | | |
| PB.2077.4 | 2103 | 9 | ENST00000379458.9 | incomplete-splice_match | 3prime_fragment | 3 | canonical | coding | 100963174 | 100967162 |
| PB.2077.2 | 2209 | 2 | ENST00000483366.5 | incomplete-splice_match | 5prime_fragment | 2 | canonical | non_coding | NA | NA |
| PB.2077.5 | 1722 | 4 | ENST00000614399.1 | full-splice_match | alternative_3end | 123 | canonical | non_coding | NA | NA |
| PB.2077.6 | 1618 | 3 | ENST00000614399.1 | incomplete-splice_match | intron_retention | 13 | canonical | non_coding | NA | NA |
| PB.2077.8 | 1399 | 3 | ENST00000614399.1 | incomplete-splice_match | 3prime_fragment | 2 | canonical | non_coding | NA | NA |
| MUC4 mRNA isoforms | | | | | | | | | | |
| PB.1631.1 | 1746 | 7 | ENST00000308466.12 | incomplete-splice_match | 3prime_fragment | 3 | canonical | coding | 195751244 | 195747176 |
| PB.1631.11 | 2028 | 10 | ENST00000308466.12 | incomplete-splice_match | 3prime_fragment | 47 | canonical | coding | 195751244 | 195747176 |
| PB.1631.14 | 2901 | 17 | ENST00000308466.12 | incomplete-splice_match | 3prime_fragment | 54 | canonical | coding | 195763636 | 195747176 |
| PB.1631.17 | 1770 | 9 | ENST00000308466.12 | incomplete-splice_match | 3prime_fragment | 11 | canonical | coding | 195753129 | 195747176 |
| PB.1631.18 | 1648 | 8 | ENST00000308466.12 | incomplete-splice_match | 3prime_fragment | 50 | canonical | coding | 195753129 | 195747176 |
| PB.1631.19 | 2727 | 15 | ENST00000308466.12 | incomplete-splice_match | 3prime_fragment | 70 | canonical | coding | 195763636 | 195747176 |
| PB.1631.22 | 1484 | 7 | ENST00000308466.12 | incomplete-splice_match | 3prime_fragment | 140 | canonical | coding | 195753129 | 195747176 |
| PB.1631.23 | 2595 | 14 | ENST00000308466.12 | incomplete-splice_match | 3prime_fragment | 4 | canonical | coding | 195761550 | 195747176 |
| PB.1631.32 | 1761 | 10 | ENST00000308466.12 | incomplete-splice_match | internal_fragment | 3 | canonical | coding | 195761550 | 195750803 |
| PB.1631.33 | 1378 | 3 | ENST00000308466.12 | incomplete-splice_match | internal_fragment | 4 | canonical | non_coding | NA | NA |

TABLE 14-continued

Classification of mucin mRNA isoforms in endotracheal mucus of COVID-19 patients with severe disease (critically ill COVID-19).

| PB_ isoform_ID | Length | Exons | Associated_ transcript | Structural_ category | Subcategory | Transcript_ count | Type of splice site | Coding? | CDS_ genomic_start | CDS_ genomic_end |
|---|---|---|---|---|---|---|---|---|---|---|
| PB.1631.4 | 2499 | 11 | ENST00000308466.12 | incomplete-splice_match | 3prime_ fragment | 4 | canonical | coding | 195761550 | 195747176 |
| PB.1631.8 | 587 | 1 | ENST00000308466.12 | incomplete-splice_match | mono-exon | 11 | NA | non_ coding | NA | NA |
| PB.1631.35 | 879 | 3 | ENST00000346145.8 | incomplete-splice_match | 5prime_ fragment | 6 | canonical | coding | 195778453 | 195773941 |
| PB.1631.10 | 3471 | 19 | ENST00000349607.8 | incomplete-splice_match | 3prime_ fragment | 11 | canonical | coding | 195769077 | 195747176 |
| PB.1631.6 | 2488 | 14 | ENST00000448861.5 | incomplete-splice_match | 3prime_ fragment | 3 | canonical | coding | 195763636 | 195753186 |
| PB.1631.12 | 3887 | 24 | ENST00000463781.8 | incomplete-splice_match | 3prime_ fragment | 11 | canonical | coding | 195778802 | 195747176 |
| PB.1631.25 | 1167 | 6 | ENST00000464234.5 | full-splice_match | alternative_ 3end5end | 42 | canonical | coding | 195751241 | 195747176 |
| PB.1631.26 | 2027 | 4 | ENST00000464234.5 | incomplete-splice_match | 3prime_ fragment | 14 | canonical | coding | 195751244 | 195747176 |
| PB.1631.27 | 1141 | 5 | ENST00000464234.5 | incomplete-splice_match | 3prime_ fragment | 6 | canonical | coding | 195751241 | 195747176 |
| PB.1631.31 | 998 | 3 | ENST00000464234.5 | incomplete-splice_match | 3prime_ fragment | 15 | canonical | coding | 195751069 | 195747176 |
| PB.1631.7 | 779 | 2 | ENST00000464234.5 | incomplete-splice_match | 3prime_ fragment | 22 | canonical | coding | 195747325 | 195747176 |
| PB.1631.42 | 1132 | 1 | ENST00000478156.5 | incomplete-splice_match | mono-exon | 2 | NA | coding | 195791294 | 195790242 |
| PB.1631.62 | 1374 | 2 | ENST00000478685.1 | full-splice_match | alternative_ 3end5end | 3 | canonical | non_ coding | NA | NA |
| PB.1631.36 | 2869 | 2 | ENST00000479406.5 | incomplete-splice_match | 5prime_ fragment | 2 | canonical | non_ coding | NA | NA |
| PB.1631.37 | 2058 | 2 | ENST00000479406.5 | incomplete-splice_match | 5prime_ fragment | 13 | canonical | coding | 195811817 | 195789639 |
| PB.1631.38 | 1904 | 2 | ENST00000479406.5 | incomplete-splice_match | 5prime_ fragment | 8 | canonical | coding | 195811817 | 195789756 |
| PB.1631.39 | 1951 | 2 | ENST00000479406.5 | incomplete-splice_match | 5prime_ fragment | 203 | canonical | non_ coding | NA | NA |
| PB.1631.43 | 1451 | 2 | ENST00000479406.5 | incomplete-splice_match | 5prime_ fragment | 347 | canonical | coding | 195811817 | 195790242 |
| MUC5AC mRNA isoforms | | | | | | | | | | |
| PB.331.1 | 1700 | 8 | ENST00000621226.2 | incomplete-splice_match | internal_ fragment | 3 | canonical | coding | 1177538 | 1182750 |
| PB.332.11 | 2397 | 15 | ENST00000621226.2 | incomplete-splice_match | 3prime_ fragment | 36 | canonical | coding | 1194562 | 1200702 |
| PB.332.12 | 2201 | 14 | ENST00000621226.2 | incomplete-splice_match | 3prime_ fragment | 62 | canonical | coding | 1195083 | 1200702 |
| PB.332.13 | 1911 | 13 | ENST00000621226.2 | incomplete-splice_match | 3prime_ fragment | 28 | canonical | coding | 1195949 | 1200702 |
| PB.332.15 | 1737 | 12 | ENST00000621226.2 | incomplete-splice_match | 3prime_ fragment | 12 | canonical | coding | 1196669 | 1200702 |
| PB.332.17 | 1645 | 11 | ENST00000621226.2 | incomplete-splice_match | 3prime_ fragment | 30 | canonical | coding | 1196669 | 1200702 |
| PB.332.18 | 1550 | 9 | ENST00000621226.2 | incomplete-splice_match | 3prime_ fragment | 62 | canonical | coding | 1197486 | 1200702 |
| PB.332.2 | 3821 | 19 | ENST00000621226.2 | incomplete-splice_match | 3prime_ fragment | 18 | canonical | coding | 1192285 | 1200702 |
| PB.332.20 | 1357 | 8 | ENST00000621226.2 | incomplete-splice_match | 3prime_ fragment | 23 | canonical | coding | 1199707 | 1200702 |
| PB.332.21 | 1263 | 7 | ENST00000621226.2 | incomplete-splice_match | 3prime_ fragment | 8 | canonical | coding | 1199707 | 1200702 |
| PB.332.22 | 1420 | 6 | ENST00000621226.2 | incomplete-splice_match | 3prime_ fragment | 38 | canonical | coding | 1198844 | 1200702 |
| PB.332.23 | 1092 | 5 | ENST00000621226.2 | incomplete-splice_match | 3prime_ fragment | 24 | canonical | coding | 1199707 | 1200702 |
| PB.332.24 | 1103 | 4 | ENST00000621226.2 | incomplete-splice_match | 3prime_ fragment | 13 | canonical | coding | 1199707 | 1200702 |
| PB.332.27 | 796 | 2 | ENST00000621226.2 | incomplete-splice_match | 3prime_ fragment | 2 | canonical | coding | 1199968 | 1200702 |
| PB.332.28 | 633 | 1 | ENST00000621226.2 | incomplete-splice_match | mono-exon | 2 | NA | non_ coding | NA | NA |
| PB.332.5 | 2952 | 18 | ENST00000621226.2 | incomplete-splice_match | 3prime_ fragment | 2 | canonical | coding | 1194349 | 1200702 |
| PB.332.7 | 2778 | 17 | ENST00000621226.2 | incomplete-splice_match | 3prime_ fragment | 11 | canonical | coding | 1194349 | 1200702 |
| PB.332.8 | 2631 | 16 | ENST00000621226.2 | incomplete-splice_match | 3prime_ fragment | 21 | canonical | coding | 1194349 | 1200702 |

TABLE 14-continued

Classification of mucin mRNA isoforms in endotracheal mucus of COVID-19 patients with severe disease (critically ill COVID-19).

| PB_ isoform_ID | Length | Exons | Associated_ transcript | Structural_ category | Subcategory | Transcript_ count | Type of splice site | Coding? | CDS_ genomic_start | CDS_ genomic_end |
|---|---|---|---|---|---|---|---|---|---|---|
| MUC5B mRNA isoforms | | | | | | | | | | |
| PB.333.1 | 1105 | 7 | ENST00000525715.5 | incomplete-splice_match | 5prime_fragment | 2 | canonical | coding | 1223124 | 1228033 |
| PB.334.2 | 1613 | 8 | ENST00000525715.5 | incomplete-splice_match | internal_fragment | 5 | canonical | coding | 1234219 | 1237272 |
| PB.334.3 | 1445 | 8 | ENST00000525715.5 | incomplete-splice_match | internal_fragment | 2 | canonical | coding | 1234219 | 1237272 |
| PB.334.10 | 2175 | 14 | ENST00000529681.5 | incomplete-splice_match | 3prime_fragment | 129 | canonical | coding | 1255112 | 1261608 |
| PB.334.11 | 1893 | 13 | ENST00000529681.5 | incomplete-splice_match | 3prime_fragment | 65 | canonical | coding | 1256696 | 1261608 |
| PB.334.12 | 1760 | 12 | ENST00000529681.5 | incomplete-splice_match | 3prime_fragment | 72 | canonical | coding | 1256696 | 1261608 |
| PB.334.13 | 1701 | 11 | ENST00000529681.5 | incomplete-splice_match | 3prime_fragment | 129 | canonical | coding | 1256696 | 1261608 |
| PB.334.17 | 1584 | 9 | ENST00000529681.5 | incomplete-splice_match | 3prime_fragment | 66 | canonical | coding | 1258978 | 1261608 |
| PB.334.18 | 1368 | 8 | ENST00000529681.5 | incomplete-splice_match | 3prime_fragment | 79 | canonical | coding | 1258978 | 1261608 |
| PB.334.19 | 1782 | 6 | ENST00000529681.5 | incomplete-splice_match | 3prime_fragment | 29 | canonical | coding | 1258978 | 1261608 |
| PB.334.20 | 1143 | 5 | ENST00000529681.5 | incomplete-splice_match | 3prime_fragment | 27 | canonical | coding | 1261411 | 1261608 |
| PB.334.21 | 1056 | 4 | ENST00000529681.5 | incomplete-splice_match | 3prime_fragment | 47 | canonical | coding | 1261411 | 1261608 |
| PB.334.24 | 718 | 1 | ENST00000529681.5 | incomplete-splice_match | mono-exon | 4 | NA | non_coding | NA | NA |
| PB.334.4 | 3507 | 19 | ENST00000529681.5 | incomplete-splice_match | 3prime_fragment | 14 | canonical | coding | 1251275 | 1261608 |
| PB.334.5 | 2928 | 18 | ENST00000529681.5 | incomplete-splice_match | 3prime_fragment | 7 | canonical | coding | 1254103 | 1261608 |
| PB.334.6 | 2715 | 17 | ENST00000529681.5 | incomplete-splice_match | 3prime_fragment | 53 | canonical | coding | 1254103 | 1261608 |
| PB.334.7 | 2558 | 16 | ENST00000529681.5 | incomplete-splice_match | 3prime_fragment | 19 | canonical | coding | 1254178 | 1261608 |
| PB.334.8 | 2369 | 15 | ENST00000529681.5 | incomplete-splice_match | 3prime_fragment | 93 | canonical | coding | 1254772 | 1261608 |
| MUC7 mRNA isoforms | | | | | | | | | | |
| PB.1681.3 | 2363 | 3 | ENST00000304887.6 | full-splice_match | reference_match | 160 | canonical | coding | 70474022 | 70481878 |
| PB.1681.4 | 2241 | 3 | ENST00000304887.6 | full-splice_match | alternative_3end | 9 | canonical | coding | 70474022 | 70481878 |
| PB.1681.7 | 1879 | 3 | ENST00000304887.6 | full-splice_match | alternative_3end | 2 | canonical | coding | 70474022 | 70481878 |
| PB.1681.11 | 2198 | 1 | ENST00000304887.6 | incomplete-splice_match | mono-exon | 120 | NA | coding | 70481831 | 70481878 |
| PB.1681.9 | 2121 | 2 | ENST00000304887.6 | incomplete-splice_match | 3prime_fragment | 2 | canonical | coding | 70481831 | 70481878 |
| PB.1681.1 | 1957 | 4 | ENST00000413702.5 | full-splice_match | alternative_3end | 2 | canonical | coding | 70474022 | 70481878 |
| PB.1681.12 | 1646 | 1 | ENST00000413702.5 | incomplete-splice_match | mono-exon | 8 | NA | coding | 70481831 | 70481878 |
| PB.1681.14 | 1434 | 1 | ENST00000413702.5 | incomplete-splice_match | mono-exon | 5 | NA | coding | 70481831 | 70481878 |
| PB.1681.8 | 1110 | 2 | ENST00000505411.5 | incomplete-splice_match | 3prime_fragment | 5 | canonical | coding | 70474022 | 70481833 |
| MUC12 mRNA isoforms | | | | | | | | | | |
| PB.2078.1 | 741 | 2 | ENST00000474482.1 | full-splice_match | alternative_5end | 6 | canonical | non_coding | NA | NA |
| MUC13 mRNA isoforms | | | | | | | | | | |
| PB.1591.22 | 2550 | 12 | ENST00000616727.4 | full-splice_match | alternative_3end | 11 | canonical | coding | 124934712 | 124908147 |
| PB.1591.25 | 2424 | 12 | ENST00000616727.4 | full-splice_match | alternative_3end | 5 | canonical | coding | 124934712 | 124908147 |
| PB.1591.26 | 2331 | 12 | ENST00000616727.4 | full-splice_match | alternative_3end | 6 | canonical | coding | 124934712 | 124908147 |
| PB.1591.28 | 1806 | 12 | ENST00000616727.4 | full-splice_match | alternative_3end | 82 | canonical | coding | 124934712 | 124908147 |
| PB.1591.5 | 2876 | 12 | ENST00000616727.4 | full-splice_match | reference_match | 658 | canonical | coding | 124934712 | 124908147 |

TABLE 14-continued

Classification of mucin mRNA isoforms in endotracheal mucus of COVID-19 patients with severe disease (critically ill COVID-19).

| PB_ isoform_ID | Length | Exons | Associated_ transcript | Structural_ category | Subcategory | Transcript_ count | Type of splice site | Coding? | CDS_ genomic_start | CDS_ genomic_end |
|---|---|---|---|---|---|---|---|---|---|---|
| PB.1591.11 | 1505 | 2 | ENST00000616727.4 | incomplete- splice_match | 3prime_ fragment | 88 | canonical | non_ coding | NA | NA |
| PB.1591.14 | 1744 | 5 | ENST00000616727.4 | incomplete- splice_match | 3prime_ fragment | 23 | canonical | coding | 124910443 | 124908147 |
| PB.1591.16 | 2281 | 10 | ENST00000616727.4 | incomplete- splice_match | 3prime_ fragment | 21 | canonical | coding | 124922235 | 124908147 |
| PB.1591.17 | 2095 | 8 | ENST00000616727.4 | incomplete- splice_match | 3prime_ fragment | 2 | canonical | coding | 124916455 | 124908147 |
| PB.1591.2 | 2196 | 9 | ENST00000616727.4 | incomplete- splice_match | 3prime_ fragment | 53 | canonical | coding | 124922235 | 124908147 |
| PB.1591.21 | 1741 | 4 | ENST00000616727.4 | incomplete- splice_match | 3prime_ fragment | 3 | canonical | non_ coding | NA | NA |
| PB.1591.24 | 1470 | 6 | ENST00000616727.4 | incomplete- splice_match | 3prime_ fragment | 2 | canonical | coding | 124910443 | 124908147 |
| PB.1591.27 | 800 | 6 | ENST00000616727.4 | incomplete- splice_match | 3prime_ fragment | 3 | canonical | coding | 124910443 | 124908147 |
| PB.1591.29 | 1157 | 10 | ENST00000616727.4 | incomplete- splice_match | 3prime_ fragment | 3 | canonical | coding | 124922235 | 124908147 |
| PB.1591.30 | 1535 | 11 | ENST00000616727.4 | incomplete- splice_match | 5prime_ fragment | 5 | canonical | coding | 124934712 | 124908192 |
| PB.1591.31 | 1390 | 11 | ENST00000616727.4 | incomplete- splice_match | 5prime_ fragment | 35 | canonical | coding | 124934712 | 124908336 |
| PB.1591.32 | 1002 | 9 | ENST00000616727.4 | incomplete- splice_match | internal_ fragment | 2 | canonical | coding | 124927649 | 124910417 |
| PB.1591.4 | 2042 | 7 | ENST00000616727.4 | incomplete- splice_match | 3prime_ fragment | 79 | canonical | coding | 124916455 | 124908147 |
| PB.1591.6 | 1836 | 6 | ENST00000616727.4 | incomplete- splice_match | 3prime_ fragment | 19 | canonical | coding | 124910443 | 124908147 |
| PB.1591.8 | 2779 | 11 | ENST00000616727.4 | incomplete- splice_match | 3prime_ fragment | 48 | canonical | coding | 124927649 | 124908147 |
| PB.1591.9 | 2380 | 3 | ENST00000616727.4 | incomplete- splice_match | 3prime_ fragment | 23 | canonical | coding | 124910662 | 124908147 |
| MUC15 mRNA isoforms | | | | | | | | | | |
| PB.354.10 | 1011 | 2 | ENST00000436318.6 | incomplete- splice_match | 3prime_ fragment | 3 | canonical | non_ coding | NA | NA |
| PB.354.16 | 1210 | 3 | ENST00000436318.6 | incomplete- splice_match | 3prime_ fragment | 10 | canonical | coding | 26561139 | 26561065 |
| PB.354.2 | 2255 | 2 | ENST00000436318.6 | incomplete- splice_match | 3prime_ fragment | 4 | canonical | non_ coding | NA | NA |
| PB.354.6 | 2672 | 3 | ENST00000436318.6 | incomplete- splice_match | 3prime_ fragment | 2 | canonical | coding | 26561139 | 26561065 |
| PB.354.9 | 1535 | 3 | ENST00000436318.6 | incomplete- splice_match | 3prime_ fragment | 5 | canonical | coding | 26561139 | 26561065 |
| PB.354.12 | 1916 | 4 | ENST00000455601.6 | full- splice_match | alternative_ 3end | 12 | canonical | coding | 26565858 | 26561065 |
| PB.354.18 | 1502 | 4 | ENST00000527569.1 | full- splice_match | alternative_ 3end | 5 | canonical | coding | 26565858 | 26561065 |
| PB.354.3 | 3178 | 4 | ENST00000527569.1 | full- splice_match | reference_ match | 4 | canonical | coding | 26565858 | 26561065 |
| PB.354.20 | 885 | 2 | ENST00000527569.1 | incomplete- splice_match | 5prime_ fragment | 2 | canonical | coding | 26565858 | 26565166 |
| PB.354.13 | 1854 | 4 | ENST00000527569.1 | full- splice_match | alternative_ 3end | 3 | canonical | coding | 26567094 | 26561065 |
| PB.354.17 | 1426 | 4 | ENST00000527569.1 | full- splice_match | reference_ match | 7 | canonical | coding | 26567094 | 26561065 |
| PB.354.19 | 1023 | 3 | ENST00000527569.1 | incomplete- splice_match | 5prime_ fragment | 68 | canonical | coding | 26567094 | 26565166 |
| PB.354.1 | 3392 | 5 | ENST00000529533.6 | full- splice_match | reference_ match | 41 | canonical | coding | 26572262 | 26561065 |
| PB.354.11 | 2005 | 5 | ENST00000529533.6 | full- splice_match | alternative_ 3end5end | 129 | canonical | coding | 26567094 | 26561065 |
| PB.354.15 | 1707 | 5 | ENST00000529533.6 | full- splice_match | alternative_ 3end | 211 | canonical | coding | 26572262 | 26561065 |
| PB.354.7 | 2658 | 5 | ENST00000529533.6 | full- splice_match | alternative_ 3end | 6 | canonical | coding | 26572262 | 26561065 |
| PB.354.8 | 2292 | 5 | ENST00000529533.6 | full- splice_match | alternative_ 3end5end | 8 | canonical | coding | 26567094 | 26561065 |
| PB.354.5 | 1817 | 1 | ENST00000529533.6 | incomplete- splice_match | mono-exon | 17 | NA | non_ coding | NA | NA |
| MUC16 mRNA isoforms | | | | | | | | | | |
| PB.1059.14 | 2218 | 21 | ENST00000397910.8 | incomplete- splice_match | 3prime_ fragment | 6 | canonical | non_ coding | NA | NA |

TABLE 14-continued

Classification of mucin mRNA isoforms in endotracheal mucus of COVID-19 patients with severe disease (critically ill COVID-19).

| PB_ isoform_ID | Length | Exons | Associated_ transcript | Structural_ category | Subcategory | Transcript_ count | Type of splice site | Coding? | CDS_ genomic_start | CDS_ genomic_end |
|---|---|---|---|---|---|---|---|---|---|---|
| PB.1059.16 | 2138 | 20 | ENST00000397910.8 | incomplete-splice_match | 3prime_fragment | 6 | canonical | non_coding | NA | NA |
| PB.1059.18 | 2056 | 19 | ENST00000397910.8 | incomplete-splice_match | 3prime_fragment | 25 | canonical | non_coding | NA | NA |
| PB.1059.19 | 1853 | 17 | ENST00000397910.8 | incomplete-splice_match | 3prime_fragment | 18 | canonical | non_coding | NA | NA |
| PB.1059.20 | 1736 | 16 | ENST00000397910.8 | incomplete-splice_match | 3prime_fragment | 15 | canonical | non_coding | NA | NA |
| PB.1059.21 | 1648 | 15 | ENST00000397910.8 | incomplete-splice_match | 3prime_fragment | 17 | canonical | non_coding | NA | NA |
| PB.1059.22 | 2603 | 25 | ENST00000397910.8 | incomplete-splice_match | 3prime_fragment | 6 | canonical | non_coding | NA | NA |
| PB.1059.26 | 1457 | 13 | ENST00000397910.8 | incomplete-splice_match | 3prime_fragment | 4 | canonical | non_coding | NA | NA |
| PB.1059.27 | 3321 | 34 | ENST00000397910.8 | incomplete-splice_match | 3prime_fragment | 3 | canonical | non_coding | NA | NA |
| PB.1059.28 | 2868 | 29 | ENST00000397910.8 | incomplete-splice_match | 3prime_fragment | 4 | canonical | non_coding | NA | NA |
| PB.1059.34 | 3122 | 31 | ENST00000397910.8 | incomplete-splice_match | 3prime_fragment | 3 | canonical | non_coding | NA | NA |
| PB.1059.6 | 2506 | 24 | ENST00000397910.8 | incomplete-splice_match | 3prime_fragment | 15 | canonical | non_coding | NA | NA |
| PB.1059.7 | 2312 | 22 | ENST00000397910.8 | incomplete-splice_match | 3prime_fragment | 2 | canonical | non_coding | NA | NA |
| PB.1067.1 | 1799 | 2 | ENST00000397910.8 | incomplete-splice_match | internal_fragment | 3 | canonical | non_coding | 8946928 | 8943473 |
| PB.1067.2 | 3409 | 2 | ENST00000397910.8 | incomplete-splice_match | internal_fragment | 4 | canonical | coding | 8948749 | 8943641 |
| PB.1067.3 | 1991 | 2 | ENST00000397910.8 | incomplete-splice_match | internal_fragment | 2 | canonical | coding | 8947372 | 8943641 |
| PB.1067.5 | 1463 | 1 | ENST00000397910.8 | incomplete-splice_match | mono-exon | 5 | NA | coding | 8948341 | 8946890 |
| PB.1068.1 | 1371 | 1 | ENST00000397910.8 | incomplete-splice_match | mono-exon | 2 | NA | coding | 8955526 | 8954177 |
| PB.1068.2 | 2381 | 1 | ENST00000397910.8 | incomplete-splice_match | mono-exon | 12 | NA | coding | 8957107 | 8954846 |
| PB.1068.3 | 3385 | 1 | ENST00000397910.8 | incomplete-splice_match | mono-exon | 6 | NA | coding | 8958172 | 8954846 |
| PB.1068.4 | 1268 | 1 | ENST00000397910.8 | incomplete-splice_match | mono-exon | 3 | NA | coding | 8956021 | 8954846 |
| PB.1068.6 | 2673 | 1 | ENST00000397910.8 | incomplete-splice_match | mono-exon | 4 | NA | coding | 8958706 | 8956040 |
| PB.1071.1 | 1978 | 1 | ENST00000397910.8 | incomplete-splice_match | mono-exon | 29 | NA | coding | 8967058 | 8965160 |
| PB.1071.12 | 3343 | 1 | ENST00000397910.8 | incomplete-splice_match | mono-exon | 16 | NA | coding | 8978822 | 8975709 |
| PB.1071.13 | 2158 | 1 | ENST00000397910.8 | incomplete-splice_match | mono-exon | 19 | NA | coding | 8977877 | 8975727 |
| PB.1071.14 | 2043 | 1 | ENST00000397910.8 | incomplete-splice_match | mono-exon | 2 | NA | coding | 8978822 | 8976927 |
| PB.1071.4 | 3320 | 3 | ENST00000397910.8 | incomplete-splice_match | 5prime_fragment | 2 | canonical | coding | 8972783 | 8965238 |
| PB.1071.7 | 1407 | 1 | ENST00000397910.8 | incomplete-splice_match | mono-exon | 2 | NA | coding | 8973077 | 8971716 |
| PB.1071.8 | 2630 | 1 | ENST00000397910.8 | incomplete-splice_match | mono-exon | 3 | NA | coding | 8974253 | 8971731 |
| PB.1059.12 | 882 | 8 | ENST00000596768.5 | incomplete-splice_match | 3prime_fragment | 4 | canonical | non_coding | NA | NA |
| PB.1059.2 | 801 | 7 | ENST00000596768.5 | incomplete-splice_match | 3prime_fragment | 2 | canonical | non_coding | NA | NA |
| PB.1059.1 | 1479 | 11 | ENST00000599436.1 | incomplete-splice_match | 3prime_fragment | 3 | canonical | non_coding | NA | NA |
| PB.1059.10 | 1008 | 9 | ENST00000599436.1 | incomplete-splice_match | 3prime_fragment | 15 | canonical | non_coding | NA | NA |
| PB.1059.25 | 2210 | 20 | ENST00000599436.1 | incomplete-splice_match | 3prime_fragment | 2 | canonical | non_coding | NA | NA |
| PB.1059.4 | 1341 | 12 | ENST00000599436.1 | incomplete-splice_match | 3prime_fragment | 18 | canonical | non_coding | NA | NA |
| PB.1059.8 | 1219 | 10 | ENST00000599436.1 | incomplete-splice_match | 3prime_fragment | 33 | canonical | non_coding | NA | NA |
| PB.1059.32 | 1286 | 11 | ENST00000601404.5 | incomplete-splice_match | 3prime_fragment | 2 | canonical | non_coding | NA | NA |

TABLE 14-continued

Classification of mucin mRNA isoforms in endotracheal mucus of COVID-19 patients with severe disease (critically ill COVID-19).

| PB_ isoform_ID | Length | Exons | Associated_ transcript | Structural_ category | Subcategory | Transcript_ count | Type of splice site | Coding? | CDS_ genomic_start | CDS_ genomic_end |
|---|---|---|---|---|---|---|---|---|---|---|
| MUC20 mRNA isoforms | | | | | | | | | | |
| PB.1629.99 | 1542 | 3 | ENST00000445522.6 | full-splice_match | alternative_5end | 51 | canonical | coding | 195726377 | 195733218 |
| PB.1629.100 | 1484 | 2 | ENST00000498018.1 | full-splice_match | alternative_5end | 32 | canonical | coding | 195726377 | 195729952 |
| MUC21 mRNA isoforms | | | | | | | | | | |
| PB.1864.115 | 881 | 1 | ENST00000376296.3 | incomplete-splice_match | mono-exon | 26 | NA | non_coding | NA | NA |
| PB.1864.96 | 2930 | 2 | ENST00000376296.3 | incomplete-splice_match | 3prime_fragment | 82 | canonical | coding | 30987538 | 30988194 |
| PB.1864.110 | 762 | 2 | ENST00000486149.2 | incomplete-splice_match | 3prime_fragment | 96 | canonical | coding | 30987538 | 30988194 |
| PB.1864.90 | 1765 | 2 | ENST00000486149.2 | incomplete-splice_match | 3prime_fragment | 1637 | canonical | coding | 30987538 | 30988194 |
| PB.1864.94 | 1587 | 2 | ENST00000486149.2 | incomplete-splice_match | 3prime_fragment | 304 | canonical | coding | 30987538 | 30988194 |
| PB.1865.1 | 6024 | 4 | ENST00000561890.1 | full-splice_match | reference_match | 3 | canonical | non_coding | NA | NA |
| PB.1865.10 | 1593 | 3 | ENST00000561890.1 | incomplete-splice_match | 3prime_fragment | 37 | canonical | non_coding | NA | NA |
| PB.1865.11 | 1820 | 3 | ENST00000561890.1 | incomplete-splice_match | 3prime_fragment | 19 | canonical | non_coding | NA | NA |
| PB.1865.12 | 2813 | 2 | ENST00000561890.1 | incomplete-splice_match | 3prime_fragment | 7 | canonical | coding | 31032243 | 31034938 |
| PB.1865.14 | 1800 | 2 | ENST00000561890.1 | incomplete-splice_match | 3prime_fragment | 32 | canonical | coding | 31032243 | 31034938 |
| PB.1865.17 | 1294 | 2 | ENST00000561890.1 | incomplete-splice_match | 3prime_fragment | 10 | canonical | coding | 31032333 | 31034938 |
| PB.1865.18 | 2158 | 2 | ENST00000561890.1 | incomplete-splice_match | 3prime_fragment | 3 | canonical | coding | 31032435 | 31034938 |
| PB.1865.19 | 2335 | 2 | ENST00000561890.1 | incomplete-splice_match | 3prime_fragment | 6 | canonical | coding | 31034819 | 31034938 |
| PB.1865.20 | 1749 | 2 | ENST00000561890.1 | incomplete-splice_match | 3prime_fragment | 7 | canonical | coding | 31034819 | 31034938 |
| PB.1865.8 | 2652 | 3 | ENST00000561890.1 | incomplete-splice_match | 3prime_fragment | 17 | canonical | non_coding | NA | NA |

TABLE 15

Classification of mucin mRNA isoforms in the blood of COVID-19 patients (mild and severe (=critically ill) disease).

| Con-dition | PB_ isoform_ ID | Length | Exons | Associated transcript | Structural_ category | Sub-category | Transcript_ count | Cod-ing? | Type of splice site | CDS_ genomic_ start | CDS_ genomic_ end |
|---|---|---|---|---|---|---|---|---|---|---|---|
| MUC1 mRNA isoforms | | | | | | | | | | | |
| Mild | PB.564.5 | 1640 | 8 | ENST00000337604.6 | full-splice_match | alternative_3end5end | 41 | coding | canonical | 155192843 | 155186135 |
| Mild | PB.564.18 | 848 | 5 | ENST00000338684.9 | incomplete-splice_match | 3prime_fragment | 17 | coding | canonical | 155187302 | 155186135 |
| Mild | PB.564.1 | 1607 | 8 | ENST00000368390.7 | full-splice_match | alternative_3end5end | 59 | coding | canonical | 155192843 | 155186135 |
| Mild | PB.564.21 | 1881 | 8 | ENST00000368392.7 | full-splice_match | alternative_3end5end | 98 | coding | canonical | 155192843 | 155186135 |
| Mild | PB.564.8 | 960 | 6 | ENST00000467134.5 | full-splice_match | alternative_3end | 14 | coding | canonical | 155192843 | 155187570 |
| Mild | PB.564.14 | 1114 | 4 | ENST00000467134.5 | incomplete-splice_match | 3prime_fragment | 20 | coding | canonical | 155188165 | 155187574 |
| Mild | PB.564.11 | 1905 | 3 | ENST00000468978.2 | full-splice_match | alternative_3end5end | 49 | coding | canonical | 155186196 | 155185873 |

TABLE 15-continued

Classification of mucin mRNA isoforms in the blood of COVID-19 patients (mild and severe (=critically ill) disease).

| Con-dition | PB_isoform_ID | Length | Exons | Associated transcript | Structural_category | Sub-category | Transcript_count | Cod-ing? | Type of splice site | CDS_genomic_start | CDS_genomic_end |
|---|---|---|---|---|---|---|---|---|---|---|---|
| Mild | PB.564.10 | 1935 | 2 | ENST00000468978.2 | incomplete-splice_match | intron_retention | 6 | coding | canonical | 155186196 | 155185873 |
| Mild | PB.564.16 | 789 | 4 | ENST00000610359.4 | incomplete-splice_match | 3prime_fragment | 29 | coding | canonical | 155187302 | 155186135 |
| Mild | PB.564.32 | 1090 | 5 | ENST00000614519.4 | incomplete-splice_match | 3prime_fragment | 2 | coding | canonical | 155188165 | 155187570 |
| Mild | PB.564.7 | 1331 | 6 | ENST00000620103.4 | incomplete-splice_match | 3prime_fragment | 127 | coding | canonical | 155188165 | 155186135 |
| Severe | PB.541.8 | 1927 | 8 | ENST00000337604.6 | full-splice_match | alternative_3end5end | 108 | coding | canonical | 155192843 | 155186135 |
| Severe | PB.541.9 | 1860 | 8 | ENST00000368390.7 | full-splice_match | alternative_3end5end | 199 | coding | canonical | 155192843 | 155186135 |
| Severe | PB.541.20 | 1588 | 8 | ENST00000368392.7 | full-splice_match | alternative_3end5end | 61 | coding | canonical | 155192843 | 155186135 |
| Severe | PB.541.26 | 2688 | 8 | ENST00000368392.7 | full-splice_match | alternative_3end5end | 29 | coding | canonical | 155192843 | 155186135 |
| Severe | PB.541.14 | 1232 | 7 | ENST00000462215.5 | incomplete-splice_match | 3prime_fragment | 8 | coding | canonical | 155188165 | 155186135 |
| Severe | PB.541.23 | 1071 | 4 | ENST00000467134.5 | incomplete-splice_match | 3prime_fragment | 7 | coding | canonical | 155188165 | 155187574 |
| Severe | PB.541.5 | 1894 | 3 | ENST00000468978.2 | full-splice_match | alternative_3end5end | 42 | coding | canonical | 155186196 | 155185873 |
| Severe | PB.541.4 | 2499 | 2 | ENST00000468978.2 | incomplete-splice_match | intron_retention | 57 | coding | canonical | 155186196 | 155185873 |
| Severe | PB.541.17 | 650 | 3 | ENST00000485118.5 | incomplete-splice_match | 3prime_fragment | 13 | coding | canonical | 155187302 | 155186135 |
| Severe | PB.541.21 | 1003 | 7 | ENST00000614519.4 | full-splice_match | alternative_5end | 2 | coding | canonical | 155188165 | 155187570 |
| Severe | PB.541.12 | 1384 | 6 | ENST00000620103.4 | incomplete-splice_match | 3prime_fragment | 241 | coding | canonical | 155188165 | 155186135 |
| Severe | PB.541.16 | 846 | 5 | ENST00000620103.4 | incomplete-splice_match | 3prime_fragment | 89 | coding | canonical | 155187302 | 155186135 |
| Severe | PB.541.18 | 715 | 4 | ENST00000620103.4 | incomplete-splice_match | 3prime_fragment | 34 | coding | canonical | 155187302 | 155186135 |
| MUC12 mRNA isoforms | | | | | | | | | | | |
| Mild | PB.7353.1 | 867 | 2 | ENST00000474482.1 | full-splice_match | alternative_5end | 49 | non_coding | canonical | NA | NA |
| Severe | PB.6235.1 | 771 | 2 | ENST00000474482.1 | full-splice_match | alternative_5end | 12 | non_coding | canonical | NA | NA |
| MUC13 mRNA isoforms | | | | | | | | | | | |
| Mild | PB.5616.2 | 1460 | 2 | ENST00000490147.1 | incomplete-splice_match | 5prime_fragment | 4 | coding | canonical | 124928033 | 124923498 |
| Mild | PB.5616.1 | 2378 | 11 | ENST00000616727.4 | incomplete-splice_match | 3prime_fragment | 16 | coding | canonical | 124922235 | 124908147 |
| MUC16 mRNA isoforms | | | | | | | | | | | |
| Mild | PB.3837.3 | 3148 | 31 | ENST00000397910.8 | incomplete-splice_match | 3prime_fragment | 3 | coding | canonical | 8889822 | 8848932 |

TABLE 15-continued

Classification of mucin mRNA isoforms in the blood of COVID-19 patients (mild and severe (=critically ill) disease).

| Con-dition | PB_isoform_ID | Length | Exons | Associated transcript | Structural_category | Sub-category | Transcript_count | Cod-ing? | Type of splice site | CDS_genomic_start | CDS_genomic_end |
|---|---|---|---|---|---|---|---|---|---|---|---|
| Mild | PB.3839.1 | 1896 | 1 | ENST00000397910.8 | incomplete-splice_match | mono-exon | 13 | coding | NA | 8948749 | 8946890 |
| Mild | PB.3839.2 | 2941 | 1 | ENST00000397910.8 | incomplete-splice_match | mono-exon | 2 | coding | NA | 8949790 | 8946890 |
| Mild | PB.3839.3 | 3046 | 1 | ENST00000397910.8 | incomplete-splice_match | mono-exon | 3 | coding | NA | 8952196 | 8949167 |
| Mild | PB.3839.4 | 2281 | 1 | ENST00000397910.8 | incomplete-splice_match | mono-exon | 7 | coding | NA | 8952892 | 8950619 |
| Mild | PB.3840.1 | 1540 | 1 | ENST00000397910.8 | incomplete-splice_match | mono-exon | 28 | coding | NA | 8956354 | 8954846 |
| Mild | PB.3841.1 | 1600 | 1 | ENST00000397910.8 | incomplete-splice_match | mono-exon | 17 | coding | NA | 8958511 | 8956916 |
| Mild | PB.3842.2 | 1553 | 1 | ENST00000397910.8 | incomplete-splice_match | mono-exon | 9 | coding | NA | 8977250 | 8975709 |
| Mild | PB.3837.4 | 833 | 7 | ENST00000596768.5 | incomplete-splice_match | 3prime_fragment | 2 | coding | canonical | 8858749 | 8848932 |
| Mild | PB.3837.1 | 1396 | 12 | ENST00000599436.1 | incomplete-splice_match | 3prime_fragment | 18 | coding | canonical | 8866116 | 8848932 |
| Severe | PB.3395.1 | 4088 | 41 | ENST00000397910.8 | incomplete-splice_match | 3prime_fragment | 5 | coding | canonical | 8896022 | 8848932 |
| Severe | PB.3396.2 | 1144 | 1 | ENST00000397910.8 | incomplete-splice_match | mono-exon | 13 | coding | NA | 8955976 | 8954846 |
| Severe | PB.3396.3 | 2944 | 1 | ENST00000397910.8 | incomplete-splice_match | mono-exon | 11 | coding | NA | 8978438 | 8975709 |
| Severe | PB.3396.4 | 1404 | 1 | ENST00000397910.8 | incomplete-splice_match | mono-exon | 74 | coding | NA | 8976770 | 8975727 |
| MUC19 mRNA isoforms | | | | | | | | | | | |
| Severe | PB.1630.25 | 579 | 3 | ENST00000427572.2 | incomplete-splice_match | 3prime_fragment | 2 | coding | canonical | 40569767 | 40570646 |
| Severe | PB.1630.11 | 3112 | 15 | ENST00000454784.9 | incomplete-splice_match | intron_retention | 12 | coding | canonical | 40550725 | 40561683 |
| Severe | PB.1624.1 | 972 | 8 | ENST00000454784.9 | incomplete-splice_match | internal_fragment | 2 | coding | canonical | 40432716 | 40433903 |
| Severe | PB.1630.26 | 1158 | 2 | ENST00000546043.2 | full-splice_match | alternative_5end | 2 | coding | canonical | 40569653 | 40570646 |
| MUC20 mRNA isoforms | | | | | | | | | | | |
| Mild | PB.5804.85 | 1740 | 3 | ENST00000445522.6 | full-splice_match | alternative_5end | 412 | coding | canonical | 195726377 | 195733218 |
| Mild | PB.5804.93 | 680 | 3 | ENST00000445522.6 | full-splice_match | alternative_5end | 16 | coding | canonical | 195726509 | 195733218 |
| Mild | PB.5804.86 | 148 | 2 | ENST00000498018.1 | full-splice_match | alternative_5end | 132 | coding | canonical | 195726377 | 195729952 |
| Severe | PB.5084.46 | 1299 | 3 | ENST00000445522.6 | full-splice_match | alternative_5end | 104 | coding | canonical | 195726377 | 195733218 |
| Severe | PB.5084.47 | 1259 | 2 | ENST00000498018.1 | full-splice_match | alternative_5end | 8 | coding | canonical | 195726377 | 195729952 |

TABLE 16

Classification of mucin mRNA isoforms in the blood of control patients (i.e. mild non-COVID-19 and post-COVID-19 (no symptoms)).

| Condition | Isoform | Length | Exons | Associated_ transcript | Structural_ category | Sub category | Transcr_ count | Type of splice site | Coding? | CDS_ genomic_ start | CDS_ genomic_ end |
|---|---|---|---|---|---|---|---|---|---|---|---|
| MUC1 mRNA isoforms | | | | | | | | | | | |
| No COVID mild | PB.3496.1 | 1693 | 8 | ENST00000337604.6 | full-splice_ match | alternative_ 3end5end | 86 | canonical | coding | 155192843 | 155186135 |
| No COVID mild | PB.3388.1 | 1636 | 8 | ENST00000368390.7 | full-splice_ match | alternative_ 3end5end | 63 | canonical | coding | 155192843 | 155186135 |
| No COVID mild | PB.3500.2 | 1887 | 8 | ENST00000368392.7 | full-splice_ match | alternative_ 3end5end | 33 | canonical | coding | 155192843 | 155186135 |
| No COVID mild | PB.3500.5 | 981 | 7 | ENST00000368392.7 | incomplete-splice_ match | 3prime_ fragment | 15 | canonical | coding | 155188165 | 155186135 |
| No COVID mild | PB.3500.4 | 1026 | 2 | ENST00000462317.5 | incomplete-splice_ match | intron_ retention | 3 | canonical | coding | 155186196 | 155185873 |
| No COVID mild | PB.3500.1 | 1802 | 3 | ENST00000468978.2 | full-splice_ match | alternative_ 3end | 33 | canonical | coding | 155187302 | 155187126 |
| No COVID mild | PB.3500.6 | 1837 | 2 | ENST00000468978.2 | incomplete-splice_ match | intron_ retention | 8 | canonical | coding | 155186196 | 155185873 |
| No COVID mild | PB.3498.1 | 1733 | 3 | ENST00000485118.5 | incomplete-splice_ match | intron_ retention | 31 | canonical | coding | 155188165 | 155188127 |
| No COVID mild | PB.3500.3 | 1504 | 6 | ENST00000620103.4 | incomplete-splice_ match | 3prime_ fragment | 94 | canonical | coding | 155188165 | 155186135 |
| No COVID mild | PB.3521.1 | 852 | 5 | ENST00000620103.4 | incomplete-splice_ match | 3prime_ fragment | 9 | canonical | coding | 155187302 | 155186135 |
| Post-COVID | PB.147.2 | 1199 | 8 | ENST00000337604.6 | full-splice_ match | alternative_ 3end | 16 | canonical | coding | 155192843 | 155186135 |
| Post-COVID | PB.147.6 | 1604 | 8 | ENST00000368390.7 | full-splice_ match | alternative_ 3end5end | 50 | canonical | coding | 155192843 | 155186135 |
| Post-COVID | PB.147.11 | 1177 | 8 | ENST00000368392.7 | full-splice_ match | alternative_ 3end | 2 | canonical | coding | 155192843 | 155186135 |
| Post-COVID | PB.147.10 | 1519 | 7 | ENST00000438413.5 | full-splice_ match | alternative_ 3end5end | 18 | canonical | coding | 155192843 | 155186135 |
| Post-COVID | PB.147.14 | 975 | 4 | ENST00000467134.5 | incomplete-splice_ match | 3prime_ fragment | 8 | canonical | coding | 155188165 | 155187574 |
| Post-COVID | PB.147.3 | 1315 | 6 | ENST00000620103.4 | incomplete-splice_ match | 3prime_ fragment | 50 | canonical | coding | 155188165 | 155186135 |
| Post-COVID | PB.147.4 | 731 | 4 | ENST00000620103.4 | incomplete-splice_ match | 3prime_ fragment | 16 | canonical | coding | 155187302 | 155186135 |
| MUC12 mRNA isoforms | | | | | | | | | | | |
| No COVID mild | PB.3810.1 | 653 | 3 | ENST00000473098.5 | full-splice_ match | alternative_ 5end | 10 | canonical | non_ coding | NA | NA |
| No COVID mild | PB.3845.1 | 865 | 2 | ENST00000474482.1 | full-splice_ match | alternative_ 5end | 12 | canonical | non_ coding | NA | NA |
| Post-COVID | PB.2206.1 | 852 | 2 | ENST00000474482.1 | full-splice_ match | alternative_ 5end | 70 | canonical | non_ coding | NA | NA |
| MUC16 mRNA isoforms | | | | | | | | | | | |
| No COVID mild | PB.3906.1 | 2056 | 19 | ENST00000397910.8 | incomplete-splice_ match | 3prime_ fragment | 38 | canonical | coding | 8876599 | 8848932 |
| No COVID mild | PB.3897.1 | 1077 | 1 | ENST00000397910.8 | incomplete-splice_ match | mono-exon | 2 | NA | coding | 8955733 | 8954855 |

TABLE 16-continued

Classification of mucin mRNA isoforms in the blood of control patients (i.e. mild non-COVID-19 and post-COVID-19 (no symptoms)).

| Condition | Isoform | Length | Exons | Associated_ transcript | Structural_ category | Sub category | Transcr_ count | Type of splice site | Coding? | CDS_ genomic_ start | CDS_ genomic_ end |
|---|---|---|---|---|---|---|---|---|---|---|---|
| No COVID mild | PB.3907.1 | 2156 | 1 | ENST00000397910.8 | incomplete-splice_ match | mono-exon | 7 | NA | coding | 8958172 | 8956040 |
| No COVID mild | PB.3956.1 | 947 | 1 | ENST00000397910.8 | incomplete-splice_ match | mono-exon | 5 | NA | coding | 8976665 | 8975721 |
| Post-COVID | PB.1139.1 | 770 | 1 | ENST00000397910.8 | incomplete-splice_ match | mono-exon | 2 | NA | coding | 8946910 | 8946146 |
| Post-COVID | PB.1140.1 | 1588 | 1 | ENST00000397910.8 | incomplete-splice_ match | mono-exon | 13 | NA | coding | 8956429 | 8954846 |
| Post-COVID | PB.1141.1 | 1195 | 1 | ENST00000397910.8 | incomplete-splice_ match | mono-exon | 11 | NA | coding | 8966137 | 8965238 |
| Post-COVID | PB.1141.2 | 4603 | 3 | ENST00000397910.8 | incomplete-splice_ match | 5prime_ fragment | 4 | canonical | coding | 8973992 | 8965238 |
| MUC19 mRNA isoforms | | | | | | | | | | | |
| No COVID mild | PB.4031.1 | 2567 | 2 | ENST00000454784.9 | incomplete-splice_ match | intron_ retention | 9 | canonical | non_ coding | NA | NA |
| Post-COVID | PB.508.1 | 966 | 3 | ENST00000427572.2 | incomplete-splice_ match | 3prime_ fragment | 5 | canonical | non_ coding | NA | NA |
| Post-COVID | PB.505.5 | 1152 | 2 | ENST00000484665.2 | incomplete-splice_ match | 3prime_ fragment | 5 | canonical | non_ coding | NA | NA |
| MUC20 mRNA isoforms | | | | | | | | | | | |
| No COVID mild | PB.4083.1 | 4298 | 3 | ENST00000445522.6 | full-splice_ match | alternative_ 3end5end | 3 | canonical | coding | 195726377 | 195733218 |
| No COVID mild | PB.4080.1 | 1538 | 3 | ENST00000445522.6 | full-splice_ match | alternative_ 5end | 177 | canonical | coding | 195726377 | 195733218 |
| No COVID mild | PB.4085.1 | 1582 | 2 | ENST00000498018.1 | full-splice_ match | alternative_ 5end | 127 | canonical | coding | 195726377 | 195729952 |

TABLE 17

Comparative analysis of mucin mRNA isoform abundance and/or presence in mucus and blood samples of COVID-19 patients and controls.

| | | COVID-19 | | | | Control | | |
|---|---|---|---|---|---|---|---|---|
| Gene | Transcript_ ID | critical COVID-19 (mucus from ETT) | critical COVID-19 (blood samples) | Mild COVID-19 (blood samples) | Combined COVID-19 (blood samples) | Mild non-COVID-19 (blood samples) | Post-COVID-19 (blood samples) | Combined control groups (blood samples) |
| MUC1 | ENST00000337604.6 | 217 | 108 | 41 | 149 | 86 | 16 | 102 |
| MUC1 | ENST00000338684.9 | 101 | 0 | 17 | 17 | 0 | 0 | 0 |
| MUC1 | ENST00000342482.8 | 8 | 0 | 0 | 0 | 0 | 0 | 0 |
| MUC1 | ENST00000343256.9 | 4 | 0 | 0 | 0 | 0 | 0 | 0 |
| MUC1 | ENST00000368390.7 | 311 | 199 | 59 | 258 | 63 | 50 | 113 |
| MUC1 | ENST00000368392.7 | 17 | 90 | 98 | 188 | 48 | 2 | 50 |
| MUC1 | ENST00000368393.7 | 4 | 0 | 0 | 0 | 0 | 0 | 0 |
| MUC1 | ENST00000438413.5 | 23 | 0 | 0 | 0 | 0 | 18 | 18 |
| MUC1 | ENST00000462215.5 | 0 | 8 | 0 | 8 | 0 | 0 | 0 |
| MUC1 | ENST00000462317.5 | 8 | 0 | 0 | 0 | 3 | 0 | 3 |
| MUC1 | ENST00000467134.5 | 5 | 7 | 34 | 41 | 0 | 8 | 8 |
| MUC1 | ENST00000468978.2 | 29 | 99 | 55 | 154 | 41 | 0 | 41 |
| MUC1 | ENST00000485118.5 | 23 | 13 | 0 | 13 | 0 | 0 | 0 |
| MUC1 | ENST00000610359.4 | 8 | 0 | 0 | 0 | 0 | 0 | 0 |
| MUC1 | ENST00000612778.4 | 11 | 0 | 0 | 0 | 0 | 0 | 0 |
| MUC1 | ENST00000614519.4 | 6 | 2 | 2 | 4 | 0 | 0 | 0 |
| MUC1 | ENST00000620103.4 | 1131 | 364 | 127 | 491 | 103 | 66 | 169 |

TABLE 17-continued

Comparative analysis of mucin mRNA isoform abundance and/or presence in mucus and blood samples of COVID-19 patients and controls.

| | | COVID-19 | | | | Control | | |
|---|---|---|---|---|---|---|---|---|
| Gene | Transcript_ ID | critical COVID-19 (mucus from ETT) | critical COVID-19 (blood samples) | Mild COVID-19 (blood samples) | Combined COVID-19 (blood samples) | Mild non-COVID-19 (blood samples) | Post-COVID-19 (blood samples) | Combined control groups (blood samples) |
| MUC2 | ENST00000361558.7 | 29 | 0 | 0 | 0 | 0 | 0 | 0 |
| MUC3A | ENST00000379458.9 | 3 | 0 | 0 | 0 | 0 | 0 | 0 |
| MUC3A | ENST00000483366.5 | 2 | 0 | 0 | 0 | 0 | 0 | 0 |
| MUC3A | ENST00000614399.1 | 138 | 0 | 0 | 0 | 0 | 0 | 0 |
| MUC4 | ENST00000308466.12 | 401 | 0 | 0 | 0 | 0 | 0 | 0 |
| MUC4 | ENST00000346145.8 | 6 | 0 | 0 | 0 | 0 | 0 | 0 |
| MUC4 | ENST00000349607.8 | 11 | 0 | 0 | 0 | 0 | 0 | 0 |
| MUC4 | ENST00000448861.5 | 3 | 0 | 0 | 0 | 0 | 0 | 0 |
| MUC4 | ENST00000463781.8 | 11 | 0 | 0 | 0 | 0 | 0 | 0 |
| MUC4 | ENST00000464234.5 | 99 | 0 | 0 | 0 | 0 | 0 | 0 |
| MUC4 | ENST00000478156.5 | 2 | 0 | 0 | 0 | 0 | 0 | 0 |
| MUC4 | ENST00000478685.1 | 3 | 0 | 0 | 0 | 0 | 0 | 0 |
| MUC4 | ENST00000479406.5 | 573 | 0 | 0 | 0 | 0 | 0 | 0 |
| MUC5AC | ENST00000621226.2 | 395 | 0 | 0 | 0 | 0 | 0 | 0 |
| MUC5B | ENST00000525715.5 | 9 | 0 | 0 | 0 | 0 | 0 | 0 |
| MUC5B | ENST00000529681.5 | 833 | 0 | 0 | 0 | 0 | 0 | 0 |
| MUC7 | ENST00000304887.6 | 293 | 0 | 0 | 0 | 0 | 0 | 0 |
| MUC7 | ENST00000413702.5 | 15 | 0 | 0 | 0 | 0 | 0 | 0 |
| MUC7 | ENST00000505411.5 | 5 | 0 | 0 | 0 | 0 | 0 | 0 |
| MUC12 | ENST00000473098.5 | 0 | 0 | 0 | 0 | 10 | 0 | 10 |
| MUC12 | ENST00000474482.1 | 6 | 12 | 49 | 61 | 12 | 70 | 82 |
| MUC13 | ENST00000616727.4 | 1171 | 0 | 16 | 16 | 0 | 0 | 0 |
| MUC13 | ENST00000490147.1 | 0 | 0 | 4 | 4 | 0 | 0 | 0 |
| MUC15 | ENST00000436318.6 | 24 | 0 | 0 | 0 | 0 | 0 | 0 |
| MUC15 | ENST00000455601.6 | 23 | 0 | 0 | 0 | 0 | 0 | 0 |
| MUC15 | ENST00000527569.1 | 78 | 0 | 0 | 0 | 0 | 0 | 0 |
| MUC15 | ENST00000529533.6 | 412 | 0 | 0 | 0 | 0 | 0 | 0 |
| MUC16 | ENST00000397910.8 | 238 | 103 | 64 | 167 | 52 | 30 | 82 |
| MUC16 | ENST00000596768.5 | 6 | 0 | 2 | 2 | 0 | 0 | 0 |
| MUC16 | ENST00000599436.1 | 71 | 0 | 18 | 18 | 0 | 0 | 0 |
| MUC16 | ENST00000601404.5 | 2 | 0 | 0 | 0 | 0 | 0 | 0 |
| MUC19 | ENST00000454784.9 | 0 | 14 | 0 | 14 | 9 | 0 | 9 |
| MUC19 | ENST00000427572.2 | 0 | 2 | 0 | 2 | 0 | 5 | 5 |
| MUC19 | ENST00000484665.2 | 0 | 0 | 0 | 0 | 0 | 5 | 5 |
| MUC19 | ENST00000546043.2 | 0 | 2 | 0 | 2 | 0 | 0 | 0 |
| MUC20 | ENST00000445522.6 | 51 | 104 | 428 | 532 | 180 | 51 | 231 |
| MUC20 | ENST00000498018.1 | 32 | 8 | 132 | 140 | 127 | 0 | 127 |
| MUC21 | ENST00000376296.3 | 108 | 0 | 0 | 0 | 0 | 0 | 0 |
| MUC21 | ENST00000486149.2 | 2037 | 0 | 0 | 0 | 0 | 0 | 0 |
| MUC22 | ENST00000561890.1 | 141 | 0 | 0 | 0 | 0 | 0 | 0 |

REFERENCES

Breugelmans T, Van Spaendonk H, De Man J G, De Schepper H U, Jauregui-Amezaga A, Macken E, Linden S K, Pintelon I, Timmermans J P, De Winter B Y, Smet A. In depth study of transmembrane mucins in association with intestinal barrier dysfunction during the course of T cell transfer and DSS-induced colitis. J Crohns Colitis 2020, jjaa015.

Corman V M, Landt O, Kaiser M, Molenkamp R, Meijer A, Chu D K, Bleicker T, Brunink S, Schneider J, Schmidt M L, Mulders D G, Haagmans B L, van der Veer B, van den Brink S, Wijsman L, Goderski G, Romette J L, Ellis J, Zambon M, Peiris M, Goossens H, Reusken C, Koopmans M P, Drosten C. Detection of 2019 novel coronavirus (2019-nCoV) by real-time RT-PCR. Euro Surveill 2020, 25(3):2000045.

d'Allessandro M, et al., 2020. Serum KL-6 concentrations as a novel biomarker of severe COVID-19. Journal of Medical Virology, 92:2216-2220.

Guan W J, Chen R C, Zhong N S. Strategies for the prevention and management of coronavirus disease 2019. Eur Respir J. 2020, 55(4):2000597.

Gupta J, Nebreda A. Analysis of Intestinal Permeability in Mice. *BIO-PROTOCOL* 2014; 4(22).

Heylen M, Deleye S, De Man J G, et al. Colonoscopy and pPET/CT are Valid Techniques to Monitor Inflammation in the Adoptive Transfer Colitis Model in Mice. *Inflamm Bowel Dis* 2013; 19(5): 967-76.

Hoffmann et al., 2020. SARS-CoV-2 cell entry depends on ACE2 and TMPRSS2 and is blocked by a clinically proven protease inhibitor. Cell, 181:271-280.

Huang C, Yeming W, Li X, Ren L et al., 2020. Clinical features of patients infected with 2019 novel coronavirus in Wuhan, China. The Lancet, 395:497-506.

Linden S, Putton P, Karlsson N, et al. Mucins in the mucosal barrier to infection. *Mucosal Immunol* 2008; 1(3): 183-97.

Moehle C, Ackermann N, Langmann T, et al. Aberrant intestinal expression and allelic variants of mucin genes associated with inflammatory bowel disease. *J Mol Med* 2006; 84(12): 1055-66.

Moreels T G, Nieuwendijk R J, De Man J G, et al. Concurrent infection with *Schistosoma mansoni* attenuates inflammation induced changes in colonic morphology, cytokine levels, and smooth muscle contractility of trinitrobenzene sulphonic acid induced colitis in rats. *Gut* 2004; 53(1): 99-107.

Obermair A, Schmid B C, Packer L M, Leodolter S, Birner P, Ward B G, Crandon A J, McGuckin M A, Zeillinger R. Expression of MUC1 splice variants in benign and malignant ovarian tumours. *Int J Cancer* 2002; 100: 166-71.

Sheng Y H, Lourie R, Linden S K, et al. The MUC13 cell-surface mucin protects against intestinal inflammation by inhibiting epithelial cell apoptosis. *Gut* 2011; 60(12): 1661-70.

Sheng Y, Triyana S, Wang R, et al. MUC1 and MUC13 differentially regulate epithelial inflammation in response to inflammatory and infectious stimuli. *Mucosal Immunol* 2012; 6(3): 557-68.

Vancamelbeke M, Vanuytsel T, Farre R, et al. Genetic and Transcriptomic Bases of Intestinal 50 Epithelial Barrier Dysfunction in Inflammatory Bowel Disease. *Inflamm Bowel Dis* 2017; 23(10): 1718-29.

Wallace J L, Keenan C M, Gale D, Shoupe T S. Exacerbation of experimental colitis by nonsteroidal anti-inflammatory drugs is not related to elevated leukotriene B4synthesis. *Gastroenterology* 1992; 102(1): 18-27.

Wenju et al., 2020. Elevated MUC1 and MUC5AC mucin protein levels in airway mucus of critical ill COVID-19 patients. J Med Virol 93:582-584.

Zaretsky J Z, Barnea I, Aylon Y, Gorivodsky M, Wreschner D H, Keydar I. MUC1 gene overexpressed in breast cancer: Structure and transcriptional activity of the MUC1 promoter and role of estrogen receptor alpha (ERa) in regulation of the MUC1 gene expression. *Mol Cancer* 2006; 5: 57.

Zrihan-Licht S, Vos H L, Baruch A, Elroy-Stein O, Sagiv D, Keydar I, Hilkens J, Wreschner D H. Characterization and Molecular Cloning of a Novel MUC1 Protein, Devoid of Tandem Repeats, Expressed in Human Breast Cancer Tissue. *Eur J Biochem* 1994; 224: 787-95.

The invention claimed is:

1. A method for diagnosing and treating a subject with a coronaviral infection, the method comprising:

providing a biological sample from the subject;

determining the presence of a mucin in the biological sample, the mucin being selected from the group consisting of MUC16, MUC21, MUC2, MUC4, MUC5AC, MUC5B, MUC6, MUC13, and MUC20;

diagnosing the subject with a coronaviral infection based on the presence of the mucin in the biological sample; and administering a treatment to the subject wherein the treatment reduces production of the mucin, wherein the treatment is selected from the group consisting of remdesivir, (hydroxy)chloroquine, favipiravir, baricitinib, anakinra, dexamethasone, and toculizumab.

2. The method of claim 1, further comprising determining the presence of MUC1 in the biological sample.

3. The method of claim 2, wherein determining the presence of the mucin in the biological sample comprises quantifying an mRNA expression level of MUC1, MUC2, MUC16, and MUC20, wherein high levels of MUC1, high levels of MUC2, high levels of MUC20, or low levels of MUC16 are indicative of a coronaviral infection.

4. The method of claim 2, wherein determining the presence of the mucin in the biological sample comprises quantifying an mRNA expression level of MUC1, MUC2, MUC4, MUC6, MUC13, MUC16, and MUC20, wherein high levels of MUC1, high levels of MUC2, low levels of MUC4, low levels of MUC6, high levels of MUC13, low levels of MUC16, or low levels of MUC20 are indicative of a coronaviral infection.

5. The method of claim 1, wherein determining the presence of the mucin in the biological sample comprises quantifying an mRNA expression level of MUC2, MUC13, MUC20, and MUC21, wherein high levels of MUC2, high levels of MUC13, high levels of MUC20, or high levels of MUC21 are indicative of a mild coronaviral infection.

6. The method of claim 1, wherein determining the presence of the mucin in the biological sample comprises quantifying an mRNA expression level of MUC2, MUC5AC, MUC5B, MUC13, MUC16, MUC20, and MUC21, wherein high levels of MUC2, high levels of MUC5AC, high levels of MUC5B, high levels of MUC13, high levels of MUC16, high levels of MUC20, or high levels of MUC21 are indicative of a mild coronaviral infection.

7. The method of claim 2, wherein determining the presence of the mucin in the biological sample comprises quantifying an mRNA expression level of MUC1, MUC5B, and MUC16, wherein high levels of MUC1, high levels of MUC5B, or low levels of MUC16 are indicative of a severe coronaviral infection.

8. The method of claim 2, wherein determining the presence of the mucin in the biological sample comprises quantifying an mRNA expression level of MUC1, MUC16, MUC20, and MUC21, wherein high levels of MUC1, low levels of MUC16, low levels of MUC20, or low levels of MUC21 are indicative of a severe coronaviral infection.

9. A method for diagnosing and treating a subject with a coronaviral infection, the method comprising:

providing a biological sample from a subject;

determining the presence of a mucin isoform in the biological sample, the mucin being selected from the group consisting of MUC16 mRNA isoforms, MUC21 mRNA isoforms, MUC2 mRNA isoforms, MUC4 mRNA isoforms, MUC5AC mRNA isoforms, MUC5B mRNA isoforms, MUC13 mRNA isoforms, MUC20 mRNA isoforms, and MUC1 mRNA isoforms;

diagnosing the subject with a coronaviral infection based on the presence of the mucin isoform in the biological sample; and administering a treatment to the subject wherein the treatment reduces production of the mucin isoform, wherein the treatment is selected from the group consisting of remdesivir, (hydroxy)chloroquine, favipiravir, baricitinib, anakinra, dexamethasone, and toculizumab.

10. The method of claim 9, further comprising determining the presence and/or quantity of one or more additional mucin isoforms in the biological sample selected from the group consisting of MUC3A mRNA isoforms, MUC6 mRNA isoforms, MUC7 mRNA isoforms, MUC8 mRNA isoforms, MUC12 mRNA isoforms, MUC15 mRNA isoforms, MUC17 mRNA isoforms, MUC19 mRNA isoforms, and MUC22 mRNA isoforms.

11. The method of claim 9, wherein determining the presence of the mucin isoform in the biological sample comprises determining the presence of two or more mucin mRNA isoforms.

12. The method of claim 9, wherein determining the presence of the mucin isoform in the biological sample comprises quantifying an mRNA expression level of MUC1 mRNA isoforms, MUC13 mRNA isoforms, MUC16 mRNA isoforms and MUC21 mRNA isoforms, and wherein the presence the of the MUC1 mRNA isoforms, the MUC13 mRNA isoforms, the MUC16 mRNA isoforms, and the MUC21 mRNA isoforms are indicative of a coronaviral infection.

13. The method of claim 9, wherein determining the presence of the mucin isoform in the biological sample comprises quantifying an mRNA expression level of MUC1 mRNA isoforms, MUC2 mRNA isoforms, MUC16 mRNA isoforms, and MUC20 mRNA isoforms, and wherein high levels of MUC1 mRNA isoforms, high levels of MUC2 mRNA isoforms, high levels of MUC20 mRNA isoforms, or low levels of MUC16 mRNA isoforms are indicative of a coronaviral infection.

14. The method of claim 9, wherein determining the presence of the mucin isoform in the biological sample comprises quantifying an mRNA expression level of MUC2 mRNA isoforms, MUC13 mRNA isoforms, MUC20 mRNA isoforms, and MUC21 mRNA, and wherein high levels of MUC2 mRNA isoforms, high levels of MUC13 mRNA isoforms, high levels of MUC20 mRNA isoforms, or high levels of MUC21 mRNA isoforms is indicative of a mild coronaviral infection.

15. The method of claim 9, wherein determining the presence of the mucin isoform in the biological sample comprises quantifying an mRNA expression level of MUC1 mRNA isoforms, MUC5B mRNA isoforms, and MUC16 mRNA isoforms, and wherein high levels of MUC1 mRNA isoforms, high levels of MUC5B mRNA isoforms, or low levels of MUC16 mRNA isoforms is indicative of a more severe coronaviral infection.

16. The method of claim 9, wherein:

the biological sample is a mucous sample; and determining the presence of the mucin isoform in the biological sample comprises quantifying an mRNA expression level of MUC1 mRNA isoforms, MUC2 mRNA isoforms, MUC3A mRNA isoforms, MUC4 mRNA isoforms, MUC5AC mRNA isoforms, MUC5B mRNA isoforms, MUC6 mRNA isoforms, MUC7 mRNA isoforms, MUC8 mRNA isoforms, MUC12 mRNA isoforms, MUC13 mRNA isoforms, MUC16 mRNA isoforms, MUC17 mRNA isoforms, MUC19 mRNA isoforms, MUC20 mRNA isoforms, MUC21 mRNA isoforms, or MUC22 mRNA isoforms, wherein the mRNA expression level of one or more of the mucin isoforms is indicative of the severity of a coronaviral infection.

17. The method of claim 9, wherein:

the biological sample is a blood sample; and determining the presence of the mucin isoform in the biological sample comprises quantifying an mRNA expression level of MUC1 mRNA isoforms, MUC3A mRNA isoforms, MUC4 mRNA isoforms, MUC5B mRNA isoforms, MUC7 mRNA isoforms, MUC12 mRNA isoforms, MUC13 mRNA isoforms, MUC15 mRNA isoforms, MUC16 mRNA isoforms, MUC17 mRNA isoforms, MUC19 mRNA isoforms, or MUC20 mRNA isoforms wherein the mRNA expression level of one or more of the mRNA isoforms is indicative of the severity of a coronaviral infection.

18. The method of claim 9 wherein the mucin isoforms are transmembrane mucins.

19. The method of claim 1, wherein the coronaviral infection is a SARS-CoV-2 infection.

* * * * *